(12) United States Patent
Bitman et al.

(10) Patent No.: US 12,121,522 B2
(45) Date of Patent: *Oct. 22, 2024

(54) METHODS OF TREATING CANCER WITH AN mTOR INHIBITOR

(71) Applicant: Revolution Medicines, Inc., Redwood City, CA (US)

(72) Inventors: Bojena Bitman, Redwood City, CA (US); W. Clay Gustafson, Redwood City, CA (US); Ed Lorenzana, Redwood City, CA (US); Justin G. Meyerowitz, Redwood City, CA (US); Yu Chi Yang, Redwood City, CA (US); Mallika Singh, Redwood City, CA (US); Zhengping Wang, Redwood City, CA (US); Zhican Wang, Redwood City, CA (US)

(73) Assignee: REVOLUTION MEDICINES, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/506,061

(22) Filed: Nov. 9, 2023

(65) Prior Publication Data
US 2024/0100056 A1    Mar. 28, 2024

Related U.S. Application Data

(63) Continuation of application No. 18/324,050, filed on May 25, 2023.

(60) Provisional application No. 63/348,263, filed on Jun. 2, 2022, provisional application No. 63/345,809, filed on May 25, 2022.

(51) Int. Cl.
| | | |
|---|---|---|
| *A61K 31/519* | (2006.01) | |
| *A61K 9/00* | (2006.01) | |
| *A61K 31/436* | (2006.01) | |
| *A61K 31/4433* | (2006.01) | |
| *A61P 29/00* | (2006.01) | |
| *A61P 35/00* | (2006.01) | |

(52) U.S. Cl.
CPC .......... *A61K 31/519* (2013.01); *A61K 9/0019* (2013.01); *A61K 31/436* (2013.01); *A61K 31/4433* (2013.01); *A61P 29/00* (2018.01); *A61P 35/00* (2018.01)

(58) Field of Classification Search
CPC ...... A61K 31/519; A61K 31/436; A61P 35/00
USPC ....................................................... 514/262.1
See application file for complete search history.

(56) References Cited

U.S. PATENT DOCUMENTS

| | | |
|---|---|---|
| 3,929,992 A | 12/1975 | Sehgal et al. |
| 4,316,885 A | 2/1982 | Rakhit |
| 4,650,803 A | 3/1987 | Stella et al. |
| 4,861,760 A | 8/1989 | Mazuel et al. |
| 4,911,920 A | 3/1990 | Jani et al. |
| 5,023,263 A | 6/1991 | Von Burg |
| 5,023,264 A | 6/1991 | Caufield et al. |
| 5,100,883 A | 3/1992 | Schiehser |
| 5,102,876 A | 4/1992 | Caufield |
| 5,118,677 A | 6/1992 | Caufield |
| 5,118,678 A | 6/1992 | Kao et al. |
| 5,120,726 A | 6/1992 | Failli et al. |
| 5,120,842 A | 6/1992 | Failli et al. |
| 5,130,307 A | 7/1992 | Failli et al. |
| 5,151,413 A | 9/1992 | Caufield et al. |
| 5,162,333 A | 11/1992 | Failli et al. |
| 5,177,203 A | 1/1993 | Failli et al. |
| 5,212,162 A | 5/1993 | Missel et al. |
| 5,221,670 A | 6/1993 | Caufield |
| 5,233,036 A | 8/1993 | Hughes |
| 5,252,579 A | 10/1993 | Skotnicki et al. |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,262,564 A | 11/1993 | Kun et al. |
| 5,302,584 A | 4/1994 | Kao et al. |
| 5,344,833 A | 9/1994 | Hughes |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |

(Continued)

FOREIGN PATENT DOCUMENTS

| | | |
|---|---|---|
| CN | 1132512 A | 10/1996 |
| CN | 106188093 A | 12/2016 |

(Continued)

OTHER PUBLICATIONS

U.S. Appl. No. 18/324,050, filed May 25, 2023, Bitman, et al.*
Al-Muhammed et al. "In-vivo studies on dexamethasone sodium phosphate liposomes", Journal of microencapsulation, Jan. 1, 1996;13(3):293-305.
Anonyous, "Scientific Discussion," EMEA, 2015, pp. 1-49.
Apsel, B. et al. (Nov. 2008, e-published Oct. 12, 2008). "Targeted polypharmacology: discovery of dual inhibitors of tyrosine and phosphoinositide kinases," Nature Chemical Biology 4(11):691-699.

(Continued)

*Primary Examiner* — Erich A Leeser
(74) *Attorney, Agent, or Firm* — Cooley LLP

(57) ABSTRACT

The present disclosure relates to methods for the treatment of diseases or disorders (e.g., cancer) with mTOR inhibitors. Specifically, the disclosure relates to methods of treating a subject having a cancer by administering a particular dosage of an mTOR inhibitor. In some embodiments this disclosure includes methods for delaying, preventing, or treating acquired resistance to RAS inhibitors using a dosage of an mTOR inhibitor. In some embodiments, this disclosure relates to methods of treating or preventing adverse events associated with administration of an mTOR inhibitor using tacrolimus.

24 Claims, 12 Drawing Sheets

Specification includes a Sequence Listing.

(56) References Cited

U.S. PATENT DOCUMENTS

| | | |
|---|---|---|
| 5,385,910 A | 1/1995 | Ocain et al. |
| 5,389,639 A | 2/1995 | Failli et al. |
| 5,391,730 A | 2/1995 | Skotnicki et al. |
| 5,403,841 A | 4/1995 | Lang et al. |
| 5,411,967 A | 5/1995 | Kao et al. |
| 5,434,260 A | 7/1995 | Skotnicki et al. |
| 5,463,048 A | 10/1995 | Skotnicki et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,527,907 A | 6/1996 | Or et al. |
| 5,563,145 A | 10/1996 | Failli et al. |
| 5,583,139 A | 12/1996 | Or et al. |
| 5,665,772 A | 9/1997 | Cottens et al. |
| 5,741,677 A | 4/1998 | Kozlowski et al. |
| 5,780,462 A | 7/1998 | Lee et al. |
| 5,985,890 A | 11/1999 | Cottens et al. |
| 6,200,985 B1 | 3/2001 | Cottens et al. |
| 6,277,983 B1 | 8/2001 | Shaw et al. |
| 6,323,201 B1 | 11/2001 | Carson et al. |
| 6,342,507 B1 | 1/2002 | Naicker et al. |
| 6,358,969 B1 | 3/2002 | Shelley et al. |
| 6,562,819 B2 | 5/2003 | Carson et al. |
| 6,720,344 B2 | 4/2004 | Kerwin et al. |
| 7,074,804 B2 | 7/2006 | Zhu et al. |
| 7,160,867 B2 | 1/2007 | Abel et al. |
| 7,241,771 B2 | 7/2007 | Zhu |
| 7,429,596 B2 | 9/2008 | Tanaka et al. |
| 7,585,868 B2 | 9/2009 | Knight et al. |
| 8,101,602 B2 | 1/2012 | Menear et al. |
| 8,410,131 B2 | 4/2013 | Lane et al. |
| 8,492,405 B2 | 7/2013 | Yasuma et al. |
| 8,604,032 B2 | 12/2013 | Ren et al. |
| 8,642,604 B2 | 2/2014 | Knight et al. |
| 8,697,709 B2 | 4/2014 | Dar et al. |
| 8,785,454 B2 | 7/2014 | Ren et al. |
| 8,980,899 B2 | 3/2015 | Korennykh et al. |
| 9,321,772 B2 | 4/2016 | Dar et al. |
| 9,358,229 B2 | 6/2016 | Vannucchi et al. |
| 9,493,467 B2 | 11/2016 | Knight et al. |
| 9,512,125 B2 | 12/2016 | Shokat et al. |
| 9,603,891 B2 | 3/2017 | Bae et al. |
| 9,629,843 B2 | 4/2017 | Shokat et al. |
| 10,117,945 B2 | 11/2018 | Shokat et al. |
| 10,160,767 B2 | 12/2018 | Zhong et al. |
| 10,980,889 B1 | 4/2021 | Pitzen |
| 11,364,300 B2 | 6/2022 | Pitzen et al. |
| 11,685,749 B2 | 6/2023 | Semko et al. |
| 2004/0235762 A1 | 11/2004 | Abel et al. |
| 2005/0085472 A1 | 4/2005 | Tanaka et al. |
| 2005/0101624 A1 | 5/2005 | Betts et al. |
| 2005/0192311 A1 | 9/2005 | Isozaki et al. |
| 2008/0249123 A1 | 10/2008 | Gu et al. |
| 2009/0074831 A1 | 3/2009 | Falotico et al. |
| 2009/0124638 A1 | 5/2009 | Shokat et al. |
| 2009/0131631 A1 | 5/2009 | Krafft et al. |
| 2009/0181988 A1 | 7/2009 | Tanaka et al. |
| 2009/0253733 A1 | 10/2009 | Rhodes et al. |
| 2009/0270426 A1 | 10/2009 | Knight et al. |
| 2009/0274739 A1 | 11/2009 | Marks et al. |
| 2009/0292118 A1 | 11/2009 | Lee et al. |
| 2009/0312319 A1 | 12/2009 | Ren et al. |
| 2010/0009963 A1 | 1/2010 | Knight et al. |
| 2010/0190749 A1 | 7/2010 | Ren et al. |
| 2010/0190980 A1 | 7/2010 | Umemiya et al. |
| 2011/0046165 A1 | 2/2011 | Ren et al. |
| 2011/0098241 A1 | 4/2011 | Sun et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0065154 A1 | 3/2012 | Tanaka et al. |
| 2012/0065426 A1 | 3/2012 | Watanabe et al. |
| 2012/0294930 A1 | 11/2012 | Ren et al. |
| 2012/0322814 A1 | 12/2012 | Korennykh et al. |
| 2012/0329776 A1 | 12/2012 | Ren et al. |
| 2013/0289271 A1 | 10/2013 | Perrin-Ninkovic et al. |
| 2014/0066462 A1 | 3/2014 | Pearce et al. |
| 2014/0288096 A1 | 9/2014 | Knight et al. |
| 2015/0031881 A1 | 1/2015 | Tanaka et al. |
| 2015/0368297 A1 | 12/2015 | Bae et al. |
| 2016/0000789 A1 | 1/2016 | Shokat et al. |
| 2016/0168151 A1 | 6/2016 | Tanaka et al. |
| 2016/0279108 A1 | 9/2016 | Forrest et al. |
| 2016/0354377 A1 | 12/2016 | Dar et al. |
| 2017/0246305 A1 | 8/2017 | Shokat et al. |
| 2019/0284146 A1 | 9/2019 | Yan et al. |
| 2019/0336609 A1 | 11/2019 | Pitzen et al. |
| 2021/0094975 A1 | 4/2021 | Aggen et al. |
| 2021/0338824 A1 | 11/2021 | Pitzen et al. |
| 2022/0340596 A1 | 10/2022 | Semko et al. |
| 2023/0055672 A1 | 2/2023 | Pitzen et al. |
| 2023/0093861 A1 | 3/2023 | Aggen et al. |

FOREIGN PATENT DOCUMENTS

| | | |
|---|---|---|
| EP | 0088593 A2 | 9/1983 |
| EP | 0467606 A1 | 1/1992 |
| EP | 1916006 A1 | 4/2008 |
| ES | 2258763 | 9/2006 |
| GB | 1459571 A | 12/1976 |
| JP | H0249775 A | 2/1990 |
| JP | H04112877 A | 4/1992 |
| JP | H04230389 A | 8/1992 |
| JP | 2004161716 A | 6/2004 |
| JP | 2008273976 A | 11/2008 |
| JP | 2009513222 A | 4/2009 |
| JP | 2012528165 A | 11/2012 |
| JP | 2016500112 A | 1/2016 |
| JP | 2017531624 A | 10/2017 |
| RU | 2152946 C1 | 7/2000 |
| RU | 2322981 C2 | 4/2008 |
| RU | 2487711 C2 | 7/2013 |
| WO | WO-9205179 A1 | 4/1992 |
| WO | WO-9311130 A1 | 6/1993 |
| WO | WO-9402136 A1 | 2/1994 |
| WO | WO-9402485 A1 | 2/1994 |
| WO | WO-1994004540 A1 | 3/1994 |
| WO | WO-9409010 A1 | 4/1994 |
| WO | WO-9411380 A1 | 5/1994 |
| WO | WO-9425072 A1 | 11/1994 |
| WO | WO-9504738 A1 | 2/1995 |
| WO | WO-9514023 A1 | 5/1995 |
| WO | WO-9516691 A1 | 6/1995 |
| WO | WO-9641807 A1 | 12/1996 |
| WO | WO-9936553 A2 | 7/1999 |
| WO | WO-0114387 A1 | 3/2001 |
| WO | WO-2004024719 A1 | 3/2004 |
| WO | WO-2004101583 A1 | 11/2004 |
| WO | WO-2005007085 A2 | 1/2005 |
| WO | WO-2005105760 A1 | 11/2005 |
| WO | WO-2006009518 A1 | 1/2006 |
| WO | WO-2006068760 A2 | 6/2006 |
| WO | WO-2006069038 A1 | 6/2006 |
| WO | WO-2006116727 A2 | 11/2006 |
| WO | WO-2007057457 A2 | 5/2007 |
| WO | WO-2007061737 A2 | 5/2007 |
| WO | WO-2007068462 A2 | 6/2007 |
| WO | WO-2007114926 A2 | 10/2007 |
| WO | WO-2007121453 A2 | 10/2007 |
| WO | WO-2008046641 A2 | 4/2008 |
| WO | WO-2008047821 A1 | 4/2008 |
| WO | WO-2008065887 A1 | 6/2008 |
| WO | WO-2008115974 A2 | 9/2008 |
| WO | WO-2008127226 A2 | 10/2008 |
| WO | WO-2009046436 A1 | 4/2009 |
| WO | WO-2009088986 A1 | 7/2009 |
| WO | WO-2009088990 A1 | 7/2009 |
| WO | WO-2009089262 A1 | 7/2009 |

(56) References Cited

FOREIGN PATENT DOCUMENTS

| | | |
|---|---|---|
| WO | WO-2009122176 A2 | 10/2009 |
| WO | WO-2009131631 A1 | 10/2009 |
| WO | WO-2010006072 A2 | 1/2010 |
| WO | WO-2010006086 A2 | 1/2010 |
| WO | WO-2010025406 A1 | 3/2010 |
| WO | WO-2010036380 A1 | 4/2010 |
| WO | WO-2010044885 A2 | 4/2010 |
| WO | WO-2010051042 A1 | 5/2010 |
| WO | WO-2010051043 A1 | 5/2010 |
| WO | WO-2010138487 A1 | 12/2010 |
| WO | WO-2011022439 A1 | 2/2011 |
| WO | WO-2011022440 A2 | 2/2011 |
| WO | WO-2011047384 A2 | 4/2011 |
| WO | WO-2011047384 A9 | 8/2011 |
| WO | WO-2012017449 A1 | 2/2012 |
| WO | WO-2012066502 A1 | 5/2012 |
| WO | WO-2012103959 A1 | 8/2012 |
| WO | WO-2012103960 A1 | 8/2012 |
| WO | WO-2012151562 A1 | 11/2012 |
| WO | WO-2012154695 A2 | 11/2012 |
| WO | WO-2013077921 A2 | 5/2013 |
| WO | WO-2014082286 A1 | 6/2014 |
| WO | WO-2015066371 A1 | 5/2015 |
| WO | WO-2015095755 A1 | 6/2015 |
| WO | WO-2015184983 A1 | 12/2015 |
| WO | WO-2016040806 A1 | 3/2016 |
| WO | WO-2016100116 A1 | 6/2016 |
| WO | WO-2017044720 A1 | 3/2017 |
| WO | WO-2017121444 A1 | 7/2017 |
| WO | WO-2018204416 A1 | 11/2018 |
| WO | WO-2019064182 A1 | 4/2019 |
| WO | WO-2019212990 A1 | 11/2019 |
| WO | WO-2019212991 A1 | 11/2019 |
| WO | WO-2020160711 A1 | 8/2020 |
| WO | WO-2021257736 A1 | 12/2021 |
| WO | WO-2022216900 A2 | 10/2022 |
| WO | WO-2023230577 A1 | 11/2023 |

OTHER PUBLICATIONS

Awad, M.M. et al., "Acquired Resistance to KRASG12C Inhibition in Cancer," The New England Journal of Medicine, Jun. 24, 2021, vol. 384, pp. 2382-2393.

Ayral-Kaloustian, S. et al. (Jan. 2010). "Hybrid inhibitors of phosphatidylinositol 3-kinase (PI3K) and the mammalian target of rapamycin (mTOR): design, synthesis, and superior antitumor activity of novel wortmannin-rapamycin conjugates," J Med Chem 53(1):452-459.

Banerjee, S.S. et al. (2012, e-published May 7, 2012). "Poly(ethylene glycol)-Prodrug Conjugates: Concept, Design, and Applications," J Drug Deliv 2012:103973, 17 pages.

Burnett L G., "Discovery of RMC-5552: A selective bi-steric inhibitor of mTORC1 that suppresses 4EBP1 phosphorylation, for the treatment of mTORC1-activated tumors including RAS pathway escape", In: Proceedings of the American Association for Cancer Research Annual Meeting 2021; Apr. 10-15, 2021 and May 17-21, 25 pages [online], Philadelphia (PA): AACR; Cancer Res 2021;81(13_Suppl):Abstract nr ND10 [retrieved on Jun. 7, 2023]. Retrieved from: https://s3-us-west-2.amazonaws.com/rvmdpubs.revmed.com/2021/04+ND10+RMC-5552.pdf.

Campanero, M. et al., "Therapeutic drug monitoring for sirolimus in whole blood of organ transplants by high-performance liquid chromatography with ultraviolet detection," Journal of Chromotography, 2004, vol. 1031, pp. 265-273.

CAS Registry No. 53123-88-9, accessed Feb. 27, 2018, 2 pages.

Choi, J. et al. (Jul. 1996). "Structure of the FKBP12-rapamycin complex interacting with the binding domain of human FRAP," Science 273(5272):239-242.

Chonn et al. "Recent advances in liposomal drug-delivery systems", Current Opinion in Biotechnology, (1995); 6(6):698-708.

Chou, "Drug Combination Studies and Their Synergy Quantification Using the Chou-Talalay Method." Cancer Research (2010); 70(2): 440-446. Published OnlineFirst Jan. 12, 2010.

Christensen, J., "The KRASG12C Inhibitor, MRTX849, Provides Insight Toward Therapeutic Susceptibility of KRAS Mutant Cancer," Presentation at AACR-NCI-EORTC International Conference, Oct. 26-30, 2019, 30 pages, audio and visual available at https://webcast.aacr.org/console/player/41715?mediaType=audio&.

ClinicalTrials.gov, "Combination Study of RMC-4630 and Sotorasib for NSCLC Subjects With KRASG12C Mutation After Failure of Prior Standard Therapies," NCT No. NCT05054725, last updated Apr. 3, 2023, 9 pages.

ClinicalTrials.gov, "Dose Escalation and Dose Expansion Study of RMC-6291 Monotherapy in Subjects with Advanced KRASG12C Mutant Solid Tumors," NCT No. NCT05462717, last updated Sep. 6, 2023, 7 pages.

ClinicalTrials.gov, "Dose Escalation of RMC-4630 Monotherapy in Relapsed/Refractory Solid Tumors," NCT No. NCT03634982, last updated Sep. 1, 2022, 8 pages.

ClinicalTrials.gov, "Dose Escalation of RMC-5552 Monotherapy in Relapsed/Refractory Solid Tumors," NCT No. NCT04774952, last updated Mar. 7, 2023, 8 pages.

ClinicalTrials.gov, "Evaluation of RMC-6236 in Subjects with Advanced Solid Tumors Harboring Specific Mutations in KRAS," NCT No. NCT05379985, last updated Dec. 27, 2022, 7 pages.

ClinicalTrials.gov, "History of Changes for Study: NCT04774952; Dose Escalation of RMC-5552 Monotherapy in Relapsed/Refractory Solid Tumors," NCT No. NCT04774952, earliest publication date of Feb. 25, 2023, 4 pages.

ClinicalTrials.gov, "Sotorasib Activity in Subjects With Advanced Solid Tumors With KRAS p.G12C Mutation (CodeBreak 101)," NCT No. NCT04185883, last updated Sep. 14, 2023, 14 pages.

Database Registry [Online], CAS Registry No. 1237826-20-8 (Aug. 23, 2010), 1 page.

Database Registry [Online], CAS Registry No. 153984-91-9 (Mar. 30, 1994), 1 page.

Dhaon, M. et al., "Synthesis, isolation, and characterization of ABT-578 equilibrium isomers," Tetrahedron Letters, Dec. 22, 2006, vol. 48, pp. 1059-1062.

Dowling, R.J. et al. (May 28, 2010). "mTORC1-mediated cell proliferation, but not cell growth, controlled by the 4E-BPs," Science 328(5982):1172-1176.

Drachman, J.G. et al. (2013). "Antibody-drug conjugates: the chemistry behind empowering antibodies to fight cancer," Hematology Am Soc Hematol Educ Program 2013:306-310.

European Search Report in EP Application No. 23164819.7, mailed Sep. 28, 2023, 18 pages.

Eyles Je, et al. "Oral delivery and fate of poly (lactic acid) microsphere-encapsulated interferon in rats", Journal of pharmacy and pharmacology, (1997); 49(7):669-674.

Feldman M.E., et al., "Active-Site Inhibitors of mTOR Target Rapamycin-Resistant Outputs of mTORC1 and mTORC2," PLoS Biology, Feb. 2009, vol. 7 (2), pp. 0371-0383.

Feldman, ME et al., "New inhibitors of the PI3K-Akt-mTOR pathway: insights into mTOR signaling from a new generation of Tor kinase domain inhibitors (TORKinibs)," Posphoinositide 3-kinase in Health and Disease, 2011, vol. 2, pp. 241-262.

Flygare, J.A. et al., "Antibody-drug conjugates for the treatment of cancer," Chem Biol Drug Des, Jan. 2013, vol. 81(1):113-121.

Fundamentals of Medical Prevention. Educational and Methodological Manual for Students and Cadets of Professional Development Cycles of State Professional Educational Institutions. Novosibirsk, 2016, UDC 614.2-084, BBC 51.1(2)2, pp. 13-21, Available online https://rcmpnso.ru/profila/m_mater/docs/osnovi_med_pomoshi.pdf?ysclid=l5wi7xgplo450927514.

Galat, "Functional diversity and pharmacological profiles of the FKBPs and their complexes with small natural ligands," Cell Mol Life Sci. Sep. 2013;70(18):3243-75.

Gao, Z.H., et al., "Controlled release of a contraceptive steroids from biodegradable and injectable gel formulations: in vitro evaluation," Pharm Res., (1995); 12(6):857-863.

(56) References Cited

OTHER PUBLICATIONS

Guo et al., "High-throughput screening using patient-derived tumor xenografts to predict clinical trial drug response," Nature Medicine, Oct. 19, 2015, vol. 21, No. 11, pp. 1318-1325.
Hackam et al. "Translation of research evidence from animals to humans", JAMA, (2006); 296(14):1727-1732.
Hara, K. et al. (Jul. 26, 2002). "Raptor, a binding partner of target of rapamycin (TOR), mediates TOR action," Cell 110(2):177-189.
Hsieh, A.C. et al. (Feb. 22, 2012). "The translational landscape of mTOR signalling steers cancer initiation and metastasis," Nature 485(7396):55-61.
Hsieh, A.C. et al. (Mar. 16, 2010). "Genetic dissection of the oncogenic mTOR pathway reveals druggable addiction to translational control via 4EBP-el F4E," Cancer Cell 17(3):249-261.
Hughes et al., "The isolation, synthesis and characterization of an isomeric form of rapamycin," Tetrahedron Letters, vol. 33, Issue 33, Aug. 11, 1992, pp. 4739-4742.
Il'ichev, Y. et al., "Degradation of rapamycin and its ring-opened isomer: role of base catalysis," ARKIVOC, May 6, 2007, vol. 12, pp. 110-131.
Infante, J. R. et al. (2013). Abstract C252: A phase 1, dose-escalation study of MLN0128, an investigational oral mammalian target of rapamycin complex 1/2 (mTORC1/2) catalytic inhibitor, in patients (pts) with advanced non-hematologic malignancies. Mol. Cancer Ther. 12; C252.
International Search Report and Written Opinion for PCT Application No. PCT/US2023/067503 dated Jul. 19, 2023, 15 pages.
International Search Report and Written Opinion in PCT/US2022/023778, mailed Nov. 25, 2022, 1-18.
International Search Report mailed on Aug. 28, 2018, for PCT Application No. PCT/US2018/030531, filed on May 1, 2018, 16 pages.
International Search Report mailed on Dec. 14, 2015, for PCT Application No. PCT/US2015/049693, filed on Sep. 11, 2015, 3 pages.
International Search Report mailed on Jun. 26, 2019, for PCT Application No. PCT/US2019/029738, filed on Apr. 29, 2019, 4 pages.
International Search Report mailed on Sep. 23, 2019, for PCT Application No. PCT/US2019/029737, filed on Apr. 29, 2019, 12 pages.
Jacinto, E. et al. (Nov. 2004, e-published Oct. 3, 2004). "Mammalian TOR complex 2 controls the actin cytoskeleton and is rapamycin insensitive," Nat Cell Biol 6(11):1122-1128.
Jordan "Tamoxifen: a most unlikely pioneering medicine", Nature Reviews Drug Discovery, (2003); 2(3):205-213.
Kallen et al., "X-ray Crystal Structure of 28-O-Methylrapamycin complexed with FKBP12: Is the Cyclohexyl Moiety Part of the Effector Domain of Rapamycin," J. Am. Chem. Soc. 1996, 118, 5857-5861.
Katritzky, A.R., et al., "QSAR modeling, synthesis and bioassay of diverse leukemia RPMI-8226 cell line active agents," Eur J Med Chem. Nov. 2010, vol. 45, No. 11, pp. 5183-5199.
Katritzky, A.R., et al., "Tautomerism in drug discovery," Journal of computer-aided molecular design, Jun. 2010, vol. 24 (6-7), pp. 475-484.
Kim, D.H. et al. (Jul. 26, 2002). "mTOR interacts with raptor to form a nutrient-sensitive complex that signals to the cell growth machinery," Cell 110(2):163-175.
Kümmerer, K., "Pharmaceuticals in the Environment", Annual Review of Environment and Resources (2010); 35: 57-75.
Kolb, H.C. et al (Jun. 1, 2001). "Click Chemistry: Diverse Chemical Function from a Few Good Reactions," Angewandte Chemie International Edition 40(11):2004-2021.
Lamming, D.W. et al. (Mar. 30, 2012). "Rapamycin-induced insulin resistance is mediated by mTORC2 loss and uncoupled from longevity," Science 335(6076):1638-1643.
Lee, BJ et al., "Selective inhibitors of mTORC1 activate 4EBP1 and suppress tumor growth," Nat Chem Biol., Oct. 2021, vol. 17, No. 10, pp. 1065-1074.
Liu et al., "Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer," J Med Chem. Oct. 14, 2010;53(19):7146-55.
Luengo et al., "Manipulation of the Rapamycin Effector Domain. Selective Nucleophilic Substitution of the C7 Methoxy Group," Org. Chem. 1994, 59, 22, 6512-6513.
Leungo, J. et al., "Studies on Selective Reductions of Rapamycin," Tetrahedron Letters, 1994, vol. 35, No. 35, pp. 6469-6472.
Mashkovsky, M.D., "Medicaments (Doctor's Manual)", 14th Edition, vol. 1., Moscow. (2001), p. 11; 6 pages with English translation.
Masuda, et al., Synthesis of Alkoxy-, (Alkylthio)-, Phenoxy-, and (Phenylthio)pyrazines and their Olfactive Properties, J. Agric. Food Chem., 1986, pp. 377-381.
McCormick, M.A. et al. (Jan. 12, 2011). "TOR and ageing: a complex pathway for a complex process," Philas Trans R Soc Land B Biol Sci 366(1561):17-27.
Moni et al., "Synthesis of rapamycin glycoconjugates via a CuAAC-based approach," Tetrahedron Letters, vol. 54, Issue 51, Dec. 18, 2013, pp. 6999-7003.
Naing, A. et al. (Sep. 25, 2012, e-published Aug. 30, 2012). "Safety, tolerability, pharmacokinetics and pharmacodynamics of AZD8055 in advanced solid tumours and lymphoma," Br J Cancer 107(7):1093-1099.
Neasta, J. et al. (Jul. 2014, e-published Apr. 19, 2014). "mTOR complex 1: a key player in neuroadaptations induced by drugs of abuse," J Neurochem 130(2):172-184.
Nelson et al., "Manipulation of the C(22)-C(27) Region of Rapamycin: Stability Issues and Biological Implications," Bioorganic & Medicinal Chemistry Letters, vol. 9, No. 2, 1999, pp. 295-300.
Nelson, F.C. et al., "A Novel Ring Contraction of Rapamycin," Tetrahedron Letters, 1994, vol. 35, No. 41, pp. 7557-7560.
Nowak et al., "Discovery of potent and selective inhibitors of the mammalian target of rapamycin (mTOR) kinase," J Med Chem. Nov. 26, 2009;52(22):7081-9.
O'Donnell, A. et al. (Apr. 1, 2008, e-published Mar. 10, 2008). "Phase I pharmacokinetic and pharmacodynamic study of the oral mammalian target of rapamycin inhibitor everolimus in patients with advanced solid tumors," J Clin Onco/ 26(10):1588-1595.
Ohbayashi, Y., et al., "Topical steroid injection for refractory oral chronic graft-versus-host disease" Rinsho Ketsueki, (2007), vol. 48, pp. 1508-1510.
O'Reilly, K.E. et al. (Feb. 1, 2006). "mTOR inhibition induces upstream receptor tyrosine kinase signaling and activates Akt," Cancer Res 66(3):1500-1508.
Ostro MJ, et al. "Use of liposomes as injectable-drug delivery systems", American Journal of Hospital Pharmacy, (1989), 46:1576-1587.
Pokrovsky, V.I., "Small Medical Encyclopedia," Medicine, 1996, V5, pp. 90-96, and English translation of relevant portion, 12 pages.
Prior, I. et al., "The Frequency f Ras Mutations in Cancer," Cancer Research, 2020, vol. 80, pp. 2969-2974.
Rao, "Recent developments of collagen-based materials for medical applications and drug delivery systems," J Biomater Sci Polym Ed. 1995;7(7):623-45.
Revolution Medicines, Inc., "Targeting KRASG12C(ON) and Potential Application to Overcoming Drug Resistance in RAS-Addicted Tumors," RAS-Targeted Drug Development, Sep. 22, 2021, 16 pages.
Revolution Medicines, Inc., "The Bi-steric mTORC1-Selective Inhibitor RMC-5552 in Tumors with Activation of mTOR Signaling: Preclinical Activity in Combination with RAS(ON) Inhibitors in RAS-Addicted Tumors, and Initial Clinical Findings from A Single Agent Phase 1/1b Study," 2022 ASCO Annual Meeting, Jun. 3-7, 2002, Chicago, IL, Abstract No. 3098, 1 page.
Ricciutelli, M. et al., "Evaluation of rapamycin chemical stability in volatile-organic solvents by HPLC," Journal of Pharmaceutical and Biomedical Analysis, Mar. 20, 2006, vol. 41, pp. 1070-1074.
Rhodes, N. et al. (Apr. 1, 2008). "Characterization of an Akt kinase inhibitor with potent pharmacodynamic and antitumor activity," Cancer Res 68(7):2366-2374.

(56) References Cited

OTHER PUBLICATIONS

Rodrik-Outmezguine, V.S. et al. (Aug. 2011, e-published Jun. 17, 2011). "mTOR kinase inhibition causes feedback-dependent biphasic regulation of AKT signaling," Cancer Discov 1(3):248-259.
Rodrik-Outmezguine, V.S., et al., "Overcoming mTOR Resistance Mutations with a New-Generation mTOR Inhibitor," Nature, Jun. 9, 2016, vol. 534(7606), 28 pages.
Ruggero, D. et al. (May 2004, e-published Apr. 18, 2004). "The translation factor elF-4E promotes tumor formation and cooperates with c-Myc in lymphomagenesis," Nat Med 10(5):484-486.
Sanchez-Martinez, Conception, "Cyclin dependent kinase (CDK) inhibitors as anticancer drugs", Bioorganic & Medicinal Chemistry Letters, Pergamon, Amsterdam, NL, 25(17), Jun. 6, 2015, pp. 3420-3435.
Sarbassov, D.D. et al. (Apr. 21, 2006). "Prolonged rapamycin treatment inhibits mTORC2 assembly and Akt/PKB," Mol Cell 22(2):159-168.
Sarbassov, D.D. et al. (Jul. 27, 2004). "Rictor, a novel binding partner of mTOR, defines a rapamycin-insensitive and raptor-independent pathway that regulates the cytoskeleton," Curr Biol 14(14):1296-1302.
Shu et al., "Synthesis of 1125 labeled photoaffinity rapamycin analogs," Journal of Labelled Compounds and Radiopharmaceuticals, vol. 38, No. 3, 1996, pp. 227-237.
Sobhani, H. et al., "A Reversed Phase High Performance Liquid Chromatographic Method for Determination of Rapamycin," Iranian Journal of Pharmaceutical Research, Feb. 2013, vol. 12 (supplement), pp. 77-81.
Strom et al., "Structural identification of SAR-943 metabolites generated by human liver microsomes in vitro using mass spectrometry in combination with analysis of fragmentation patterns," J. Mass. Spectrom. 2011, 46, 615-624.
Su, K. Y. et al. (Feb. 1, 2012). "Pretreatment epidermal growth factor receptor (EGFR) T790M mutation predicts shorter EGFR tyrosine kinase inhibitor response duration in patients with non-small-cell lung cancer," J Clin Oncol 30(4):433-440.
Tallarida, R.J., "Quantitative methods for assessing drug synergism," Genes and cancer, Nov. 2011, vol. 2, No. 11, pp. 1003-1008.
Tanaka, N. et al., "Clinical Acquired Resistance to KRASG12C Inhibition through a Novel KRAS Switch-II Pocket Mutation and Polyclonal Alterations Converging on RAS-MAPK Reactivation," AACR Cancer Discovery, Aug. 2021, vol. 11, No. 8, pp. 1913-1922.
Thoreen C.C., et al., "An ATP-competitive Mammalian Target of Rapamycin Inhibitor Reveals Rapamycin-resistant Functions of mTORC1," Journal of Biological Chemistry, Mar. 2009, vol. 284 (12), pp. 8023-8032.
Umeda, N. et al. (Jan. 12, 2011, e-published Dec. 13, 2010). "A photocleavable rapamycin conjugate for spatiotemporal control of small GTPase activity," J Am Chem Soc 133(1):12-14.
Vengerovskiy, A. I., "Pharmacological incompatibility", Bulletin of Siberian Medicine (2003); 2(3): 49-56; 16 pages (English translation of Russian Office Action for Russian Application No. 2013107378/13(010962) attached).
Viale, PH., "The American Cancer Society's Facts & Figures: 2020 Edition," Journal of the Advanced Practitioner in Oncology, Mar. 2020, vol. 11, No. 2, pp. 135-136.
Wagner, R. et al., "Rapamycin analogs with reduced systemic exposure," Bioorganic Medicinal Chemistry Letters, Sep. 26, 2005, vol. 15, pp. 5340-5343.
Wood, E.R. et al. (Sep. 15, 2004). "A unique structure for epidermal growth factor receptor bound to GW572016 (Lapatinib): relationships among protein conformation, inhibitor off-rate, and receptor activity in tumor cells," Cancer Res 64(18):6652-6659.
Written Opinion mailed on Dec. 14, 2015, or PCT Application No. PCT/US2015/049693, filed on Sep. 11, 2015, 7 pages.
Wyeth Laboratories, Rapamune® (sirolimus) Oral Solution Tablets, 2007, 37 pages, retrieved from https://www.accessdata.fda.gov/drugsatfda_docs/label/2007/021083s030,021110s038lbl.pdf.
Xie et al., "Design, Synthesis and Biological Evaluation of Novel Rapamycin Benzothiazole Hybrids as mTOR Targeted Anti-cancer Agents," Chem Pharm Bull (Tokyo). 2016;64(4):346-55.
Xie et al., "Synthesis of Rapamycin Derivatives Containing the Triazole Moiety Used as Potential mTOR-Targeted Anticancer Agents," Arch Pharm (Weinheim). Jun. 2016;349(6):428-41.
Xu, C.X. et al. (2011, e-published Jun. 14, 2011). "The combination of RAD001 and NVP-BEZ235 exerts synergistic anticancer activity against non-small cell lung cancer in vitro and in vivo," PLoS One 6(6):e20899.
Yamanishi, et al., Syntheses of trimethylpyrazines and their antibacterial properties, Yakugaku Zasshi, 1967, pp. 105-107.
Yang, H. et al. (May 9, 2013, e-published May 1, 2013). "mTOR kinase structure, mechanism and regulation," Nature 497(7448):217-223.
Yohannes, D. et al., "Degradation of Rapamycin Retrieval of Major Intact Subunits," Tetraheron Letters, Jan. 1, 1992, vol. 33, No. 49, pp. 7469-7472.
Zeng, H. et al. (Jul. 25, 2013, e-published Jun. 30, 2013). "mTORC1 couples immune signals and metabolic programming to establish T(reg)-cell function," Nature (7459):485-490.
Dorwald, F.Z., "Side Reactions in Organic Synthesis: A Guide to Successful Synthesis Design," Weinheim: Wiley-VCH Verlag GmbH & Co. KGaA, Preface, Mar. 2006, 4 printed pages.
Extended European Search Report in EP Application No. 23164819.7, mailed Jan. 25, 2024, 20 pages.
Wood et al., "Developmental Pharmacology—Drug Disposition, Action, and Therapy in Infants and Children," New England Journal of Medicine, Sep. 18, 2003, vol. 349, No. 12, pp. 1157-1167.
Revolution Medicines, Inc., "On Target to Outsmart Cancer™," Corporate Presentation, Jan. 10, 2023, 32 pages.
Revolution Medicines, Inc., "On Target to Outsmart Cancer™," Corporate Presentation, Jan. 11, 2022, 33 pages.
Revolution Medicines, Inc., "Revolution Medicines Announces Publication Describing Design and Synthesis of RMC-5552, a First-in- Class, Bi-Steric mTORC1-Selective Inhibitor," Press Release dated Dec. 19, 2022, 2 pages.

\* cited by examiner

METHODS OF TREATING CANCER WITH AN mTOR INHIBITOR

CROSS-REFERENCE TO RELATED APPLICATIONS

This application is a continuation of U.S. application Ser. No. 18/324,050, filed May 25, 2023, which claims priority to U.S. Provisional Application Ser. No. 63/348,263, filed Jun. 2, 2022, and U.S. Provisional Application Ser. No. 63/345,809, filed May 25, 2022, each of which are herein incorporated by reference in their entirety for all purposes.

REFERENCE TO A SEQUENCE LISTING

The contents of the electronic sequence listing (REME_032_03US_SeqList_ST26.xml; Size: 17,326 bytes; and Date of Creation: Oct. 25, 2023) are herein incorporated by reference in its entirety.

FIELD OF DISCLOSURE

The present disclosure relates to methods for the treatment of diseases or disorders (e.g., cancer) with mTOR inhibitors. Specifically, in some embodiments this disclosure relates to methods of treating a subject having a cancer by administering a dosage of an mTOR inhibitor. In some embodiments this disclosure includes methods for delaying, preventing, or treating acquired resistance to RAS inhibitors using a dosage of an mTOR inhibitor. In some embodiments, this disclosure relates to methods of treating or preventing adverse events associated with administration of an mTOR inhibitor using tacrolimus.

BACKGROUND

The mammalian target of rapamycin (mTOR) is a serine-threonine kinase related to the lipid kinases of the phosphoinositide 3-kinase (PI3K) family. mTOR exists in two complexes, mTORC1 and mTORC2, which are differentially regulated, have distinct substrate specificities, and are differentially sensitive to rapamycin. mTORC1 integrates signals from growth factor receptors with cellular nutritional status and controls the level of cap-dependent mRNA translation by modulating the activity of key translational components such as the cap-binding protein and oncogene eIF4E.

First-generation mTOR inhibitors, as well as pan- and isoform-selective PI3K inhibitors, have been evaluated for the treatment of cancers dependent on activation of PI3K/mTOR signaling. Rapalogs and pan-mTOR active-site inhibitors do not inhibit mTORC1-mediated phosphorylation of 4EBP1 completely at clinically achievable exposures, and thus can be considered "incomplete" pathway inhibitors. This is thought to be, at least in part, consistent with the minimal clinical success of these agents. In addition, pan-mTOR active-site inhibitors exhibit a lack of selectivity and likely inhibit lipid kinases. There is a significant group of cancers with dysregulation of PI3K/mTOR signaling with unmet medical needs that are not currently addressed by extant inhibitor treatment strategies.

Currently, most subjects with mutations/rearrangements that confer activation of the mTOR pathway do not have approved targeted therapeutic options. This represents a subject population that could potentially benefit from treatment. In addition, resistance to currently approved and emerging targeted therapies presents another potential subject population. Treatment options for both subject populations primarily include chemotherapy regimens, which provide modest benefit, and are often associated with deleterious side-effects. Thus, there is a need for new treatment options for these subjects.

SUMMARY

The present disclosure relates to methods for the treatment of diseases or disorders (e.g., cancer) with mTOR inhibitors (e.g., RMC-5552). In particular, the present disclosure provides methods comprising administering a particular dosage of an mTOR inhibitor (e.g., RMC-5552). Such methods were surprisingly found both to be both efficacious and tolerable to the subject.

The present disclosure provides a method of treating a subject having a cancer, the method comprising administering a dosage of about 3 mg/week to about 25 mg/week of a compound to the subject;

wherein the compound is RMC-5552:

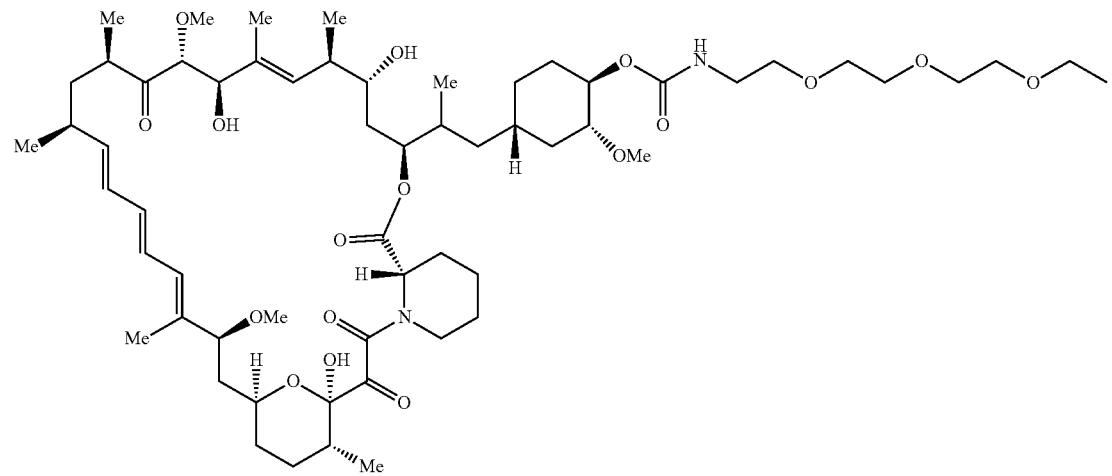

-continued

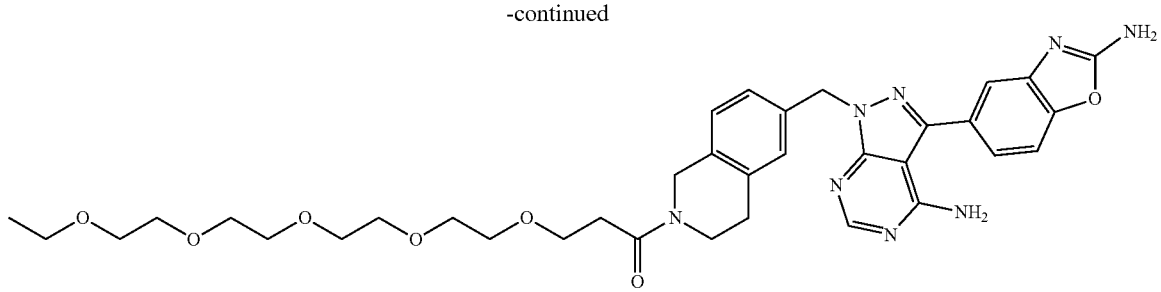

or a stereoisomer, tautomer, or oxepane isomer thereof, or pharmaceutically acceptable salt of any of the foregoing.

The present disclosure also provides a method of treating a subject having salivary gland cancer, the method comprising administering a dosage of about 3 mg/week to about 25 mg/week of a compound to the subject;
wherein the compound is RMC-5552 or a stereoisomer, tautomer, or oxepane isomer thereof, or pharmaceutically acceptable salt of any of the foregoing.

The present disclosure also provides a method for delaying or preventing acquired resistance to a RAS inhibitor in a subject in need thereof, comprising administering to the subject about 3 mg/week to about 25 mg/week of a compound, wherein the subject has already received or will receive administration of the RAS inhibitor;
wherein the compound is RMC-5552 or a stereoisomer, tautomer, or oxepane isomer thereof, or pharmaceutically acceptable salt of any of the foregoing.

The present disclosure also provides a method of treating acquired resistance to a RAS inhibitor in a subject in need thereof, comprising administering to the subject about 3 mg/week to about 25 mg/week of a compound;
wherein the compound is RMC-5552 or a stereoisomer, tautomer, or oxepane isomer thereof, or pharmaceutically acceptable salt of any of the foregoing.

The present disclosure also provides a use of a compound in a treatment of cancer, wherein the treatment comprises administering a dosage of about 3 mg/week to about 25 mg/week of the compound to a subject in need thereof;
wherein the compound is RMC-5552 or a stereoisomer, tautomer, or oxepane isomer thereof, or pharmaceutically acceptable salt of any of the foregoing.

The present disclosure also provides a use of a compound in the manufacture of a medicament for treatment of cancer, wherein the treatment comprises administering the medicament to a subject in need thereof to deliver a dosage of about 3 mg/week to about 25 mg/week of the compound;
wherein the compound is RMC-5552 or a stereoisomer, tautomer, or oxepane isomer thereof, or pharmaceutically acceptable salt of any of the foregoing.

The present disclosure also provides a compound for use in a method of treating cancer, the method comprising administering a dosage of about 3 mg/week to about 25 mg/week of the compound to a subject in need thereof;
wherein the compound is RMC-5552 or a stereoisomer, tautomer, or oxepane isomer thereof, or pharmaceutically acceptable salt of any of the foregoing.

The present disclosure also provides a medicament for treatment of cancer, the medicament comprising a compound, wherein the treatment comprises administering the medicament to deliver a dosage of about 3 mg/week to about 25 mg/week of the compound to a subject in need thereof;
wherein the compound is RMC-5552 or a stereoisomer, tautomer, or oxepane isomer thereof, or pharmaceutically acceptable salt of any of the foregoing.

The present disclosure also provides a compound for use in a method treating cancer in a subject having acquired resistance to a RAS inhibitor, the method comprising administering a dosage of about 3 mg/week to about 25 mg/week of the compound to the subject, wherein the subject has already received or will receive administration of the RAS inhibitor;
wherein the compound is RMC-5552 or a stereoisomer, tautomer, or oxepane isomer thereof, or pharmaceutically acceptable salt of any of the foregoing.

The present disclosure also provides a combination of compound and a RAS inhibitor for simultaneous, separate, or sequential use in a method of treating cancer in a subject having acquired resistance to the RAS inhibitor, the method comprising administering a dosage of about 3 mg/week to about 25 mg/week of the compound to a subject in need thereof;
wherein the compound is RMC-5552 or a stereoisomer, tautomer, or oxepane isomer thereof, or pharmaceutically acceptable salt of any of the foregoing.

The present disclosure also provides a use of a compound in a treatment for delaying or preventing acquired resistance to a RAS inhibitor in a subject in need thereof, comprising administering to the subject about 3 mg/week to about 25 mg/week of a compound, wherein the subject has already received or will receive administration of the RAS inhibitor;
wherein the compound is RMC-5552 or a stereoisomer, tautomer, or oxepane isomer thereof, or pharmaceutically acceptable salt of any of the foregoing.

The present disclosure also provides a use of a compound in the manufacture of a medicament for treatment for delaying or preventing acquired resistance to a RAS inhibitor, wherein the treatment comprises administering the medicament to a subject in need thereof to deliver a dosage of about 3 mg/week to about 25 mg/week of the compound, wherein the subject has already received or will receive administration of the RAS inhibitor; wherein the compound is RMC-5552 or a stereoisomer, tautomer, or oxepane isomer thereof, or pharmaceutically acceptable salt of any of the foregoing.

The present disclosure also provides a compound for use in a method of delaying or preventing acquired resistance to a RAS inhibitor, the method comprising administering a dosage of about 3 mg/week to about 25 mg/week of the compound to a subject in need thereof, wherein the subject has already received or will receive administration of the RAS inhibitor;
wherein the compound is RMC-5552 or a stereoisomer, tautomer, or oxepane isomer thereof, or pharmaceutically acceptable salt of any of the foregoing.

The present disclosure also provides a medicament for treatment for delaying or preventing acquired resistance to a RAS inhibitor, the medicament comprising a compound, wherein the treatment comprises administering the medicament to deliver a dosage of about 3 mg/week to about 25 mg/week of the compound to a subject in need thereof, wherein the subject has already received or will receive administration of the RAS inhibitor;

wherein the compound is RMC-5552 or a stereoisomer, tautomer, or oxepane isomer thereof, or pharmaceutically acceptable salt of any of the foregoing.

The present disclosure also provides a use of a compound in a treatment of acquired resistance to a RAS inhibitor, wherein the treatment comprises administering a dosage of about 3 mg/week to about 25 mg/week of the compound to a subject in need thereof;

wherein the compound is RMC-5552 or a stereoisomer, tautomer, or oxepane isomer thereof, or pharmaceutically acceptable salt of any of the foregoing.

The present disclosure also provides a use of a compound in the manufacture of a medicament for treatment of acquired resistance to a RAS inhibitor, wherein the treatment comprises administering the medicament to a subject in need thereof to deliver a dosage of about 3 mg/week to about 25 mg/week of the compound;

wherein the compound is RMC-5552 or a stereoisomer, tautomer, or oxepane isomer thereof, or pharmaceutically acceptable salt of any of the foregoing.

The present disclosure also provides a compound for use in a method of treating acquired resistance to a RAS inhibitor, the method comprising administering a dosage of about 3 mg/week to about 25 mg/week of the compound to a subject in need thereof;

wherein the compound is RIC-5552 or a stereoisomer, tautomer, or oxepane isomer thereof, or pharmaceutically acceptable salt of any of the foregoing.

The present disclosure also provides a medicament for treatment of acquired resistance to a RAS inhibitor, the medicament comprising a compound, wherein the treatment comprises administering the medicament to deliver a dosage of about 3 mg/week to about 25 mg/week of the compound to a subject in need thereof;

wherein the compound is RIC-5552 or a stereoisomer, tautomer, or oxepane isomer thereof, or pharmaceutically acceptable salt of any of the foregoing.

The present disclosure also provides a method of treating or preventing mucositis in a subject in need thereof that has been, is being, or will be treated with an mTOR inhibitor, the method comprising administering a tacrolimus solution to the subject.

The present disclosure also provides a use of a tacrolimus solution in a method of treating or preventing mucositis, wherein the treatment comprises administering the tacrolimus solution to a subject in need thereof that has been, is being, or will be treated with an mTOR inhibitor.

The present disclosure also provides a use of a tacrolimus solution in the manufacture of a medicament for treatment or prevention of mucositis, wherein the treatment comprises administering the medicament to a subject in need thereof that has been, is being, or will be treated with an mTOR inhibitor.

The present disclosure also provides a tacrolimus solution for use in a method of treating or preventing mucositis, the method comprising administering the tacrolimus solution to a subject in need thereof that has been, is being, or will be treated with an mTOR inhibitor.

The present disclosure also provides a medicament for treatment or prevention of mucositis, the medicament comprising a tacrolimus solution, wherein the treatment comprises administering the medicament to a subject in need thereof that has been, is being, or will be treated with an mTOR inhibitor.

BRIEF DESCRIPTION OF THE DRAWINGS

FIG. 1A shows mean tumor responses from 1, 3, 10, or 30 mg/kg QW IP administration of RMC-5552 in transcutol/solutol formulation (n=12/group). ***P<0.0001, 1-way ANOVA. FIG. 1B shows waterfall plot of individual end-of-study responses. Each animal represented as a separate bar. Number of animals per group=12. Numbers indicate number of regressions at respective doses (defined as >10% reduction in tumor volume from starting volume) in each group.

FIG. 2A shows mean tumor responses from 3 and 10 mg/kg QW IP administration of RMC-5552 in transcutol/solutol formulation (n=10, or n=5 in 3 mg/kg dosing arm). ***P<0.0001, 1-way ANOVA. FIG. 2B shows waterfall plot of individual tumor volumes at Day 29, control animal end point. Each animal represented as a separate bar. Number of animals per group=10, or n=5 in 3 mg/kg dosing arm. Numbers indicate number of regressions at respective doses (defined as >10% reduction in tumor volume from starting volume) in each group. FIG. 2C shows duration of tumor response following 4 doses of 3 or 10 mg/kg QW IP RMC-5552. FIG. 2D reflects Kaplan-Meier survival analysis of the time for TOV21G tumors to regrow to a tumor volume of 300 mm$^3$ following treatment cessation. Median time to regrowth in RMC-5552 3 mg/kg arm is 61 days, while 10 mg/kg dose survival time was undefined, extending past 73 days. Dotted horizontal line indicates time to regrowth of 50% of the tumors in a treatment.

FIG. 3A shows mean volume plot for RMC-5552 dosed at 3 or 10 mg/kg QW via IP administration of RMC-5552. P<0.01, *P<0.001, 1-way ANOVA. FIG. 3B shows waterfall plot of individual tumor responses, all groups on Day 51 postimplant. Each animal represented as a separate bar. The number of tumor regressions out of total mice in that group is shown (tumor regression defined as >10% reduction in tumor volume from starting volume) in each group.

PK=pharmacokinetic; pS6RP=phosphorylated S6 ribosomal protein; u=unbound. FIG. 4A shows dose-dependent modulation of tumor p4EBP1 following IP administration of a single dose of RMC-5552 to MCF7 tumor-bearing nude mice (lefty-axis), graphed against PK unbound plasma concentration (nM), with mouse plasma unbound fraction at 0.004 (right axis). Data represent means±standard errors (n=3).

FIG. 4B shows PK-pharmacodynamic relationship for modulation of tumor p4EBP1 and plasma concentration for RMC-5552 derived from data from individual animals. Colors of symbols denote time of tissue harvest following IP administration of a single dose of RMC-5552. FIG. 4C shows dose-dependent modulation of tumor pS6RP following IP administration of a single dose of RMC-5552 to MCF7 tumor-bearing nude mice (lefty-axis), graphed against PK unbound plasma concentration (nM) (right axis). Data represent means standard errors (n=3).

DETAILED DESCRIPTION

Figure 1A:
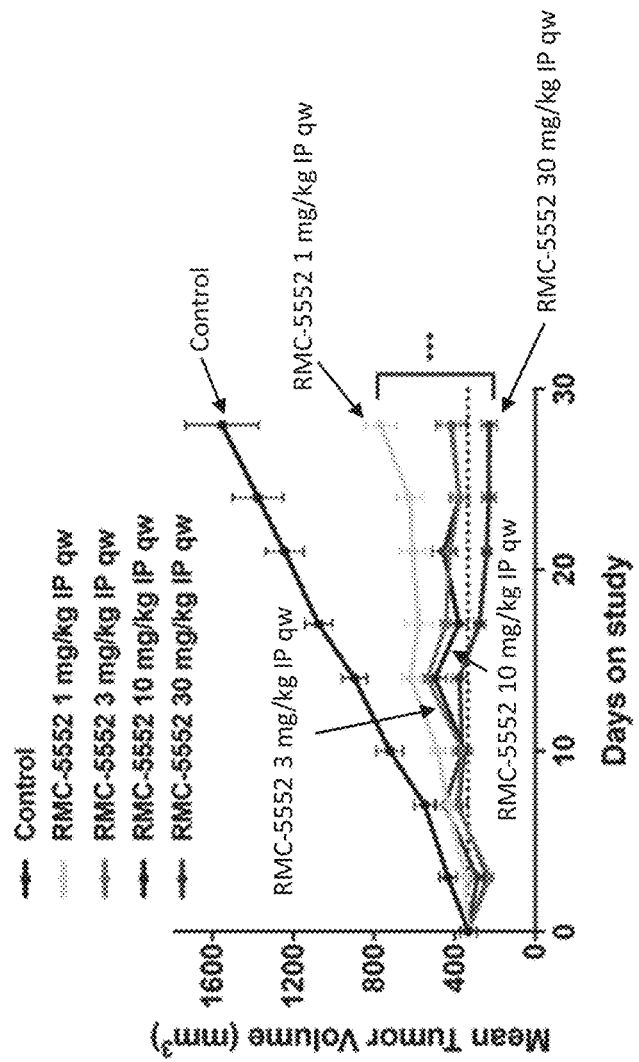
FIGS. 1A-1B show Dose-Dependent Antitumor Effects of Repeated RMC-5552 Weekly Treatment in the MCF7 Xenograft Model of Human Estrogen Receptor Positive Breast Cancer in Athymic Nude Mice. Abbreviations: ANOVA=analysis of variance; IP=intraperitoneal; QW=once weekly.

The present disclosure relates to methods for treating a disease or disorder (e.g., cancer) with a compound (e.g., RMC-5552). In some embodiments, the present disclosure provides methods for delaying, preventing, or treating acquired resistance to a RAS inhibitor (e.g., a KRAS$^{G12C}$ inhibitor) by administering a compound (e.g., RMC-5552).

The methods include administering the compound (e.g., RMC-5552) at a particular dosage. For example, in some embodiments the compound (e.g., RMC-5552) is administered at a dosage of about 3 mg/week to about 25 mg/week.

Dosages of the compound (i.e., RMC-5552) as described herein were surprisingly found to be both efficacious at treating a disease or disorder of a subject while remaining tolerable for the subject. A common point of failure for a drug therapy is inability of the subject to tolerate side-effects of the drug while continuing usage of the drug at amounts effective at treatment of the disease. Low doses of the drug may reduce or eliminate side effects but may result in ineffective disease treatment. For example, side-effects associated with various cancer treatments include stomatitis/mucositis, decreased appetite and fatigue, anemia, dehydration, hyponatremia, nausea, and vomiting. Dosages of the compound (i.e., RMC-5552) of the present disclosure surprisingly were found not to produce such side-effects at severities necessitating reduction of the drug usage below therapeutically effective amounts.

As used above, and throughout this disclosure, the following terms, unless otherwise indicated, shall be understood to have the following meanings. If a term is missing, the conventional term as known to one skilled in the art controls.

As used herein, the terms "including," "containing," and "comprising" are used in their open, non-limiting sense.

The articles "a" and "an" are used in this disclosure to refer to one or more than one (i.e., to at least one) of the grammatical object of the article. By way of example, "an element" means one element or more than one element.

The term "and/or", as used herein, refers to either "and" or "or", or both.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The term "disorder" is used in this disclosure to mean, and is used interchangeably with, the terms disease, condition, or illness, unless otherwise indicated.

The term "inhibitor" means a compound that prevents a biomolecule, (e.g., a protein, nucleic acid) from completing or initiating a reaction. An inhibitor can inhibit a reaction by competitive, uncompetitive, or non-competitive means. Exemplary inhibitors include, but are not limited to, nucleic acids, DNA, RNA, shRNA, siRNA, proteins, protein mimetics, peptides, peptidomimetics, antibodies, small molecules, chemicals, analogs that mimic the binding site of an enzyme, receptor, or other protein, e.g., that is involved in signal transduction, therapeutic agents, pharmaceutical compositions, drugs, and combinations of these. In some embodiments, the inhibitor can be nucleic acid molecules including, but not limited to, siRNA that reduce the amount of functional protein in a cell. Accordingly, compounds said to be "capable of inhibiting" a particular protein, e.g., mTOR or RAS, comprise any such inhibitor.

The term "therapeutic agent", as used herein, refers to any substance, e.g., a compound or composition, capable of treating a disease or disorder. In some embodiments, therapeutic agents that are useful in connection with the present disclosure include without limitation mTOR inhibitors, RAS inhibitors such as, e.g., KRAS inhibitors (e.g., KRAS[G12C] inhibitors), and certain cancer chemotherapeutics.

The term "treatment" or "treating" with regard to a subject, as used herein, refers to improving at least one symptom, pathology or marker of the subject's disease or disorder, either directly or by enhancing the effect of another treatment. Treating includes curing, improving, or at least partially ameliorating the disorder, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

mTOR Inhibitors

The terms "mTOR inhibitor", as used herein, refers to a compound that inhibits the activity of mTOR (e.g., kinase activity). Examples of mTOR inhibitors include, but are not limited to, RMC-5552, everolimus, sirolimus, nab-sirolimus, INK128, PP242, PP121, MLN0128, AZD8055, AZD2014, NVP-BEZ235, BGT226, SF1126, Torin 1, Torin 2, WYE 687, WYE 687 salt (e.g., hydrochloride), PF04691502, PI-103, CC-223, OSI-027, XL388, KU-0063794, GDC-0349, and PKI-587. In some embodiments, the mTOR inhibitor is a more selective inhibitor of mTORC1 versus mTORC2. In some embodiments, the mTOR inhibitor is a more selective inhibitor of mTORC2 versus mTORC1. In embodiments, the mTOR inhibitor is an active site mTOR inhibitor. As used herein, "active site mTOR inhibitor" refers to a compound that inhibits the activity of mTOR (e.g., kinase activity) and binds to the active site of mTOR (e.g., the ATP binding site, overlapping with the ATP binding site, blocking access by ATP to the ATP binding site of mTOR).

In some embodiments, a compound employed in embodiments of the present disclosure (e.g., RMC-5552) may sometimes be referred to herein as a "bi-steric mTOR inhibitor" or "bi-steric inhibitor of mTOR". The terms "bi-steric mTOR inhibitor" and "bi-steric inhibitor of mTOR" are used interchangeably in this disclosure to refer to two pharmacophores in a single compound. One pharmacophore binds to the well-known FRB (FKBP12-rapamycin binding) site on mTORCT and the other binds to the mTOR kinase active site. As a result of these two binding interactions, such compounds exhibit two biologically useful features: (1) selectivity for mTORCT over mTORC2, which is characteristic of the natural compound rapamycin, and (2) deep inhibition of mTORC1, which is characteristic of known active site inhibitors. These properties enable selective inhibition of phosphorylation of mTORCT substrates, including 4EBP1. Non-limiting examples of bi-steric mTOR inhibitors may be found in WO 2019212991, WO 2019212990, and WO 2018204416, incorporated herein by reference in their entireties. In some embodiments, a bi-steric mTOR inhibitor has a molecular weight of between 1600 and 2100 Da, inclusive, and exhibits selective (>10-fold) inhibition of mTORC1 over mTORC2. In some embodiments, the two pharmacophores are joined by a linker. The linker may be any suitable linker, for example a PEG linker, or the linkers described in Hoang Thi, Thai Thanh et al. "The Importance of Poly(ethylene glycol) Alternatives for Overcoming PEG Immunogenicity in Drug Delivery and Bioconjugation." Polymers vol. 12,2 298. 2 Feb. 2020.

In some embodiments the mTOR inhibitor is a compound of Formula Ic:

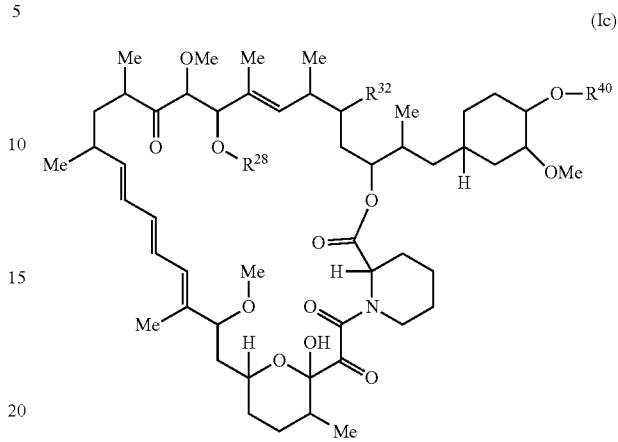

(Ic)

or a stereoisomer, tautomer, or oxepane isomer thereof, or a pharmaceutically acceptable salt of any of the foregoing, wherein.

$R^{32}$ is —H, =O, —$OR^3$, —$N_3$, or —O—C(=$Z^1$)—$R^{32a}$;

$R^{21}$ is —H, ($C_1$-$C_6$)alkyl, or —C(=$Z^1$)—$R^{28a}$.

$R^{40}$ is —H or —C(=$Z_1$)—$R^{40a}$.

wherein when $R^{28}$ and $R^{40}$ are H, then $R^{32}$ is not =O;

each $Z^1$ is independently O or S;

$R^{28a}$, $R^{32a}$, and $R^{40a}$ are independently -$A^1$-$L^1$-$A^2$-B; -$A^1$-$A^2$-B; -$L^2$-$A^1$-$L^1$-$A^2$-$L^3$-B; —O—($C_1$-$C_6$)alkyl; or —O—($C_6$-$C_{10}$)aryl; wherein the aryl of —O—($C_6$-$C_{10}$)aryl is unsubstituted or substituted with 1-5 substituents selected from —$NO_2$ and halogen;

$A^1$ and $A^2$ are independently absent or are independently selected from

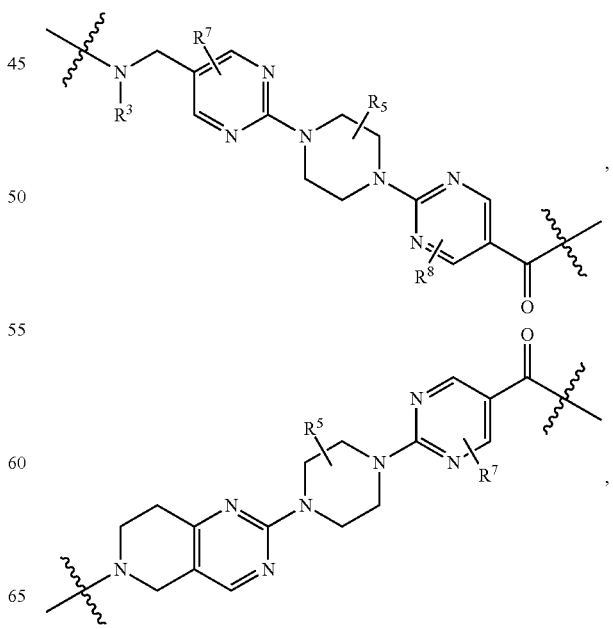

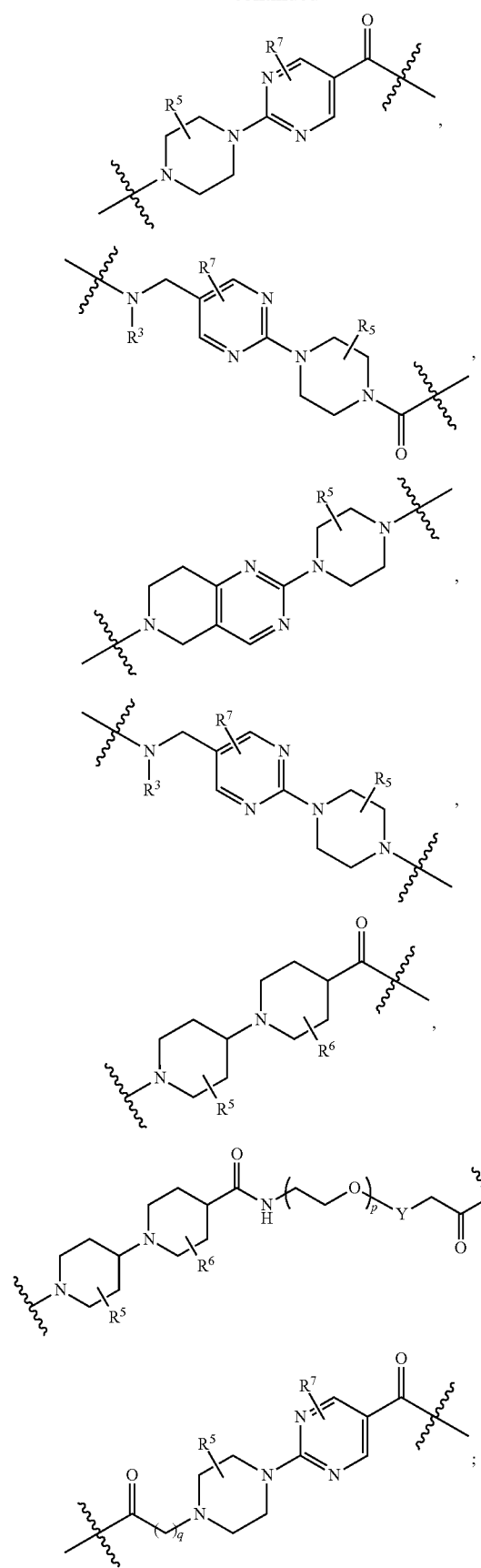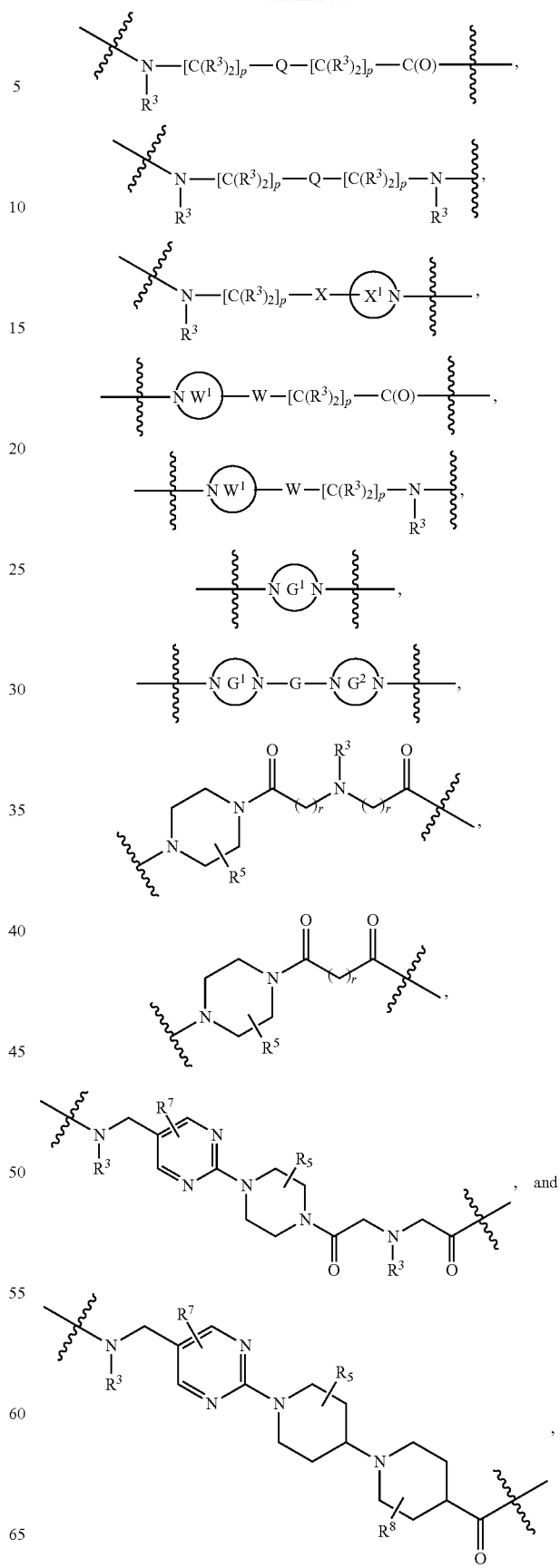

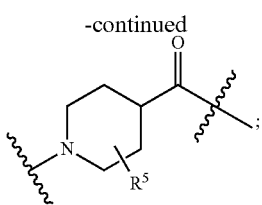

wherein the bond on the left side of A¹, as drawn, is bound to —C(=Z¹)— or L²; and wherein the bond on the right side of the A² moiety, as drawn, is bound to B or L³;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each X¹ is independently a heteroarylene or heterocyclylene ring;

each W is independently absent or 1 to 2 rings selected from arylene, cycloalkylene, heteroarylene, and heterocyclylene;

each W¹ is independently a heteroarylene or heterocyclylene ring;

each G is independently absent or a ring selected from arylene, cycloalkylene, heteroarylene, and heterocyclylene;

each G¹ and G² are independently heteroarylene or heterocyclylene ring;

each L¹ is independently selected from

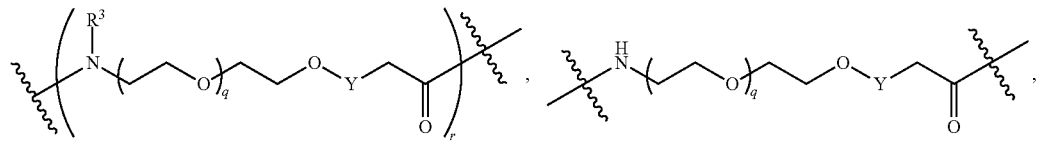

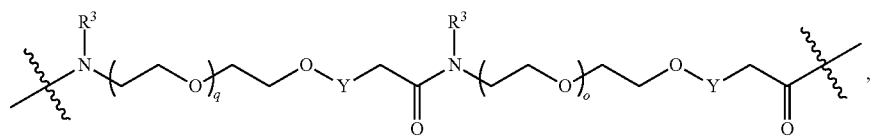

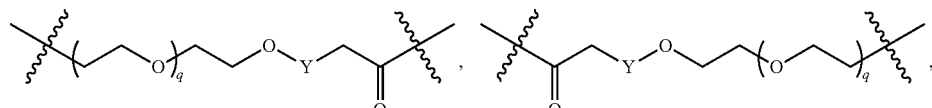

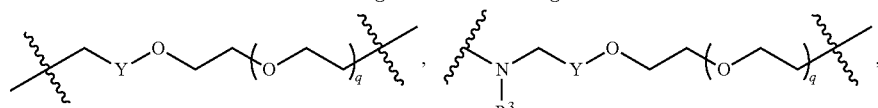

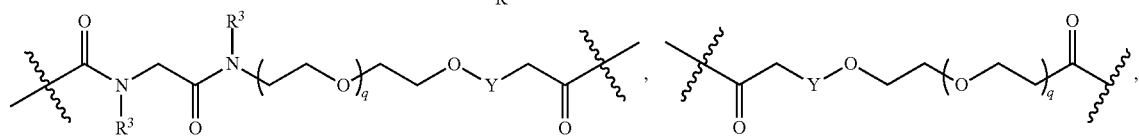

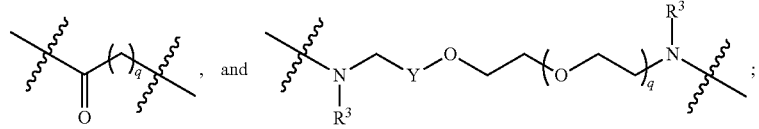

L² and L³ are independently absent or are independently selected from

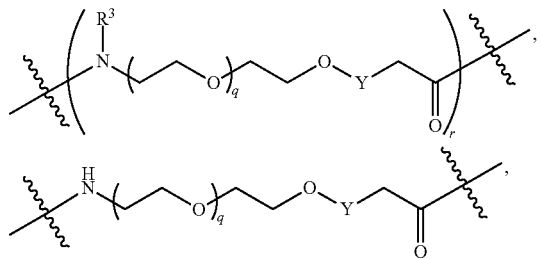

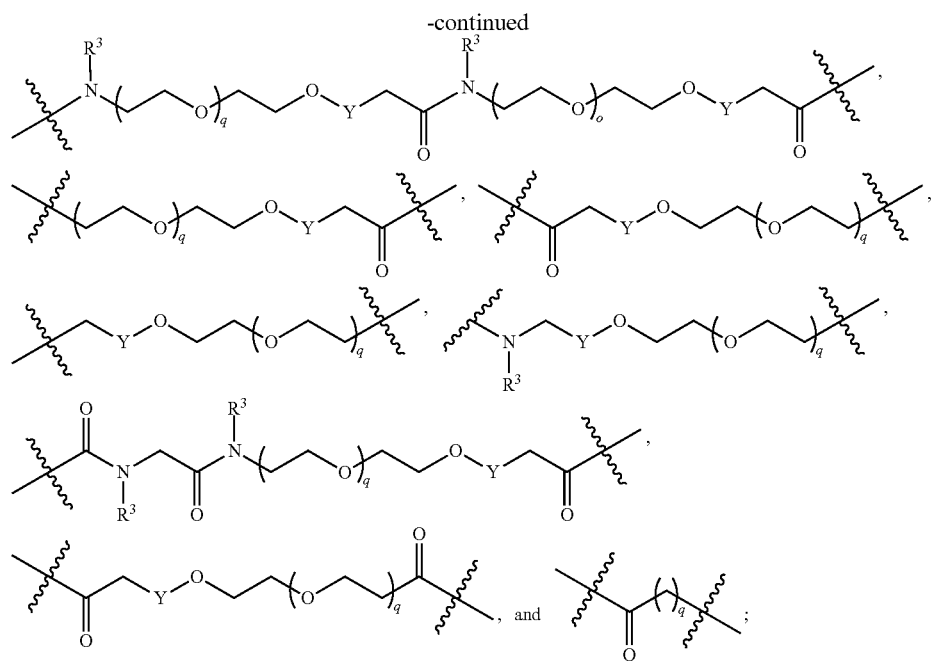
each B is independently selected from
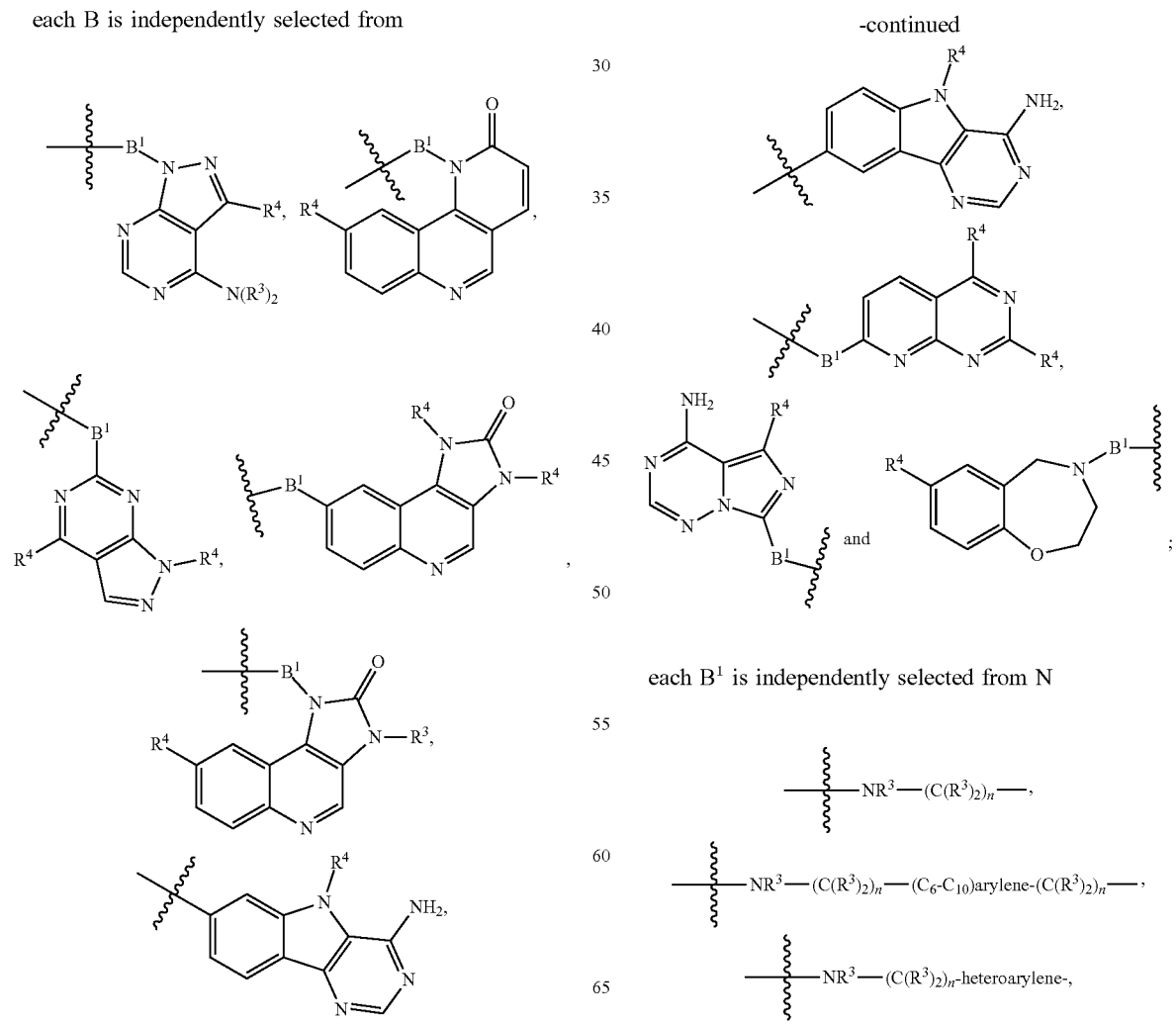
each $B^1$ is independently selected from N -continued

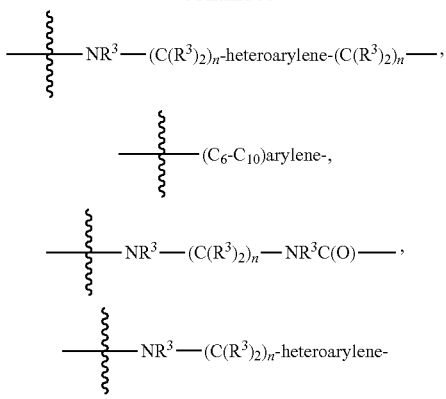

heteroarylene-heterocyclylene-(C₆-C₁₀)arylene-,

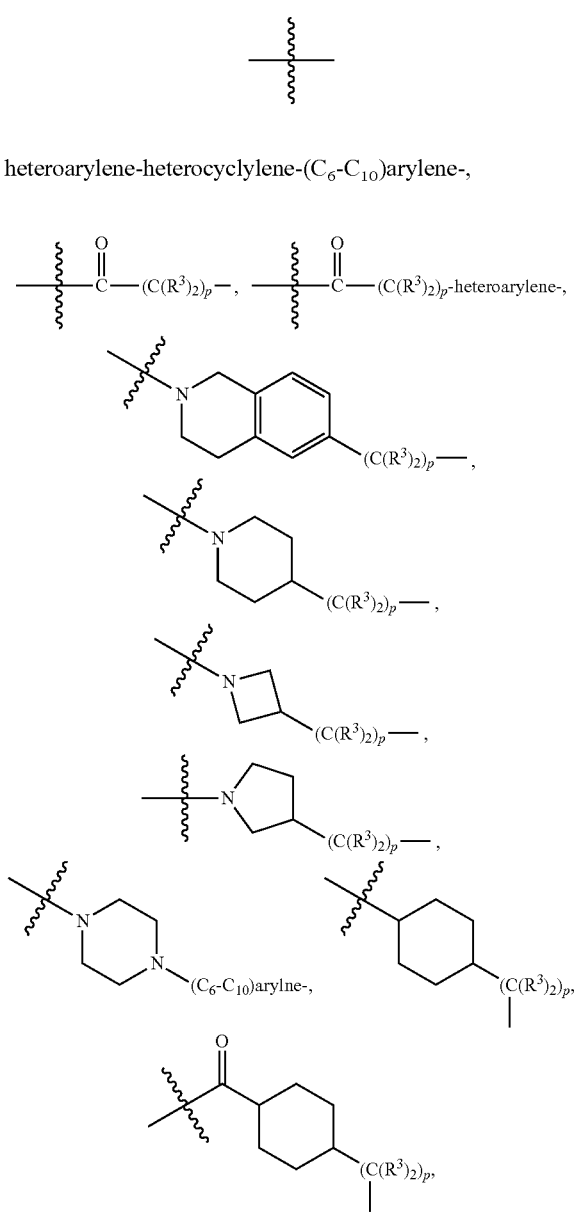

-continued

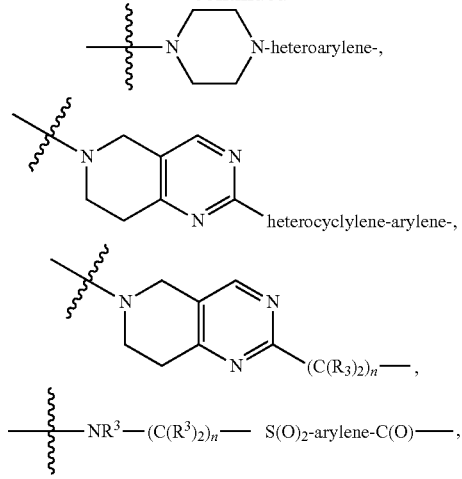

wherein the

bond on the left side of $B^1$, as drawn, is bound to $A^2$, $L^3$, or $L^1$; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are optionally substituted with —N$(R^3)_2$, —OR$^3$, halogen, $(C_1\text{-}C_6)$alkyl, —$(C_1\text{-}C_6)$alkylene-heteroaryl, —$(C_1\text{-}C_6)$alkylene-CN, —C(O)NR$^3$-heteroaryl, or —C(O)NR$^3$-heterocyclyl;

each $R^5$ is independently H, $(C_1\text{-}C_6)$alkyl, —C(O)OR$^3$, or —N$(R^3)_2$, wherein the alkyl of $(C_1\text{-}C_6)$alkyl is optionally substituted with —N$(R^3)_2$ or —OR$^3$;

each $R^6$ is independently H, $(C_1\text{-}C_6)$alkyl, —C(O)OR$^3$, or —N$(R^3)_2$, wherein the alkyl of $(C_1\text{-}C_6)$alkyl is optionally substituted with —N$(R^3)_2$ or —OR$^3$;

each $R^7$ is independently H, $(C_1\text{-}C_6)$alkyl, —C(O)OR$^3$, or —N$(R^3)_2$, wherein the alkyl of $(C_1\text{-}C_6)$alkyl is optionally substituted with —N$(R^3)_2$ or —OR$^3$;

each $R^8$ is independently H, $(C_1\text{-}C_6)$alkyl, —C(O)OR$^3$, or —N$(R^3)_2$, wherein the alkyl of $(C_1\text{-}C_6)$alkyl is optionally substituted with —N$(R^3)_2$ or —OR$^3$;

each Y is independently $C(R^3)_2$ or a bond;

each n is independently an integer from one to 12;

each o is independently an integer from zero to 30;

each p is independently an integer from zero to 12;

each q is independently an integer from zero to 30; and each r is independently an integer from one to 6. See, e.g., WO 2019212990, incorporated by reference herein in its entirety.

In some embodiments, the two pharmacophores described in Formula Ic are joined by a linker, such as one of the linkers described in Hoang Thi, Thai Thanh et al. "The Importance of Poly(ethylene glycol) Alternatives for Overcoming PEG Immunogenicity in Drug Delivery and Bioconjugation." Polymers vol. 12,2 298. 2 Feb. 2020.

In another embodiment of the present disclosure, the mTOR inhibitor (e.g., a bi-steric mTOR inhibitor, e.g., RMC-5552) is an enantiomer. In some embodiments, a compound is an (S)-enantiomer. In other embodiments, a compound is an (R)-enantiomer. In yet other embodiments, the compound is a (+) or (−) enantiomer.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

The mTOR inhibitor (e.g., a bi-steric mTOR inhibitor, e.g., RMC-5552) may contain asymmetric or chiral centers, and, therefore, exist in different stereoisomeric forms. It is intended that the methods of the present disclosure consider all stereoisomeric forms of the mTOR inhibitors (e.g., a bi-steric mTOR inhibitor, e.g., RMC-5552) as well as mixtures thereof, including racemic mixtures. In addition, the present disclosure embraces methods comprising all geometric and positional isomers. For example, if an mTOR inhibitor (e.g., a bi-steric mTOR inhibitor, e.g., RMC-5552) incorporates a double bond or a fused ring, both the cis- and trans-forms, as well as mixtures, are embraced within the scope of the present disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

The term "tautomers", as used herein, may refer to a set of compounds that have the same number and type of atoms, but differ in bond connectivity and are in equilibrium with one another. A "tautomer" is a single member of this set of compounds. Typically, a single tautomer is drawn but it may be understood that this single structure may represent all possible tautomers that might exist. Examples may include enol-ketone tautomerism. When a ketone is drawn it may be understood that both the enol and ketone forms are part of the disclosure. The mTOR inhibitor (e.g., a bi-steric mTOR inhibitor, e.g., RMC-5552) of the present disclosure may exist in their tautomeric form (for example, as an amide or imino ether). All such tautomeric forms are contemplated herein as part of the methods of the present disclosure.

In addition to tautomers that may exist at all amide, carbonyl, and oxime groups within the mTOR inhibitors of the present disclosure, compounds in this family readily interconvert via a ring-opened species between two major isomeric forms, known as the pyran and oxepane isomers (shown below). This interconversion can be promoted by magnesium ions, mildly acidic conditions, or alkylamine salts, as described in the following references: i) Hughes, P. F.; Musser, J.; Conklin, M.; Russo, R. 1992. *Tetrahedron Lett.* 33(33): 4739-32. ii) Zhu, T. 2007. U.S. Pat. No. 7,241,771; Wyeth. iii) Hughes, P. F. 1994. U.S. Pat. No. 5,344,833; American Home Products Corp. The scheme below shows an interconversion between the pyran and oxepane isomers in compounds, including compounds according to Formula Ic.

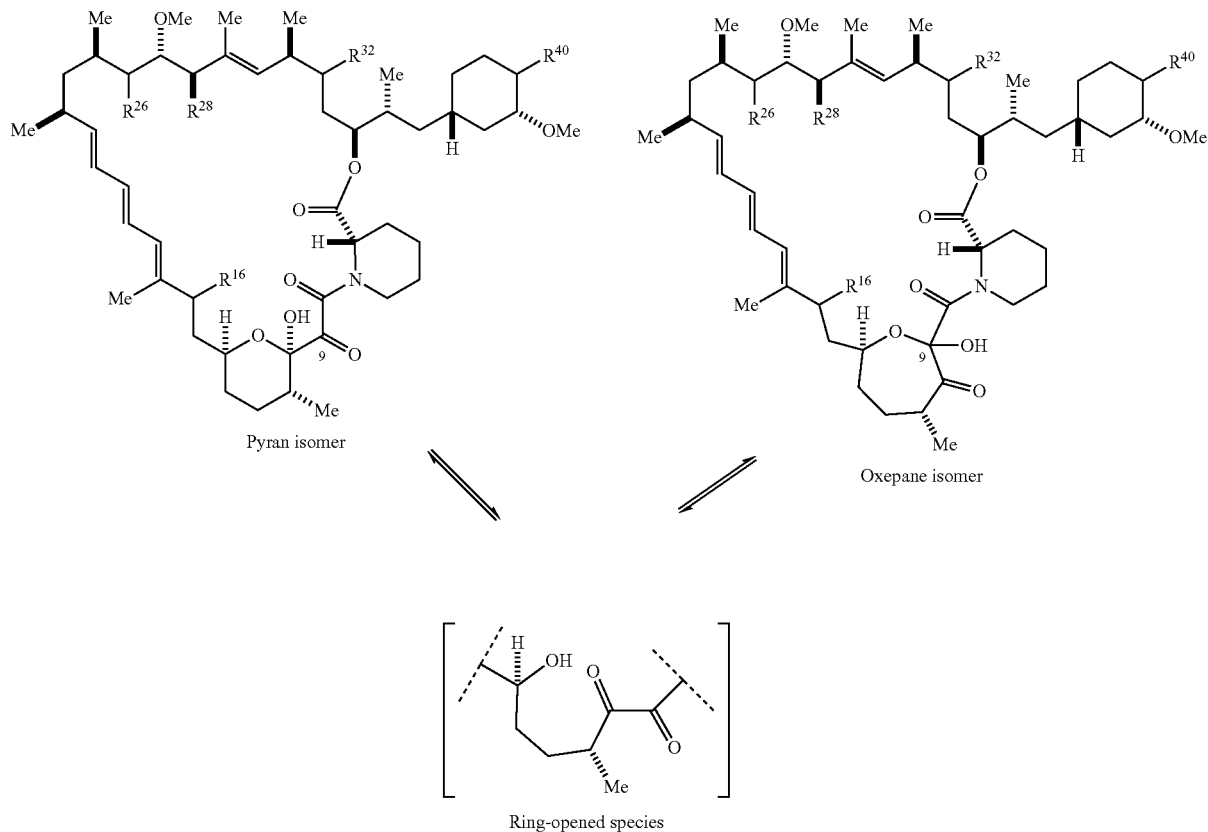

As this interconversion occurs under mild condition, and the thermodynamic equilibrium position may vary between different members of compounds of Formula Ic, both isomers are contemplated for the compounds of Formula Ic. For the sake of brevity, the pyran isomer form of all intermediates and compounds of Formula Ic is shown, however it is understood the mTOR inhibitor (e.g., a bi-steric mTOR inhibitor, e.g., RMC-5552) may exist in their oxepane form. All such oxepane forms are contemplated herein as part of the methods of the present disclosure.

The term "solvate" refers to a complex of variable stoichiometry formed by a solute and solvent. Such solvents for the purpose of the present disclosure may not interfere with the biological activity of the solute. Examples of suitable solvents include, but are not limited to, water, methanol, ethanol, and acetic acid. Solvates wherein water is the solvent molecule are typically referred to as hydrates. Hydrates include compositions containing stoichiometric amounts of water, as well as compositions containing variable amounts of water.

The term "salt(s)", as employed herein, denotes acidic salts formed with inorganic and/or organic acids, as well as basic salts formed with inorganic and/or organic bases. In addition, when a compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of an mTOR inhibitor (e.g., a bi-steric mTOR inhibitor, e.g., RMC-5552)(e.g., a bi-steric mTOR inhibitor, e.g., RMC-5552) may be formed, for example, by reacting a compound with an amount of acid or base, such as an equivalent amount, in a medium such as one in which the salt precipitates or in an aqueous medium followed by lyophilization. The compounds of the disclosure may include pharmaceutically acceptable salts of the compounds disclosed herein. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Pharmaceutically acceptable salt" may also include both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Unless otherwise stated, structures depicted herein may also include compounds which differ only in the presence of one or more isotopically enriched atoms. For example, compounds having the present structure except for the replacement of a hydrogen atom by deuterium or tritium, or the replacement of a carbon atom by 13C or 14C, or the replacement of a nitrogen atom by 15N, or the replacement of an oxygen atom with 17O or 18O are within the scope of the disclosure. Such isotopically labeled compounds are useful as research or diagnostic tools.

The term RMC-6272 refers to a bi-steric mTOR inhibitor which has the following structure:

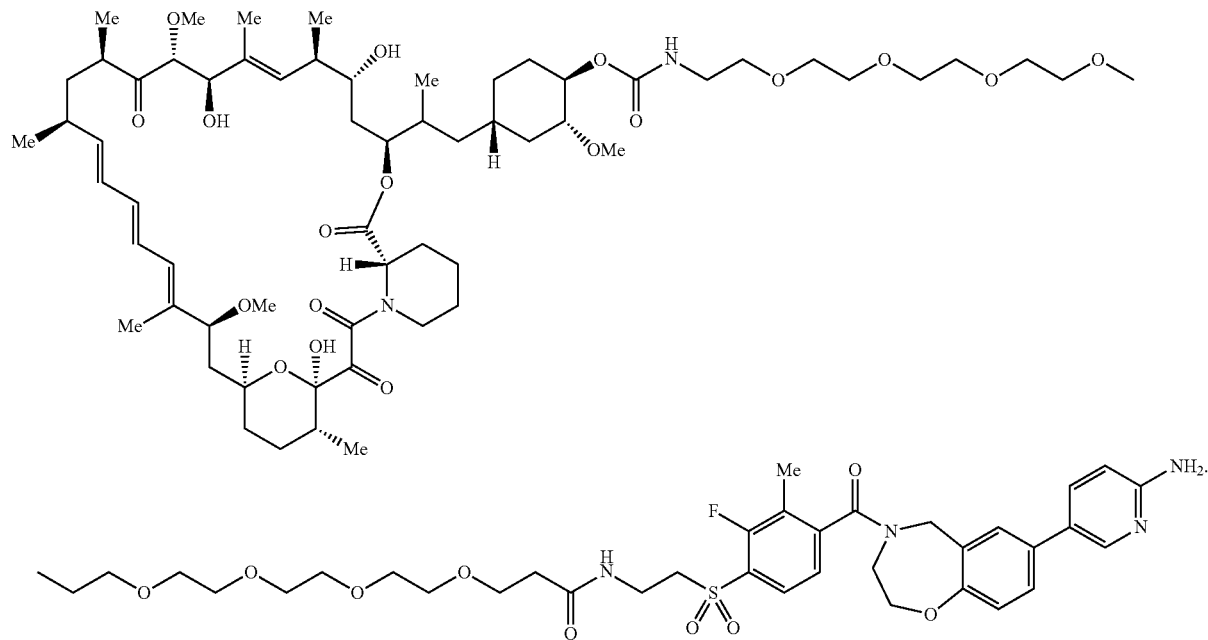

RMC-6272 exhibits potent and selective (>10-fold) inhibition of mTORC1 over mTORC2. Also contemplated herein are stereoisomers, tautomers, and oxepane isomers of RMC-6272, or a pharmaceutically acceptable salt of any of the foregoing.

The term RMC-5552 refers to a bi-steric mTOR inhibitor which has the following structure:

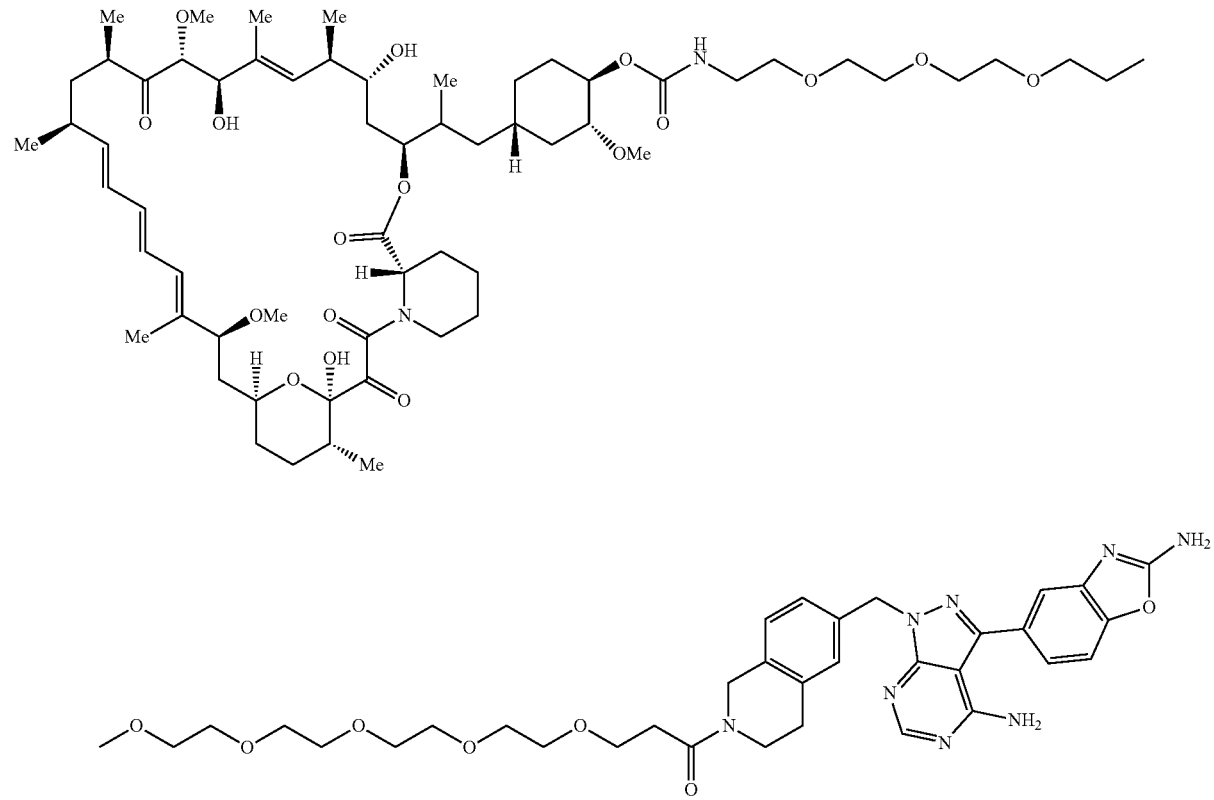

In some embodiments, the bi-steric mTOR inhibitor is
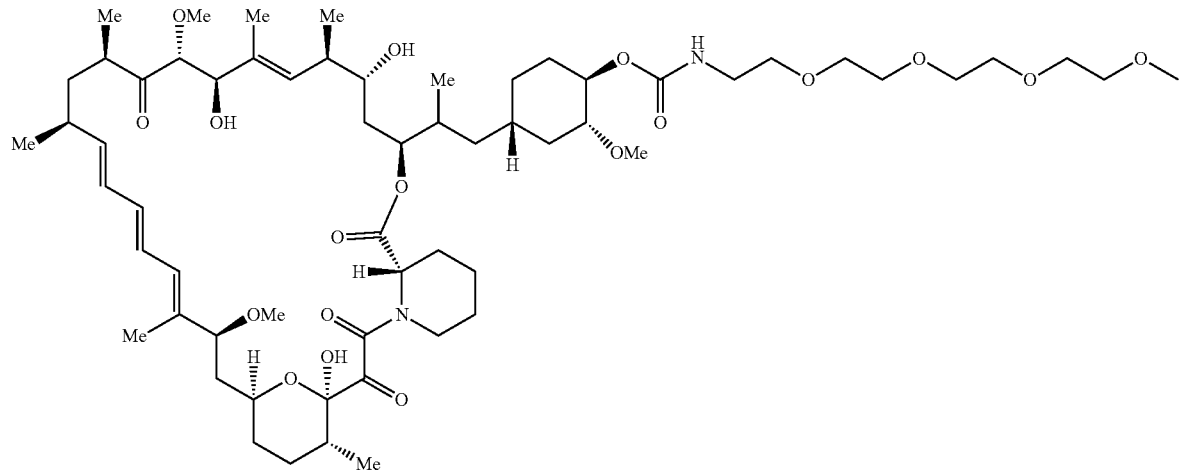
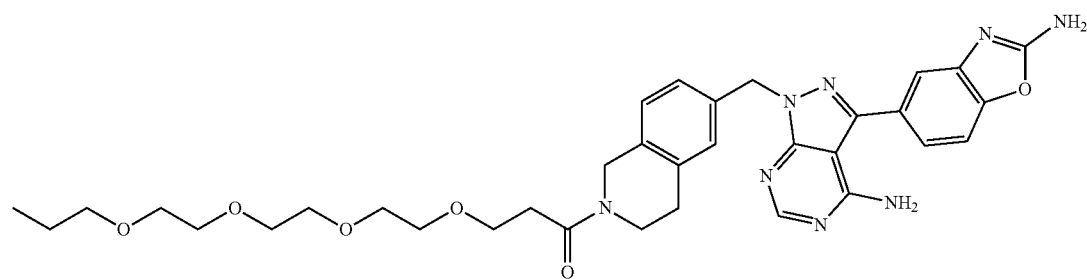
or a stereoisomer, tautomer, or oxepane isomer thereof, or pharmaceutically acceptable salt of any of the foregoing.
In some embodiments, the bi-steric mTOR inhibitor is
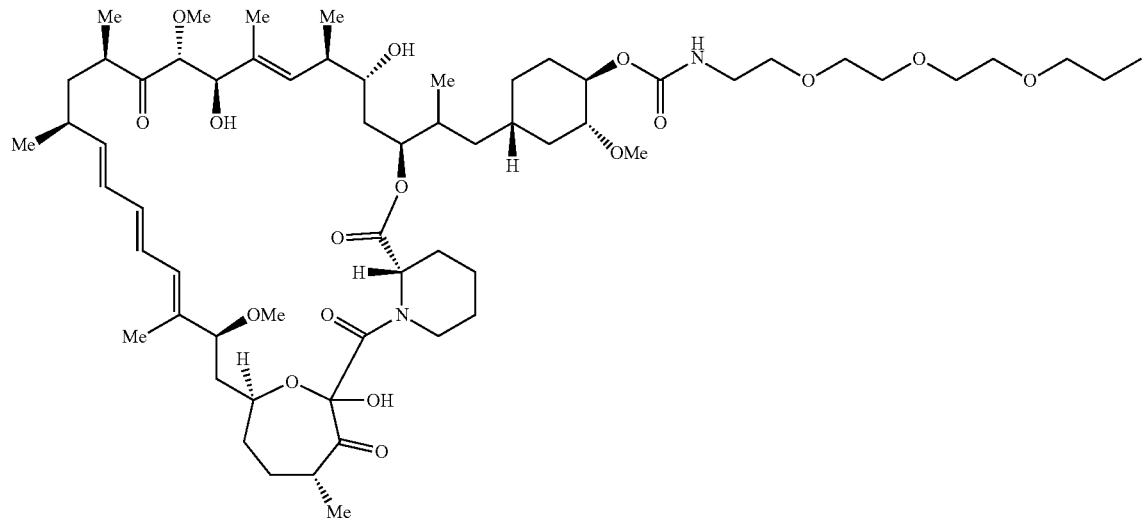

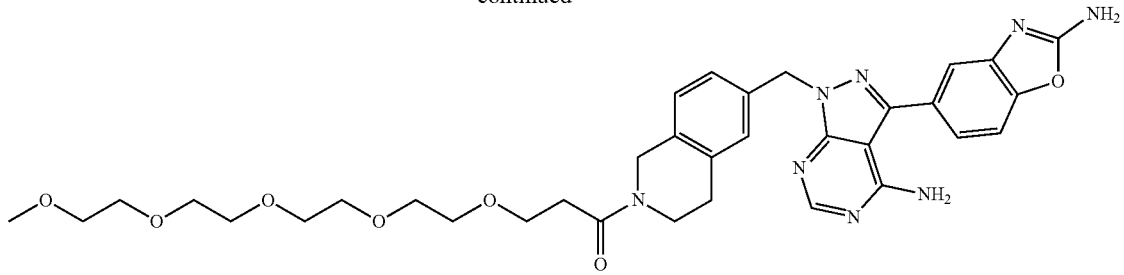

or a stereoisomer or tautomer thereof, or a pharmaceutically acceptable salt of any of the foregoing.

Mechanistic Target of Rapamycin (mTOR)

The term "mTOR" refers to the protein "mechanistic target of rapamycin (serine/threonine kinase)" or "mammalian target of rapamycin." The term "mTOR" may refer to the nucleotide sequence or protein sequence of human mTOR (e.g., Entrez 2475, Uniprot P42345, RefSeq NM_004958, or RefSeq NP_004949) (SEQ ID NO: 1). The term "mTOR" may include both the wild-type form of the nucleotide sequences or proteins as well as any mutants thereof. In some embodiments, "mTOR" is wild-type mTOR. In some embodiments, "mTOR" is one or more mutant forms. The term "mTOR" XYZ may refer to a nucleotide sequence or protein of a mutant mTOR wherein the Y numbered amino acid of mTOR that normally has an X amino acid in the wildtype, instead has a Z amino acid in the mutant. In some embodiments, an mTOR is the human mTOR. In some embodiments, the mTOR has the nucleotide sequence corresponding to reference number GL206725550 (SEQ ID NO:2). In some embodiments, the mTOR has the nucleotide sequence corresponding to RefSeq NM_004958.3 (SEQ ID NO:2). In some embodiments, the mTOR has the protein sequence corresponding to reference number GL4826730 (SEQ ID NO: 1). In some embodiments, the mTOR has the protein sequence corresponding to RefSeq NP_004949.1 (SEQ ID NO: 1). In some embodiments, the mTOR has the following amino acid sequence:

```
                                          (SEQ ID NO: 1)
MLGTGPAAATTAATTSSNVSVLQQFASGLKSRNEETRAKAAKELQHYVTM

ELREMSQEESTRFYDQLNHHIFELVSSSDANERKGGILAIASLIGVEGGN

ATRIGRFANYLRNLLPSNDPWMEMASKAIGRLAMAGDTFTAEYVEFEVKR

ALEWLGADRNEGRRHAAVLVLRELAISVPTFFFQQVQPFFDNIFVAVWDP

KQAIREGAVAALRACLILTTQREPKEMQKPQWYRHTFEEAEKGFDETLAK

EKGMNRDDRIHGALLILNELVRISSMEGERLREEMEEITQQQLVHDKYCK

DLMGFGTKPRHITPFTSFQAVQPQQSNALVGLLGYSSHQGLMGFGTSPSP

AKSTLVESRCCRDLMEEKFDQVCQWVLKCRNSKNSLIQMTILNLLPRLAA

FRPSAFTDTQYLQDTMNHVLSCVKKEKERTAAFQALGLLSVAVRSEFKVY

LPRVLDIIRAALPPKDFAHKRQKAMQVDATVFTCISMLARAMGPGIQQDI

KELLEPMLAVGLSPALTAVLYDLSRQIPQLKKDIQDGLLKMLSLVLMHKP

LRHPGMPKGLAHQLASPGLTTLPEASDVGSITLALRTLGSFEFEGHSLTQ

FVRHCADHFLNSEHKEIRMEAARTCSRLLTPSIHLISGHAHVVSQTAVQV

VADVLSKLLWGITDPDPDIRYCVLASLDERFDAHLAQAENLQALFVALND

QVFEIRELAICTVGRLSSMNPAFVMPFLRKMLIQILTELEHSGIGRIKEQ

SARMLGHLVSNAPRLIRPYMEPILKALILKLKDPDPDPNPGVINNVLATI

GELAQVSGLEMRKWVDELFIIIMDMLQDSSLLAKRQVALWTLGQLVASTG

YVVEPYRKYPTLLEVLLNFLKTEQNQGTRREAIRVLGLLGALDPYKHKVN

IGMIDQSRDASAVSLSESKSSQDSSDYSTSEMLVNMGNLPLDEFYPAVSM

VALMRIFRDQSLSHHHTMVVQAITFIFKSLGLKCVQFLPQVMPTFLNVIR

VCDGAIREFLFQQLGMLVSFVKSHIRPYMDEIVTLMREFWVMNTSIQSTI

ILLIEQIVVALGGEFKLYLPQLIPHMLRVFMHDNSPGRIVSIKLLAAIQL

FGANLDDYLHLLLPPIVKLFDAPEAPLPSRKAALETVDRLTESLDFTDYA

SRIIHPIVRTLDQSPELRSTAMDTLSSLVFQLGKKYQIFIPMVNKVLVRH

RINHQRYDVLICRIVKGYTLADEEEDPLIYQHRMLRSGQGDALASGPVET

GPMKKLHVSTINLQKAWGAARRVSKDDWLEWLRRLSLELLKDSSSPSLRS

CWALAQAYNPMARDLFNAAFVSCWSELNEDQQDELIRSIELALTSQDIAE

VTQTLLNLAEFMEHSDKGPLPLRDDNGIVLLGERAAKCRAYAKALHYKEL

EFQKGPTPAILESLISINNKLQQPEAAAGVLEYAMKHFGELEIQATWYEK

LHEWEDALVAYDKKMDTNKDDPELMLGRMRCLEALGEWGQLHQQCCEKWT

LVNDETQAKMARMAAAAAWGLGQWDSMEEYTCMIPRDTHDGAFYRAVLAL

HQDLFSLAQQCIDKARDLLDAELTAMAGESYSRAYGAMVSCHMLSELEEV

IQYKLVPERREIIRQIWWERLQGCQRIVEDWQKILMVRSLVVSPHEDMRT

WLKYASLCGKSGRLALAHKTLVLLLGVDPSRQLDHPLPTVHPQVTYAYMK

NMWKSARKIDAFQHMQHFVQTMQQQAQHAIATEDQQHKQELHKLMARCFL

KLGEWQLNLQGINESTIPKVLQYYSAATEHDRSWYKAWHAWAVMNFEAVL

HYKHQNQARDEKKKLRHASGANITNATTAATTAATATTTASTEGSNSESE

AESTENSPTPSPLQKKVTEDLSKTLLMYTVPAVQGFFR SISLSRGNNLQ

DTLRVLTLWFDYGHWPDVNEALVEGVKAIQIDTWLQVIPQLIARIDTPRP

LVGRLIHQLLTDIGRYHPQALIYPLTVASKSTTTARHNAANKILKNMCEH

SNTLVQQAMMVSEELIRVAILWHEMWHEGLEEASRLYFGERNVKGMFEVL

EPLHAMMERGPQTLKETSFNQAYGRDLMEAQEWCRKYMKSGNVKDLTQA

WDLYYHVFRRISKQLPQLTSLELQYVSPKLLMCRDLELAVPGTYDPNQPI

IRIQSIAPSLQVITSKQRPRKLTLMGSNGHEFVFLLKGHEDLRQDERVMQ

LFGLVNTLLANDPTSLRKNLSIQRYAVIPLSTNSGLIGWVPHCDTLHALI

RDYREKKKILLNIEHRIMLRMAPDYDHLTLMQKVEVFEHAVNNTAGDDLA
```

-continued

KLLWLKSPSSEVWFDRRTNYTRSLAVMSMVGYILGLGDRHPSNLMLDRLS

GKILHIDFGDCFEVAMTREKFPEKIPFRLTRMLTNAMEVTGLDGNYRITC

HTVMEVLREHKDSVMAVLEAFVYDPLLNWRLMDTNTKGNKRSRTRTDSYS

AGQSVEILDGVELGEPAHKKTGTTVPESIHSFIGDGLVKPEALNKKAIQI

INRVRDKLTGRDFSHDDTLDVPTQVELLIKQATSHENLCQCYIGWCPFW

In some embodiments, the mTOR is a mutant mTOR. In some embodiments, the mutant mTOR is associated with a disease that is not associated with wildtype mTOR. In some embodiments, the mTOR may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to the sequence above.

The term "mTORC1" refers to the protein complex including mTOR and Raptor (regulatory-associated protein of mTOR). mTORC1 may also include MLST8 (mammalian lethal with SEC 13 protein 8), PRAS40, and/or DEPTOR. mTORC1 may function as a nutrient/energy/redox sensor and regulator of protein synthesis. The term "mTORC1 pathway" or "mTORC1 signal transduction pathway" may refer to a cellular pathway including mTORC1. An mTORC1 pathway includes the pathway components upstream and downstream from mTORC1. An mTORC1 pathway is a signaling pathway that is modulated by modulation of mTORC1 activity. In some embodiments, an mTORC1 pathway is a signaling pathway that is modulated by modulation of mTORC1 activity but not by modulation of mTORC2 activity. In some embodiments, an mTORC1 pathway is a signaling pathway that is modulated to a greater extent by modulation of mTORC1 activity than by modulation of mTORC2 activity.

The term "mTORC2" refers to the protein complex including mTOR and RICTOR (rapamycin-insensitive companion of mTOR). mTORC2 may also include GOL, mSIN1 (mammalian stress-activated protein kinase interacting protein 1), Protor 1/2, DEPTOR, TTI1, and/or TEL2. mTORC2 may regulate cellular metabolism and the cytoskeleton. The term "mTORC2 pathway" or "mTORC2 signal transduction pathway" may refer to a cellular pathway including mTORC2. An mTORC2 pathway includes the pathway components upstream and downstream from mTORC2. An mTORC2 pathway is a signaling pathway that is modulated by modulation of mTORC2 activity. In some embodiments, an mTORC2 pathway is a signaling pathway that is modulated by modulation of mTORC2 activity but not by modulation of mTORC1 activity. In some embodiments, an mTORC2 pathway is a signaling pathway that is modulated to a greater extent by modulation of mTORC2 activity than by modulation of mTORC1 activity.

The term "rapamycin" or "sirolimus" refers to a macrolide produced by the bacteria *Streptomyces hygroscopicus*. Rapamycin may prevent the activation of T cells and B cells. Rapamycin has the IUPAC name (3S,6R,7E,9R,10R, 12R, 14S, 15E, 17E, 19E,21S,23S,26R,27R,34aS)-9, 10, 12, 13, 14,21,22,23,24,25,26,27,32,33,34,34a-hexadecahydro-9,27-dihydroxy-3-[(1R)-2-[(1 S,3R,4R)-4-hydroxy-3-methoxy-cyclohexyl]-1-methylethyl]-10,21-dimethoxy-6,8,12,14,20, 26-hexamethyl-23,27-epoxy-3H-pyrido[2, 1-c][1,4]-oxaazacyclohentriacontine-1,5,11,28,29(4H,6H,31H)-pentone. Rapamycin has the CAS number 53123-88-9. Rapamycin may be produced synthetically (e.g., by chemical synthesis) or through use of a production method that does not include use of *Streptomyces hygroscopicus*.

"Analog" is used in accordance with its plain ordinary meaning within chemistry and biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof.

The term "rapamycin analog" or "rapalog" refers to an analog or derivative (e.g., a prodrug) of rapamycin.

The term "FKBP" refers to the protein Peptidyl-prolyl cis-trans isomerase. For non-limiting examples of FKBP, see Cell Mol Life Sci. 2013 September; 70(18):3243-75. In some embodiments, "FKBP" may refer to "FKBP-12" or "FKBP 12" or "FKBP 1 A." In some embodiments, "FKBP" may refer to the human protein. Included in the term "FKBP" is the wildtype and mutant forms of the protein. In some embodiments, "FKBP" may refer to the wildtype human protein. In some embodiments, "FKBP" may refer to the wildtype human nucleic acid. In some embodiments, the FKBP is a mutant FKBP. In some embodiments, the mutant FKBP is associated with a disease that is not associated with wildtype FKBP. In some embodiments, the FKBP includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype FKBP.

The term "FKBP-12" or "FKBP 12" or "FKBP1A" may refer to the protein "Peptidyl-prolyl cis-trans isomerase FKBP 1 A." In some embodiments, "FKBP-12" or "FKBP 12" or "FKBP 1 A" may refer to the human protein. Included in the term "FKBP-12" or "FKBP 12" or "FKBP 1 A" are the wildtype and mutant forms of the protein. In some embodiments, "FKBP-12" or "FKBP 12" or "FKBP 1 A" may refer to the protein associated with Entrez Gene 2280, OMIM 186945, UniProt P62942, and/or RefSeq (protein) NP_000792 (SEQ ID NO:3). In some embodiments, the reference numbers immediately above may refer to the protein, and associated nucleic acids, known as of the date of filing of this application. In some embodiments, "FKBP-12" or "FKBP 12" or "FKBP 1 A" may refer to the wildtype human protein. In some embodiments, "FKBP-12" or "FKBP 12" or "FKBP1A" may refer to the wildtype human nucleic acid. In some embodiments, the FKBP-12 is a mutant FKBP-12. In some embodiments, the mutant FKBP-12 is associated with a disease that is not associated with wildtype FKBP-12. In some embodiments, the FKBP-12 may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype FKBP-12. In some embodiments, the FKBP-12 has the protein sequence corresponding to reference number GI: 206725550. In some embodiments, the FKBP-12 has the protein sequence corresponding to RefSeq NP_000792.1 (SEQ ID NO:3).

The term "4E-BP1" or "4EBP1" or "EIF4EBP1" refers to the protein "Eukaryotic translation initiation factor 4E-binding protein 1." In some embodiments, "4E-BP1" or "4EBP1" or "EIF4EBP 1" may refer to the human protein. Included in the term "4E-BP 1" or "4EBP 1" or "EIF4EBP1" are the wildtype and mutant forms of the protein. In some embodiments, "4E-BP1" or "4EBP1" or "EIF4EBP1" may refer to the protein associated with Entrez Gene 1978, OMIM 602223, UniProt Q13541, and/or RefSeq (protein) NP_004086 (SEQ ID NO:4). In some embodiments, the reference numbers immediately above may refer to the protein, and associated nucleic acids, known as of the date of filing of this application. In some embodiments, "4E-BP 1" or "4EBP1" or "EIF4EBP1" may refer to the wildtype human protein. In some embodiments, "4E-BP1" or "4EBP1" or "EIF4EBP1" may refer to the wildtype human nucleic acid. In some embodiments, the 4EBP1 is a mutant 4EBP1. In some embodiments, the mutant 4EBP1 is associated with a disease that is not associated with wildtype 4EBP1. In some embodiments, the 4EBP1 may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype 4EBP1. In some embodiments, the 4EBP1 has the protein sequence corresponding to reference number GL4758258. In some embodiments, the 4EBP1 has the protein sequence corresponding to RefSeq NP_004086.1 (SEQ ID NO:4).

The term "Akt" refers to the serine/threonine specific protein kinase involved in cellular processes such as glucose metabolism, apoptosis, proliferation, and other functions, also known as "protein kinase B" (PKB) or "Akt1." In some embodiments, "Akt" or "AM" or "PKB" may refer to the human protein. Included in the term "Akt" or "Akt1" or "PKB" are the wildtype and mutant forms of the protein. In some embodiments, "Akt" or "Akt1" or "PKB" may refer to the protein associated with Entrez Gene 207, OMIM 164730, UniProt P31749, and/or RefSeq (protein) NP_005154 (SEQ ID NO:5). In some embodiments, the reference numbers immediately above may refer to the protein, and associated nucleic acids, known as of the date of filing of this application. In some embodiments, "Akt" or "Akt1" or "PKB" may refer to the wildtype human protein. In some embodiments, "Akt" or "Akt1" or "PKB" may refer to the wildtype human nucleic acid. In some embodiments, the Akt is a mutant Akt. In some embodiments, the mutant Akt is associated with a disease that is not associated with wildtype Akt. In some embodiments, the Akt may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype Akt. In some embodiments, the Akt has the protein sequence corresponding to reference number GI: 62241011. In some embodiments, the Akt has the protein sequence corresponding to RefSeq NP_005154.2 (SEQ ID NO:5).

The term "mutation" as used herein indicates any modification of a nucleic acid and/or polypeptide which results in an altered nucleic acid or polypeptide. The term "mutation" may include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences, as well as amplifications and/or chromosomal breaks or translocations.

Reference to a "subtype" of a cell (e.g., a KRAS$^{G12C}$ subtype, a KRAS$^{G12S}$ subtype, a KRAS$^{G12D}$ subtype, a KRAS$^{G12V}$ subtype) means that the cell contains a gene mutation encoding a change in the protein of the type indicated. For example, a cell classified as a "KRAS$^{G12C}$ subtype" contains at least one KRAS allele that encodes an amino acid substitution of cysteine for glycine at position 12 ($^{G12C}$); and, similarly, other cells of a particular subtype (e.g., KRAS$^{G12D}$ KRAS$^{G12S}$ and KRAS$^{G12V}$ subtypes) contain at least one allele with the indicated mutation (e.g., a KRAS$^{G12D}$ mutation, a KRAS$^{G12S}$ mutation or a KRAS$^{G12V}$ mutation, respectively). Unless otherwise noted, all amino acid position substitutions referenced herein (such as, e.g., "$^{G12C}$" in KRAS$^{G12C}$) correspond to substitutions in the human version of the referenced protein, i.e., KRAS$^{G12C}$ refers to a G→C substitution in position 12 of human KRAS.

Methods of Treatment

The present disclosure provides a method of treating a disease or disorder mediated by mTOR by administering, to the subject suffering from or susceptible to developing a disease or disorder mediated by mTOR, a dosage of an mTOR inhibitor (e.g., a bi-steric mTOR inhibitor such as RMC-5552).

In some embodiments, the methods comprise administering an mTOR inhibitor (e.g., a bi-steric mTOR inhibitor, e.g., RMC-5552)(e.g., a bi-steric mTOR inhibitor, e.g., RMC-5552) as a monotherapy. The term "monotherapy" refers to a method of treatment comprising administering to a subject a single therapeutic agent, optionally as a pharmaceutical composition.

Some embodiments are directed to a method of treating a subject having a cancer by administering a dosage of about 3 mg/week to about 25 mg/week of a bi-steric mTOR inhibitor to the subject;

wherein the bi-steric mTOR inhibitor is

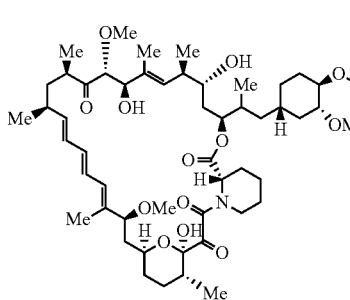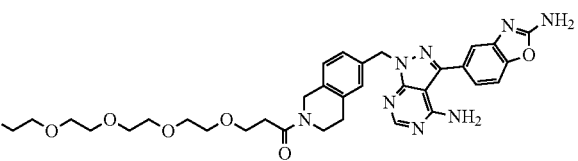

or a stereoisomer, tautomer, or oxepane isomer thereof, or pharmaceutically acceptable salt of any of the foregoing.

In some embodiments, the cancer is salivary gland cancer and the method comprises administering a dosage of about 3 mg/week to about 25 mg/week of a bi-steric mTOR inhibitor to the subject;

wherein the bi-steric mTOR inhibitor is

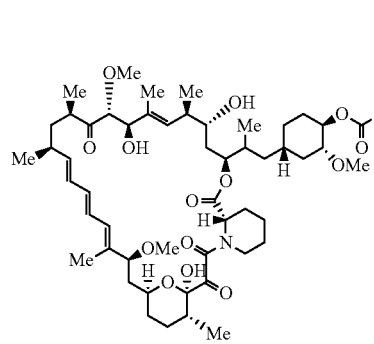
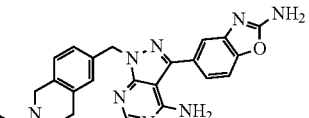

or a stereoisomer, tautomer, or oxepane isomer thereof, or pharmaceutically acceptable salt of any of the foregoing.

In some embodiments, the dosage is about 4 mg/week to about 25 mg/week, about 4 mg/week to about 20 mg/week, about 4 mg/week to about 16 mg/week, about 4 mg/week to about 14 mg/week, about 4 mg/week to about 12 mg/week, about 4 mg/week to about 10 mg/week, about 4 mg/week to about 9 mg/week, about 4 mg/week to about 8 mg/week, about 4 mg/week to about 7 mg/week, about 4 mg/week to about 6 mg/week, about 5 mg/week to about 25 mg/week, about 5 mg/week to about 20 mg/week, about 5 mg/week to about 16 mg/week, about 5 mg/week to about 14 mg/week, about 5 mg/week to about 12 mg/week, about 5 mg/week to about 10 mg/week, about 5 mg/week to about 9 mg/week, about 5 mg/week to about 8 mg/week, about 5 mg/week to about 7 mg/week, about 5 mg/week to about 6 mg/week, about 6 mg/week to about 25 mg/week, about 6 mg/week to about 20 mg/week, about 6 mg/week to about 16 mg/week, about 6 mg/week to about 14 mg/week, about 6 mg/week to about 12 mg/week, about 6 mg/week to about 10 mg/week, about 6 mg/week to about 9 mg/week, about 6 mg/week to about 8 mg/week, about 6 mg/week to about 7 mg/week, about 7 mg/week to about 25 mg/week, about 7 mg/week to about 20 mg/week, about 7 mg/week to about 16 mg/week, about 7 mg/week to about 14 mg/week, about 7 mg/week to about 12 mg/week, about 6 mg/week to about 10 mg/week, about 7 mg/week to about 9 mg/week, about 7 mg/week to about 8 mg/week, about 8 mg/week to about 25 mg/week, about 8 mg/week to about 20 mg/week, about 8 mg/week to about 16 mg/week, about 8 mg/week to about 14 mg/week, about 8 mg/week to about 12 mg/week, about 8 mg/week to about 10 mg/week, about 9 mg/week to about 25 mg/week, about 9 mg/week to about 20 mg/week, about 9 mg/week to about 16 mg/week, about 9 mg/week to about 14 mg/week, about 9 mg/week to about 12 mg/week, about 10 mg/week to about 25 mg/week, about 10 mg/week to about 20 mg/week, about 10 mg/week to about 16 mg/week, about 10 mg/week to about 14 mg/week, about 10 mg/week to about 12 mg/week, about 11 mg/week to about 25 mg/week, about 11 mg/week to about 20 mg/week, about 11 mg/week to about 16 mg/week, about 11 mg/week to about 14 mg/week, or about 11 mg/week to about 12 mg/week.

In some embodiments, the dosage is about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week.

It was surprisingly observed that a dosage of 1.6 mg/week to 6 mg/week of a bi-steric mTOR inhibitor (i.e., RMC-5552) exhibited a dose-proportional increase in exposure, while a dosage of above 6 mg/week exhibited a more than dose-proportional increase. A dose-proportional increase is generally preferable in dosage regimens as it affords greater control over target exposure and is often associated with desirable drug clearance. These concerns are often balanced against the need for high dosage to afford efficacy in disease treatment. Accordingly, in some embodiments, the dosage is at or near the dose-proportional inflection point of 6 mg/week (e.g., about 5 mg/week to about 9 mg/week, about 6 mg/week to about 9 mg/week, about 6 mg/week to about 8 mg/week, about 5 mg/week, about 5.5 mg/week, about 6 mg/week, about 6.5 mg/week, about 7 mg/week, about 7.5 mg/week, about 8 mg/week, about 8.5 mg/week, or about 9 mg/week).

It was also surprisingly observed that a steep dose-response relationship exists above a dosage of about 6 mg/week (e.g., between 6 mg/week to 12 mg/week.) Accordingly, in some embodiments, a dosage above about 6 mg/week is used. Dosages at these ranges can be intolerable due to side effects (e.g., mucositis.) As described herein, tacrolimus (e.g., a tacrolimus mouthwash; see extended discussion of tacrolimus below) was surprisingly able to mitigate side effects and thereby enable a higher dosage. Accordingly, in some embodiments, a dosage above about 6 mg/week is used in combination with tacrolimus.

In some embodiments, a high dosage (e.g., above about 6 mg/week) is used initially before lowering the dosage. For example, in some embodiments a dosage above about 6 mg/week (i.e., above the dose-proportional increase threshold) is administered for one week or for several weeks and is followed by a dosage below about 6 mg/week (i.e., near or below the dose-proportional increase threshold.) In some embodiments, there is a break (e.g., 1, 2, 3, 4, or 5 weeks) between the high dosage and the low dosage. In some embodiments, the dosage in a first 1, 2, 3, 4, or 5 week(s) is higher than the dosage in following weeks. In some embodiments, the dosage in the first week is higher than the dosage in following weeks.

In some embodiments, the dosage in the first 1, 2, 3, 4, or 5 weeks is about 6 mg/week to about 25 mg/week, about 6 mg/week to about 20 mg/week, about 6 mg/week to about 16 mg/week, about 6 mg/week to about 14 mg/week, about 6 mg/week to about 12 mg/week, about 6 mg/week to about 10 mg/week, about 8 mg/week to about 25 mg/week, about 8 mg/week to about 20 mg/week, about 8 mg/week to about 16 mg/week, about 8 mg/week to about 14 mg/week, about 8 mg/week to about 12 mg/week, about 8 mg/week to about 10 mg/week, about 10 mg/week to about 25 mg/week, about 10 mg/week to about 20 mg/week, about 10 mg/week to about 16 mg/week, about 10 mg/week to about 14 mg/week, or about 10 mg/week to about 12 mg/week. In some embodiments, dosage in the first 1, 2, 3, 4, or 5 week(s) is about 10 mg/week to about 12 mg/week. In some embodiments, dosage in the first week is about 10 mg/week to about 12 mg/week.

In some embodiments, the dosage in the first 1, 2, 3, 4, or 5 week(s) is about 6 mg/week, about 6.5 mg/week, about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week. In some embodiments, the dosage in the first 1, 2, 3, 4, or 5 week(s) is about 10 mg/week. In some embodiments, the dosage in the first 1, 2, 3, 4, or 5 week(s) is about 11 mg/week. In some embodiments, the dosage in the first 1, 2, 3, 4, or 5 week(s) is about 12 mg/week. In some embodiments, the dosage in the first week is about 10 mg/week. In some embodiments, the dosage in the first week is about 11 mg/week. In some embodiments, the dosage in the week is about 12 mg/week.

In some embodiments, the dosage in the first 1, 2, 3, 4, or 5 week(s) is followed by 1, 2, 3, 4, or 5 weeks without administration. In some embodiments, the dosage in the first week is followed by 1, 2, 3, 4, or 5 weeks without administration.

In some embodiments, the dosage after 1, 2, 3, 4, 5, 6, 7, 8, 9, or 10 week(s) is about 3 mg/week to about 12 mg/week, about 3 mg/week to about 10 mg/week, about 3 mg/week to about 8 mg/week, about 3 mg/week to about 6 mg/week, about 4 mg/week to about 12 mg/week, about 4 mg/week to about 10 mg/week, about 4 mg/week to about 8 mg/week, about 4 mg/week to about 6 mg/week, about 5 mg/week to about 12 mg/week, about 5 mg/week to about 10 mg/week, about 5 mg/week to about 8 mg/week, about 5 mg/week to about 6 mg/week, about 6 mg/week to about 12 mg/week, about 6 mg/week to about 10 mg/week, about 6 mg/week to about 8 mg/week, about 6 mg/week to about 7 mg/week, about 7 mg/week to about 12 mg/week, about 7 mg/week to about 10 mg/week, about 7 mg/week to about 8 mg/week, about 8 mg/week to about 12 mg/week, or about 8 mg/week to about 10 mg/week. In some embodiments, the dosage after 1, 2, 3, 4, 5, 6, 7, 8, 9, or 10 week(s) is about 3 mg/week to about 12 mg/week.

In some embodiments, the dosage after 1, 2, 3, 4, 5, 6, 7, 8, 9, or 10 week(s) is about 3 mg/week, about 3.5 mg/week, about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, or about 10 mg/week. In some embodiments, the dosage after 1, 2, 3, 4, 5, 6, 7, 8, 9, or 10 week(s) is about 6 mg/week.

For example, in some embodiments, the dosage in a first 1, 2, 3, 4, 5 or week(s) is about 6 mg/week, about 6.5 mg/week, about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week;
followed by 0, 1, 2, 3, 4, or 5 weeks without administration;
followed by a dosage of about 3 mg/week to about 12 mg/week, about 3 mg/week to about 10 mg/week, about 3 mg/week to about 8 mg/week, about 3 mg/week to about 6 mg/week, about 4 mg/week to about 12 mg/week, about 4 mg/week to about 10 mg/week, about 4 mg/week to about 8 mg/week, about 4 mg/week to about 6 mg/week, about 5 mg/week to about 12 mg/week, about 5 mg/week to about 10 mg/week, about 5 mg/week to about 8 mg/week, about 5 mg/week to about 6 mg/week, about 6 mg/week to about 12 mg/week, about 6 mg/week to about 10 mg/week, about 6 mg/week to about 8 mg/week, about 6 mg/week to about 7 mg/week, about 7 mg/week to about 12 mg/week, about 7 mg/week to about 10 mg/week, about 7 mg/week to about 8 mg/week, about 8 mg/week to about 12 mg/week, or about 8 mg/week to about 10 mg/week.

Also for example, in some embodiments, the dosage in a first 1, 2, 3, 4, 5 or week(s) is about 6 mg/week to about 25 mg/week, about 6 mg/week to about 20 mg/week, about 6 mg/week to about 16 mg/week, about 6 mg/week to about 14 mg/week, about 6 mg/week to about 12 mg/week, about 6 mg/week to about 10 mg/week, about 8 mg/week to about 25 mg/week, about 8 mg/week to about 20 mg/week, about 8 mg/week to about 16 mg/week, about 8 mg/week to about 14 mg/week, about 8 mg/week to about 12 mg/week, about 8 mg/week to about 10 mg/week, about 10 mg/week to about 25 mg/week, about 10 mg/week to about 20 mg/week, about 10 mg/week to about 16 mg/week, about 10 mg/week to about 14 mg/week, or about 10 mg/week to about 12 mg/week;
followed by 0, 1, 2, 3, 4, or 5 weeks without administration;
followed by a dosage of about 3 mg/week, about 3.5 mg/week, about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, or about 10 mg/week.

In some embodiments, after several (e.g., 1, 2, 3, 4, or 5) weeks of administration of the lower dosage, there may be another break in administration (e.g., 0, 1, 2, 3, 4, or 5 weeks without administration) and/or another decrease in the dosage. In some embodiments, this is followed by more breaks and/or decreases in dosage. In some embodiments, the dosage is progressively lowered over the course of treatment. In some embodiments, the dosage is lowered by about 1 mg/week, about 2 mg/week, about 3 mg/week, about 4 mg/week, about 5 mg/week, or about 6 mg/week every 1, 2, 3, 4, or 5 weeks. In some embodiments, there is a break in administration between each lowering of the dosage.

Administration of the disclosed compounds or compositions can be accomplished via any mode of administration for therapeutic agents. These modes may include systemic or local administration such as oral, nasal, parenteral, transdermal, subcutaneous, vaginal, buccal, rectal, topical, intrathecal, or intracranial administration modes.

In some embodiments, administering can include oral administration, administration as a suppository, topical contact, intravenous, parenteral, intraperitoneal, intramuscular, intralesional, intrathecal, intracranial, intranasal, or subcutaneous administration, or the implantation of a slow-release device, e.g., a mini-osmotic pump, to a subject. Administration can be by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. The compositions of the present disclosure can be delivered transdermally, by a topical route, and by formulation as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, J. Biomater Set Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of an mTOR inhibitor into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46: 1576-1587, 1989). In some embodiments, an mTOR inhibitor (e.g., a bi-steric mTOR inhibitor, e.g., RMC-5552)(e.g., a bi-steric mTOR inhibitor, e.g., RMC-5552) is delivered by nanoparticles.

Depending on the intended mode of administration, an mTOR inhibitor (e.g., a bi-steric mTOR inhibitor, e.g., RMC-5552)(e.g., a bi-steric mTOR inhibitor, e.g., RMC-5552) can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, an mTOR inhibitor (e.g., a bi-steric mTOR inhibitor, e.g., RMC-5552) can be administered in intravenous (both bolus and infusion), intraperitoneal, intrathecal, subcutaneous, and intramuscular forms, and all using forms well known to those skilled in the pharmaceutical arts.

Illustrative pharmaceutical compositions are tablets and gelatin capsules comprising a an mTOR inhibitor (e.g., a bi-steric mTOR inhibitor, e.g., RMC-5552) and a pharmaceutically acceptable carrier such as a) diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

The term "carrier", as used herein, encompasses carriers, excipients, and diluents, and means a material, composition, or vehicle, such as a liquid or solid filler, diluent, excipient, solvent, or encapsulating material, involved in carrying or transporting a pharmaceutical agent from one organ, or portion of the body, to another organ, or portion of the body of a subject. Excipients should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, spray-dried dispersions, and the like.

The term "pharmaceutically compatible carrier materials" may comprise, e.g., acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

Liquid, particularly injectable, compositions can, for example, be prepared by dissolution, dispersion, etc. For example, an mTOR inhibitor (e.g., a bi-steric mTOR inhibitor, e.g., RMC-5552) is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize an mTOR inhibitor (e.g., a bi-steric mTOR inhibitor, e.g., RMC-5552).

An mTOR inhibitor (e.g., a bi-steric mTOR inhibitor, e.g., RMC-5552) can be also formulated as a suppository that can be prepared from fatty emulsions or suspensions; using polyalkylene glycols such as propylene glycol, as the carrier.

An mTOR inhibitor (e.g., a bi-steric mTOR inhibitor, e.g., RMC-5552) can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

An mTOR inhibitor (e.g., a bi-steric mTOR inhibitor, e.g., RMC-5552) can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular, or intravenous injections and infusions. Injectables can be prepared in conventional forms, either as liquid solutions or suspensions or solid forms suitable for dissolving in liquid prior to injection.

In some embodiments, the dosage is administered via an intravenous ("IV") infusion. In some embodiments, the dosage is administered over about 0.5 hour to about 2 hours, over about 0.5 hour to about 1.5 hours, over about 0.5 hour to about 1 hour, over about 1 hour to about 2 hours, or over about 1 hour to about 1.5 hours. In some embodiments, the dosage is administered over about 0.5 hour, about 1 hour, about 1.5 hours, or about 2 hours. In some embodiments, the dosage is administered over about 1 hour.

In some embodiments, the dosage is about 4 mg/week to about 25 mg/week, about 4 mg/week to about 14 mg/week, about 4 mg/week to about 12 mg/week, about 5 mg/week to about 25 mg/week, about 5 mg/week to about 14 mg/week, about 5 mg/week to about 12 mg/week, about 5 mg/week to about 10 mg/week, about 6 mg/week to about 25 mg/week, about 6 mg/week to about 14 mg/week, about 6 mg/week to about 12 mg/week, about 6 mg/week to about 9 mg/week, about 6 mg/week to about 8 mg/week, about 7 mg/week to about 25 mg/week, about 7 mg/week to about 14 mg/week, about 7 mg/week to about 12 mg/week, about 7 mg/week to about 8 mg/week, about 8 mg/week to about 25 mg/week, about 8 mg/week to about 14 mg/week, about 8 mg/week to about 12 mg/week, or about 8 mg/week to about 10 mg/week and the dosage is administered over about 0.5 hour to about 2 hours, over about 0.5 hour to about 1.5 hours, over about 0.5 hour to about 1 hour, over about 1 hour to about 2 hours, or over about 1 hour to about 1.5 hours. In some embodiments, the dosage is about 3 mg/week to about 25 mg/week and is administered over about 0.5 hour to about 2 hours.

In some embodiments, the dosage is about 4 mg/week to about 25 mg/week, about 4 mg/week to about 14 mg/week, about 4 mg/week to about 12 mg/week, about 5 mg/week to about 25 mg/week, about 5 mg/week to about 14 mg/week, about 5 mg/week to about 12 mg/week, about 5 mg/week to about 10 mg/week, about 6 mg/week to about 25 mg/week, about 6 mg/week to about 14 mg/week, about 6 mg/week to about 12 mg/week, about 6 mg/week to about 9 mg/week, about 6 mg/week to about 8 mg/week, about 7 mg/week to about 25 mg/week, about 7 mg/week to about 14 mg/week, about 7 mg/week to about 12 mg/week, about 7 mg/week to about 8 mg/week, about 8 mg/week to about 25 mg/week, about 8 mg/week to about 14 mg/week, about 8 mg/week to about 12 mg/week, or about 8 mg/week to about 10 mg/week and the dosage is administered over about 0.5 hour, about 1 hour, about 1.5 hours, or about 2 hours. In some embodiments, the dosage is about 3 mg/week to about 25 mg/week and is administered over about 1 hour.

In some embodiments, the dosage is about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week and is administered over about 0.5 hour to about 2 hours, over about 0.5 hour to about 1.5 hours, over about 0.5 hour to about 1 hour, over about 1 hour to about 2 hours, or over about 1 hour to about 1.5 hours. In some embodiments, the dosage is about 6 mg/week or about 8 mg/week and is administered over about 0.5 hour to about 2 hours.

In some embodiments, the dosage is about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week and is administered over about 0.5 hour, about 1 hour, about 1.5 hours, or about 2 hours. In some embodiments, the dosage is about 6 mg/week or about 8 mg/week and is administered over about 1 hour.

In some embodiments, the dosage is administered once-weekly. For example, in some embodiments, a dosage of about 3 mg/week to about 25 mg/week is administered via a once-weekly IV infusion. In some embodiments, a dosage of about 6 mg/week or about 8 mg/week is administered via a once-weekly IV infusion. In some embodiments, the dosage is administered once-weekly over about 0.5 hour to about 2 hours. In some embodiments, the dosage is administered once-weekly over about 1 hour.

In some embodiments, the dosage is administered over multiple weekly administrations (e.g., multiple IV infusions). The sum of mTOR inhibitor (e.g., a bi-steric mTOR inhibitor, e.g., RMC-5552) administered over the multiple weekly administrations is the dosage. In some embodiments, the dosage is administered twice-weekly, thrice-weekly, or quadrice-weekly. For example, in some embodiments, a dosage of about 3 mg/week to about 25 mg/week is administered over twice-weekly or thrice-weekly IV infusions. In some embodiments, a dosage of about 6 mg/week or about 8 mg/week is administered over twice-weekly or thrice-weekly IV infusions. In some embodiments, the dosage is administered twice-weekly or thrice-weekly over about 0.5 hour to about 2 hours. In some embodiments, the dosage is administered twice-weekly or thrice-weekly over IV infusions of about 0.5 hour to about 1 hour each.

As used herein, the term "subject" encompasses mammals and non-mammals. Examples of mammals include, but are not limited to, any member of the class Mammalia: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. In some embodiments, the subject is human.

A "patient" is a mammal, e.g., a human, mouse, rat, guinea pig, dog, cat, horse, cow, pig, or non-human primate, such as a monkey, chimpanzee, baboon, or rhesus. "Patient" includes both human and animals.

Adverse Events

A challenge associated with many cancer drug treatments is administration of sufficient amounts of the drug to a subject without inducing intolerable side-effects in the subject. Surprisingly, it has been found that providing and/or administering a mouthwash (e.g., a tacrolimus mouthwash) to the subject and/or ice to the mouth the subject in conjunction with an mTOR inhibitor (such as bi-steric mTOR inhibitors (e.g., RMC-5552) and allosteric mTOR inhibitors (e.g., everolimus, sirolimus, and nab-sirolimus)) provides the ability to administer higher dosages and/or results in a reduction of side-effects.

In some embodiments, the methods of the present disclosure treat and/or prevent one or more side effects associated with administration of an mTOR inhibitor (e.g., RMC-5552, everolimus, sirolimus, and nab-sirolimus). Such side effects include but are not limited to anemia, nausea, mucositis (e.g., stomatitis), vomiting, diarrhea, fatigue, decreased appetite, hyponatremia, hyperglycemia, headache, dyspnoea, and rash.

For example, using a solution as described below (e.g., a mouthwash) and/or ice chips, dosages of the mTOR inhibitor (e.g., RMC-5552, everolimus, sirolimus, and nab-sirolimus) could be administered without inducing intolerable stomatitis and/or mucositis.

Mucositis, as used herein, refers to inflammation and/or ulceration of the mucous membranes lining the digestive tract, usually painful. Mucositis is often seen as an adverse effect of chemotherapy and radiotherapy treatment for cancer. Mucositis can occur anywhere along the gastrointestinal tract, but oral mucositis is particularly common and refers to inflammation and ulceration that occurs in the mouth. Given the prevalence of oral mucositis, sometimes the term "mucositis" is used to refer to "oral mucositis". Oral mucositis is also known as stomatitis.

In some embodiments, the methods further comprise providing and/or administering a solution (e.g., mouthwash) to the subject and/or ice to the mouth of the subject. In some embodiments when employing the solution (e.g., mouthwash) and/or ice, the subject tolerates a higher dosage of the mTOR inhibitor (e.g., RMC-5552, everolimus, sirolimus, and nab-sirolimus) than when not employing the solution and/or ice.

In some embodiments, employing the solution (e.g., mouthwash) and/or ice, is done before the administration of an mTOR inhibitor (e.g., a bi-steric mTOR inhibitor, e.g., RMC-5552). In some embodiments, the dosage of a bi-steric mTOR inhibitor (e.g., RMC-5552) is about 6 mg/week to about 25 mg/week, about 6 mg/week to about 20 mg/week, about 6 mg/week to about 16 mg/week, about 6 mg/week to about 14 mg/week, about 6 mg/week to about 12 mg/week, about 6 mg/week to about 10 mg/week, about 8 mg/week to about 25 mg/week, about 8 mg/week to about 20 mg/week, about 8 mg/week to about 16 mg/week, about 8 mg/week to about 14 mg/week, about 8 mg/week to about 12 mg/week, about 8 mg/week to about 10 mg/week, about 10 mg/week to about 25 mg/week, about 10 mg/week to about 20 mg/week, about 10 mg/week to about 16 mg/week, about 10 mg/week to about 14 mg/week, or about 10 mg/week to about 12 mg/week. In some embodiments, dosage is about 10 mg/week to about 12 mg/week. In some embodiments, dosage is about 10 mg/week to about 12 mg/week. In some embodiments, the dosage is about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week. In some embodiments, the dosage is about 10 mg/week. In some embodiments, the dosage is about 11 mg/week. In some embodiments, the dosage is about 12 mg/week. In some embodiments, the dosage is about 10 mg/week. In some embodiments, the dosage is about 11 mg/week. In some embodiments, the dosage is about 12 mg/week.

In some embodiments, the methods of the present disclosure further comprise administering a dexamethasone solution (e.g., mouthwash) to the subject.

In some embodiments, the dexamethasone solution (e.g., mouthwash) comprises about 0.1 mg/5 mL to about 1 mg/5 mL, about 0.5 m/5 mL to about 5 mg/5 mL, or about 0.5 mg/5 mL to about 20 mg/5 mL dexamethasone. In some embodiments, the dexamethasone solution (e.g., mouthwash) comprises about 0.5 mg/5 mL, about 1 mg/5 mL, about 5 mg/5 mL, about 10 mg/5 mL, or about 20 mg/5 mL dexamethasone. In some embodiments, the dexamethasone solution (e.g., mouthwash) comprises about 0.5 mg/5 mL dexamethasone.

In some embodiments, the subject is administered about 2.5 mL, about 5 mL, or about 10 mL of a dexamethasone solution (e.g., mouthwash). In some embodiments, the subject is administered about 2.5 mL of the dexamethasone solution (e.g., mouthwash). In some embodiments, the dexamethasone solution (e.g., mouthwash) is administered 1, 2, 3, or 4 times daily.

In some embodiments, the methods of the present disclosure further comprise administering tacrolimus to the subject. For example, in some embodiments, tacrolimus is administered as gel or as an ointment (e.g., as a 0.1% or as a 0.03% ointment), as a solution (e.g., a mouthwash), or as a tablet, pill, or capsule. Without being bound by any theory, it is believed that tacrolimus has the added benefit of directly binding to the mTORC1 complex at the same binding site as a bi-steric mTOR inhibitor (e.g., RMC-5552) disclosed herein, blocking one of the two binding sites, or in the case of an allosteric mTOR inhibitor (e.g., everolimus, sirolimus, and nab-sirolimus) it is believed that tacrolimus beneficially competes against the allosteric mTOR inhibitor for presenter protein binding (e.g., FKBP12), thereby selectively reducing the efficacy of the mTOR inhibitor to inhibit mTOR signaling in a tissue of the subject which has been contacted with tacrolimus and as a result mitigates mTOR inhibitor induced adverse event in said tissue.

In some embodiments, the methods further comprise administering a tacrolimus solution (e.g., a mouthwash) to the subject. In some embodiments, the tacrolimus solution (e.g., mouthwash) comprises about 0.1 mg/mL to about 1 mg/mL tacrolimus. In some embodiments, the tacrolimus solution (e.g., mouthwash) comprises about 0.1 mg/mL, about 0.5 mg/mL, about 1 mg/mL, about 5 mg/mL, about 10 mg/mL, or about 20 mg/mL of solution (e.g., mouthwash). In some embodiments, the tacrolimus solution (e.g., mouthwash) comprises about 0.5 mg/mL tacrolimus. In some embodiments, the tacrolimus solution (e.g., mouthwash) comprises about 0.1 mg/mL tacrolimus.

In some embodiments, the subject is administered about 2.5 mL, about 5 mL, or about 10 mL of the tacrolimus solution (e.g., mouthwash). In some embodiments, the subject is administered about 2.5 mL of the tacrolimus solution (e.g., mouthwash). In some embodiments, the tacrolimus solution (e.g., mouthwash) is administered 1, 2, 3, or 4 times daily. In some embodiments, the tacrolimus solution (e.g., mouthwash) is administered on the day of administering an mTOR inhibitor (e.g., a bi-steric mTOR inhibitor such as RMC-5552) or just prior to administering the mTOR inhibitor (e.g., RMC-5552). In some embodiments, the tacrolimus solution (e.g., mouthwash) is administered on the day of IV infusion or just prior to IV infusion. In some embodiments, the tacrolimus solution (e.g., mouthwash) is administered only on the day of administering the mTOR inhibitor (e.g., RMC-5552) or only just prior to the administering the mTOR inhibitor (e.g., RMC-5552). In some embodiments, the tacrolimus solution (e.g., mouthwash) is administered only on the day of IV infusion or only just prior to IV infusion.

In some embodiments, the method further comprises administering a combination solution (e.g., mouthwash) to the subject, wherein the combination solution (e.g., mouthwash) comprises dexamethasone and tacrolimus.

In some embodiments, the combination solution (e.g., mouthwash) comprises about 0.1 mg/5 mL to about 1 mg/5 mL, about 0.5 m/5 mL to about 5 mg/5 mL, or about 0.5 mg/5 mL to about 20 mg/5 mL dexamethasone. In some embodiments, the dexamethasone solution (e.g., mouthwash) comprises about 0.5 mg/5 mL, about 1 mg/5 mL, about 5 mg/5 mL, about 10 mg/5 mL, or about 20 mg/5 mL dexamethasone. In some embodiments, the combination solution (e.g., mouthwash) comprises about 0.5 mg/5 mL dexamethasone.

In some embodiments, the combination solution (e.g., mouthwash) comprises about 0.1 mg/mL to about 1 mg/mL tacrolimus. In some embodiments, the combination solution (e.g., mouthwash) comprises about 0.1 mg/mL, about 0.5 mg/mL, about 1 mg/mL, about 5 mg/mL, about 10 mg/mL, or about 20 mg/mL of tacrolimus. In some embodiments, the combination solution (e.g., mouthwash) comprises about 0.5 mg/mL tacrolimus. In some embodiments, the combination solution (e.g., mouthwash) comprises about 0.1 mg/mL tacrolimus.

In some embodiments, the subject is administered about 2.5 mL of the combination solution (e.g., mouthwash). In some embodiments, the combination solution (e.g., mouthwash) is administered 1, 2, 3, or 4 times daily. In some embodiments, the combination solution (e.g., mouthwash) is administered on the day of administering an mTOR inhibitor (e.g., a bi-steric mTOR inhibitor, e.g., RMC-5552) or just prior to administering an mTOR inhibitor (e.g., a bi-steric mTOR inhibitor, e.g., RMC-5552). In some embodiments, the combination solution (e.g., mouthwash) is administered on the day of IV infusion or just prior to IV infusion. In some embodiments, the combination solution (e.g., mouthwash) is administered only on the day of administering an mTOR inhibitor (e.g., a bi-steric mTOR inhibitor, e.g., RMC-5552) or only just prior to administering an mTOR inhibitor (e.g., a bi-steric mTOR inhibitor, e.g., RMC-5552). In some embodiments, the combination solution (e.g., mouthwash) is administered only on the day of IV infusion or only just prior to mTOR inhibitor (e.g., bi-steric mTOR inhibitor, e.g., RMC-5552) IV infusion.

In some embodiments, the method of treating a subject having cancer further comprises providing and/or administering ice to the mouth of the subject. The ice may be applied before administering an mTOR inhibitor (e.g., a bi-steric mTOR inhibitor such as RMC-5552), while administering the mTOR inhibitor (e.g., RMC-5552), after administering the mTOR inhibitor (e.g., RMC-5552), or some combination of the foregoing. In some embodiments, the ice is applied for about 1 to about 60, for about 1 to about 30, or for about 1 to about 10 minutes before administering the mTOR inhibitor (e.g., RMC-5552), or for about 1, about 5, about 10, about 15, about 20, about 30, or about 60 minutes before administering the mTOR inhibitor (e.g., RMC-5552). In some embodiments, the ice is applied during administering the mTOR inhibitor (e.g., RMC-5552). In some embodiments, the ice is applied for about 1 to about 60, for about 1 to about 30, or for about 1 to about 10 minutes after administering the mTOR inhibitor (e.g., RMC-5552), or for about 1, about 5, about 10, about 15, about 20, about 30, or about 60 minutes after administering the mTOR inhibitor (e.g., RMC-5552). In some embodiments, the ice is applied for about 10 minutes before administering the mTOR inhibitor (e.g., RMC-5552), during administering the mTOR inhibitor (e.g., RMC-5552), and for about 10 minutes after administering the mTOR inhibitor (e.g., RMC-5552). In some embodiments, the ice is applied for about 1 to about 60, for about 1 to about 30, or for about 1 to about 10 minutes before IV infusion, or for about 1, about 5, about 10, about 15, about 20, about 30, or about 60 minutes before IV infusion. In some embodiments, the ice is applied during IV infusion. In some embodiments, the ice is applied for about 1 to about 60, for about 1 to about 30, or for about 1 to about 10 minutes after IV infusion, or for about 1, about 5, about 10, about 15, about 20, about 30, or about 60 minutes after IV infusion. In some embodiments, the ice is applied for about 10 minutes before IV infusion, during IV infusion, and for about 10 minutes after IV infusion.

In some embodiments, the present disclosure is directed to a method of treating or preventing mucositis (e.g., stomatitis) in a subject in need thereof, the method comprising administering an effective amount of tacrolimus (e.g., a tacrolimus solution such as a tacrolimus mouthwash.) In some embodiments, the mucositis (e.g., stomatitis) is associated with administration of mTOR inhibitor (e.g., RMC-5552, everolimus, sirolimus, and nab-sirolimus.) In some embodiments, the subject in need thereof is undergoing, has underwent, or will undergo treatment with an mTOR inhibitor (e.g., RMC-5552, everolimus, sirolimus, and nab-sirolimus.) In some embodiments, the tacrolimus is administered as gel or as an ointment (e.g., as a 0.1% or as a 0.03% ointment), as a solution (e.g., a mouthwash), or as a tablet, pill, or capsule. In some embodiments, the tacrolimus is administered as a tacrolimus solution (e.g., a mouthwash) to the subject. In some embodiments, the tacrolimus solution (e.g., mouthwash) comprises about 0.1 mg/mL to about 1 mg/mL tacrolimus. In some embodiments, the tacrolimus solution (e.g., mouthwash) comprises about 0.1 mg/mL, about 0.5 mg/mL, about 1 mg/mL, about 5 mg/mL, about 10 mg/mL, or about 20 mg/mL of solution (e.g., mouthwash). In some embodiments, the tacrolimus solution (e.g., mouthwash) comprises about 0.5 mg/mL tacrolimus. In some embodiments, the tacrolimus solution (e.g., mouthwash) comprises about 0.1 mg/mL tacrolimus. In some embodiments, the subject is administered about 2.5 mL, about 5 mL, or about 10 mL of the tacrolimus solution (e.g., mouthwash). In some embodiments, the subject is administered about 2.5 mL of the tacrolimus solution (e.g., mouthwash). In some embodiments, the tacrolimus solution (e.g., mouthwash) is administered 1, 2, 3, or 4 times daily. In some embodiments, the tacrolimus solution (e.g., mouthwash) is administered on the day of administering the mTOR inhibitor (e.g., RMC-5552, everolimus, sirolimus, and nab-sirolimus) or just prior to administering the mTOR inhibitor (e.g., RMC-5552, everolimus, sirolimus, and nab-sirolimus). In some embodiments, the tacrolimus solution (e.g., mouthwash) is administered on the day of IV infusion or just prior to IV infusion. In some embodiments, the tacrolimus solution (e.g., mouthwash) is administered only on the day of administering the mTOR inhibitor (e.g., RMC-5552, everolimus, sirolimus, and nab-sirolimus) or only just prior to the administering the mTOR inhibitor (e.g., RMC-5552, everolimus, sirolimus, and nab-sirolimus). In some embodiments, the tacrolimus solution (e.g., mouthwash) is administered only on the day of IV infusion or only just prior to IV infusion.

Combination Therapy

In some methods, an mTOR inhibitor (e.g., a bi-steric mTOR inhibitor such as RMC-5552) is used in combination with one or more additional therapeutic agents. In these embodiments, the dosages of the one or more additional therapeutic agents may be reduced from their standard dosages (i.e., when they are administered alone).

The term "combination therapy" refers to a method of treatment comprising administering to a subject at least two therapeutic agents, optionally as one or more pharmaceutical compositions. When used in combination therapy, an mTOR inhibitor (e.g., a bi-steric mTOR inhibitor, e.g., RMC-5552) may be administered with one or more therapeutic agents simultaneously or separately. This administration in combination can include simultaneous administration of the mTOR inhibitor (e.g., a bi-steric mTOR inhibitor, e.g., RMC-5552) and the one or more therapeutic agents in the same dosage form, simultaneous administration in separate dosage forms, and separate administration. That is, the mTOR inhibitor (e.g., a bi-steric mTOR inhibitor, e.g., RMC-5552) and any of the one or more therapeutic agents described herein can be formulated together in the same dosage form and administered simultaneously. Alternatively, the mTOR inhibitor (e.g., a bi-steric mTOR inhibitor, e.g., RMC-5552) and the one or more therapeutic agents can be in separate formulations administered simultaneously. In another alternative, the mTOR inhibitor (e.g., a bi-steric mTOR inhibitor, e.g., RMC-5552) can be administered and followed by the one or more therapeutic agents, or vice versa. In some embodiments of the separate administration protocol, the mTOR inhibitor (e.g., a bi-steric mTOR inhibitor, e.g., RMC-5552) and the one or more therapeutic agents are administered a few minutes apart, or a few hours apart, or a few days apart.

In some embodiments an mTOR inhibitor (e.g., a bi-steric mTOR inhibitor, e.g., RMC-5552) and one or more additional therapeutic agents are administered simultaneously or sequentially, in either order. The mTOR inhibitor (e.g., a bi-steric mTOR inhibitor, e.g., RMC-5552) may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours, up to 24 hours, or up to 1-7, 1-14, 1-21 or 1-30 days before or after the one or more additional therapeutic agents.

The additional therapeutic agent may be administered in an effective amount. The additional therapeutic agent may be administered in a therapeutically effective amount. In some embodiments, the effective amount of one or more of the additional therapeutic agents may be lower when used in a combination therapy than the therapeutic amount of the same therapeutic agent when it is used as a monotherapy, e.g., due an additive or synergistic effect of combining the two or more therapeutics.

The terms "effective amount" or "therapeutically effective amount" when used in connection with a compound refer to a sufficient amount of the compound to provide the desired biological result. That result can be reduction and/or alleviation of the signs, symptoms, or causes of a disease, or any other desired alteration of a biological system. For example, an "effective amount" for therapeutic use of the one or more additional therapeutic agents is the amount of the one or more additional therapeutic agents required to provide a clinically significant decrease in a disease.

In some embodiments, the methods include administration of one or more additional therapeutic agents. In some embodiments, the methods include administration of the additional therapeutic agent in a therapeutically effective amount. In some embodiments, the additional therapeutic agent is an anti-cancer agent. In some embodiments, the additional therapeutic agent is an immunotherapeutic agent. In some embodiments, the additional therapeutic agent is an immune-oncological agent. In some embodiments, the additional therapeutic agent is an anti-autoimmune disease agent. In some embodiments, the additional therapeutic agent is an anti-inflammatory disease agent. In some embodiments, the additional therapeutic agent is an anti-neurodegenerative disease agent. In some embodiments, the additional therapeutic agent is an anti-metabolic disease agent. In some embodiments, the additional therapeutic agent is an anti-cardiovascular disease agent. In some embodiments, the additional therapeutic agent is an anti-aging agent. In some embodiments, the additional therapeutic agent is a longevity agent. In some embodiments, the additional therapeutic agent is an agent for treating or preventing transplant rejection. In some embodiments, the additional therapeutic agent is an agent for treating or preventing fungal infection. In some embodiments, the additional therapeutic agent is immune system repressor. In some embodiments, the additional therapeutic agent is an mTOR modulator. In some embodiments, the additional therapeutic agent is an mTOR inhibitor. In some embodiments, the additional therapeutic agent is an active site mTOR inhibitor. In some embodiments, the additional therapeutic agent is a rapamycin. In some embodiments, the additional therapeutic agent is a rapamycin analog. In some embodiments, the additional therapeutic agent is an mTOR pathway inhibitor. In some embodiments, the additional therapeutic agent is a CDK4/6 inhibitor or an anti-PD1/PD-L1, PI3K inhibitor. In some embodiments, the additional therapeutic agent is a RAS inhibitor.

In some embodiments, the one or more additional therapeutic agents in the combination therapy includes a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, fiuclornnide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with an mTOR inhibitor (e.g., RMC-5552) include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/02871.

A therapeutic agent may be a biologic (e.g., cytokine (e.g., interferon or an interleukin such as IL-2)) used in treatment of cancer or symptoms associated therewith. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a T-cell checkpoint inhibitor. In some embodiments, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PDL-1. In some embodiments, the checkpoint inhibitor is an inhibitor or antagonist (e.g., an inhibitory antibody or Fc fusion or small molecule inhibitor) of PDL-2 (e.g., a PDL-2/Ig fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene) or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MEDI0680, BMS936559, MED14736, MPDL3280A, MSB0010718C, BMS986016, IMP321, lirilumab, IPH2101, 1-7F9, and KW-6002.

A therapeutic agent may be an anti-TIGIT antibody, such as MBSA43, BMS-986207, MK-7684, COM902, AB154, MTIG7192A or OMP-313M32 (etigilimab).

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents.

Anti-cancer agents include mitotic inhibitors, intercalating antibiotics, growth factor inhibitors, cell cycle inhibitors, enzymes, topoisomerase inhibitors, biological response modifiers, alkylating agents, antimetabolites, folic acid analogs, pyrimidine analogs, purine analogs and related inhibitors, *vinca* alkaloids, epipodophyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapeutic agents include two or more anti-cancer agents. The two or more anti-cancer agents can be used in a cocktail to be administered in combination or administered separately. Suitable dosing regimens of combination anti-cancer agents are known in the art and described in, for example, Saltz et al., *Proc. Am. Soc. Clin. Oncol.* 18:233a (1999), and Douillard et al., *Lancet* 355 (9209):1041-1047 (2000).

Other non-limiting examples of anti-cancer agents that may be used in the combination therapies described herein include Gleevec® (Imatinib Mesylate); Kyprolis® (carfilzomib); Velcade® (bortezomib); Casodex (bicalutanide); Iressa® (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammall and calicheamicin omegall (see, e.g., *Agnew, Chem. Intl. Ed Engl.* 33:183-186 (1994)); dynemicin such as dynemicin A; bisphosphonates such as clodronate; an esperamicin; neocarzinostatin chromophore and related chromoprotein enediyne antibiotic chromophores, aclacinomysins, actinomycin, authramycin, azaserine, bleomycins, cactinomycin, calicheamicin, carabicin, caminomycin, carminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., Taxol® (paclitaxel), Abraxane® (cremophor-free, albumin-engineered nanoparticle formulation of paclitaxel), and Taxotere® (doxetaxel); chloranbucil; tamoxifen (Nolvadex™); raloxifene; aromatase inhibiting 4(5)-imidazoles; 4-hydroxytamoxifen trioxifene; keoxifene; LY 117018; onapnistone; toremifene (Fareston®); flutamide, nilutamide, bicalutamide, leuprolide, goserelin; chlorambucil; Gemzar® gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; Navelbine® (vinorelbine); novantrone; teniposide; edatrexate; daunomycin; aminopterin; ibandronate; irinotecan (e.g., CPT-11); topoisomerase inhibitor RFS 2000; difluoromethylornithine (DMFO); retinoids such as retinoic acid; esperamicins; capecitabine (e.g., Xeloda®); and pharmaceutically acceptable salts of any of the above.

Additional non-limiting examples of anti-cancer agents that may be used in the combination therapies disclosed herein include trastuzumab (Herceptin®), bevacizumab (Avastin®), cetuximab (Erbitux®), rituximab (Rituxan®), Taxol®, Arimidex®, ABVD, avicine, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

Further non-limiting examples of anti-cancer agents that may be used in the combination therapies described herein include natural products such as *vinca* alkaloids (e.g., vinblastine, vincristine, and vinorelbine), epipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexamethylmelamine and thiotepa), CDK inhibitors (e.g., a CDK4/6 inhibitor such as abemaciclib, ribociclib, palbociclib; seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), KSP (Eg5) inhibitors (e.g., Array 520), DNA binding agents (e.g., Zalypsis®), PI3K inhibitors such as PI3K delta inhibitor (e.g., GS-1101 and TGR-1202), PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HU-MAX-CD38), anti-CSl (e.g., elotuzumab), HSP90 inhibitors (e.g., 17 AAG and KOS 953), PI3K/Akt inhibitors (e.g., perifosine), Akt inhibitors (e.g., GSK-2141795), PKC inhibitors (e.g., enzastaurin), FTIs (e.g., Zarnestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine®, sorafenib, or any analog or derivative variant of the foregoing.

In some embodiments, the anti-cancer agent is a HER2 inhibitor. Non-limiting examples of HER2 inhibitors include monoclonal antibodies such as trastuzumab (Herceptin®) and pertuzumab (Perjeta®); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, and JNJ-26483327.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TNO155, RMC-4550, RMC-4630, JAB-3068, JAB-3312, RLY-1971, ERAS-601, or BBP-398), an SOS1 inhibitor (e.g., BI-1701963, BI-3406, or RMC-5845), a Raf inhibitor, a MEK inhibitor, an ERK inhibitor, a PI3K inhibitor, a PTEN inhibitor, or an AKT inhibitor. In some embodiments, the anti-cancer agent is JAB-3312.

In some embodiments, a therapeutic agent that may be combined with an mTOR inhibitor (e.g., a bi-steric mTOR inhibitor, e.g., RMC-5552) is an inhibitor of the MAP kinase (MAPK) pathway (or "MAPK inhibitor"). MAPK inhibitors include, but are not limited to, one or more MAPK inhibitor described in Cancers (Basel) 2015 September; 7(3): 1758-1784. For example, the MAPK inhibitor may be selected from one or more of trametinib, binimetinib, selumetinib, cobimetinib, LErafAON (NeoPharm), ISIS 5132; vemurafenib, pimasertib, TAK733, R04987655 (CH4987655); CI-1040; PD-0325901; CH5126766; MAP855; AZD6244; refametinib (RDEA 119/BAY 86-9766); GDC-0973/XL581; AZD8330 (ARRY-424704/ARRY-704); RO5126766 (Roche, described in PLoS One. 2014 Nov. 25; 9(11)); and GSK1120212 (or JTP-74057, described in Clin Cancer Res. 2011 Mar. 1; 17(5):989-1000). The MAPK inhibitor may be PLX8394, LXH254, GDC-5573, or LY3009120.

In some embodiments, an anti-cancer agent is a disrupter or inhibitor of the RAS-RAF-ERK or PI3K-AKT-TOR or PI3K-AKT signaling pathways. The PI3K/AKT inhibitor may include, but is not limited to, one or more PI3K/AKT inhibitor described in Cancers (Basel) 2015 September; 7(3): 1758-1784. For example, the PI3K/AKT inhibitor may be selected from one or more of NVP-BEZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist.

In some embodiments, additional therapeutic agents include ALK inhibitors, HER2 inhibitors, EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies. In some embodiments, a therapeutic agent may be a pan-RTK inhibitor, such as afatinib.

IGF-1R inhibitors include linsitinib, or a pharmaceutically acceptable salt thereof.

EGFR inhibitors include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15:59(8):1935-40; and Yang et al., Cancer Res. 1999, 59:1236-1243. The EGFR inhibitor can be monoclonal antibody Mab E7.6.3 (Yang, 1999 supra), or Mab $C_{225}$ (ATCC Accession No. HB-8508), or an antibody or antibody fragment having the binding specificity thereof.

Small molecule antagonists of EGFR include gefitinib (Iressa®), erlotinib (Tarceva®), and lapatinib (TykerB®). See, e.g., Yan et al., Pharmacogenetics and Pharmacogenomics in Oncology Therapeutic Antibody Development, BioTechniques 2005, 39(4):565-8; and Paez et al., EGFR Mutations in Lung Cancer Correlation with Clinical Response to Gefitinib Therapy, Science 2004, 304(5676): 1497-500. In some embodiments, the EGFR inhibitor is osimertinib (Tagrisso®). Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747,498; WO96/30347; EP 0787772; WO97/30034; WO97/30044; WO97/38994; WO97/49688; EP 837063; WO98/02434; WO97/38983; WO95/19774; WO95/19970; WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8(12):1599-1625.

MEK inhibitors include, but are not limited to, pimasertib, selumetinib, cobimetinib (Cotellic®), trametinib (Mekinist®), and binimetinib (Mektovi®). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from ΔE51-Q58; ΔF53-Q58; E203K; L177M; C121S; F53L; K57E; Q56P; and K57N.

PI3K inhibitors include, but are not limited to, wortmannin; 17-hydroxywortmannin analogs described in WO06/044453; 4-[2-(1H-Indazol-4-yl)-6-[[4-(methylsulfonyl)piperazin-1-yl]methyl]thieno[3,2-d]pyrimidin-4-yl]morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in WO06/122806); (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in WO08/070740); LY294002 (2-(4-morpholinyl)-8-phenyl-4H-1-benzopyran- 4-one (available from Axon Medchem); PI 103 hydrochloride (3-[4-(4-morpholinylpyrido-[3',2':4,5]furo[3,2-d]pyrimidin-2-yl] phenol hydrochloride (available from Axon Medchem); PIK 75 (2-methyl-5-nitro-2-[(6-bromoimidazo[1,2-a]pyridin-3-yl)methylene]-1-methylhydrazide-benzenesulfonic acid, monohydrochloride) (available from Axon Medchem); PIK 90 (N-(7,8-dimethoxy-2,3-dihydro-imidazo[1,2-c]quinazolin-5-yl)-nicotinamide (available from Axon Medchem); AS-252424 (5-[1-[5-(4-fluoro-2-hydroxy-phenyl)-furan-2-yl]-meth-(Z)-ylidene]-thiazolidine-2,4-dione (available from Axon Medchem); TGX-221 (7-methyl-2-(4-morpholinyl)-9-[1-(phenylamino)ethyl]-4H-pyrido-[1,2-a]pyrirnidin-4-one (available from Axon Medchem); XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits Akt1) (Barnett et al., Biochem. J. 2005, 385 (Pt. 2): 399-408); Akt-1-1,2 (inhibits Akl and 2) (Barnett et al., Biochem. J. 2005, 385 (Pt. 2): 399-408); API-59CJ-Ome (e.g., Jin et al., Br. J. Cancer 2004, 91:1808-12); 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134 (12 Suppl): 34935-34985); perifosine (e.g., interferes with Akt membrane localization; Dasmahapatra et al. Clin. Cancer Res. 2004, 10(15):5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

BRAF inhibitors that may be used in combination with an mTOR inhibitor (e.g., a bi-steric mTOR inhibitor, e.g., RMC-5552) include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E.

MCL-1 inhibitors include, but are not limited to, AMG-176, MIK665, and 563845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung, and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian and breast cancer). Thus, combination therapy involving a SHP2 inhibitor with a RAS pathway inhibitor could be a general strategy for preventing tumor resistance in a wide range of malignancies.

Non-limiting examples of such SHP2 inhibitors that are known in the art, include: Chen et al. *Mol Pharmacol.* 2006, 70, 562; Sarver et al., *J. Med. Chem.* 2017, 62, 1793; Xie et al., *J. Med. Chem.* 2017, 60, 113734; and Igbe et al., *Oncotarget*, 2017, 8, 113734; and: WO 2023282702, WO 2023280283, WO 2023280237, WO 2023018155, WO 2023011513, WO 2022271966, WO 2022271964, WO 2022271911, WO 2022259157, WO 2022242767, WO 2022241975, WO 2022237676, WO 2022237367, WO 2022237178, WO 2022235822, WO 2022234409, WO 2022208408, WO 2022207924, WO 2022167682, WO 2022166844, WO 2022161222, WO 2022156765, WO 2022135568, WO 2022089406, WO 2022089389, WO 2022063190, WO 2022043685, WO 2022042331, WO 2022033430, WO 2022033430, WO 2022017444, WO 2022007869, WO 2021259077, WO 2021249449, WO 2021249057, WO 2021244659, WO 2021218755, WO 2021281752, WO 2021197542, WO 2021176072, WO 2021149817, WO 2021148010, WO 2021147879, WO 2021143823, WO 2021143701, WO 2021143680, WO 2021121397, WO 2021119525, WO 2021115286, WO 2021110796, WO 2021088945, WO 2021073439, WO 2021061706, WO 2021061515, WO 2021043077, WO 2021033153, WO 2021028362, WO 2021033153, WO 2021028362, WO 2021018287, WO 2020259679, WO 2020249079, WO 2020210384, WO 2020201991, WO 2020181283, WO 2020177653, WO 2020165734, WO 2020165733, WO 2020165732, WO 2020156243, WO 2020156242, WO 2020108590, WO 2020104635, WO 2020094104, WO 2020094018, WO 2020081848, WO 2020073949, WO 2020073945, WO 2020072656, WO 2020065453, WO 2020065452, WO 2020063760, WO 2020061103, WO 2020061101, WO 2020033828, WO 2020033286, WO 2020022323, WO 2019233810, WO 2019213318, WO 2019183367, WO 2019183364, WO 2019182960, WO 2019167000, WO 2019165073, WO 2019158019, WO 2019152454, WO 2019051469, WO 2019051084, WO 2018218133, WO 2018172984, WO 2018160731, WO 2018136265, WO 2018136264, WO 2018130928, WO 2018129402, WO 2018081091, WO 2018057884, WO 2018013597, WO 2017216706, WO 2017211303, WO 2017210134, WO 2017156397, WO 2017100279, WO 2017079723, WO 2017078499, WO 2016203406, WO 2016203405, WO 2016203404, WO 2016196591, WO 2016191328, WO 2015107495, WO 2015107494, WO 2015107493, WO 2014176488, WO 2014113584, US 20210085677, U.S. Ser. No. 10/858,359, U.S. Ser. No. 10/934,302, U.S. Ser. No. 10/954,243, U.S. Ser. No. 10/988,466, U.S. Ser. No. 11/001,561, U.S. Ser. No. 11/033,547, U.S. Ser. No. 11/034,705, U.S. Ser. No. 11/044,675, U.S. Ser. No. 11/179,397, CN 115677661, CN 115677660, CN 115611869, CN 115521305, CN 115490697, CN 115466273, CN 115394612, CN 115304613, CN 115304612, CN 115300513, CN 115197225, CN 114957162, CN 114920759, CN 114716448, CN 114671879, CN 114539223, CN 114524772, CN 114213417, CN 114163457, CN 113896710, CN 113248521, CN 113248449, CN 113135924, CN 113024508, CN 112920131, CN 112823796, CN 112402385, CN 111848599, CN 111704611, CN 111265529, and CN 108113848, or a pharmaceutically acceptable salt, solvate, isomer (e.g., stereoisomer), prodrug, or tautomer thereof, each of which is incorporated herein by reference in its entirety.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TNO155. In some embodiments, the SHP2 inhibitor is RMC-4550. In some embodiments, the SHP2 inhibitor is RMC-4630, whose structure is shown below:

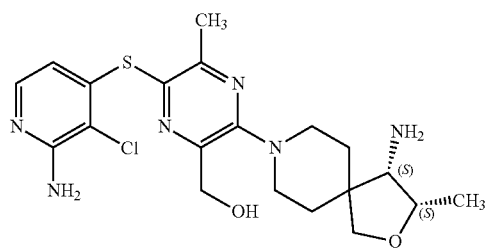

In some embodiments, the SHP2 inhibitor is JAB-3068, JAB-3312, RLY-1971, ERAS-601, or BBP-398.

In some embodiments, the additional therapeutic agent is selected from the group consisting of a HER2 inhibitor, a SHP2 inhibitor, a CDK4/6 inhibitor, an SOS1 inhibitor, and a PD-L1 inhibitor. See, e.g., Hallin et al., Cancer Discovery, DOI: 10.1158/2159-8290 (Oct. 28, 2019) and Canon et al., Nature, 575:217 (2019).

Proteasome inhibitors include, but are not limited to, carfilzomib (Kyprolis®), bortezomib (Velcade®), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PDL-1, anti-CTLA4, anti-LAG1, and anti-OX40 agents).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110(1):186-192; Thompson et al., Clin. Cancer Res. 2007, 13(6):1757-1761; and WO06/121168 A1), as well as described elsewhere herein.

GITR agonists include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO05/115451, and WO2011/051726.

Another example of a therapeutic agent that may be used in combination an mTOR inhibitor (e.g., a bi-steric mTOR inhibitor, e.g., RMC-5552) is an anti-angiogenic agent. Anti-angiogenic agents are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapeutic agents include an anti-angiogenic agent.

Anti-angiogenic agents can be MMP-2 (matrix-metalloproteinase 2) inhibitors, MMP-9 (matrix-metalloproteinase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF (e.g., bevacizumab), or soluble VEGF receptors or a ligand binding region thereof) such as VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix® (panitumumab), erlotinib (Tarceva®), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA); XL 784 (Exelixis, USA); XL 647 (Exelixis, USA); MAb, alpha5beta3 integrin, second generation (Applied Molecular Evolution, USA and MedImmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Childrens' Hospital, USA); ATN 161 (Attenuon, USA); 2-methoxyestradiol (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Childrens Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sima, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists (ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with a an mTOR inhibitor (e.g., RMC-5552) include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met.

Another example of a therapeutic agent that may be used in combination with the mTOR inhibitor (e.g., RMC-5552) is an autophagy inhibitor. Autophagy inhibitors include, but are not limited to chloroquine, 3-methyladenine, hydroxychloroquine (Plaquenil™) bafilomycin Al, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used. In some embodiments, the one or more additional therapeutic agents include an autophagy inhibitor.

Another example of a therapeutic agent that may be used in combination with an mTOR inhibitor (e.g., RMC-5552) is an anti-neoplastic agent. In some embodiments, the one or more additional therapeutic agents include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-Nl, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, or zoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with an mTOR inhibitor (e.g., RMC-5552) include ipilimumab (Yervoy®); tremelimumab; galiximab; nivolumab, also known as BMS-936558 (Opdivo®); pembrolizumab (Keytruda®); avelumab (Bavencio®); AMP224; BMS-936559; MPDL3280A, also known as RG7446; MEDI-570; AMG557; MGA271; IMP321; BMS-663513; PF-05082566; CDX-1127; anti-OX40 (Providence Health Services); huMAbOX40L; atacicept; CP-870893; lucatumumab; dacetuzumab; muromonab-CD3; ipilumumab; MEDI4736 (Imfinzi®); MSB0010718C; AMP 224; adalimumab (Humira®); ado-trastuzumab emtansine (Kadcyla®); aflibercept (Eylea®); alemtuzumab (Campath®); basiliximab (Simulect®); belimumab (Benlysta®); basiliximab (Simulect®); belimumab (Benlysta®); brentuximab vedotin (Adcetris®); canakinumab (Ilaris®); certolizumab pegol (Cimzia®); daclizumab (Zenapax®); daratumumab (Darzalex®); denosumab (Prolia®); eculizumab (Soliris®); efalizumab (Raptiva®); gemtuzumab ozogamicin (Mylotarg®); golimumab (Simponi®); ibritumomab tiuxetan (Zevalin®); infliximab (Remicade®); motavizumab (Numax®); natalizumab (Tysabri®); obinutuzumab (Gazyva®); ofatumumab (Arzerra®); omalizumab (Xolair®); palivizumab (Synagis®); pertuzumab (Perjeta®); pertuzumab (Perjeta®); ranibizumab (Lucentis®); raxibacumab (Abthrax®); tocilizumab (Actemra®); tositumomab; tositumomab-i-131; tositumomab and tositumomab-i-131 (Bexxar®); ustekinumab (Stelara®); AMG 102; AMG 386; AMG 479; AMG 655; AMG 706; AMG 745; and AMG 951.

Effective dosage amounts of an ALK inhibitor, when used for the indicated effects, range from about 0.5 mg to about 5000 mg as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In some embodiments, the compositions are in the form of a tablet that can be scored.

Effective dosage amounts of an EGFR inhibitor, when used for the indicated effects, range from about 0.5 mg to about 5000 mg as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In some embodiments, the compositions are in the form of a tablet that can be scored.

Effective dosage amounts of an MEK inhibitor, when used for the indicated effects, range from about 0.05 mg to about 5000 mg as needed to treat the condition. Compositions for in vivo or in vitro use can contain about 0.05, 0.1, 0.2, 0.3, 0.4, 0.5, 0.6, 0.7, 0.8, 0.9, 1, 2, 5, 20, 50, 75, 100, 150, 250, 500, 750, 1000, 1250, 2500, 3500, or 5000 mg of the disclosed compound, or, in a range of from one amount to another amount in the list of doses. In some embodiments, the compositions are in the form of a tablet that can be scored.

In some embodiments, at least one of the additional therapeutic agents is a RAS inhibitor. The terms "RAS inhibitor" and "inhibitor of [a] RAS" are used interchangeably to refer to any inhibitor that targets a RAS protein. In various embodiments, these terms include RAS(OFF) and RAS(ON) inhibitors such as, e.g., the KRAS(OFF) and KRAS(ON) inhibitors disclosed herein. The term "RAS (OFF) inhibitor" refers to any inhibitor that binds to a RAS protein in its GDP-bound "OFF" position, as further defined herein. The term "RAS(ON) inhibitor" refers to any inhibitor that binds to a RAS protein in its GDP-bound "ON" position, as further defined herein. In some embodiments, a RAS inhibitor has a molecular weight of under 700 Da. In some embodiments, the RAS inhibitor is selected from the group consisting of AMG 510, MRTX1257, JNJ-74699157 (ARS-3248), LY3537982, LY3499446, ARS-853, ARS-1620, GDC-6036, BPI-421286, JDQ443, JAB-21000, JAB-22000, JAB-23000, RSC-1255, ERAS-3490, D-1553, JAB-21822, GH-35, ICP-915, 1B1351, and B11823911. A RAS inhibitor may be a RAS vaccine, or another therapeutic modality designed to directly or indirectly decrease the oncogenic activity of RAS.

The terms "RAS pathway" and "RAS/MAPK pathway" are used interchangeably herein to refer to a signal transduction cascade downstream of various cell surface growth factor receptors in which activation of RAS (and its various isoforms and alleotypes) is a central event that drives a variety of cellular effector events that determine the proliferation, activation, differentiation, mobilization, and other functional properties of the cell. SHP2 conveys positive signals from growth factor receptors to the RAS activation/deactivation cycle, which is modulated by guanine nucleotide exchange factors (GEFs, such as SOS1) that load GTP onto RAS to produce functionally active GTP-bound RAS as well as GTP-accelerating proteins (GAPs, such as NF1) that facilitate termination of the signals by conversion of GTP to GDP. GTP-bound RAS produced by this cycle conveys essential positive signals to a series of serine/threonine kinases including RAF and MAP kinases, from which emanate additional signals to various cellular effector functions.

In some embodiments, the RAS inhibitor targets KRAS, NRAS, or HRAS. In some embodiments the RAS inhibitor is a RAS mutant specific inhibitor. In some embodiments, the RAS mutant is selected from:
(a) the following K-Ras mutants: G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V, and combinations thereof;
(b) the following H-Ras mutants: Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R, and combinations thereof; and
(c) the following N-Ras mutants: Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T, and combinations thereof.

Mutations at these positions may result in RAS-driven tumors.

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C or other KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

In some embodiments, at least one of the additional therapeutic agents is a RAS(OFF) inhibitor. In various embodiments, at least one of the additional therapeutic agents is a KRAS(OFF) inhibitor (e.g., any one or more KRAS(OFF) inhibitor disclosed herein or known in the art). In some embodiments, at least one of the additional therapeutic agents is a KRAS$^{G12C}$(OFF) inhibitor (e.g., any one or more of the KRAS$^{G12C}$(OFF) inhibitors disclosed herein or known in the art). In some embodiments, at least one of the additional therapeutic agents is AMG 510, MRTX849, JDQ443, MRTX1133, ERAS-3490, ERAS-4, BPI-421286, D-1553, JAB-21822, GH-35, ICP-915, 1B1351, LY3537982, GDC-6036, B11823911, RSC-1255, or a pharmaceutically acceptable salt of any of the foregoing. In some embodiments, the at least one of the additional therapeutic agents is selected from AMG 510 and MRTX849. In some embodiments, the therapeutic agent is AMG 510. In some embodiments, the therapeutic agent is MRTX849. In various embodiments, at least one of the additional therapeutic agents is an mTOR inhibitor (e.g., a bi-steric mTOR inhibitor, e.g., RMC-5552) and one of the additional therapeutic agents is a KRAS$^{G12C}$ inhibitor.

As used herein, the term "RAS(OFF) inhibitor" refers to an inhibitor that targets, that is, selectively binds to or inhibits the GDP-bound, inactive state of RAS (e.g., selective over the GTP-bound, active state of RAS). Inhibition of the GDP-bound, inactive state of RAS includes, for example, sequestering the inactive state by inhibiting the exchange of GDP for GTP, thereby inhibiting RAS from adopting the active conformation. In some embodiments, RAS(OFF) inhibitors may also bind to or inhibit the GTP-bound, active state of RAS (e.g., with a lower affinity or inhibition constant than for the GDP-bound, inactive state of RAS). In some embodiments, a RAS(OFF) inhibitor has a molecular weight of under 700 Da. The term "KRAS(OFF) inhibitor" refers to any inhibitor that binds to KRAS in its GDP-bound "OFF" position. Reference to the term KRAS (OFF) inhibitor includes, for example, AMG 510, MRTX849, JDQ443 and MRTX1133. In some embodiments, the KRAS(OFF) inhibitor is selected from AMG 510 and MRTX849. In some embodiments, the KRAS(OFF) inhibitor is AMG 510. In some embodiments, the KRAS (OFF) inhibitor is MRTX849. In some embodiments, the RAS(OFF) inhibitor is selected from sotorasib (AMG 510), adagrasib (MRTX849), MRTX1257, JNJ-74699157 (ARS-3248), LY3537982, LY3499446, ARS-853, ARS-1620, GDC-6036, JDQ443, BPI-421286, JAB-21000, RSC-1255, ERAS-3490, D-1553, JAB-21822, GH-35, ICP-915, IBI351, and BI1823911. In some embodiments, reference to the term RAS(OFF) inhibitor includes any such RAS(OFF) inhibitor disclosed in any one of the following patent applications: WO 2023287896, WO 2023287730, WO 2023284881, WO 2023284730, WO 2023284537, WO 2023283933, WO 2023283213, WO 2023280960, WO 2023280280, WO 2023280136, WO 2023280026, WO 2023278600, WO 2023274383, WO 2023274324, WO 2023034290, WO 2023020523, WO 2023020521, WO 2023020519, WO 2023020518, WO 2023018812, WO 2023018810, WO 2023018809, WO 2023018699, WO 2023015559, WO 2023014979, WO 2023014006, WO 2023010121, WO 2023009716, WO 2023009572, WO 2023004102, WO 2023003417, WO 2023001141, WO 2023001123, WO 2022271923, WO 2022271823, WO 2022271810, WO 2022271658, WO 2022269508, WO 2022266167, WO 2022266069, WO 2022266015, WO 2022265974, WO 2022261154, WO 2022261154, WO 2022251576, WO 2022251296, WO 2022237815, WO 2022232332, WO 2022232331, WO 2022232320, WO 2022232318, WO 2022223037, WO 2022221739, WO 2022221528, WO 2022221386, WO 2022216762, WO 2022192794, WO 2022192790, WO 2022188729, WO 2022187411, WO 2022184178, WO 2022173870, WO 2022173678, WO 2022135346, WO 2022133731, WO 2022133038, WO 2022133345, WO 2022132200, WO 2022119748, WO 2022109485, WO 2022109487, WO 2022098625, WO 2022095960, WO 2022093856, WO 2022089219, WO 2022087624, WO 2022087375, WO 2022087371, WO 2022083616, WO 2022083569, WO 2022081655, WO 2022076917, WO 2022072783, WO 2022066805, WO 2022066646, WO 2022063297, WO 2022061251, WO 2022056307, WO 2022052895, WO 2022048545, WO 2022047093, WO 2022042630, WO 2022040469, WO 2022037631, WO 2022037560, WO 2022031678, WO 2022028492, WO 2022028346, WO 2022026726, WO 2022026723, WO 2022015375, WO 2022002102, WO 2022002018, WO 2021259331, WO 2021257828, WO 2021252339, WO 2021248095, WO 2021248090, WO 2021248083, WO 2021248082, WO 2021248079, WO 2021248055, WO 2021245051, WO 2021244603, WO 2021239058, WO 2021231526, WO 2021228161, WO 2021219090, WO 2021219090, WO 2021219072, WO 2021218939, WO 2021217019, WO 2021216770, WO 2021215545, WO 2021215544, WO 2021211864, WO 2021190467, WO 2021185233, WO 2021180181, WO 2021175199, 2021173923, WO 2021169990, WO 2021169963, WO 2021168193, WO 2021158071, WO 2021155716, WO 2021152149, WO 2021150613, WO 2021147967, WO 2021147965, WO 2021143693, WO 2021142252, WO 2021141628, WO 2021139748, WO 2021139678, WO 2021129824, WO 2021129820, WO 2021127404, WO 2021126816, WO 2021126799, WO 2021124222, WO 2021121371, WO 2021121367, WO 2021121330, WO 2021088458, WO 2021086833, WO 2021085653, WO 2021084765, WO 2021081212, WO 2021058018, WO 2021057832, WO 2021055728, WO 2021031952, WO 2021027911, WO 2021023247, WO 2020259513, WO 2020259432, WO 2020234103, WO 2020233592, WO 2020216190, WO 2020178282, WO 2020146613, WO 2020118066, WO 2020113071, WO 2020106647, WO 2020102730, WO 2020101736, WO 2020097537, WO 2020086739, WO 2020081282, WO 2020050890, WO 2020047192, WO 2020035031, WO 2020028706, WO 2019241157, WO 2019232419, WO 2019217691, WO 2019217307, WO 2019215203, WO 2019213526, WO 2019213516, WO 2019155399, WO 2019150305, WO 2019110751, WO 2019099524, WO 2019051291, WO 2018218070, WO 2018218071, WO 2018218069, WO 2018217651, WO 2018206539, WO 2018143315, WO 2018140600, WO 2018140599, WO 2018140598, WO 2018140514, WO 2018140513, WO 2018140512, WO 2018119183, WO 2018112420, WO 2018068017, WO 2018064510, WO 2017201161, WO 2017172979, WO 2017100546, WO 2017087528, WO 2017058807, WO 2017058805, WO 2017058728, WO 2017058902, WO 2017058792, WO 2017058768, WO 2017058915, WO 2017015562, WO 2016168540, WO 2016164675, WO 2016049568, WO 2016049524, WO 2015054572, WO 2014152588, WO 2014143659, WO 2013155223, CN 114437084, CN 114195788, CN 114437107, CN 114409653, CN 114380827, CN 114195804, CN 114057776, CN 114057744, CN 114057743, CN 113999226, CN 113980032, CN 113980014, CN 113960193, CN 113929676, CN 113754653, CN 113683616, CN 113563323, CN 113527299, CN 113527294, CN 113527293, CN 113493440, CN 113429405, CN 113248521, CN 113321654, CN 113087700, CN 113024544, CN 113004269, CN 112920183, CN 112778284, CN 112390818, CN 112390788, CN 112300196, CN 112300194, CN 112300173, CN 112225734, CN 112142735, CN 112110918, CN 112094269, CN 112047937, and CN 109574871, or a pharmaceutically acceptable salt, solvate, isomer (e.g., stereoisomer), prodrug, or tautomer thereof, each of which is incorporated herein by reference in its entirety. Reference to "AMG 510" and "MRTX849" herein means the following compounds:

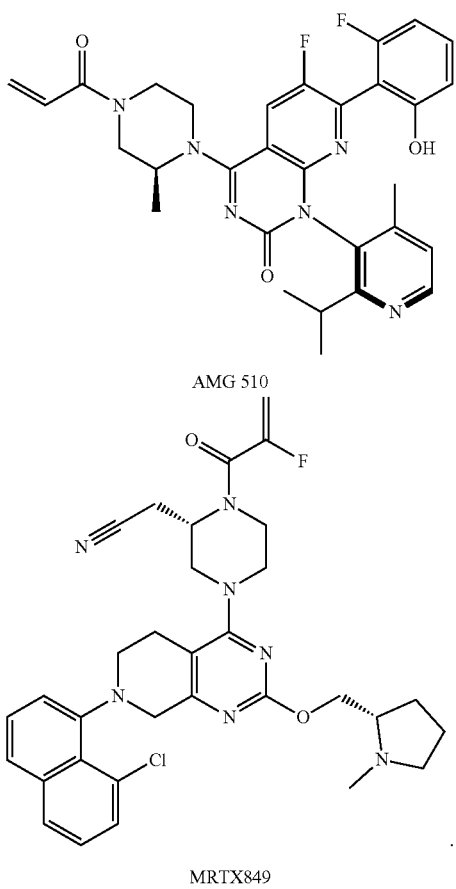

AMG 510

MRTX849

In some embodiments, at least one of the additional therapeutic agents is a RAS(ON) inhibitor. In various embodiments, at least one of the additional therapeutic agents is a KRAS(ON) inhibitor (e.g., any one or more KRAS(ON) inhibitor disclosed herein or known in the art). In some embodiments, at least one of the additional therapeutic agents is RMC-6236 (a RAS$^{MULTI}$(ON) inhibitor), RMC-6291 (a KRAS$^{G12C}$(ON) inhibitor), RMC-9805 (a KRAS$^{G12D}$(ON) inhibitor), RMC-8839 (a KRAS$^{G13C}$(ON) inhibitor), RMC-0708 (a KRAS$^{Q61H}$(ON) inhibitor) or a pharmaceutically acceptable salt of any of the foregoing. In some embodiments, at least one of the additional therapeutic agents is a KRAS$^{G12C}$(ON) inhibitor (e.g., any one or more of the KRAS$^{G12C}$(ON) inhibitors disclosed herein or known in the art). In some embodiments, the KRAS$^{G12C}$(ON) inhibitor is RMC-6291 or a pharmaceutically acceptable salt thereof.

As used herein, the term "RAS(ON) inhibitor" refers to an inhibitor that targets, that is, selectively binds to or inhibits, the GTP-bound, active state of RAS (e.g., selective over the GDP-bound, inactive state of RAS). Inhibition of the GTP-bound, active state of RAS includes, for example, the inhibition of oncogenic signaling from the GTP-bound, active state of RAS. In some embodiments, the RAS(ON) inhibitor is an inhibitor that selectively binds to and inhibits the GTP-bound, active state of RAS. In some embodiments, RAS(ON) inhibitors may also bind to or inhibit the GDP-bound, inactive state of RAS (e.g., with a lower affinity or inhibition constant than for the GTP-bound, active state of RAS). In some embodiments, a RAS(ON) inhibitor has a molecular weight of between 800 and 1100 Da, inclusive.

The term "KRAS(ON) inhibitor" refers to any inhibitor that binds to KRAS in its GDP-bound "ON" position. Reference to the term RAS(ON) inhibitor includes, without limitation, any one or more RAS(ON) inhibitors selected from the RAS(ON) inhibitors disclosed in PCT/US2023/060288, 2023060253, WO 2022235870, WO 2022235864, WO 2022060836, WO 2021257736, WO 2021091982, WO 2021091967, or WO 2021091956, or a pharmaceutically acceptable salt, solvate, isomer (e.g., stereoisomer), prodrug, or tautomer thereof, or a combination of any such RAS(ON) inhibitors.

Indications

The present disclosure provides methods of treating a disease or disorder mediated by mTOR in a subject in need thereof. The present disclosure also provides methods of preventing a disease or disorder mediated by mTOR in a subject in need thereof. The present disclosure also provides methods of reducing the risk of a disease or disorder mediated by mTOR in a subject in need thereof.

In some embodiments, the disease is cancer or an immune-mediated disease. In some embodiments, the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors. In some embodiments, the disorder is liver cirrhosis. In some embodiments, the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis. In certain embodiments, the disease is tuberous sclerosis complex (TSC). In certain embodiments, the disease is pancreatic neuroendocrine tumor (PNET), mantle cell lymphoma (MCL), colorectal cancer or bowel cancer (CRC), uterine cancer, ovarian cancer, bladder cancer, genitourinary tract cancer, or renal cell carcinoma (RCC).

In some embodiments, the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors. In some embodiments, the disorder is liver cirrhosis. In certain embodiments, the disease is tuberous sclerosis complex (TSC). In certain embodiments, the disease is pancreatic neuroendocrine tumor (PNET), mantle cell lymphoma (MCL), colorectal cancer or bowel cancer (CRC), uterine cancer, ovarian cancer, bladder cancer, genitourinary tract cancer, or renal cell carcinoma (RCC).

In some embodiments, cancer includes human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In certain embodiments, the disease is multiple myeloma. In certain embodiments, the disease is breast cancer. In certain embodiments, the disease is triple negative breast cancer.

In some embodiments, cancer includes cancer, neoplasm or malignant tumors found in mammals (e.g., humans), including leukemia, carcinomas, and sarcomas. Exemplary cancers that may be treated with a compound or method provided herein include cancer of the prostate, thyroid, endocrine system, brain, breast, cervix, colon, head and neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

In some embodiments, the disease is leukemia. The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of aberrant cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

In some embodiments, the disease is melanoma. The term "melanoma" is taken to mean a tumor arising from the melanocyte system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

In some embodiments, the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

In some embodiments, the disease is autoimmune disease. As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressier's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

In some embodiments, the disclosed compositions or compounds can be used with regard to immunosenescence. Immunosenescence may refer to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria. Immunosenescence is a multifactorial condition leading to many pathologically significant health problems, e.g., in the aged population. Age-dependent biological changes such as depletion of hematopoietic stem cells, an increase in PD1+ lymphocytes, a decline in the total number of phagocytes and NK cells and a decline in humoral immunity contribute to the onset of immunosenescence. In one aspect, immunosenescence can be measured in an individual by measuring telomere length in immune cells (See, e.g., U.S. Pat. No. 5,741,677). Immunosenescence can also be determined by documenting in an individual a lower than normal number of naive CD4 and/or CD8 T cells, T cell repertoire, the number of PD1-expressing T cells, e.g., a lower than normal number of PD-1 negative T cells, or response to vaccination in a subject greater than or equal to 65 years of age. In certain embodiments, mTOR selective modulation of certain T-cell populations may improve vaccine efficacy in the aging population and enhance effectiveness of cancer immunotherapy. The present disclosure provides a method of treating immunosenescence comprising administering to the subject a therapeutically effective amount of one or more disclosed compositions or compounds.

In some embodiments, the disease is organ or tissue transplant rejection (e.g., heart, lung, liver, kidney, pancreatic, skin or corneal transplants; graft-versus-host disease), restenosis, Hamartoma syndromes (e.g., tuberous sclerosis or Cowden Disease), Lymphangioleiomyomatosis, Retinitis pigmentosis, encephalomyelitis, insulin-dependent diabetes mellitus, lupus, dermatomyositis, arthritis, rheumatic diseases, Steroid-resistant acute Lymphoblastic Leukemia, fibrosis, scleroderma, pulmonary fibrosis, renal fibrosis, cystic fibrosis, Pulmonary hypertension, Multiple sclerosis, VHL syndrome, Carney complex, Familial adenonamtous polyposis, Juvenile polyposis syndrome, Birt-Hogg-Duke syndrome, Familial hypertrophic cardiomyopathy, Wolf-Parkinson-White syndrome, Parkinson's disease, Huntingtin's disease, Alzheimer's disease, dementias caused by tau mutations, spinocerebellar ataxia type 3, motor neuron disease caused by SOD1 mutations, neuronal ceroid lipofucinoses/Batten disease (pediatric neurodegeneration), wet macular degeneration, dry macular degeneration, muscle wasting (atrophy, cachexia), myopathies (e.g., Danon's disease), bacterial infection, viral infection, *M. tuberculosis*, group A *streptococcus*, HSV type I, HIV infection, Neurofibromatosis (e.g., Neurofibromatosis type 1), or Peutz-Jeghers syndrome.

In some embodiments, the disease is neurodegenerative disease. As used herein, the term "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes *dorsalis*.

In some embodiments, the disease is metabolic disease. As used herein, the term "metabolic disease" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

In some embodiments, the disease is inflammatory disease. As used herein, the term "inflammatory disease" refers to a disease or condition characterized by aberrant inflammation (e.g., an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

In some embodiments, the disease is cardiovascular disease. As used herein, the term "cardiovascular disease" refers to a disease or condition in which the function of a subject's cardiovascular system becomes impaired. Examples of cardiovascular diseases that may be treated with a compound, pharmaceutical composition, or method described herein include congestive heart failure; arrhythmogenic syndromes (e.g., paroxysmal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

The present disclosure also provides methods of treating an age-related condition comprising administering in a subject in need thereof. In certain embodiments, the age related condition is selected from sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

In particular, various embodiments of the present disclosure involve methods, uses, and medicaments directed to the treatment of the following cancers.

In some embodiments, the cancer is ampullary cancer, appendiceal cancer, bile duct cancer, bladder cancer, blood proliferative disorders, bone cancer, brain and neurovascular tumors, breast cancer, cancer of unknown primary origin, cervical cancer, colorectal cancer, endometrial cancer, esophagogastric cancer, gastrointestinal cancer, germ cell cancer, glioblastoma, head and neck cancer, kidney cancer, liver cancer, lung cancer, mesothelioma, cancer of neurologic origin, neuroendocrine tumors, ocular cancer, ovarian cancer, ovarian endometriosis, pancreatic cancer, peritoneal cancer, penile cancer, prostate cancer, rhabdomyosarcoma, sarcoma, sex cord stromal tumor, skin cancer, soft tissue cancer, testicular cancer, uterine cancer, and vulvar cancer. In some embodiments, the cancer is selected from the group consisting of bladder cancer, breast cancer, colorectal cancer, endometrial cancer, glioma, head and neck cancer, hematological cancer, liver cancer, lung cancer, neuro-endocrine cancer, ovarian cancer, pancreatic cancer, renal cancer, and rhabdomyosarcoma. In some embodiments, the cancer is breast cancer. In some embodiments, the breast cancer is triple negative breast cancer.

In some embodiments, the cancer is head and neck cancer. In some embodiments, the head and neck cancer is head and neck squamous cell carcinoma, salivary gland cancer, or thyroid cancer. In some embodiments, the thyroid cancer is thyroid gland adenocarcinoma. In some embodiments, the head and neck cancer is salivary gland cancer. As described herein, dosages of the bi-steric mTOR inhibitor RMC-5552 were surprisingly efficacious for treatment of salivary gland cancer, with 1 subject exhibiting 63% reduction in tumor size.

In some embodiments, the cancer is hematological cancer. In some embodiments, the hematological cancer is leukemia, lymphoma, myeloproliferative diseases, multiple myeloma, or a myelodysplastic syndrome. In some embodiments, the leukemia is acute myeloid leukemia (AML), acute lymphocytic leukemia (ALL), or chronic myeloid leukemia (CML). In some embodiments, the lymphoma is mantle cell lymphoma (MCL), B-acute lymphoblastic lymphoma, non-Hodgkin's lymphomas (e.g., Burkitt's, Small Cell, and Large Cell lymphomas), or Hodgkin's lymphoma.

In some embodiments, the cancer is gastrointestinal cancer. In some embodiments, the gastrointestinal cancer is GI neuroendocrine cancer, gastrointestinal stromal tumors, stomach cancer, anal cancer, rectal cancer, colorectal cancer (CRC), bowel cancer, or small bowel cancer. In some embodiments, the gastrointestinal cancer is colorectal cancer.

In some embodiments, the cancer is kidney cancer. In some embodiments, the kidney cancer is renal cell carcinoma (RCC).

In some embodiments, the cancer is liver cancer. In some embodiments, the liver cancer is hepatobiliary cancer, hepatocellular carcinoma, cholangiocarcinoma, hepatoblastoma, angiosarcoma, hepatocellular adenoma, or hemangioma. In some embodiments, the liver cancer is hepatocellular carcinoma. In some embodiments, the liver cancer is hepatoblastoma.

In some embodiments, the cancer is lung cancer. In some embodiments, the lung cancer is non-small cell lung cancer. In some embodiments, the lung cancer is squamous cell lung carcinoma.

In some embodiments, the cancer is ovarian cancer.

In some embodiments, the cancer is pancreatic cancer. In some embodiments, the pancreatic cancer is pancreatic neuroendocrine tumor (PNET).

In some embodiments, the cancer is prostate cancer.

In some embodiments, the cancer is skin cancer. In some embodiments, the skin cancer is melanoma. In some embodiments, the skin cancer is basal cell carcinoma, squamous cell carcinoma, Kaposi's sarcoma, moles dysplastic nevi, lipoma, angioma, dermatofibroma, keloids, or psoriasis.

In some embodiments, the cancer is uterine cancer.

In some embodiments, the cancer is a sarcoma. The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

In some embodiments, the cancer is a carcinoma. The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

In some embodiments, the cancer is a solid tumor.

In some embodiments, the cancer is characterized by a genotypic aberration that activates the mammalian target of rapamycin (mTOR) pathway. In some embodiments, the cancer comprises a mutation in the mTOR pathway.

In some embodiments, the genotypic aberration or the mutation is of mTOR, STK11, PIK3CA, PTEN, KEAP1, TSC1, or TSC2, or a combination thereof.

In some embodiments, the genotypic aberration or the mutation is of PTEN. In some embodiments, the PTEN mutation is a dominant negative mutation. As described herein, dosages of the bi-steric mTOR inhibitor RMC-5552 were efficacious for treatment of a cancer with a PTEN mutation, with 1 subject exhibiting a Partial Response (PR) and 2 subjects exhibiting a response of Stable Disease (SD).

In some embodiments, the genetic aberration is a mutation of PIK3CA. As described herein, dosages of the bi-steric mTOR inhibitor RMC-5552 were efficacious for treatment of cancer with a mutation of PIK3CA, with 3 subjects exhibiting a response of Stable Disease (SD).

In some embodiments, the genetic aberration is a mutation of TSC2. As described herein, dosages of the bi-steric mTOR inhibitor RMC-5552 were efficacious for treatment of cancer comprising a mutation of TSC2, with 2 subjects exhibiting a response of Stable Disease (SD).

In some embodiments, the cancer comprises a $KRAS^{G12C}$ mutation. In some embodiments, the cancer comprises co-occurring $KRAS^{G12C}$ and STK11 mutations. As described herein, dosages of the bi-steric mTOR inhibitor RMC-5552 were efficacious for treatment of cancer with a mutation of STK11 and a $KRAS^{G12C}$ mutation, with 1 subject exhibiting a response of Stable Disease (SD). In some embodiments, the cancer comprises co-occurring $KRAS^{G12C}$ and $PIK3CA^{E545K}$ mutations.

In some embodiments, the cancer is characterized by increased mTORC1 activity. In some embodiments, the cancer is characterized by decreased 4EBP1 activity.

In some embodiments, the cancer comprises a mutation of the Myc family. In some embodiments, the cancer comprises an amplification of MYC, MYCL, MYCN, or a combination thereof and/or dependence on MYC, MYCL, MYCN, or a combination thereof. In some embodiments, the cancer comprises an amplification of MYC. As described herein, dosages of the bi-steric mTOR inhibitor RMC-5552 were efficacious for treatment of cancer with an amplification of MYC, with 1 subject exhibiting a response of Stable Disease (SD).

In some embodiments, the cancer comprises a mutation of NFE2L2 (also known as NRF2). As described herein, dosages of the bi-steric mTOR inhibitor RMC-5552 were efficacious for treatment of cancer comprising a mutation of NFE2L2, with 1 subject exhibiting a response of Stable Disease (SD).

In some embodiments, the cancer comprises a BRAF fusion. As described herein, dosages of the bi-steric mTOR inhibitor RMC-5552 were efficacious for treatment of cancer comprising a BRAF fusion, with 1 subject exhibiting a response of Stable Disease (SD).

In some embodiments, the cancer is colorectal cancer and comprises a mutation of PIK3CA. In some embodiments, the cancer is colorectal cancer and comprises an amplification of MYC. In some embodiments, the cancer is colorectal cancer and comprises a mutation of PIK3CA and an amplification of MYC. As described herein, dosages of the bi-steric mTOR inhibitor RMC-5552 were efficacious for treatment of colorectal cancer comprising a mutation of PIK3CA and an amplification of MYC, with 1 subject exhibiting a response of Stable Disease (SD).

In some embodiments, the cancer is head and neck cancer and comprises a mutation of PIK3CA. As described herein, dosages of the bi-steric mTOR inhibitor RMC-5552 were efficacious for treatment of head and neck cancer comprising a mutation of PIK3CA, with 1 subject exhibiting a response of Stable Disease (SD). In some embodiments, the cancer is head and neck cancer and comprises a mutation of PTEN. As described herein, dosages of the bi-steric mTOR inhibitor RMC-5552 were efficacious for treatment of head and neck cancer comprising a mutation of PTEN, with 1 subject exhibiting a Partial Response (PR). In some embodiments, the cancer is head and neck cancer and comprises a mutation of PIK3CA and a mutation of PTEN.

In some embodiments, the cancer is liver cancer and comprises a mutation of NFE2L2. In some embodiments, the cancer is hepatocellular carcinoma and comprises a mutation of NFE2L2. As described herein, dosages of the bi-steric mTOR inhibitor RMC-5552 were efficacious for treatment of hepatocellular carcinoma comprising a mutation of NFE2L2, with 1 subject exhibiting a response of Stable Disease (SD).

In some embodiments, the cancer is ovarian cancer and comprises a mutation of TSC2. As described herein, dosages of the bi-steric mTOR inhibitor RMC-5552 were efficacious for treatment of ovarian cancer comprising a mutation of TSC2, with 1 subject exhibiting a response of Stable Disease (SD).

In some embodiments, the cancer is pancreatic cancer and comprises a mutation of STK11. In some embodiments, the cancer is pancreatic cancer and comprises a $KRAS^{G12C}$ mutation. In some embodiments, the cancer is pancreatic cancer and comprises a mutation of STK11 and a $KRAS^{G12C}$ mutation. As described herein, dosages of the bi-steric mTOR inhibitor RMC-5552 were efficacious for treatment of pancreatic cancer comprising a mutation of STK11 and a $KRAS^{G12C}$ mutation, with 1 subject exhibiting a response of Stable Disease (SD).

In some embodiments, the cancer is prostate cancer and comprises a mutation of PTEN. As described herein, dosages of the bi-steric mTOR inhibitor RMC-5552 were efficacious for treatment of prostate cancer comprising a mutation of PTEN, with 1 subject exhibiting a response of Stable Disease (SD).

In some embodiments, the cancer is uterine cancer and comprises a mutation of PIK3CA. In some embodiments, the cancer is uterine cancer and comprises a mutation of PTEN. In some embodiments, the cancer is uterine cancer and comprises a mutation of PIK3CA and a mutation of PTEN. In some embodiments, the cancer is uterine cancer and comprises a mutation of TSC2. In some embodiments, the cancer is uterine cancer and comprises a mutation of PIK3CA and a mutation of TSC2. In some embodiments, the cancer is uterine cancer and comprises a mutation of PIK3CA, a mutation of PTEN, and a mutation of TSC2. As described herein, dosages of the bi-steric mTOR inhibitor RMC-5552 were efficacious for treatment of uterine cancer comprising a mutation of PIK3CA, a mutation of PTEN, and a mutation of TSC2, with 1 subject exhibiting a response of Stable Disease (SD).

In some embodiments, the cancer is lung cancer and comprises a BRAF fusion. As described herein, dosages of the bi-steric mTOR inhibitor RMC-5552 were efficacious for treatment of lung cancer comprising a BRAF fusion, with 1 subject exhibiting a response of Stable Disease (SD).

In some embodiments, the cancer comprises a RAS mutation. In some embodiments, the cancer is colorectal cancer, non-small cell lung cancer, small-cell lung cancer, pancreatic cancer, appendiceal cancer, melanoma, acute myeloid leukemia, small bowel cancer, ampullary cancer, germ cell cancer, cervical cancer, cancer of unknown primary origin, endometrial cancer, esophagogastric cancer, GI neuroendocrine cancer, ovarian cancer, sex cord stromal tumor cancer, hepatobiliary cancer, or bladder cancer.

In some embodiments, the cancer comprises greater than about 40%, about 45%, about 50%, about 55%, about 60%, about 65%, about 70%, about 75%, about 80%, about 85%, about 90%, about 95%, greater than about 99% clonality of pathogenic variants in PIK3CA, PTEN, TSC1, or TSC2. In some embodiments, the cancer comprises greater than about 40%, about 45%, about 50%, about 55%, about 60%, about 65%, about 70%, about 75%, about 80%, about 85%, about 90%, about 95%, greater than about 99% clonality of pathogenic variants in PTEN. In some embodiments, the cancer comprises greater than about 90% clonality of pathogenic variants in PTEN. In some embodiments, the cancer comprises greater than about 40%, about 45%, about 50%, about 55%, about 60%, about 65%, about 70%, about 75%, about 80%, about 85%, about 90%, about 95%, greater than about 99% clonality of pathogenic variants in TSC1. In some embodiments, the cancer comprises greater than about 90% lonality of pathogenic variants in TSC1. In some embodiments, the cancer comprises greater than about 90% clonality of pathogenic variants in PTEN. In some embodiments, the cancer comprises greater than about 40%, about 45%, about 50%, about 55%, about 60%, about 65%, about 70%, about 75%, about 80%, about 85%, about 90%, about 95%, greater than about 99% clonality of pathogenic variants in TSC2. In some embodiments, the cancer comprises greater than about 90% clonality of pathogenic variants in TSC2. In some embodiments, the cancer comprises greater than about 40%, about 45%, about 50%, about 55%, about 60%, about 65%, about 70%, about 75%, about 80%, about 85%, about 90%, about 95%, greater than about 99% clonality of pathogenic variants in PIK3CA. In some embodiments, the cancer comprises greater than about 90% clonality of pathogenic variants in PIK3CA.

In some embodiments, the methods result in tumor regression. In some embodiments, the methods result in tumor apoptosis.

Preventing or Treating Acquired Resistance to a RAS Inhibitor

In some embodiments, the methods include delaying, preventing, or treating acquired resistance to a RAS inhibitor (e.g., a $KRAS^{G12C}$ inhibitor) by administering the RAS inhibitor (e.g., a $KRAS^{G12C}$ inhibitor) in combination with an mTOR inhibitor (e.g., a bi-steric steric mTOR inhibitor, e.g., RMC-5552). In some embodiments, the present disclosure includes methods for inducing apoptosis of a cell (e.g., a tumor cell) by contacting the cell with a RAS inhibitor (e.g., a KRAS(OFF) inhibitor such as a $KRAS^{G12C}$ inhibitor) in combination with an mTOR inhibitor (e.g., a bi-steric mTOR inhibitor, e.g., RMC-5552). In some embodiments, the present disclosure includes methods for inducing apoptosis of a cell (e.g., a tumor cell) by contacting the cell with a RAS inhibitor (e.g., a RAS(ON) inhibitor such as a KRAS $^{G12C}$(ON) inhibitor) in combination with an mTOR inhibitor (e.g., a bi-steric mTOR inhibitor, e.g., RMC-5552)

The term "preventing acquired resistance," as used herein, means avoiding the occurrence of acquired or adaptive resistance. Thus, e.g., the use of an mTOR inhibitor (e.g., a bi-steric mTOR inhibitor, e.g., RMC-5552) described herein in preventing acquired/adaptive resistance to a $KRAS^{G12C}$ inhibitor means that the mTOR inhibitor (e.g., a bi-steric mTOR inhibitor, e.g., RMC-5552) is administered prior to any detectable existence of resistance to the $KRAS^{G12C}$ inhibitor and the result of such administration of the mTOR inhibitor (e.g., a bi-steric mTOR inhibitor, e.g., RMC-5552) is that no resistance to the $KRAS^{G12C}$ inhibitor occurs.

The present disclosure provides methods for delaying or preventing acquired resistance to a RAS inhibitor in a subject in need thereof, comprising administering to the. subject about 3 mg/week to about 25 mg/week of a bi-steric mTOR inhibitor, wherein the subject has already received or will receive administration of the RAS inhibitor;

wherein the bi-steric mTOR inhibitor is

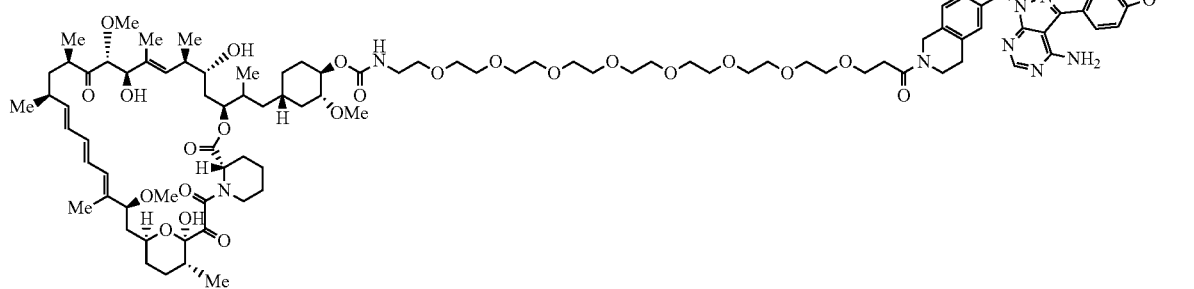

or a stereoisomer, tautomer, or oxepane isomer thereof, or pharmaceutically acceptable salt of any of the foregoing.

The present disclosure provides methods for treating acquired resistance to a RAS inhibitor in a subject in need thereof, comprising administering to the subject about 3 mg/week to about 25 mg/week of a bi-steric mTOR inhibitor;

wherein the bi-steric mTOR inhibitor is

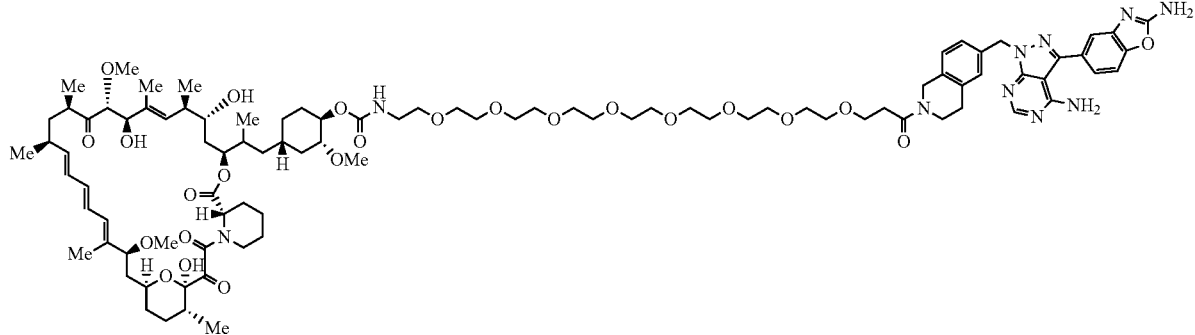 [SMILES: CO[C@H]1C[C@@H]2CC[C@@H](C)[C@@](O)(O2)C(=O)C(=O)N2CCCC[C@H]2C(=O)O[C@H](C(C)C[C@@H]2CC[C@@H](OC(=O)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]

or a stereoisomer, tautomer, or oxepane isomer thereof, or pharmaceutically acceptable salt of any of the foregoing.

In some embodiments, the methods of delaying, preventing, or treating acquired resistance to a RAS inhibitor comprise administering to the subject an effective amount of the RAS inhibitor. RAS inhibitors are described in more detail in the Combinations section of the present disclosure, and all such RAS inhibitors are contemplated in relation to the methods of delaying, preventing, or treating acquired resistance to a RAS inhibitor.

In some embodiments, the RAS inhibitor targets a specific RAS mutation. In some embodiments, the RAS inhibitor targets a KRAS mutation. In some embodiments, the RAS inhibitor targets the $KRAS^{G12C}$ mutation.

In some embodiments, the RAS inhibitor is a KRAS (OFF) inhibitor. In some embodiments, the KRAS(OFF) inhibitor is AMG 510, MRTX849, JDQ443, MRTX1133, ERAS-3490, ERAS-4, BPI-421286, D-1553, JAB-21822, GH-35, ICP-915, IBI351, LY3537982, GDC-6036, BI1823911, RSC-1255, or a pharmaceutically acceptable salt of any of the foregoing.

In some embodiments, the RAS inhibitor is a RAS(ON) inhibitor. In some embodiments, the RAS(ON) inhibitor is a KRAS(ON) inhibitor. In some embodiments, the KRAS (ON) inhibitor is RMC-6236, RMC-6291, RMC-9805, RMC-8839, RMC-0708, or a pharmaceutically acceptable salt of any of the foregoing. In some embodiments, the KRAS(ON) inhibitor is a $KRAS^{G12C}$(ON) inhibitor. In some embodiments, the $KRAS^{G12C}$(ON) inhibitor is RMC-6291 or a pharmaceutically acceptable salt thereof.

In some embodiments, the subject is administered the RAS inhibitor to treat or prevent a cancer. In some embodiments, the cancer comprises a $KRAS^{G12C}$ mutation. In some embodiments, the cancer comprises co-occurring $KRAS^{G12C}$ and STK11 mutations. In some embodiments, the cancer is a non-small cell lung cancer (NSCLC) or a colorectal cancer. In some embodiments, the cancer comprises co-occurring $KRAS^{G12C}$ and $PIK3CA^{E545K}$ mutations. In some embodiments, the cancer is a colorectal cancer.

In some embodiments, the method results in tumor regression. In some embodiments, the method results in tumor apoptosis.

EXEMPLARY EMBODIMENTS

Embodiment I-1. A method of treating a subject having a cancer, the method comprising administering a dosage of about 3 mg/week to about 25 mg/week of a bi-steric mTOR inhibitor to the subject;

wherein the bi-steric mTOR inhibitor is

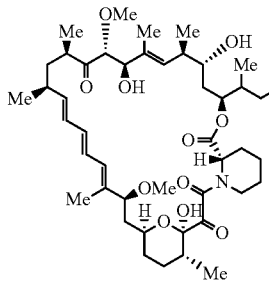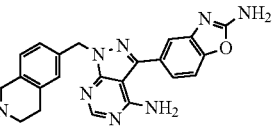

or a stereoisomer, tautomer, or oxepane isomer thereof, or pharmaceutically acceptable salt of any of the foregoing.

Embodiment I-2. A method of treating a subject having salivary gland cancer, the method comprising administering a dosage of about 3 mg/week to about 25 mg/week of a bi-steric mTOR inhibitor to the subject;

wherein the bi-steric mTOR inhibitor is

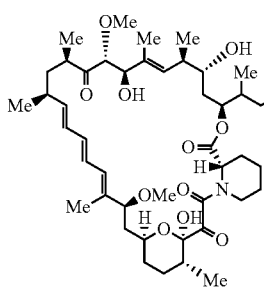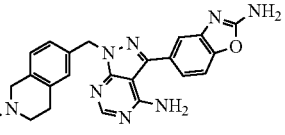

or a stereoisomer, tautomer, or oxepane isomer thereof, or pharmaceutically acceptable salt of any of the foregoing.

Embodiment I-3. The method of embodiment I-1 or I-2, wherein the dosage is about 4 mg/week to about 12 mg/week, about 5 mg/week to about 10 mg/week, about 6 mg/week to about 9 mg/week, about 6 mg/week to about 8 mg/week, or about 7 mg/week to about 8 mg/week.

Embodiment I-4. The method of any one of embodiments I-1 to I-3, wherein the dosage is about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, or about 10 mg/week.

Embodiment I-5. The method of any one of embodiments I-1 to I-4, wherein the dosage is administered via IV infusion.

Embodiment I-6. The method of embodiment I-5, wherein the dosage is administered over about 0.5 hour to about 2 hours, over about 0.5 hour to about 1.5 hours, over about 0.5 hour to about 1 hour, over about 1 hour to about 2 hours, or over about 1 hour to about 1.5 hours.

Embodiment I-7. The method of embodiment I-5 or I-6, wherein the dosage is administered over about 1 hour.

Embodiment I-8. The method of any one of embodiments I-1 to I-7, wherein the cancer is characterized by a genotypic aberration that activates the mammalian target of rapamycin (mTOR) pathway.

Embodiment I-9. The method of any one of embodiments I-1 to I-8, wherein the cancer comprises a mutation in the mTOR pathway.

Embodiment I-10. The method of embodiment I-8 or I-9, wherein the genotypic aberration or the mutation is of mTOR, STK11, PIK3CA, PTEN, KEAP1, TSC1, or TSC2, or a combination thereof.

Embodiment I-11. The method of any one of embodiments I-8 to I-10, wherein the genotypic aberration or the mutation is of PTEN.

Embodiment I-12. The method of embodiment I-10 or I-11, wherein the PTEN mutation is a dominant negative mutation.

Embodiment I-13. The method of any one of embodiments I-1 to I-12, wherein the cancer is characterized by increased mTORC1 activity.

Embodiment I-14. The method of any one of embodiments I-1 to I-13, wherein the cancer is characterized by decreased 4EBP1 activity.

Embodiment I-15. The method of any one of embodiments I-1 to I-14, wherein the cancer comprises a mutation of the Myc family.

Embodiment I-16. The method of embodiment I-15, wherein the cancer comprises an amplification of MYC, MYCL, MYCN, or a combination thereof and/or dependence on MYC, MYCL, MYCN, or a combination thereof.

Embodiment I-17. The method of any one of embodiments I-1 to I-16, wherein the cancer comprises a mutation of NFE2L2.

Embodiment I-18. The method of any one of embodiments I-1 to I-17, wherein the cancer comprises a BRAF fusion.

Embodiment I-19. The method of any one of embodiments I-1 or I-3 to I-18, wherein cancer is selected from the group consisting of bladder cancer, breast cancer, colorectal cancer, endometrial cancer, glioma, head and neck cancer, hematological cancer, liver cancer, lung cancer, neuro-endocrine cancer, ovarian cancer, pancreatic cancer, renal cancer, and rhabdomyosarcoma.

Embodiment I-20. The method of any one of embodiments I-1 or I-3 to I-19, wherein the cancer is a solid tumor.

Embodiment I-21. The method of any one of embodiments I-1 or I-3 to I-20, wherein the cancer is head and neck cancer.

Embodiment I-22. The method of embodiment I-21, wherein the cancer is salivary gland cancer.

Embodiment I-23. The method of any one of embodiments I-1 to I-22, wherein the subject is human.

Embodiment I-24. The method of any one of embodiments I-1 to I-23, wherein the method further comprises administering a dexamethasone mouthwash to the subject.

Embodiment I-25. The method of embodiment I-24, wherein the dexamethasone mouthwash comprises about 0.5 mg/5 mL dexamethasone.

Embodiment I-26. The method of embodiment I-24 or I-25, wherein the subject is administered about 2.5 mL of the dexamethasone mouthwash.

Embodiment I-27. The method of any one of embodiments I-24 to I-26, wherein the dexamethasone mouthwash is administered 1, 2, 3, or 4 times daily.

Embodiment I-28. The method of any one of embodiments I-1 to I-27, wherein the method further comprises administering a tacrolimus mouthwash to the subject.

Embodiment I-29. The method of embodiment I-28, wherein the tacrolimus mouthwash comprises about 0.5 mg/mL tacrolimus.

Embodiment I-30. The method of embodiment I-28 or I-29, wherein the subject is administered about 2.5 mL of the tacrolimus mouthwash.

Embodiment I-31. The method of any one of embodiments I-28 to I-30, wherein the tacrolimus mouthwash is administered 1, 2, 3, or 4 times daily.

Embodiment I-32. The method of any one of embodiments I-28 to I-31, wherein the tacrolimus mouthwash is administered on the day of administering the bi-steric mTOR inhibitor or just prior to administering the bi-steric mTOR inhibitor.

Embodiment I-33. The method of any one of embodiments I-1 to I-23, wherein the method further comprises administering a combination mouthwash to the subject, wherein the combination mouthwash comprises dexamethasone and tacrolimus.

Embodiment I-34. The method of embodiment I-33, wherein the combination mouthwash comprises about 0.5 mg/5 mL dexamethasone.

Embodiment I-35. The method of embodiment I-33 or I-34, wherein the combination mouthwash comprises about 0.5 mg/mL tacrolimus.

Embodiment I-36. The method of any one of embodiments I-33 to I-35, wherein the subject is administered about 2.5 mL of the combination mouthwash.

Embodiment I-37. The method of any one of embodiments I-33 to I-36, wherein the combination mouthwash is administered 1, 2, 3, or 4 times daily.

Embodiment I-38. The method of any one of embodiments I-33 to I-37, wherein the combination mouthwash is administered on the day of administering the bi-steric mTOR inhibitor or just prior to administering the bi-steric mTOR inhibitor.

Embodiment I-39. The method of any one of embodiments I-1 to I-38, wherein the method further comprises ice being applied to the mouth of the subject.

Embodiment I-40. The method of embodiment I-39, wherein the ice is applied for about 10 minutes before administering the bi-steric mTOR inhibitor, during administering the bi-steric mTOR inhibitor, and for about 10 minutes after administering the bi-steric mTOR inhibitor.

Embodiment I-41. The method of any one of embodiments I-24 to I-40, wherein the dosage is about 7 mg/week, about 7.5 mg/week, about 8 mg/week, about 8.5 mg/week, or about 9 mg/week.

Embodiment I-42. The method of any one of embodiments I-1 to I-41, wherein the method further comprises administering a RAS inhibitor to the subject.

Embodiment I-43. The method of embodiment I-42, wherein the RAS inhibitor targets a specific RAS mutation.

Embodiment I-44. The method of embodiment I-42 or I-43, wherein the RAS inhibitor targets a KRAS mutation.

Embodiment I-45. The method of any one of embodiments I-42 to I-44, wherein the RAS inhibitor targets the $KRAS^{G12C}$ mutation.

Embodiment I-46. The method of any one of embodiments I-42 to I-45, wherein the RAS inhibitor is a KRAS (OFF) inhibitor.

Embodiment I-47. The method of embodiment I-46, wherein the KRAS(OFF) inhibitor is AMG 510, MRTX849, JDQ443, MRTX1133, ERAS-3490, ERAS-4, BPI-421286, D-1553, JAB-21822, GH-35, ICP-915, IBI351, LY3537982, GDC-6036, BI1823911, RSC-1255, or a pharmaceutically acceptable salt of any of the foregoing.

Embodiment I-48. The method of any one of embodiments I-42 to I-45, wherein the RAS inhibitor is a RAS(ON) inhibitor.

Embodiment I-49. The method of embodiment I-48, wherein the RAS(ON) inhibitor is a KRAS(ON) inhibitor.

Embodiment I-50. The method of embodiment I-49, wherein the KRAS(ON) inhibitor is RMC-6236, RMC-6291, RMC-9805, RMC-8839, or a pharmaceutically acceptable salt of any of the foregoing.

Embodiment I-51. The method of embodiment I-49 or I-50, wherein the KRAS(ON) inhibitor is a $KRAS^{G12C}$ (ON) inhibitor.

Embodiment I-52. The method of embodiment I-51, wherein the $KRAS^{G12C}$ (ON) inhibitor is RMC-6291 or a pharmaceutically acceptable salt thereof.

Embodiment I-53. The method of any one of embodiments I-1 to I-52, wherein the cancer comprises a $KRAS^{G12C}$ mutation.

Embodiment I-54. The method of any one of embodiments I-1 to I-53, wherein the cancer comprises co-occurring $KRAS^{G12C}$ and STK11 mutations.

Embodiment I-55. The method of any one of embodiments I-1 to I-54, wherein the cancer comprises co-occurring $KRAS^{G12C}$ and $PIK3CA^{E545K}$ mutations.

Embodiment I-56. The method of any one of embodiments I-1 to I-20 and I-23 to I-55, wherein the cancer is colorectal cancer and comprises a mutation of PIK3CA, an amplification of MYC, or a mutation of PIK3CA and an amplification of MYC.

Embodiment I-57. The method of any one of embodiments I-1 to I-21 and I-23 to I-55, wherein the cancer is head and neck cancer and comprises a mutation of PIK3CA, a mutation of PTEN, or a mutation of PIK3CA and a mutation of PTEN.

Embodiment I-58. The method of any one of embodiments I-1 to I-20 and I-23 to I-55, wherein the cancer is hepatocellular carcinoma and comprises a mutation of NFE2L2.

Embodiment I-59. The method of any one of embodiments I-1 to I-20 and I-23 to I-55, wherein the cancer is ovarian cancer and comprises a mutation of TSC2.

Embodiment I-60. The method of any one of embodiments I-1 to I-20 and I-23 to I-55, wherein the cancer is pancreatic cancer and comprises a mutation of STK11, a $KRAS^{G12C}$ mutation, or a mutation of STK11 and a $KRAS^{G12C}$ mutation.

Embodiment I-61. The method of any one of embodiments I-1 to I-20 and I-23 to I-55, wherein the cancer is prostate cancer and comprises a mutation of PTEN.

Embodiment I-62. The method of any one of embodiments I-1 to I-20 and I-23 to I-55, wherein the cancer is uterine cancer and comprises a mutation of PIK3CA, a mutation of PIK3CA, a mutation of TSC2, or a combination thereof.

Embodiment I-63. The method of any one of embodiments I-1 to I-20 and I-23 to I-55, wherein the cancer is lung cancer and comprises a BRAF fusion.

Embodiment I-64. The method of any one of embodiments I-1 to I-63, wherein the method results in tumor regression.

Embodiment I-65. The method of any one of embodiments I-1 to I-64, wherein the method results in tumor apoptosis.

Embodiment I-66. A method for delaying or preventing acquired resistance to a RAS inhibitor in a subject in need thereof, comprising administering to the subject about 3 mg/week to about 25 mg/week of a bi-steric mTOR inhibitor, wherein the subject has already received or will receive administration of the RAS inhibitor;

wherein the bi-steric mTOR inhibitor is

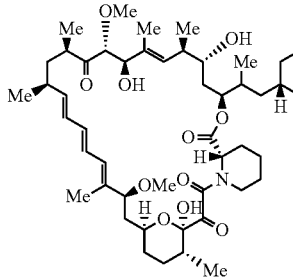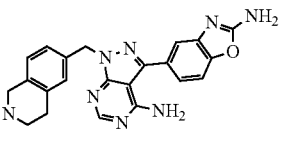

or a stereoisomer, tautomer, or oxepane isomer thereof, or pharmaceutically acceptable salt of any of the foregoing.

Embodiment I-67. A method of treating acquired resistance to a RAS inhibitor in a subject in need thereof, comprising administering to the subject about 3 mg/week to about 25 mg/week of a bi-steric mTOR inhibitor;
wherein the bi-steric mTOR inhibitor is

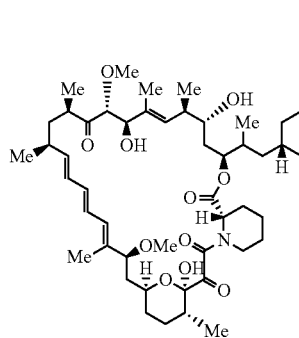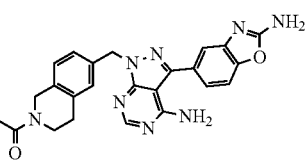

or a stereoisomer, tautomer, or oxepane isomer thereof, or pharmaceutically acceptable salt of any of the foregoing.

Embodiment I-68. The method of embodiment I-66 or I-67, further comprising administering to the subject an effective amount of the RAS inhibitor.

Embodiment I-69. The method of embodiment I-68, wherein the RAS inhibitor targets a specific RAS mutation.

Embodiment I-70. The method of any one of embodiments I-66 to I-69, wherein the RAS inhibitor targets a KRAS mutation.

Embodiment I-71. The method of any one of embodiments I-66 to I-70, wherein the RAS inhibitor targets the KRAS$^{G12C}$ mutation.

Embodiment I-72. The method of any one of embodiments I-66 to I-71, wherein the RAS inhibitor is a KRAS (OFF) inhibitor.

Embodiment I-73. The method of embodiment I-72, wherein the KRAS(OFF) inhibitor is AMG 510, MRTX849, JDQ443, MRTX1133, ERAS-3490, ERAS-4, BPI-421286, D-1553, JAB-21822, GH-35, ICP-915, IBI351, LY3537982, GDC-6036, BI1823911, RSC-1255, or a pharmaceutically acceptable salt of any of the foregoing.

Embodiment I-74. The method of any one of embodiments I-66 to I-71, wherein the RAS inhibitor is a RAS(ON) inhibitor.

Embodiment I-75. The method of embodiment I-74, wherein the RAS(ON) inhibitor is a KRAS(ON) inhibitor.

Embodiment I-76. The method of embodiment I-75, wherein the KRAS(ON) inhibitor is RMC-6236, RMC-6291, RMC-9805, RMC-8839, or a pharmaceutically acceptable salt of any of the foregoing.

Embodiment I-77. The method of embodiment I-75 or I-76, wherein the KRAS(ON) inhibitor is a KRAS$^{G12C}$(ON) inhibitor.

Embodiment I-78. The method of embodiment I-77, wherein the KRAS$^{G12C}$(ON) inhibitor is RMC-6291 or a pharmaceutically acceptable salt thereof.

Embodiment I-79. The method of any one of embodiments I-66 to I-78, wherein the subject is administered the RAS inhibitor to treat or prevent a cancer.

Embodiment I-80. The method of embodiment I-79, wherein the cancer comprises a KRAS$^{G12C}$ mutation.

Embodiment I-81. The method of embodiment I-79 or I-80, wherein the cancer comprises co-occurring KRAS$^{G12C}$ and STK11 mutations.

Embodiment I-82. The method of any one of embodiments I-79 to I-81, wherein the cancer is a non-small cell lung cancer (NSCLC) or a colorectal cancer.

Embodiment I-83. The method of any one of embodiments I-79 to I-82, wherein the cancer comprises co-occurring KRAS$^{G12C}$ and PIK3CA$^{E545K}$ mutations.

Embodiment I-84. The method of any one of embodiments I-79 to I-81 and I-83, wherein the cancer is a colorectal cancer.

Embodiment I-85. The method of any one of embodiments I-66 to I-84, wherein the method results in tumor regression.

Embodiment I-86. The method of any one of embodiments I-66 to I-84, wherein the method results in tumor apoptosis.

Embodiment I-87. Use of a bi-steric mTOR inhibitor in a treatment of cancer, wherein the treatment comprises administering a dosage of about 3 mg/week to about 25 mg/week of the bi-steric mTOR inhibitor to a subject in need thereof;
wherein the hi-steric mTOR inhibitor is

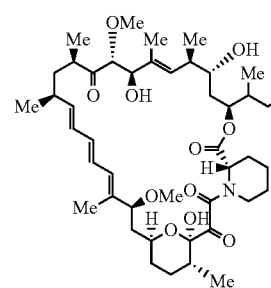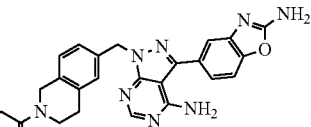

or a stereoisomer, tautomer, or oxepane isomer thereof, or pharmaceutically acceptable salt of any of the foregoing.

Embodiment I-88. Use of a bi-steric mTOR inhibitor in the manufacture of a medicament for treatment of cancer, wherein the treatment comprises administering the medicament to a subject in need thereof to deliver a dosage of about 3 mg/week to about 25 mg/week of the bi-steric mTOR inhibitor;

wherein the bi-steric mTOR inhibitor is

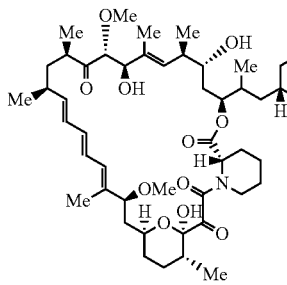
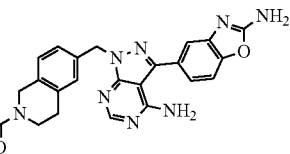

or a stereoisomer, tautomer, or oxepane isomer thereof, or pharmaceutically acceptable salt of any of the foregoing.

Embodiment I-89. A bi-steric mTOR inhibitor for use in a method of treating cancer, the method comprising administering a dosage of about 3 mg/week to about 25 mg/week of the bi-steric mTOR inhibitor to a subject in need thereof;

wherein the bi-steric mTOR inhibitor is

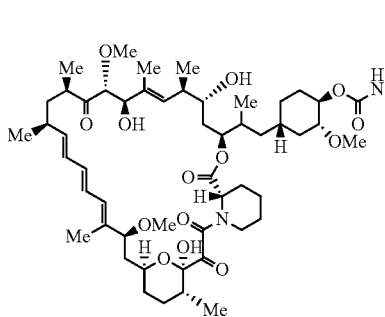

or a stereoisomer, tautomer, or oxepane isomer thereof, or pharmaceutically acceptable salt of any of the foregoing.

Embodiment I-90. A medicament for treatment of cancer, the medicament comprising a bi-steric mTOR inhibitor, wherein the treatment comprises administering the medicament to deliver a dosage of about 3 mg/week to about 25 mg/week of the bi-steric mTOR inhibitor to a subject in need thereof;

wherein the bi-steric mTOR inhibitor is

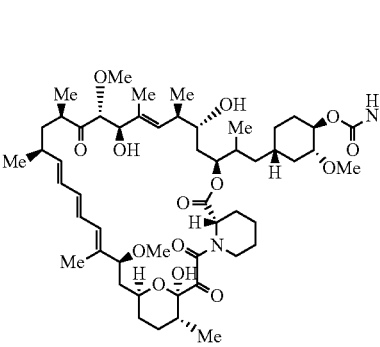
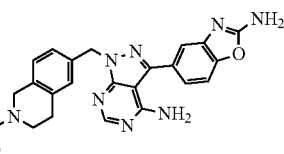

or a stereoisomer, tautomer, or oxepane isomer thereof, or pharmaceutically acceptable salt of any of the foregoing.

Embodiment I-91. The use, the bi-steric mTOR inhibitor for use, or the medicament for treatment of any one of embodiments I-87 to I-90, wherein the dosage is about 4 mg/week to about 12 mg/week, about 5 mg/week to about 10 mg/week, about 6 mg/week to about 9 mg/week, about 6 mg/week to about 8 mg/week, or about 7 mg/week to about 8 mg/week.

Embodiment I-92. The use, the bi-steric mTOR inhibitor for use, or the medicament for treatment of any one of embodiments I-87 to I-91, wherein the dosage is about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, or about 10 mg/week.

Embodiment I-93. The use, the bi-steric mTOR inhibitor for use, or the medicament for treatment of any one of embodiments I-87 to I-92, wherein the dosage is administered via IV infusion.

Embodiment I-94. The use, the bi-steric mTOR inhibitor for use, or the medicament for treatment of embodiment I-93, wherein the dosage is administered over about 0.5 hour to about 2 hours, over about 0.5 hour to about 1.5 hours, over about 0.5 hour to about 1 hour, over about 1 hour to about 2 hours, or over about 1 hour to about 1.5 hours.

Embodiment I-95. The use, the bi-steric mTOR inhibitor for use, or the medicament for treatment of embodiment I-93 or I-94, wherein the dosage is administered over about 1 hour.

Embodiment I-96. The use, the bi-steric mTOR inhibitor for use, or the medicament for treatment of any one of embodiments I-87 to I-95, wherein the cancer is characterized by a genotypic aberration that activates the mammalian target of rapamycin (mTOR) pathway.

Embodiment I-97. The use, the bi-steric mTOR inhibitor for use, or the medicament for treatment of any one of embodiments I-87 to I-96, wherein the cancer comprises a mutation in the mTOR pathway.

Embodiment I-98. The use, the bi-steric mTOR inhibitor for use, or the medicament for treatment of embodiment I-96 or I-97, wherein the genotypic aberration or the mutation is of mTOR, STK11, PIK3CA, PTEN, KEAP1, TSC1, or TSC2, or a combination thereof.

Embodiment I-99. The use, the bi-steric mTOR inhibitor for use, or the medicament for treatment of any one of embodiments I-96 to I-98, wherein the genotypic aberration or the mutation is of PTEN.

Embodiment I-100. The use, the bi-steric mTOR inhibitor for use, or the medicament for treatment of embodiment I-96 or I-99, wherein the PTEN mutation is a dominant negative mutation.

Embodiment I-101. The use, the bi-steric mTOR inhibitor for use, or the medicament for treatment of any one of embodiments I-87 to I-100, wherein the cancer is characterized by increased mTORC1 activity.

Embodiment I-102. The use, the bi-steric mTOR inhibitor for use, or the medicament for treatment of any one of embodiments I-87 to I-101, wherein the cancer is characterized by decreased 4EBP1 activity.

Embodiment I-103. The use, the bi-steric mTOR inhibitor for use, or the medicament for treatment of any one of embodiments I-87 to I-102, wherein the cancer comprises a mutation of the Myc family.

Embodiment I-104. The use, the bi-steric mTOR inhibitor for use, or the medicament for treatment of embodiment I-103, wherein the cancer comprises an amplification of MYC, MYCL, MYCN, or a combination thereof and/or dependence on MYC, MYCL, MYCN, or a combination thereof.

Embodiment I-105. The use, the bi-steric mTOR inhibitor for use, or the medicament for treatment of any one of embodiments I-87 to I-104, wherein the cancer comprises a mutation of NFE2L2.

Embodiment I-106. The use, the bi-steric mTOR inhibitor for use, or the medicament for treatment of any one of embodiments I-87 to I-105, wherein the cancer comprises a BRAF fusion.

Embodiment I-107. The use, the bi-steric mTOR inhibitor for use, or the medicament for treatment of any one of embodiments I-87 to I-106, wherein the cancer is selected from the group consisting of bladder cancer, breast cancer, colorectal cancer, endometrial cancer, glioma, head and neck cancer, hematological cancer, liver cancer, lung cancer, neuro-endocrine cancer, ovarian cancer, pancreatic cancer, renal cancer, and rhabdomyosarcoma.

Embodiment I-108. The use, the bi-steric mTOR inhibitor for use, or the medicament for treatment of any one of embodiments I-87 to I-107, wherein the cancer is a solid tumor.

Embodiment I-109. The use, the bi-steric mTOR inhibitor for use, or the medicament for treatment of any one of embodiments I-87 to I-108, wherein the cancer is head and neck cancer.

Embodiment I-110. The use, the bi-steric mTOR inhibitor for use, or the medicament for treatment of embodiment I-109, wherein the cancer is salivary gland cancer.

Embodiment I-111. The use, the bi-steric mTOR inhibitor for use, or the medicament for treatment of any one of embodiments I-87 to I-110, wherein the subject is human.

Embodiment I-112. The use, the bi-steric mTOR inhibitor for use, or the medicament for treatment of any one of embodiments I-87 to I-111, wherein the method or the treatment further comprises administering a dexamethasone mouthwash to the subject.

Embodiment I-113. The use, the bi-steric mTOR inhibitor for use, or the medicament for treatment of embodiment I-112, wherein the dexamethasone mouthwash comprises about 0.5 mg/5 mL dexamethasone.

Embodiment I-114. The use, the bi-steric mTOR inhibitor for use, or the medicament for treatment of embodiment I-112 or I-113, wherein the subject is administered about 2.5 mL of the dexamethasone mouthwash.

Embodiment I-115. The use, the bi-steric mTOR inhibitor for use, or the medicament for treatment of any one of embodiments I-112 to I-114, wherein the dexamethasone mouthwash is administered 1, 2, 3, or 4 times daily.

Embodiment I-116. The use, the bi-steric mTOR inhibitor for use, or the medicament for treatment of any one of embodiments I-87 to I-115, wherein the method or the treatment further comprises administering a tacrolimus mouthwash to the subject.

Embodiment I-117. The use, the bi-steric mTOR inhibitor for use, or the medicament for treatment of embodiment I-116, wherein the tacrolimus mouthwash comprises about 0.5 mg/mL tacrolimus.

Embodiment I-118. The use, the bi-steric mTOR inhibitor for use, or the medicament for treatment of embodiment I-116 or I-117, wherein the subject is administered about 2.5 mL of the tacrolimus mouthwash.

Embodiment I-119. The use, the bi-steric mTOR inhibitor for use, or the medicament for treatment of any one of embodiments I-116 to I-118, wherein the tacrolimus mouthwash is administered 1, 2, 3, or 4 times daily.

Embodiment I-120. The use, the bi-steric mTOR inhibitor for use, or the medicament for treatment of any one of embodiments I-116 to I-119, wherein the tacrolimus mouthwash is administered on the day of administering the bi-steric mTOR inhibitor or just prior to administering the bi-steric mTOR inhibitor.

Embodiment I-121. The use, the bi-steric mTOR inhibitor for use, or the medicament for treatment of any one of embodiments I-87 to I-111, wherein the method or the treatment further comprises administering a combination mouthwash to the subject, wherein the combination mouthwash comprises dexamethasone and tacrolimus.

Embodiment I-122. The use, the bi-steric mTOR inhibitor for use, or the medicament for treatment of embodiment I-121, wherein the combination mouthwash comprises about 0.5 mg/5 mL dexamethasone.

Embodiment I-123. The use, the bi-steric mTOR inhibitor for use, or the medicament for treatment of embodiment I-121 or I-122, wherein the combination mouthwash comprises about 0.5 mg/mL tacrolimus.

Embodiment I-124. The use, the bi-steric mTOR inhibitor for use, or the medicament for treatment of any one of embodiments I-121 to I-123, wherein the subject is administered about 2.5 mL of the combination mouthwash.

Embodiment I-125. The use, the bi-steric mTOR inhibitor for use, or the medicament for treatment of any one of embodiments I-121 to I-124, wherein the combination mouthwash is administered 1, 2, 3, or 4 times daily.

Embodiment I-126. The use, the bi-steric mTOR inhibitor for use, or the medicament for treatment of any one of embodiments I-121 to I-125, wherein the combination mouthwash is administered on the day of administering the bi-steric mTOR inhibitor or just prior to administering the bi-steric mTOR inhibitor.

Embodiment I-127. The use, the bi-steric mTOR inhibitor for use, or the medicament for treatment of any one of embodiments I-87 to I-126, wherein the method or the treatment further comprises ice being applied to the mouth of the subject.

Embodiment I-128. The use, the bi-steric mTOR inhibitor for use, or the medicament for treatment of embodiment I-127, wherein the ice is applied for about 10 minutes before administering the bi-steric mTOR inhibitor, during administering the bi-steric mTOR inhibitor, and for about 10 minutes after administering the bi-steric mTOR inhibitor.

Embodiment I-129. The use, the bi-steric mTOR inhibitor for use, or the medicament for treatment of any one of embodiments I-112 to I-128, wherein the dosage is about 7 mg/week, about 7.5 mg/week, about 8 mg/week, about 8.5 mg/week, or about 9 mg/week.

Embodiment I-130. The use, the bi-steric mTOR inhibitor for use, or the medicament for treatment of any one of embodiments I-87 to I-129, wherein the method or the treatment further comprises administering a RAS inhibitor to the subject.

Embodiment I-131. The use, the bi-steric mTOR inhibitor for use, or the medicament for treatment of embodiment I-130, wherein the RAS inhibitor targets a specific RAS mutation.

Embodiment I-132. The use, the bi-steric mTOR inhibitor for use, or the medicament for treatment of embodiment I-130 or I-131, wherein the RAS inhibitor targets a KRAS mutation.

Embodiment I-133. The use, the bi-steric mTOR inhibitor for use, or the medicament for treatment of any one of embodiments I-130 to I-132, wherein the RAS inhibitor targets the $KRAS^{G12C}$ mutation.

Embodiment I-134. The use, the bi-steric mTOR inhibitor for use, or the medicament for treatment of any one of embodiments I-130 to I-133, wherein the RAS inhibitor is a KRAS(OFF) inhibitor.

Embodiment I-135. The use, the bi-steric mTOR inhibitor for use, or the medicament for treatment of embodiment 1-134, wherein the KRAS(OFF) inhibitor is AMG 510, MRTX849, JDQ443, MRTX1133, ERAS-3490, ERAS-4, BPI-421286, D-1553, JAB-21822, GH-35, ICP-915, IBI351, LY3537982, GDC-6036, BI1823911, RSC-1255, or a pharmaceutically acceptable salt of any of the foregoing.

Embodiment I-136. The use, the bi-steric mTOR inhibitor for use, or the medicament for treatment of any one of embodiments I-130 to I-133, wherein the RAS inhibitor is a RAS(ON) inhibitor.

Embodiment I-137. The use, the bi-steric mTOR inhibitor for use, or the medicament for treatment of embodiment I-136, wherein the RAS(ON) inhibitor is a KRAS(ON) inhibitor.

Embodiment I-138. The use, the bi-steric mTOR inhibitor for use, or the medicament for treatment of embodiment 1-137, wherein the KRAS(ON) inhibitor is RMC-6236, RMC-6291, RMC-9805, RMC-8839, or a pharmaceutically acceptable salt of any of the foregoing.

Embodiment I-139. The use, the bi-steric mTOR inhibitor for use, or the medicament for treatment of embodiment 1-137 or 1-138, wherein the KRAS(ON) inhibitor is a $KRAS^{G12C}$ (ON) inhibitor.

Embodiment I-140. The use, the bi-steric mTOR inhibitor for use, or the medicament for treatment of embodiment 1-139, wherein the $KRAS^{G12C}$ (ON) inhibitor is RMC-6291 or a pharmaceutically acceptable salt thereof.

Embodiment I-141. The use, the bi-steric mTOR inhibitor for use, or the medicament for treatment of any one of embodiments I-87 to I-140, wherein the cancer comprises a $KRAS^{G12C}$ mutation.

Embodiment I-142. The use, the bi-steric mTOR inhibitor for use, or the medicament for treatment of any one of embodiments I-87 to I-141, wherein the cancer comprises co-occurring $KRAS^{G12C}$ and STK11 mutations.

Embodiment I-143. The use, the bi-steric mTOR inhibitor for use, or the medicament for treatment of any one of embodiments I-87 to I-142, wherein the cancer comprises co-occurring $KRAS^{G12C}$ and $PIK3CA^{E545K}$ mutations.

Embodiment I-144. The method of any one of embodiments I-87 to I-108 and I-111 to I-143, wherein the cancer is colorectal cancer and comprises a mutation of PIK3CA, an amplification of MYC, or a mutation of PIK3CA and an amplification of MYC.

Embodiment I-145. The method of any one of embodiments I-87 to I-109 and I-111 to I-143, wherein the cancer is head and neck cancer and comprises a mutation of PIK3CA, a mutation of PTEN, or a mutation of PIK3CA and a mutation of PTEN.

Embodiment I-146. The method of any one of embodiments I-87 to I-108 and I-111 to I-143, wherein the cancer is hepatocellular carcinoma and comprises a mutation of NFE2L2.

Embodiment I-147. The method of any one of embodiments I-87 to I-108 and I-111 to I-143, wherein the cancer is ovarian cancer and comprises a mutation of TSC2.

Embodiment I-148. The method of any one of embodiments I-87 to I-108 and I-111 to I-143, wherein the cancer is pancreatic cancer and comprises a mutation of STK11, a KRAS$^{G12C}$ mutation, or a mutation of STK11 and a KRAS$^{G12C}$ mutation.

Embodiment I-149. The method of any one of embodiments I-87 to I-108 and I-111 to I-143, wherein the cancer is prostate cancer and comprises a mutation of PTEN.

Embodiment I-150. The method of any one of embodiments I-87 to I-108 and I-111 to I-143, wherein the cancer is uterine cancer and comprises a mutation of PIK3CA, a mutation of PIK3CA, a mutation of TSC2, or a combination thereof.

Embodiment I-151. The method of any one of embodiments I-87 to I-108 and I-111 to I-143, wherein the cancer is lung cancer and comprises a BRAF fusion.

Embodiment I-152. The use, the bi-steric mTOR inhibitor for use, or the medicament for treatment of any one of embodiments I-87 to I-151, wherein the method or the treatment results in tumor regression.

Embodiment I-153. The use, the bi-steric mTOR inhibitor for use, or the medicament for treatment of any one of embodiments I-87 to I-152, wherein the method or the treatment results in tumor apoptosis.

Embodiment I-154. A bi-steric mTOR inhibitor for use in a method treating cancer in a subject having acquired resistance to a RAS inhibitor, the method comprising administering a dosage of about 3 mg/week to about 25 mg/week of the bi-steric mTOR inhibitor to the subject, wherein the subject has already received or will receive administration of the RAS inhibitor;

wherein the bi-steric mTOR inhibitor is

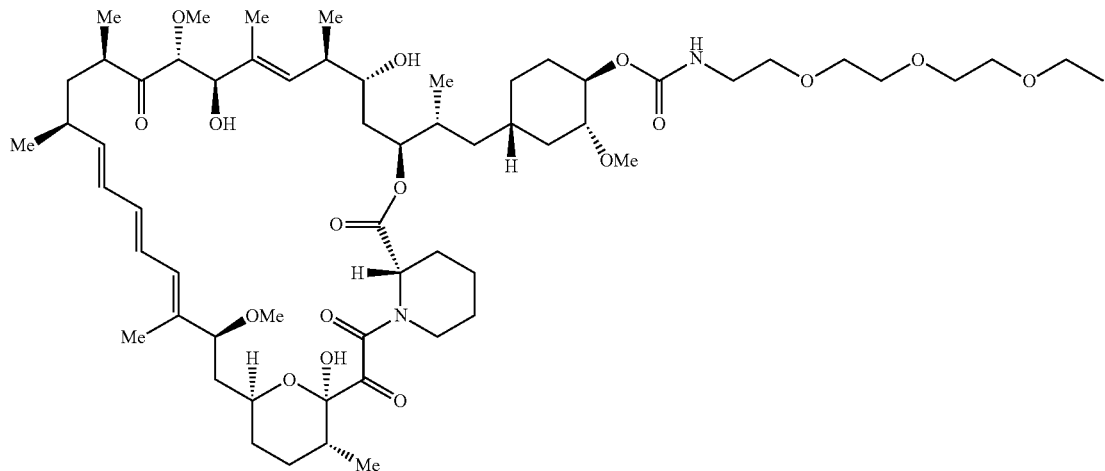

or a stereoisomer, tautomer, or oxepane isomer thereof, or pharmaceutically acceptable salt of any of the foregoing Embodiment I-155. A combination of bi-steric mTOR inhibitor and a RAS inhibitor for simultaneous, separate, or sequential use in a method of treating cancer in a subject having acquired resistance to the RAS inhibitor, the method comprising administering a dosage of about 3 mg/week to about 25 mg/week of the bi-steric mTOR inhibitor to a subject in need thereof;

wherein the bi-steric mTOR inhibitor is

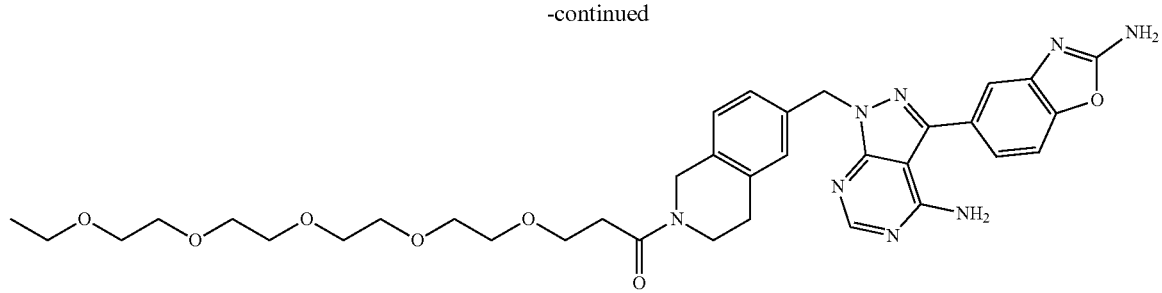

or a stereoisomer, tautomer, or oxepane isomer thereof, or pharmaceutically acceptable salt of any of the foregoing Embodiment I-156. Use of a bi-steric mTOR inhibitor in a treatment for delaying or preventing acquired resistance to a RAS inhibitor in a subject in need thereof, comprising administering to the subject about 3 mg/week to about 25 mg/week of a bi-steric mTOR inhibitor, wherein the subject has already received or will receive administration of the RAS inhibitor;

wherein the bi-steric mTOR inhibitor is

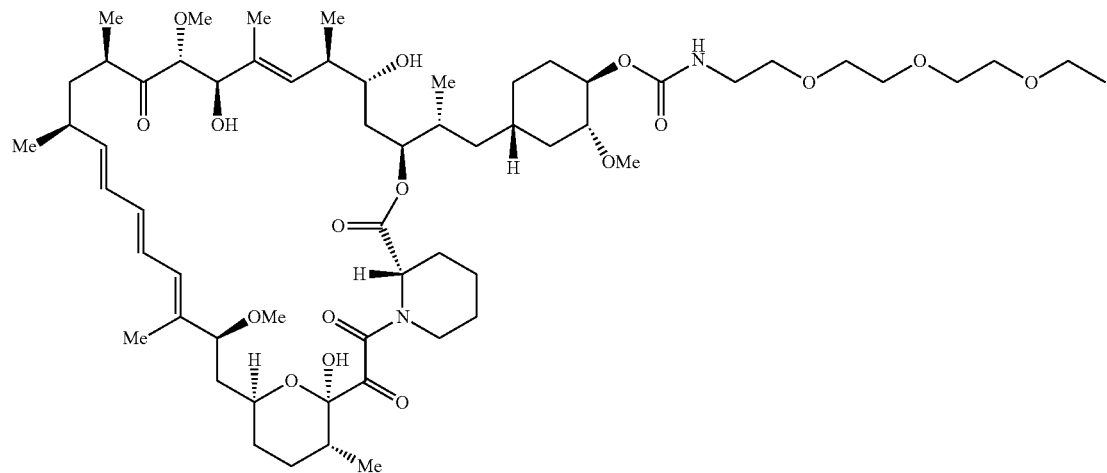

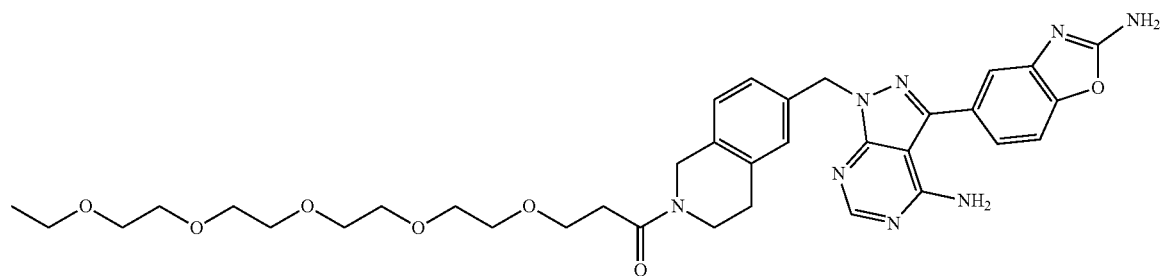

or a stereoisomer, tautomer, or oxepane isomer thereof, or pharmaceutically acceptable salt of any of the foregoing.

Embodiment I-157. Use of a bi-steric mTOR inhibitor in the manufacture of a medicament for treatment for delaying or preventing acquired resistance to a RAS inhibitor, wherein the treatment comprises administering the medicament to a subject in need thereof to deliver a dosage of about 3 mg/week to about 25 mg/week of the bi-steric mTOR inhibitor, wherein the subject has already received or will receive administration of the RAS inhibitor;

wherein the bi-steric mTOR inhibitor is

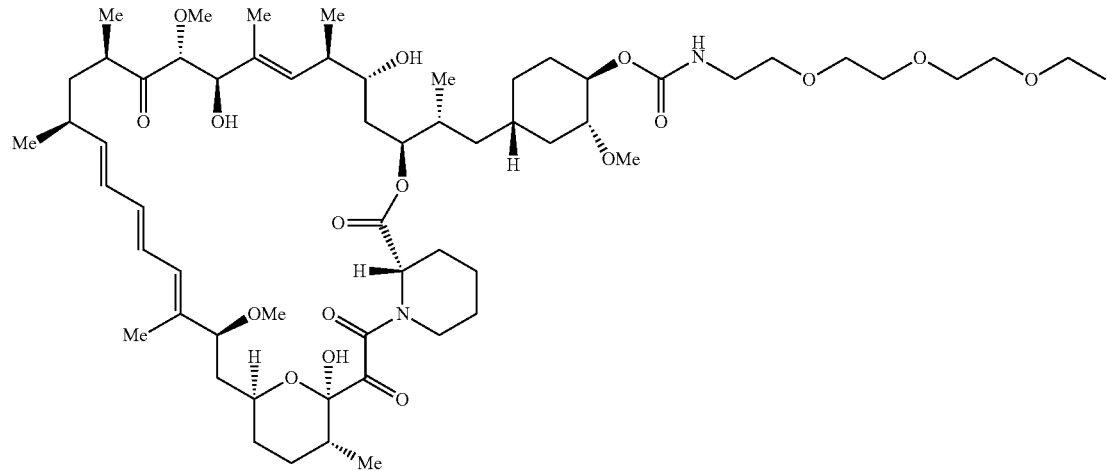
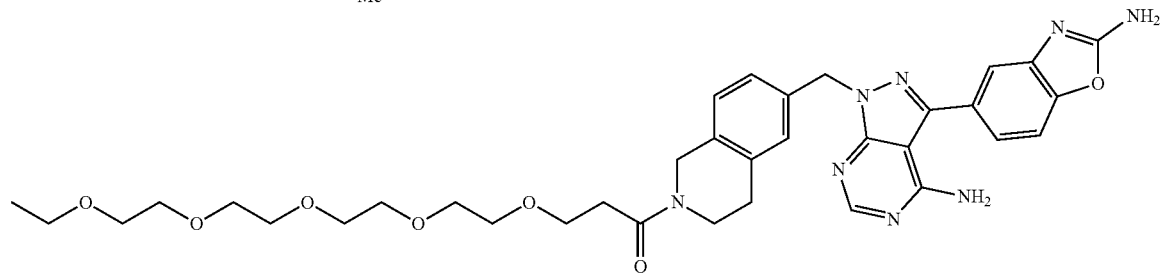

or a stereoisomer, tautomer, or oxepane isomer thereof, or pharmaceutically acceptable salt of any of the foregoing.

Embodiment I-158. A bi-steric mTOR inhibitor for use in a method of delaying or preventing acquired resistance to a RAS inhibitor, the method comprising administering a dosage of about 3 mg/week to about 25 mg/week of the bi-steric mTOR inhibitor to a subject in need thereof, wherein the subject has already received or will receive administration of the RAS inhibitor;

wherein the bi-steric mTOR inhibitor is

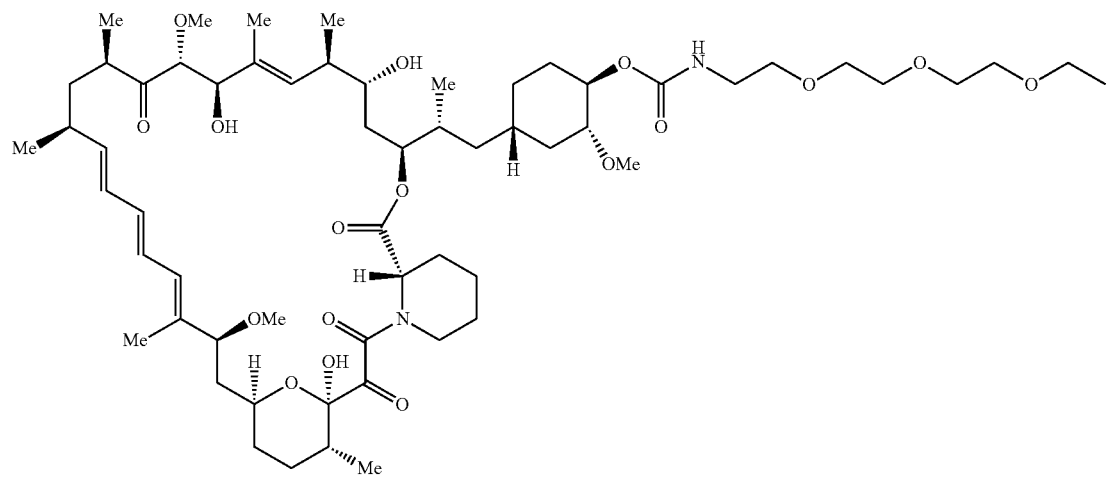

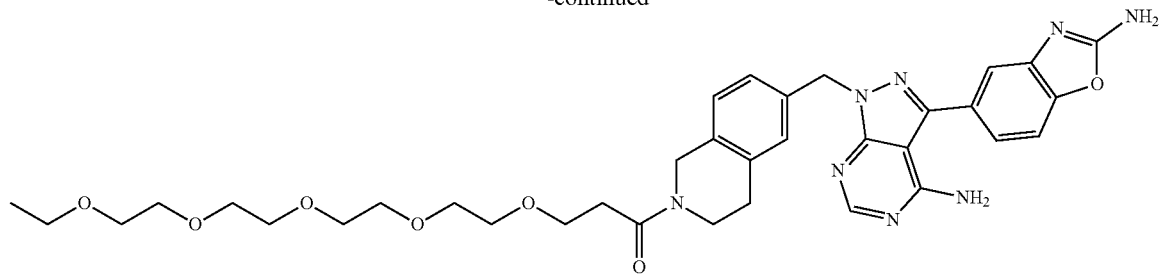

or a stereoisomer, tautomer, or oxepane isomer thereof, or pharmaceutically acceptable salt of any of the foregoing.

Embodiment I-159. A medicament for treatment for delaying or preventing acquired resistance to a RAS inhibitor, the medicament comprising a bi-steric mTOR inhibitor, wherein the treatment comprises administering the medicament to deliver a dosage of about 3 mg/week to about 25 mg/week of the bi-steric mTOR inhibitor to a subject in need thereof, wherein the subject has already received or will receive administration of the RAS inhibitor;

wherein the bi-steric mTOR inhibitor is

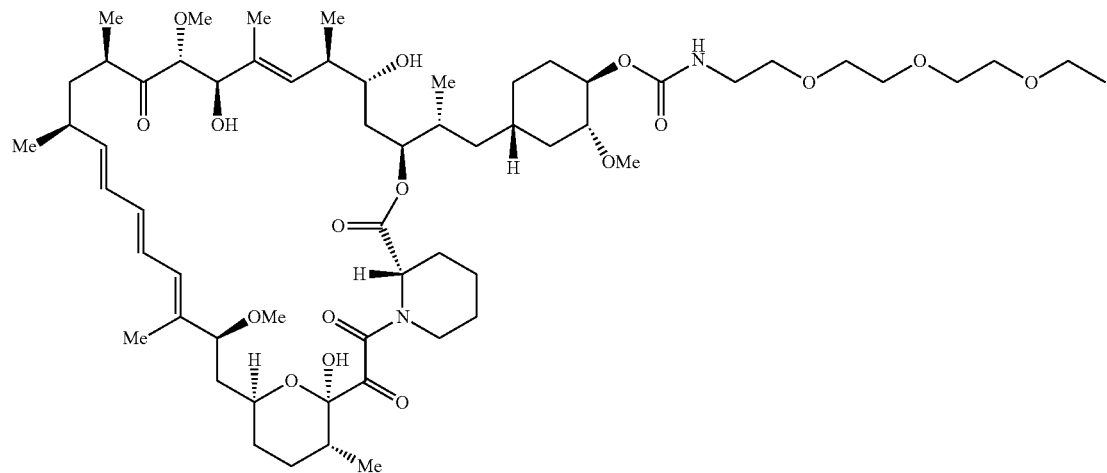

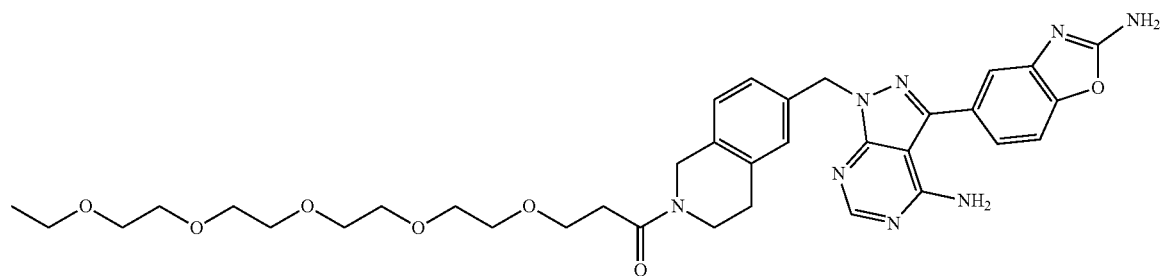

or a stereoisomer, tautomer, or oxepane isomer thereof, or pharmaceutically acceptable salt of any of the foregoing.

Embodiment I-160. Use of a bi-steric mTOR inhibitor in a treatment of acquired resistance to a RAS inhibitor, wherein the treatment comprises administering a dosage of about 3 mg/week to about 25 mg/week of the bi-steric mTOR inhibitor to a subject in need thereof;
wherein the bi-steric mTOR inhibitor is

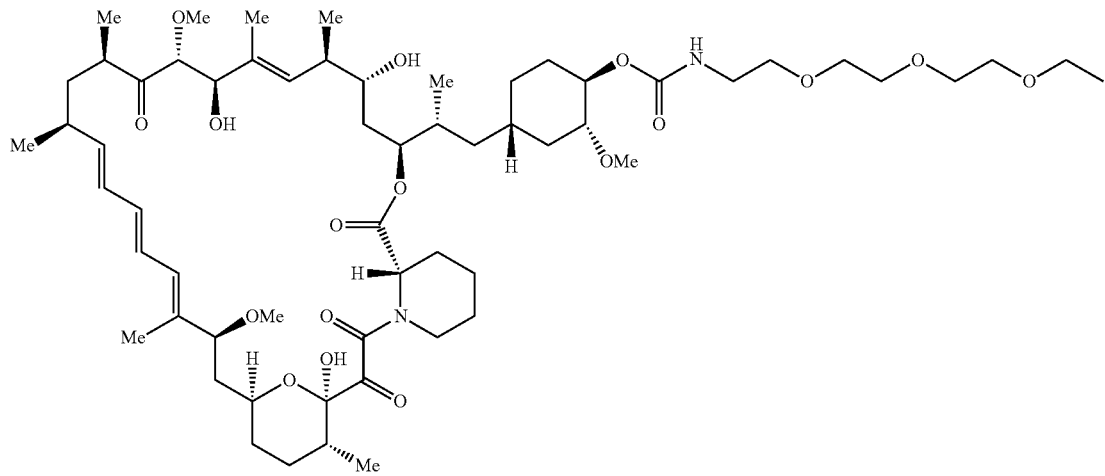

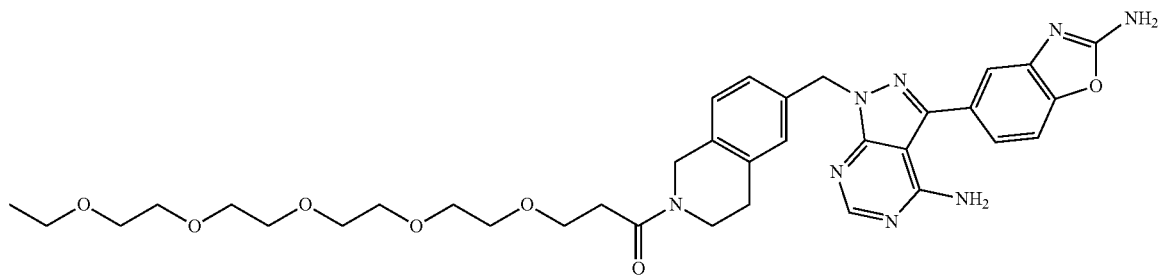

or a stereoisomer, tautomer, or oxepane isomer thereof, or pharmaceutically acceptable salt of any of the foregoing.

Embodiment I-161. Use of a bi-steric mTOR inhibitor in the manufacture of a medicament for treatment of acquired resistance to a RAS inhibitor, wherein the treatment comprises administering the medicament to a subject in need thereof to deliver a dosage of about 3 mg/week to about 25 mg/week of the bi-steric mTOR inhibitor;
wherein the bi-steric mTOR inhibitor is

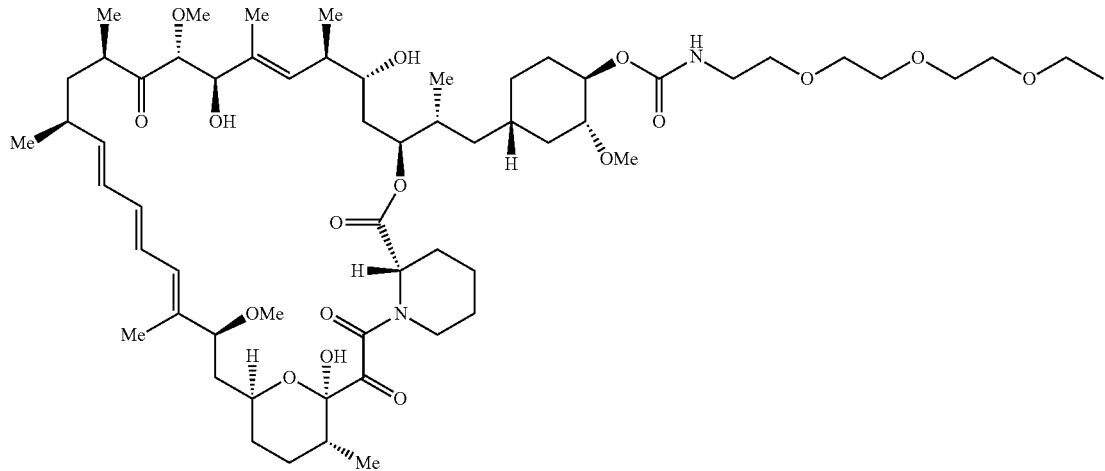

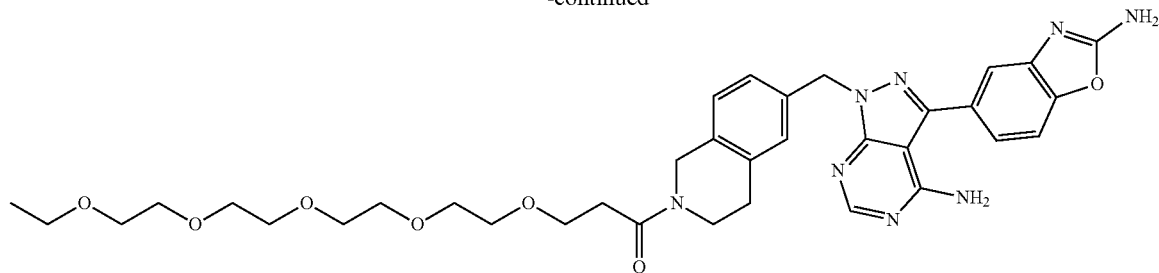

or a stereoisomer, tautomer, or oxepane isomer thereof, or pharmaceutically acceptable salt of any of the foregoing.

Embodiment I-162. A bi-steric mTOR inhibitor for use in a method of treating acquired resistance to a RAS inhibitor, the method comprising administering a dosage of about 3 mg/week to about 25 mg/week of the bi-steric mTOR inhibitor to a subject in need thereof;

wherein the bi-steric mTOR inhibitor is

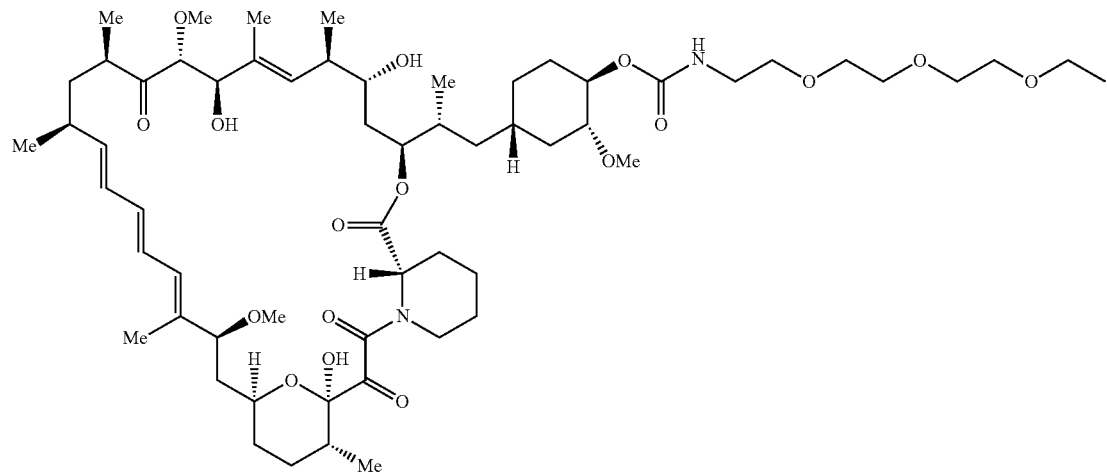

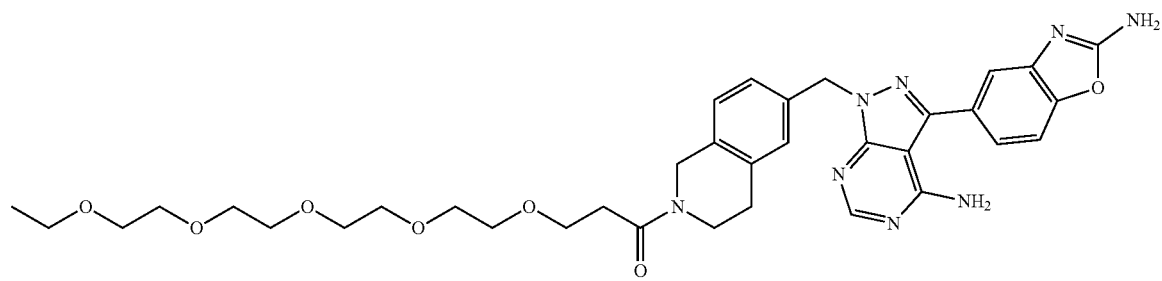

or a stereoisomer, tautomer, or oxepane isomer thereof, or pharmaceutically acceptable salt of any of the foregoing.

Embodiment I-163. A medicament for treatment of acquired resistance to a RAS inhibitor, the medicament comprising a bi-steric mTOR inhibitor, wherein the treatment comprises administering the medicament to deliver a dosage of about 3 mg/week to about 25 mg/week of the bi-steric mTOR inhibitor to a subject in need thereof;

wherein the bi-steric mTOR inhibitor is

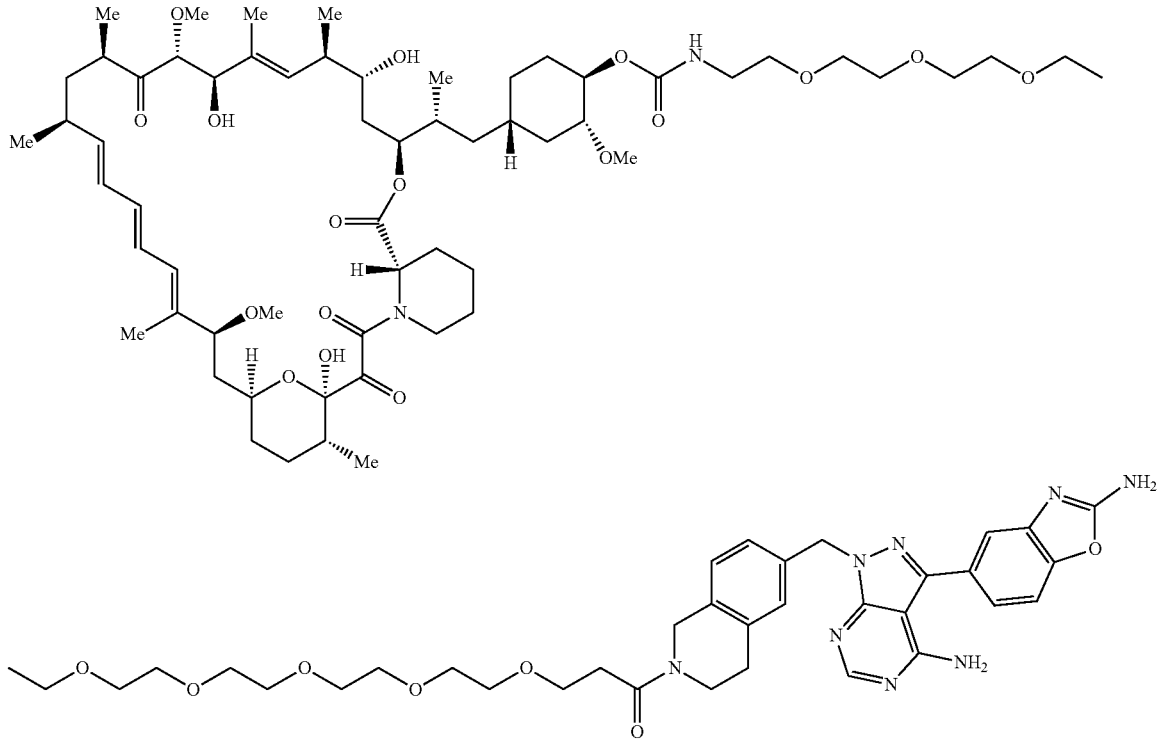

or a stereoisomer, tautomer, or oxepane isomer thereof, or pharmaceutically acceptable salt of any of the foregoing.

Embodiment I-164. The use, the bi-steric mTOR inhibitor for use, or the medicament for treatment of any one of embodiments I-154 to I-163, wherein the method or the treatment further comprises administering to the subject an effective amount of the RAS inhibitor.

Embodiment I-165. The use, the bi-steric mTOR inhibitor for use, or the medicament for treatment of any one of embodiments I-154 to I-164, wherein the RAS inhibitor targets a specific RAS mutation.

Embodiment I-166. The use, the bi-steric mTOR inhibitor for use, or the medicament for treatment of any one of embodiments I-154 to I-165, wherein the RAS inhibitor targets a KRAS mutation.

Embodiment I-167. The use, the bi-steric mTOR inhibitor for use, or the medicament for treatment of any one of embodiments I-154 to I-166, wherein the RAS inhibitor targets the $KRAS^{G12C}$ mutation.

Embodiment I-168. The use, the bi-steric mTOR inhibitor for use, or the medicament for treatment of any one of embodiments I-154 to I-167, wherein the RAS inhibitor is a KRAS(OFF) inhibitor.

Embodiment I-169. The use, the bi-steric mTOR inhibitor for use, or the medicament for treatment of embodiment 1-168, wherein the KRAS(OFF) inhibitor is AMG 510, MRTX849, JDQ443, MRTX1133, ERAS-3490, ERAS-4, BPI-421286, D-1553, JAB-21822, GH-35, ICP-915, IB1351, LY3537982, GDC-6036, BI1823911, RSC-1255, or a pharmaceutically acceptable salt of any of the foregoing.

Embodiment I-170. The use, the bi-steric mTOR inhibitor for use, or the medicament for treatment of any one of embodiments I-154 to I-167, wherein the RAS inhibitor is a RAS(ON) inhibitor.

Embodiment I-171. The use, the bi-steric mTOR inhibitor for use, or the medicament for treatment of embodiment I-170, wherein the RAS(ON) inhibitor is a KRAS(ON) inhibitor.

Embodiment I-172. The use, the bi-steric mTOR inhibitor for use, or the medicament for treatment of embodiment 1-171, wherein the KRAS(ON) inhibitor is RMC-6236, RMC-6291, RMC-9805, RMC-8839, or a pharmaceutically acceptable salt of any of the foregoing.

Embodiment I-173. The use, the bi-steric mTOR inhibitor for use, or the medicament for treatment of embodiment 1-171 or 1-172, wherein the KRAS(ON) inhibitor is a $KRAS^{G12C}$ (ON) inhibitor.

Embodiment I-174. The use, the bi-steric mTOR inhibitor for use, or the medicament for treatment of embodiment 1-173, wherein the $KRAS^{G12C}$ (ON) inhibitor is RMC-6291 or a pharmaceutically acceptable salt thereof.

Embodiment I-175. The use, the bi-steric mTOR inhibitor for use, or the medicament for treatment of any one of embodiments I-154 to I-174, wherein the subject is administered the RAS inhibitor to treat or prevent a cancer.

Embodiment I-176. The use, the bi-steric mTOR inhibitor for use, or the medicament for treatment of any one of embodiments I-156 to I-175, wherein the subject has a cancer.

Embodiment I-177. The use, the bi-steric mTOR inhibitor for use, or the medicament for treatment of any one of embodiments 1-154, 1-155, 1-175, and I-176, wherein the cancer comprises a KRAS$^{G12C}$ mutation.

Embodiment I-178. The use, the bi-steric mTOR inhibitor for use, or the medicament for treatment of any one of embodiments 1-154, 1-155, and I-175 to I-177, wherein the cancer comprises co-occurring KRAS$^{G12C}$ and STK11 mutations.

Embodiment I-179. The use, the bi-steric mTOR inhibitor for use, or the medicament for treatment of any one of embodiments 1-154, 1-155, and I-175 to I-178, wherein the cancer is a non-small cell lung cancer (NSCLC) or a colorectal cancer.

Embodiment I-180. The use, the bi-steric mTOR inhibitor for use, or the medicament for treatment of any one of embodiments 1-154, 1-155, 1-175 to I-179, wherein the cancer comprises co-occurring KRAS$^{G12C}$ and PIK3CA$^{E545K}$ mutations.

Embodiment I-181. The use, the bi-steric mTOR inhibitor for use, or the medicament for treatment of any one of embodiments 1-154, 1-155, 1-175 to I-178, and I-180 wherein the cancer is a colorectal cancer.

Embodiment I-182. The use, the bi-steric mTOR inhibitor for use, or the medicament for treatment of any one of embodiments I-154 to I-181, wherein the method or the treatment results in tumor regression.

Embodiment I-183. The use, the bi-steric mTOR inhibitor for use, or the medicament for treatment of any one of embodiments I-154 to I-182, wherein the method or the treatment results in tumor apoptosis.

Embodiment II-1. A method of treating a subject having a cancer, the method comprising administering a dosage of about 3 mg/week to about 25 mg/week of a compound to the subject;

wherein the compound is

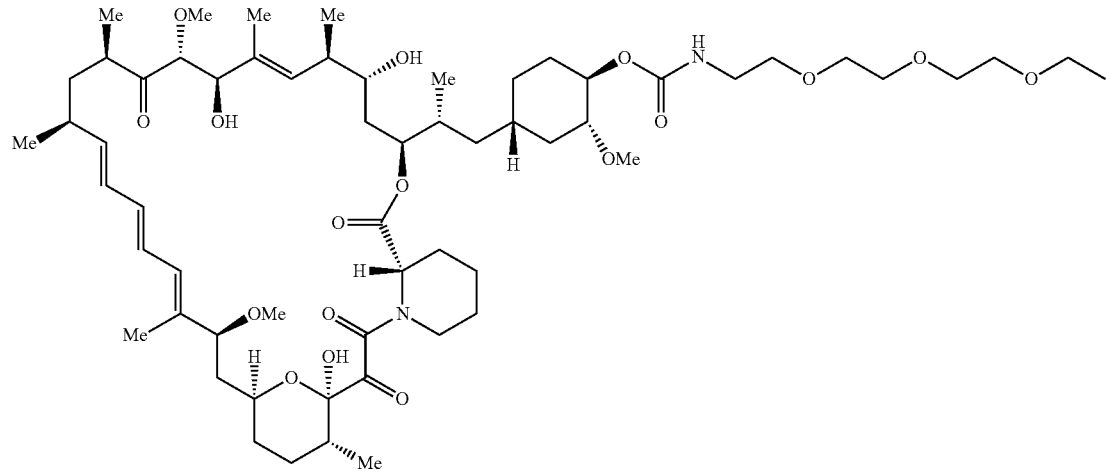

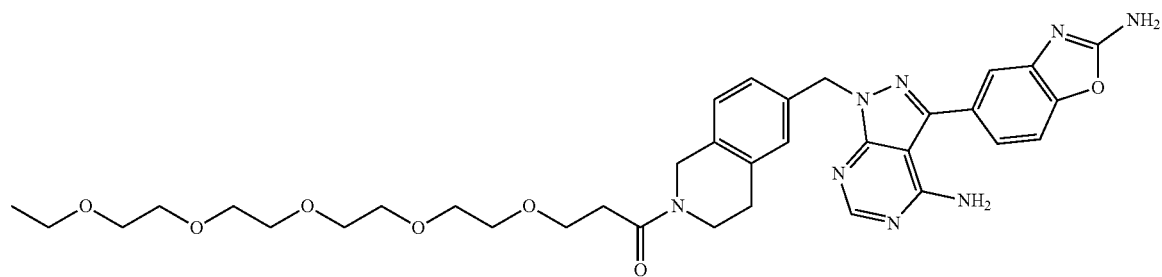

or a stereoisomer, tautomer, or oxepane isomer thereof, or pharmaceutically acceptable salt of any of the foregoing.

Embodiment II-2. Use of a compound in a treatment of cancer, wherein the treatment comprises administering a dosage of about 3 mg/week to about 25 mg/week of the compound to a subject in need thereof;

wherein the compound is

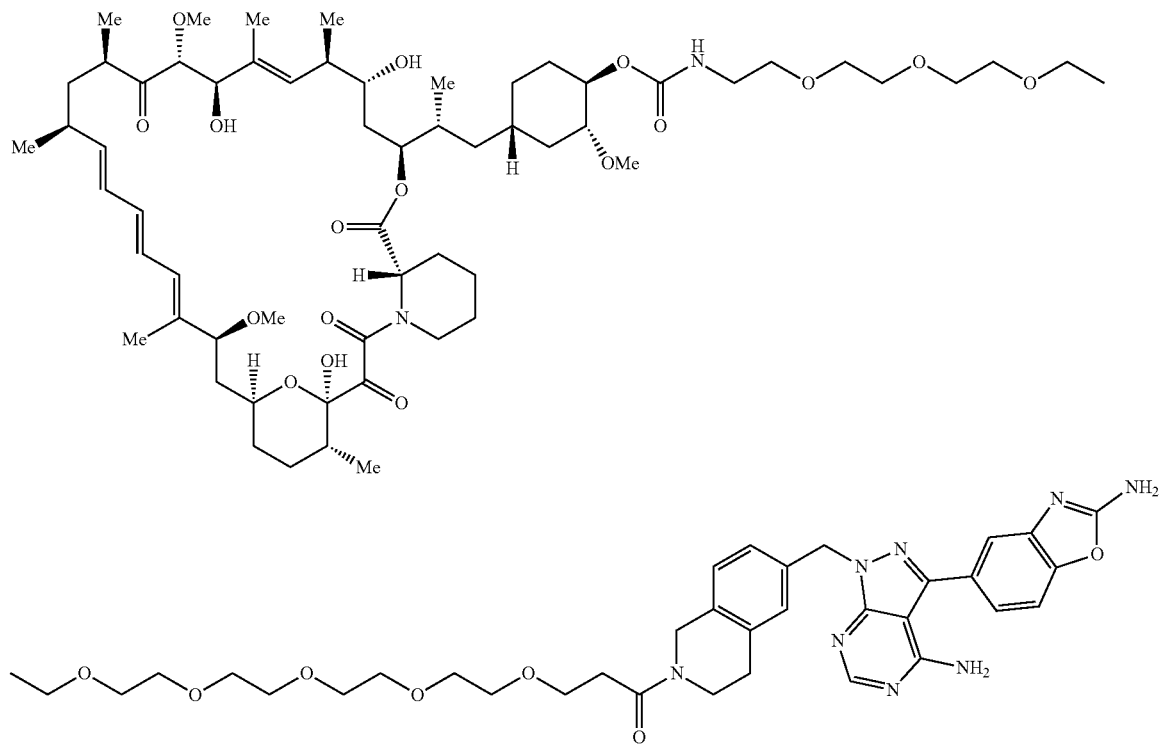

or a stereoisomer, tautomer, or oxepane isomer thereof, or pharmaceutically acceptable salt of any of the foregoing.

Embodiment II-3. Use of a compound in the manufacture of a medicament for treatment of cancer, wherein the treatment comprises administering the medicament to a subject in need thereof to deliver a dosage of about 3 mg/week to about 25 mg/week of the compound;

wherein the compound is

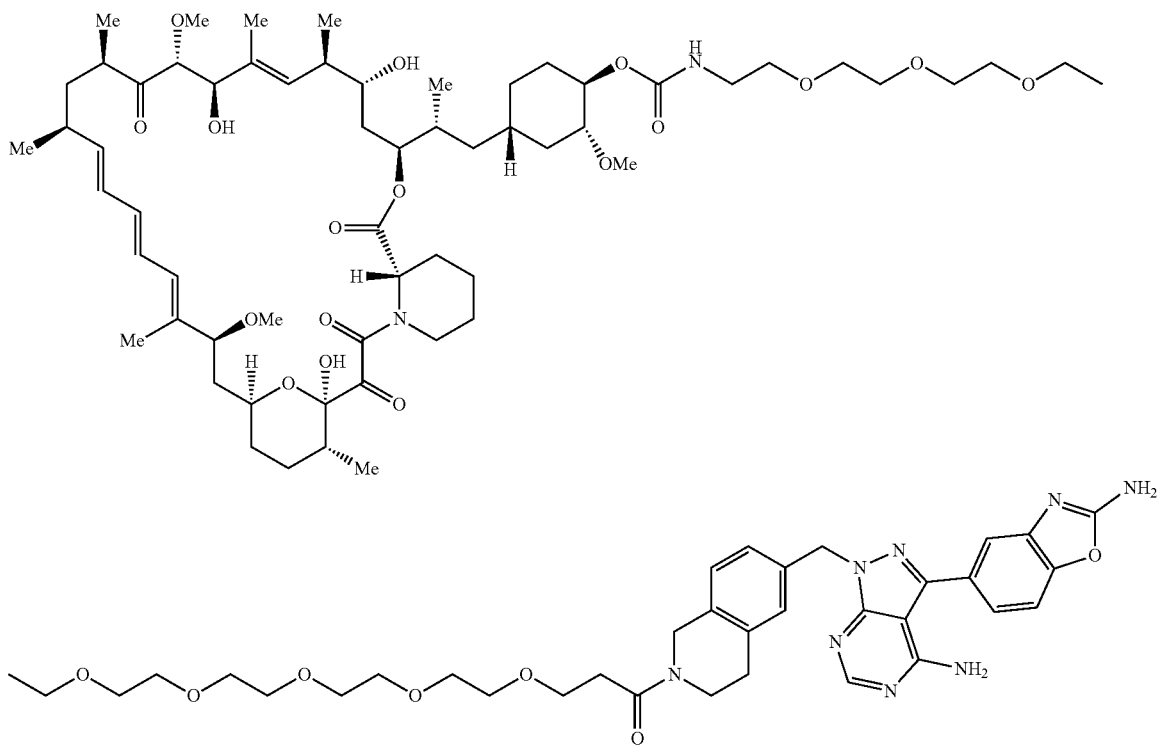

or a stereoisomer, tautomer, or oxepane isomer thereof, or pharmaceutically acceptable salt of any of the foregoing.

Embodiment II-4. A compound for use in a method of treating cancer, the method comprising administering a dosage of about 3 mg/week to about 25 mg/week of the compound to a subject in need thereof;

wherein the compound is

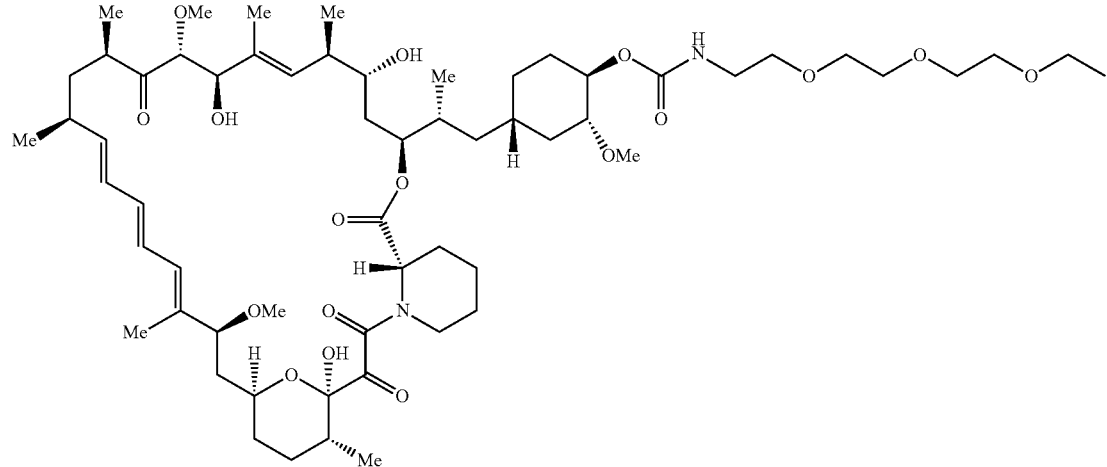

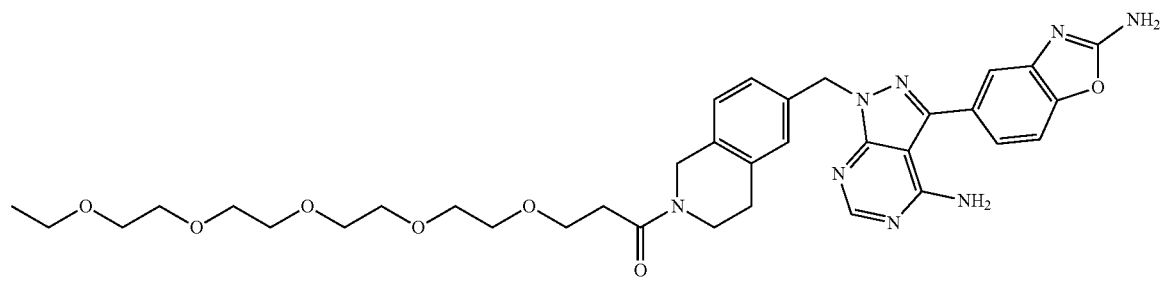

or a stereoisomer, tautomer, or oxepane isomer thereof, or pharmaceutically acceptable salt of any of the foregoing.

Embodiment II-5. A medicament for treatment of cancer, the medicament comprising a compound, wherein the treatment comprises administering the medicament to deliver a dosage of about 3 mg/week to about 25 mg/week of the compound to a subject in need thereof;

wherein the compound is

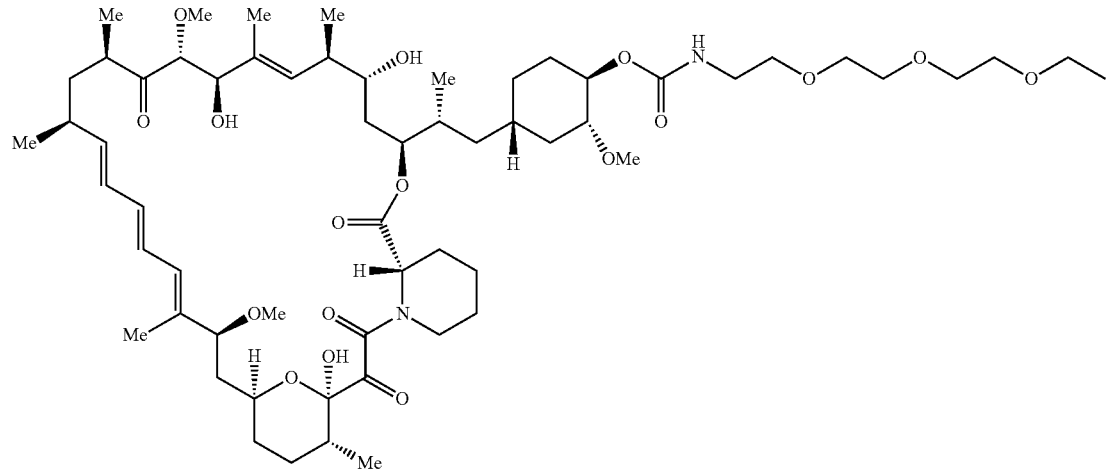

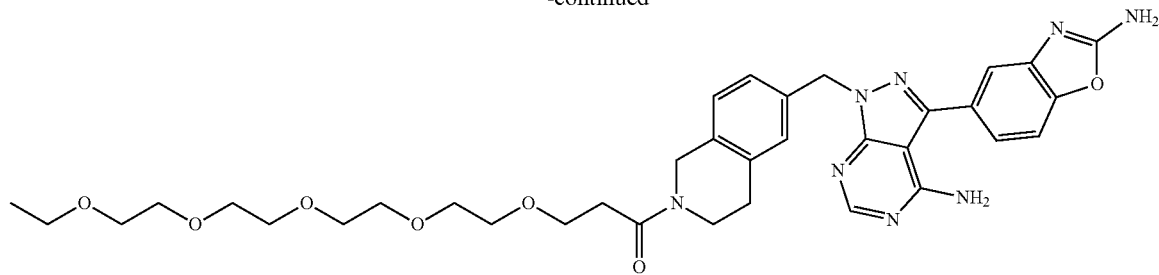

or a stereoisomer, tautomer, or oxepane isomer thereof, or pharmaceutically acceptable salt of any of the foregoing.

Embodiment II-6. A method of treating a subject having salivary gland cancer, the method comprising administering a dosage of about 3 mg/week to about 25 mg/week of a compound to the subject;
wherein the compound is

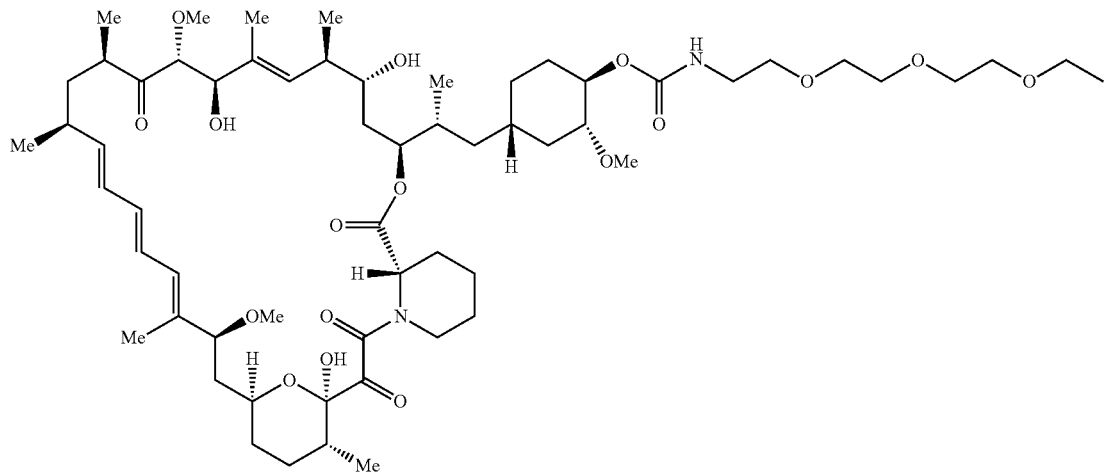

or a stereoisomer, tautomer, or oxepane isomer thereof, or pharmaceutically acceptable salt of any of the foregoing.

Embodiment II-7. A method for delaying or preventing acquired resistance to a RAS inhibitor in a subject in need thereof, comprising administering to the subject about 3 mg/week to about 25 mg/week of a compound, wherein the subject has already received or will receive administration of the RAS inhibitor;

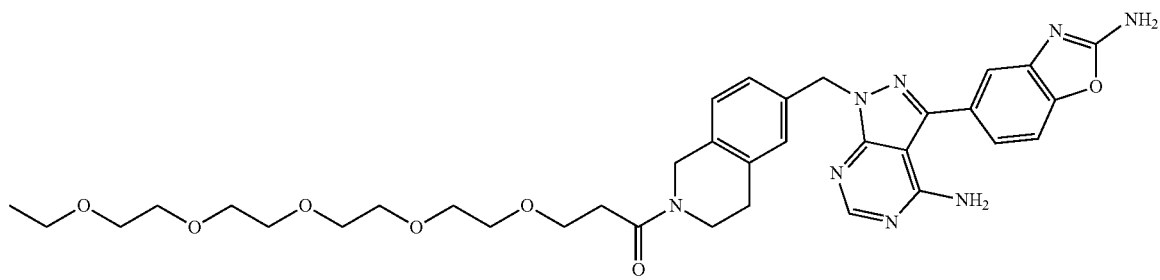

wherein the compound is
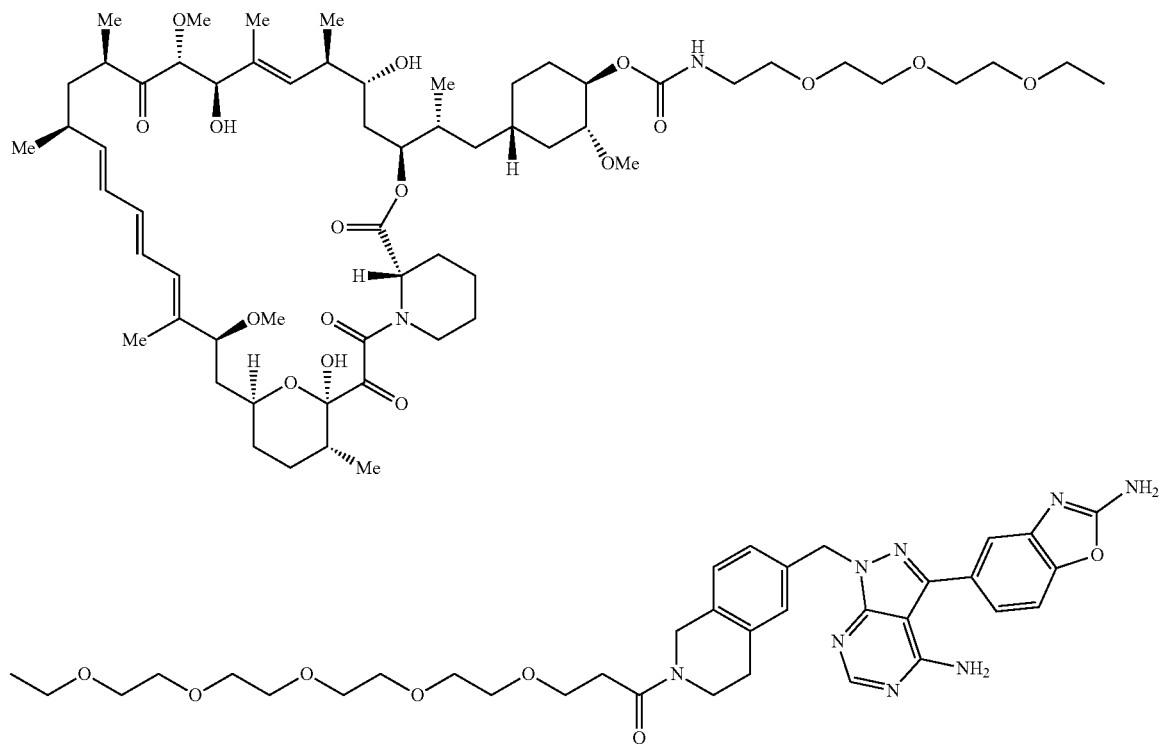
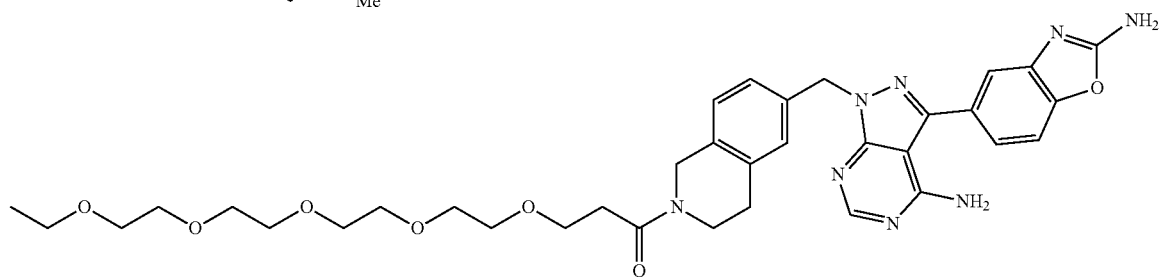
or a stereoisomer, tautomer, or oxepane isomer thereof, or pharmaceutically acceptable salt of any of the foregoing.
Embodiment II-8. A method of treating acquired resistance to a RAS inhibitor in a subject in need thereof, comprising administering to the subject about 3 mg/week to about 25 mg/week of a compound;
wherein the compound is
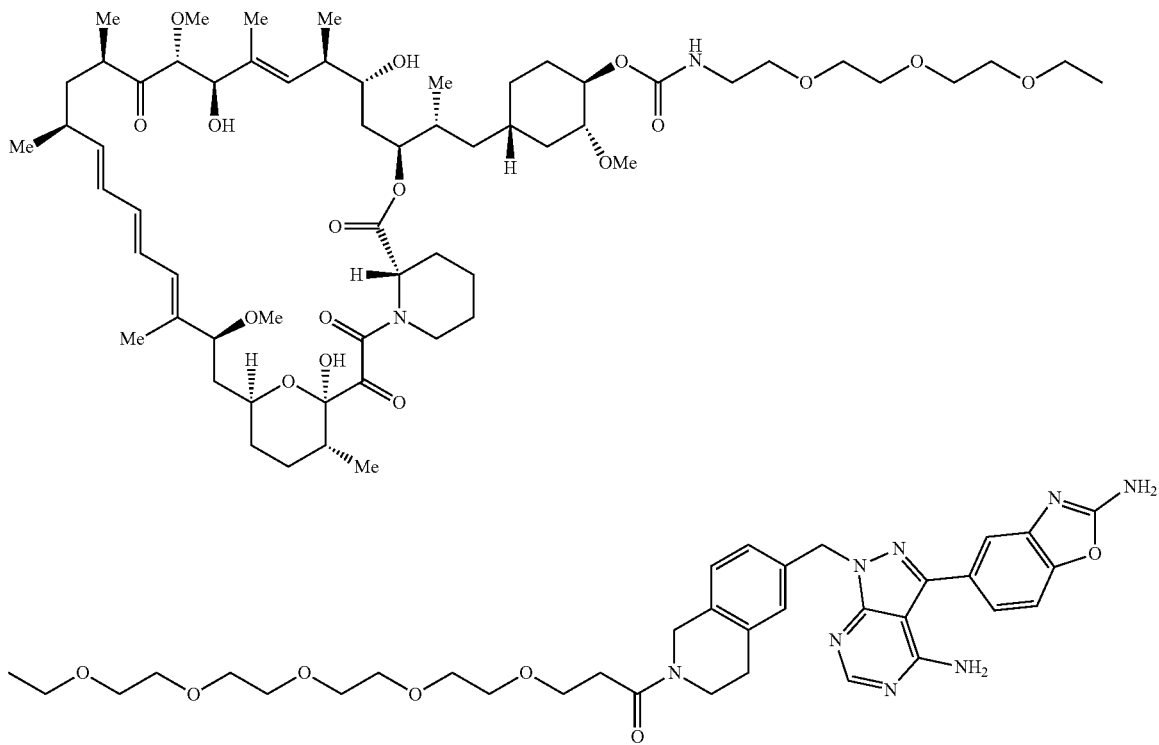

or a stereoisomer, tautomer, or oxepane isomer thereof, or pharmaceutically acceptable salt of any of the foregoing.

Embodiment II-9. A compound for use in a method treating cancer in a subject having acquired resistance to a RAS inhibitor, the method comprising administering a dosage of about 3 mg/week to about 25 mg/week of the compound to the subject, wherein the subject has already received or will receive administration of the RAS inhibitor; wherein the compound is

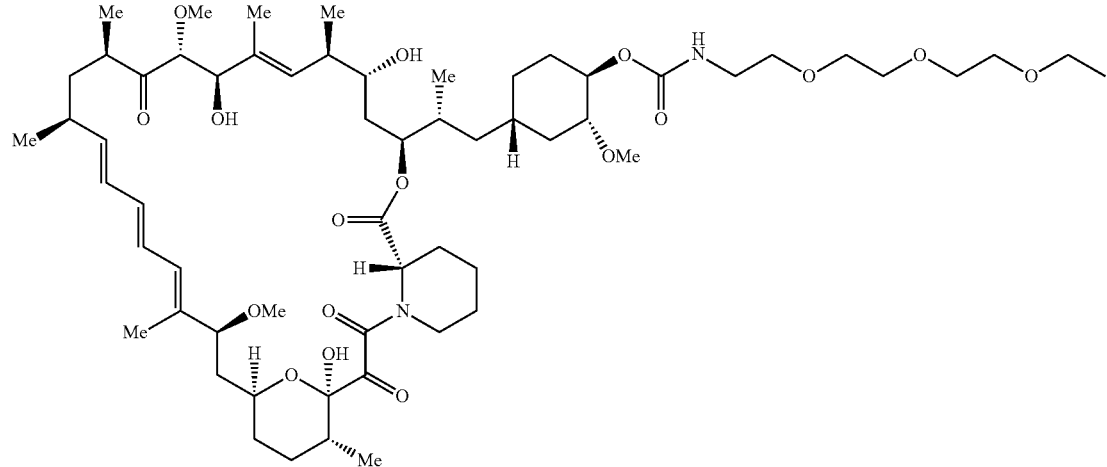

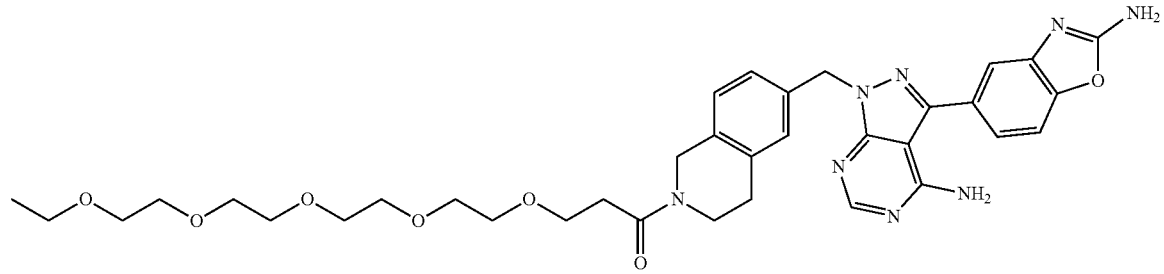

or a stereoisomer, tautomer, or oxepane isomer thereof, or pharmaceutically acceptable salt of any of the foregoing.

Embodiment II-10. A combination of compound and a RAS inhibitor for simultaneous, separate, or sequential use in a method of treating cancer in a subject having acquired resistance to the RAS inhibitor, the method comprising administering a dosage of about 3 mg/week to about 25 mg/week of the compound to a subject in need thereof; wherein the compound is

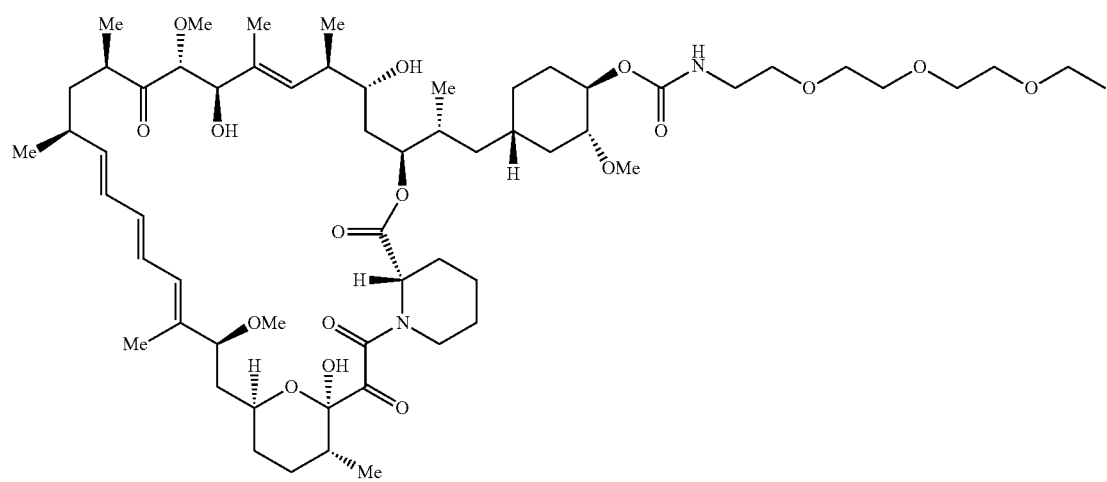

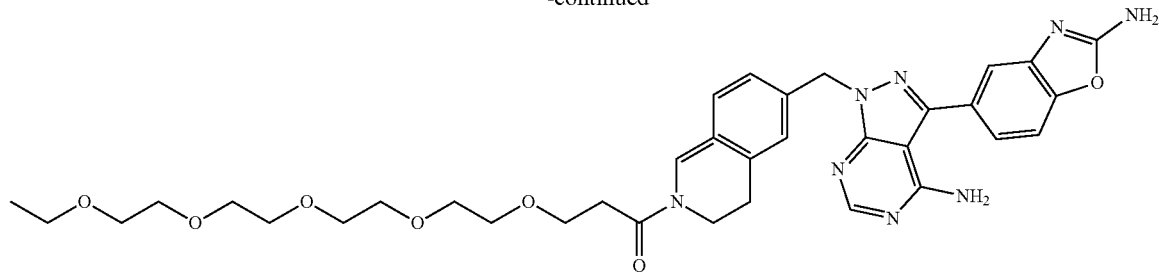

or a stereoisomer, tautomer, or oxepane isomer thereof, or pharmaceutically acceptable salt of any of the foregoing.

Embodiment II-11. Use of a compound in a treatment for delaying or preventing acquired resistance to a RAS inhibitor in a subject in need thereof, comprising administering to the subject about 3 mg/week to about 25 mg/week of a compound, wherein the subject has already received or will receive administration of the RAS inhibitor;

wherein the compound is

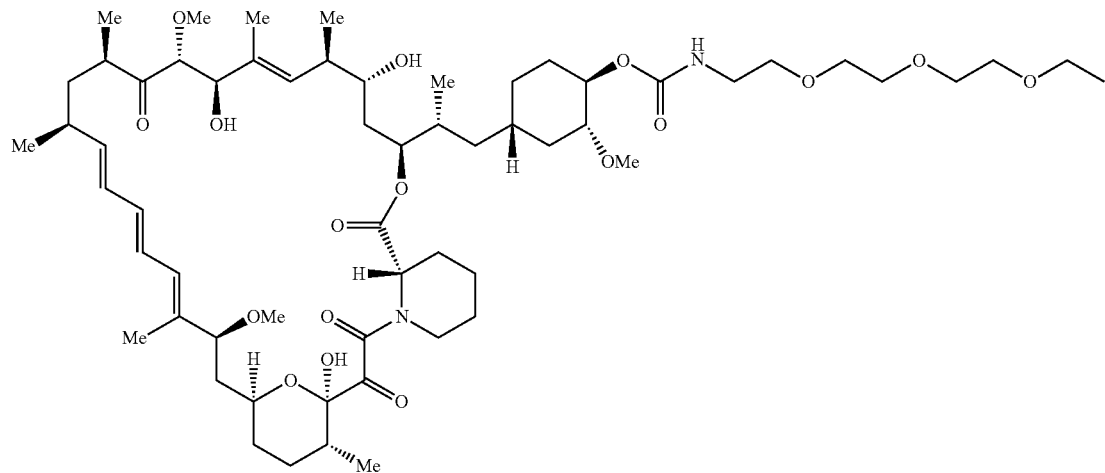

or a stereoisomer, tautomer, or oxepane isomer thereof, or pharmaceutically acceptable salt of any of the foregoing.

Embodiment II-12. Use of a compound in the manufacture of a medicament for treatment for delaying or preventing acquired resistance to a RAS inhibitor, wherein the treatment comprises administering the medicament to a subject in need thereof to deliver a dosage of about 3 mg/week to about 25 mg/week of the compound, wherein the subject has already received or will receive administration of the RAS inhibitor;

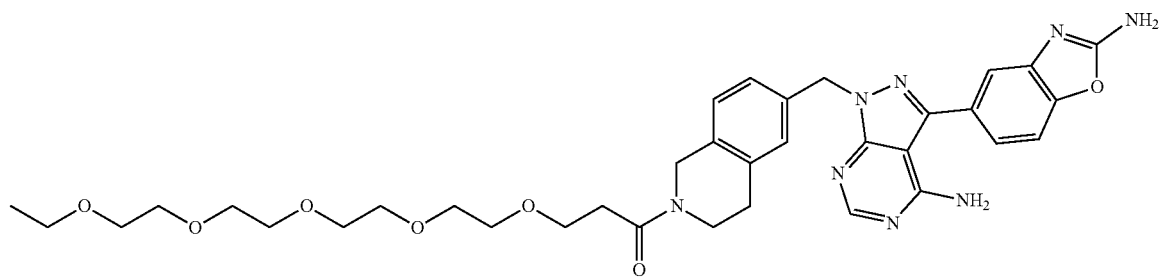

wherein the compound is

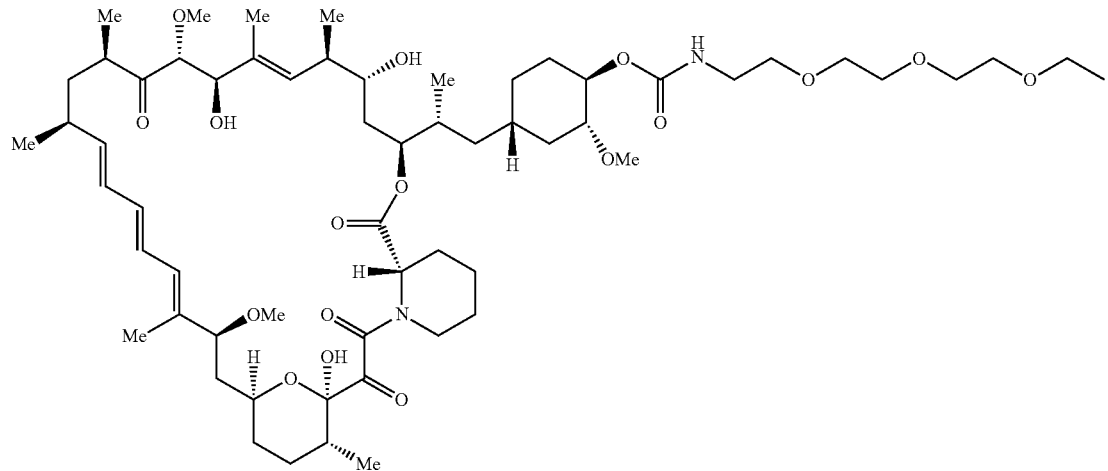

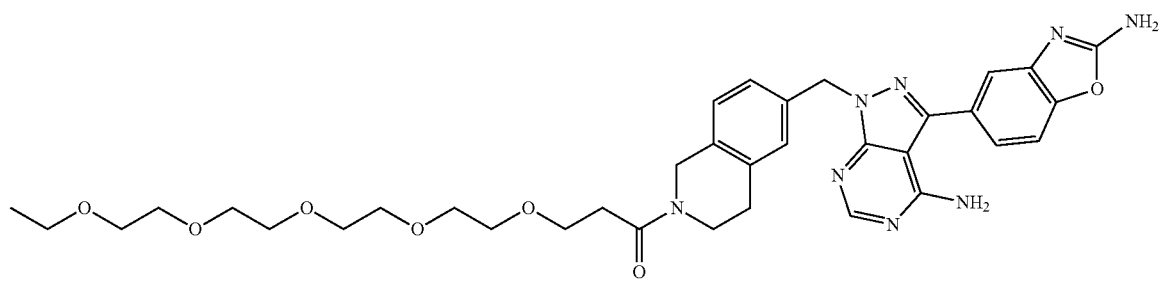

or a stereoisomer, tautomer, or oxepane isomer thereof, or pharmaceutically acceptable salt of any of the foregoing.

Embodiment II-13. A compound for use in a method of delaying or preventing acquired resistance to a RAS inhibitor, the method comprising administering a dosage of about 3 mg/week to about 25 mg/week of the compound to a subject in need thereof, wherein the subject has already received or will receive administration of the RAS inhibitor; wherein the compound is

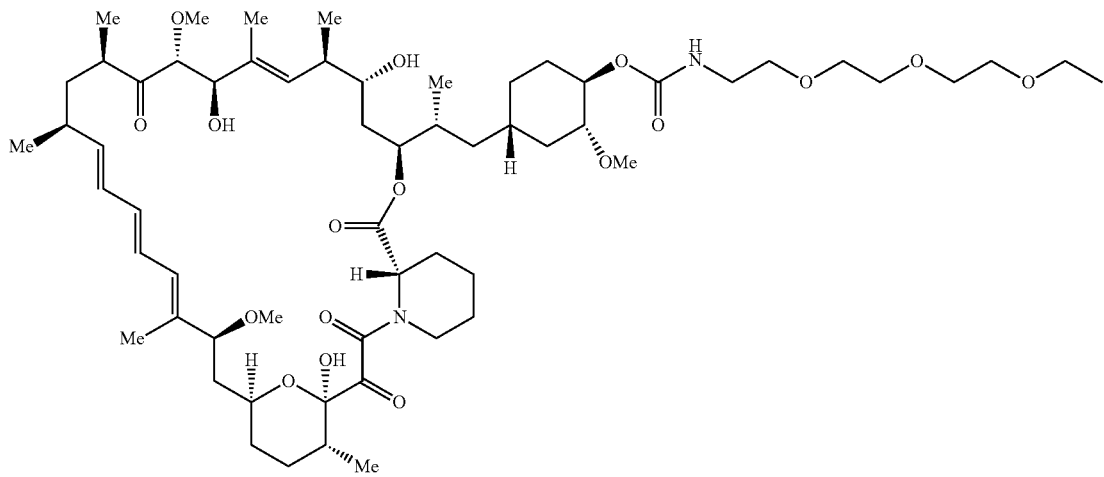

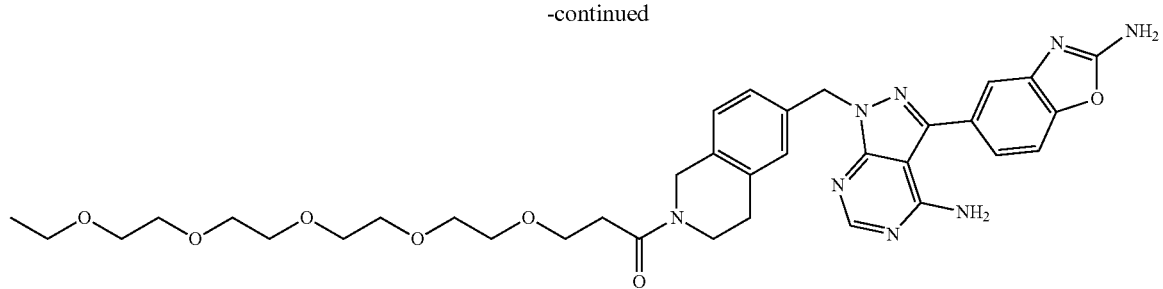

or a stereoisomer, tautomer, or oxepane isomer thereof, or pharmaceutically acceptable salt of any of the foregoing.

Embodiment II-14. A medicament for treatment for delaying or preventing acquired resistance to a RAS inhibitor, the medicament comprising a compound, wherein the treatment comprises administering the medicament to deliver a dosage of about 3 mg/week to about 25 mg/week of the compound to a subject in need thereof, wherein the subject has already received or will receive administration of the RAS inhibitor; wherein the compound is

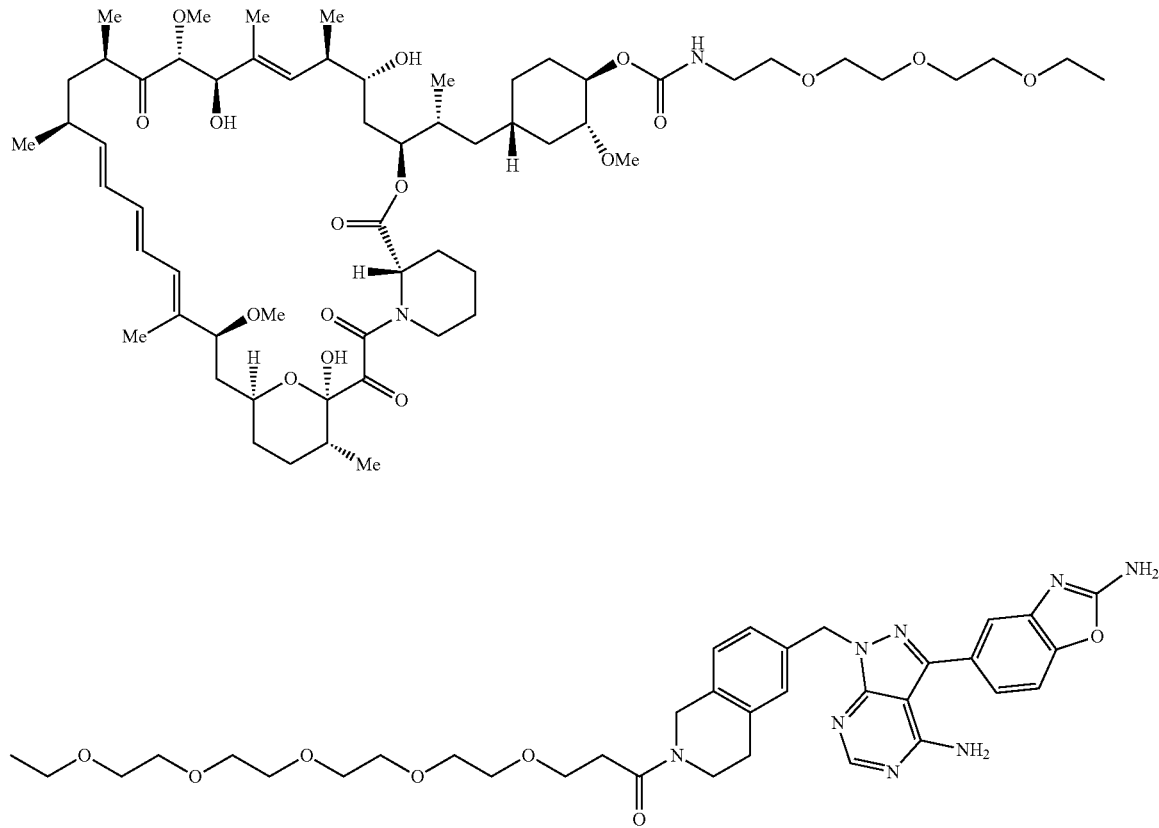

or a stereoisomer, tautomer, or oxepane isomer thereof, or pharmaceutically acceptable salt of any of the foregoing.

Embodiment II-15. Use of a compound in a treatment of acquired resistance to a RAS inhibitor, wherein the treatment comprises administering a dosage of about 3 mg/week to about 25 mg/week of the compound to a subject in need thereof;

wherein the compound is

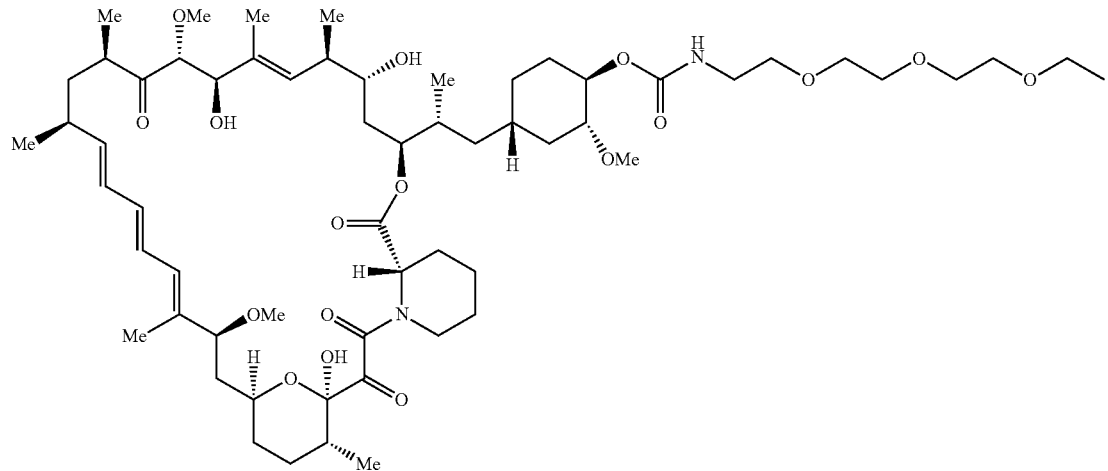

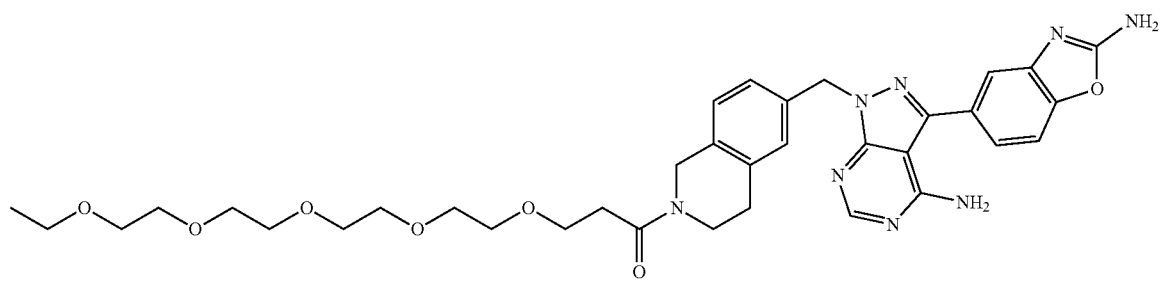

or a stereoisomer, tautomer, or oxepane isomer thereof, or pharmaceutically acceptable salt of any of the foregoing.

Embodiment II-16. Use of a compound in the manufacture of a medicament for treatment of acquired resistance to a RAS inhibitor, wherein the treatment comprises administering the medicament to a subject in need thereof to deliver a dosage of about 3 mg/week to about 25 mg/week of the compound;

wherein the compound is

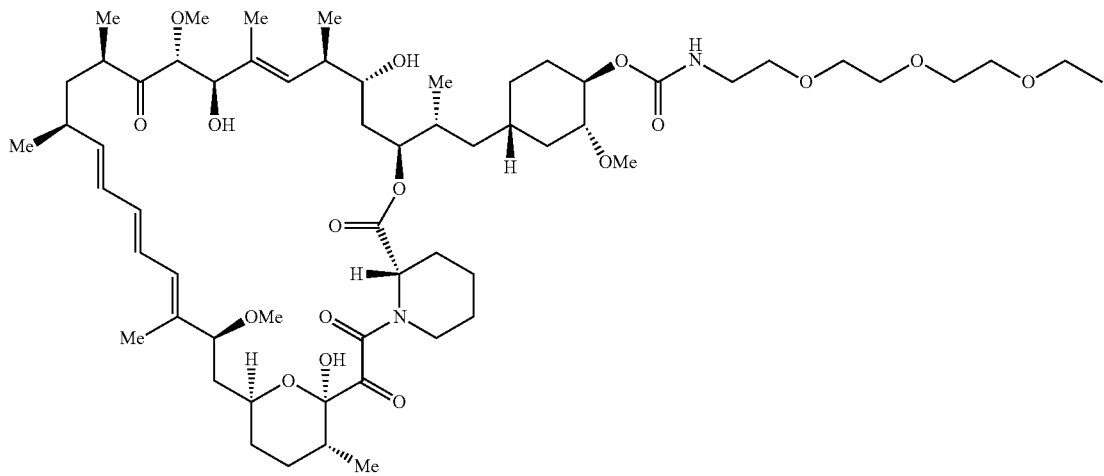

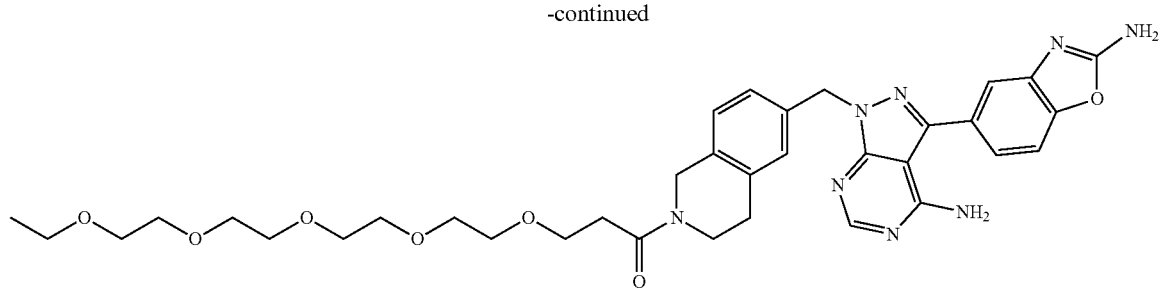

or a stereoisomer, tautomer, or oxepane isomer thereof, or pharmaceutically acceptable salt of any of the foregoing.

Embodiment II-17. A compound for use in a method of treating acquired resistance to a RAS inhibitor, the method comprising administering a dosage of about 3 mg/week to about 25 mg/week of the compound to a subject in need thereof;

wherein the compound is

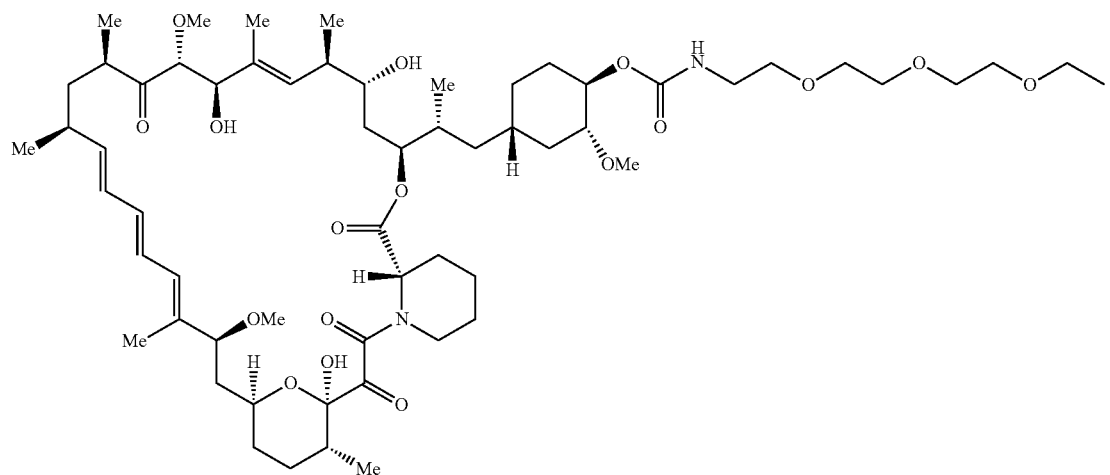

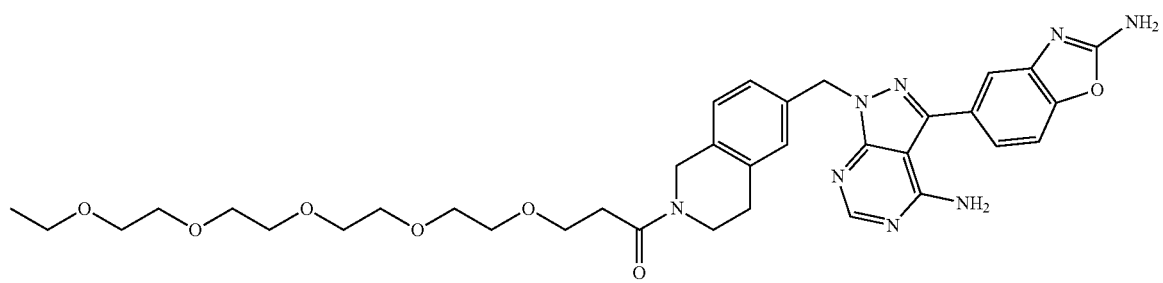

or a stereoisomer, tautomer, or oxepane isomer thereof, or pharmaceutically acceptable salt of any of the foregoing.

Embodiment II-18. A medicament for treatment of acquired resistance to a RAS inhibitor, the medicament comprising a compound, wherein the treatment comprises administering the medicament to deliver a dosage of about 3 mg/week to about 25 mg/week of the compound to a subject in need thereof;

wherein the compound is

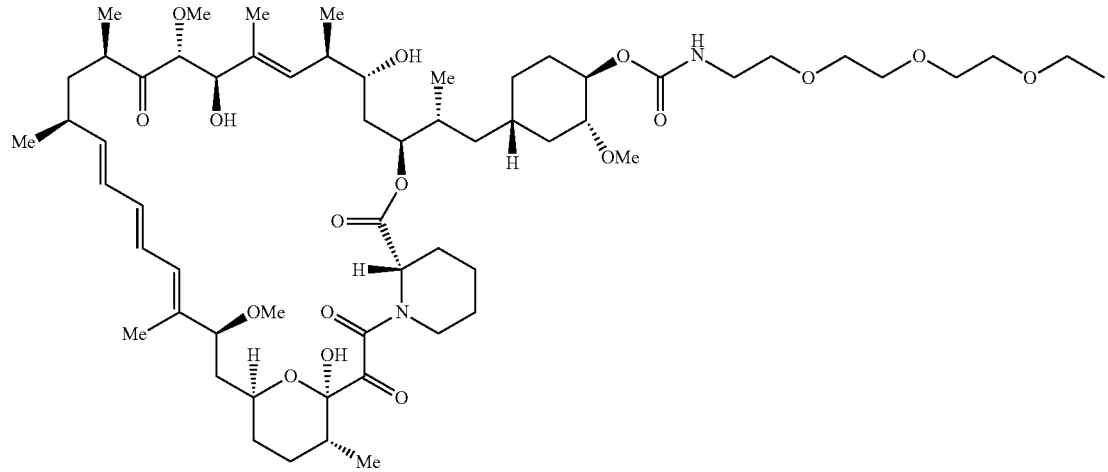

or a stereoisomer, tautomer, or oxepane isomer thereof, or pharmaceutically acceptable salt of any of the foregoing.

Embodiment II-19. A method of treating or preventing mucositis in a subject in need thereof that has been, is being, or will be treated with an mTOR inhibitor, the method comprising administering a tacrolimus solution to the subject.

Embodiment II-20. Use of a tacrolimus solution in a method of treating or preventing mucositis, wherein the treatment comprises administering the tacrolimus solution to a subject that has been, is being, or will be treated with an mTOR inhibitor.

Embodiment II-21. Use of a tacrolimus solution in the manufacture of a medicament for treatment or prevention of mucositis, wherein the treatment comprises administering the medicament to a subject that has been, is being, or will be treated with an mTOR inhibitor.

Embodiment II-22. A tacrolimus solution for use in a method of treating or preventing mucositis, the method comprising administering the tacrolimus solution to a subject that has been, is being, or will be treated with an mTOR inhibitor.

Embodiment II-23. A medicament for treatment or prevention of mucositis, the medicament comprising a tacrolimus solution, wherein the treatment comprises administering the medicament to a subject that has been, is being, or will be treated with an mTOR inhibitor.

Embodiment II-24. The method, use, tacrolimus solution, and medicament of embodiments II-19 to II-23, wherein the mucositis is stomatitis.

Embodiment II-25. The method, use, tacrolimus solution, and medicament of embodiments II-19 to II-24, wherein the mTOR inhibitor is everolimus, sirolimus, and nab-sirolimus, or a combination of the foregoing.

Embodiment II-26. The method, use, tacrolimus solution, and medicament of embodiments II-19 to II-24, wherein the mTOR inhibitor is a compound of the structure

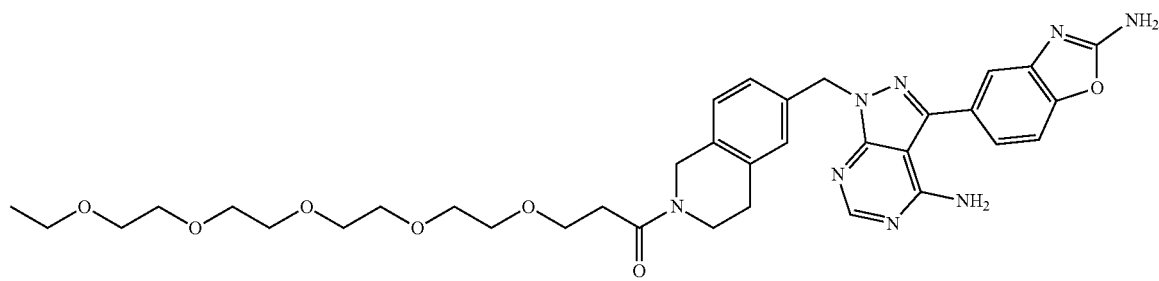

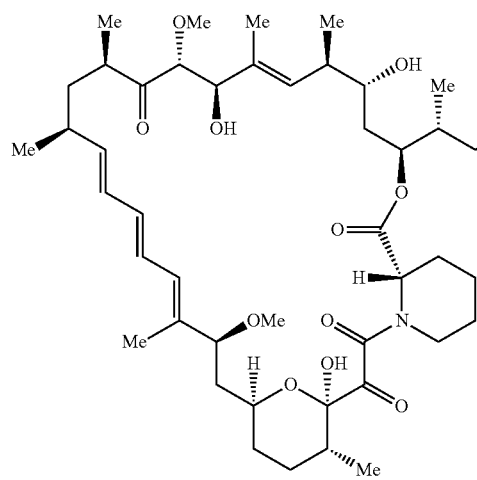

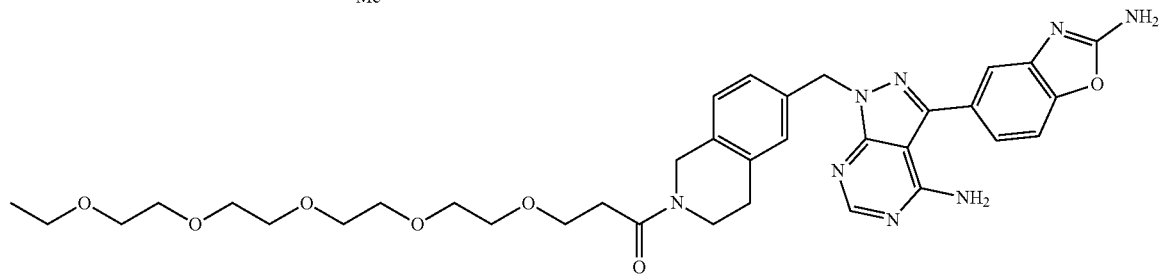

or a stereoisomer, tautomer, or oxepane isomer thereof, or pharmaceutically acceptable salt of any of the foregoing.

Embodiment II-27. The method, use, tacrolimus solution, and medicament of embodiment II-26, wherein the subject is administered a dosage of about 3 mg/week to about 25 mg/week of the compound, or a stereoisomer, tautomer, or oxepane isomer thereof, or pharmaceutically acceptable salt of any of the foregoing.

Embodiment II-28. The method, use, compound, medicament, combination, and tacrolimus solution of embodiments II-1 to II-18 and II-27, wherein the dosage is about 4 mg/week to about 25 mg/week, about 4 mg/week to about 14 mg/week, about 4 mg/week to about 12 mg/week, about 5 mg/week to about 25 mg/week, about 5 mg/week to about 14 mg/week, about 5 mg/week to about 12 mg/week, about 5 mg/week to about 10 mg/week, about 6 mg/week to about 25 mg/week, about 6 mg/week to about 14 mg/week, about 6 mg/week to about 12 mg/week, about 6 mg/week to about 9 mg/week, about 6 mg/week to about 8 mg/week, about 7 mg/week to about 25 mg/week, about 7 mg/week to about 14 mg/week, about 7 mg/week to about 12 mg/week, about 7 mg/week to about 8 mg/week, about 8 mg/week to about 25 mg/week, about 8 mg/week to about 14 mg/week, about 8 mg/week to about 12 mg/week, or about 8 mg/week to about 10 mg/week.

Embodiment II-29. The method, use, compound, medicament, combination, and tacrolimus solution of embodiments II-1 to II-18, II-27, and II-28 wherein the dosage is about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week.

Embodiment II-30. The method, use, compound, medicament, combination, and tacrolimus solution of embodiments 11-1 to 11-18 and 11-27 to 11-30, wherein the dosage in a first 1, 2, 3, 4, or 5 week(s) is higher than the dosage in following weeks.

Embodiment II-31. The method, use, compound, medicament, combination, and tacrolimus solution of embodiment II-30, wherein the dosage in the first 1, 2, 3, 4, or 5 weeks is about 6 mg/week to about 25 mg/week, about 6 mg/week to about 20 mg/week, about 6 mg/week to about 16 mg/week, about 6 mg/week to about 14 mg/week, about 6 mg/week to about 12 mg/week, about 6 mg/week to about 10 mg/week, about 8 mg/week to about 25 mg/week, about 8 mg/week to about 20 mg/week, about 8 mg/week to about 16 mg/week, about 8 mg/week to about 14 mg/week, about 8 mg/week to about 12 mg/week, about 8 mg/week to about 10 mg/week, about 10 mg/week to about 25 mg/week, about 10 mg/week to about 20 mg/week, about 10 mg/week to about 16 mg/week, about 10 mg/week to about 14 mg/week, or about 10 mg/week to about 12 mg/week.

Embodiment II-32. The method, use, compound, medicament, combination, and tacrolimus solution of embodiment 11-30 or 11-31, wherein the dosage in the first 1, 2, 3, 4, or 5 weeks is about 6 mg/week, about 6.5 mg/week, about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week.

Embodiment II-33. The method, use, compound, medicament, combination, and tacrolimus solution of embodiments II-30 to II-32, wherein the dosage in the first week is higher than the dosage in following weeks.

Embodiment II-34. The method, use, compound, medicament, combination, and tacrolimus solution of embodiments 11-30 to 11-33, wherein the dosage in the first 1, 2, 3, 4, or 5 week(s) is followed by 1, 2, 3, 4, or 5 weeks without administration.

Embodiment II-35. The method, use, compound, medicament, combination, and tacrolimus solution of embodiments II-30 to II-34, wherein the dosage after 1, 2, 3, 4, 5, 6, 7, 8, 9, or 10 week(s) is about 3 mg/week to about 12 mg/week, about 3 mg/week to about 10 mg/week, about 3 mg/week to about 8 mg/week, about 3 mg/week to about 6 mg/week, about 4 mg/week to about 12 mg/week, about 4 mg/week to about 10 mg/week, about 4 mg/week to about 8 mg/week, about 4 mg/week to about 6 mg/week, about 5 mg/week to about 12 mg/week, about 5 mg/week to about 10 mg/week, about 5 mg/week to about 8 mg/week, about 5 mg/week to about 6 mg/week, about 6 mg/week to about 12 mg/week, about 6 mg/week to about 10 mg/week, about 6 mg/week to about 8 mg/week, about 6 mg/week to about 7 mg/week, about 7 mg/week to about 12 mg/week, about 7 mg/week to about 10 mg/week, about 7 mg/week to about 8 mg/week, about 8 mg/week to about 12 mg/week, or about 8 mg/week to about 10 mg/week.

Embodiment II-36. The method, use, compound, medicament, combination, and tacrolimus solution of embodiments II-30 to II-35, wherein the dosage after 1, 2, 3, 4, 5, 6, 7, 8, 9, or 10 week(s) is about 3 mg/week, about 3.5 mg/week, about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, or about 10 mg/week.

Embodiment II-37. The method, use, compound, medicament, combination, and tacrolimus solution of embodiments 11-30 to 11-36, wherein:
the dosage in a first 1, 2, 3, 4, 5 or week(s) is about 6 mg/week to about 25 mg/week, about 6 mg/week to about 20 mg/week, about 6 mg/week to about 16 mg/week, about 6 mg/week to about 14 mg/week, about 6 mg/week to about 12 mg/week, about 6 mg/week to about 10 mg/week, about 8 mg/week to about 25 mg/week, about 8 mg/week to about 20 mg/week, about 8 mg/week to about 16 mg/week, about 8 mg/week to about 14 mg/week, about 8 mg/week to about 12 mg/week, about 8 mg/week to about 10 mg/week, about 10 mg/week to about 25 mg/week, about 10 mg/week to about 20 mg/week, about 10 mg/week to about 16 mg/week, about 10 mg/week to about 14 mg/week, or about 10 mg/week to about 12 mg/week;
followed by 0, 1, 2, 3, 4, or 5 weeks without administration;
followed by a dosage of about 3 mg/week to about 12 mg/week, about 3 mg/week to about 10 mg/week, about 3 mg/week to about 8 mg/week, about 3 mg/week to about 6 mg/week, about 4 mg/week to about 12 mg/week, about 4 mg/week to about 10 mg/week, about 4 mg/week to about 8 mg/week, about 4 mg/week to about 6 mg/week, about 5 mg/week to about 12 mg/week, about 5 mg/week to about 10 mg/week, about 5 mg/week to about 8 mg/week, about 5 mg/week to about 6 mg/week, about 6 mg/week to about 12 mg/week, about 6 mg/week to about 10 mg/week, about 6 mg/week to about 8 mg/week, about 6 mg/week to about 7 mg/week, about 7 mg/week to about 12 mg/week, about 7 mg/week to about 10 mg/week, about 7 mg/week to about 8 mg/week, about 8 mg/week to about 12 mg/week, or about 8 mg/week to about 10 mg/week.

Embodiment II-38. The method, use, compound, medicament, combination, and tacrolimus solution of embodiments 11-30 to 11-37, wherein:
the dosage in a first 1, 2, 3, 4, 5 or week(s) is about 6 mg/week, about 6.5 mg/week, about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week;
followed by 0, 1, 2, 3, 4, or 5 weeks without administration;
followed by a dosage of about 3 mg/week, about 3.5 mg/week, about 4 mg/week, about 4.5 mg/week, about 5 mg/week, about 5.5 mg/week, about 6 mg/week, about 6.5 mg/week, about 7 mg/week, about 7.5 mg/week, about 8 mg/week, about 8.5 mg/week, about 9 mg/week, about 9.5 mg/week, or about 10 mg/week.

Embodiment II-39. The method, use, compound, medicament, combination, and tacrolimus solution of embodiments 11-1 to 11-18 and 11-27 to 11-38, wherein the dosage is administered via IV infusion.

Embodiment II-40. The method, use, compound, medicament, combination, and tacrolimus solution of embodiment II-39, wherein the dosage is administered over about 0.5 hour to about 2 hours, over about 0.5 hour to about 1.5 hours, over about 0.5 hour to about 1 hour, over about 1 hour to about 2 hours, or over about 1 hour to about 1.5 hours.

Embodiment II-41. The method, use, compound, medicament, combination, or tacrolimus solution of embodiment II-38 or 40, wherein the dosage is administered over about 1 hour.

Embodiment II-42. The method, use, compound, medicament, combination, and tacrolimus solution of embodiments II-1 to II-41, wherein the subject is human.

Embodiment II-43. The method, use, compound, medicament, combination, and tacrolimus solution of embodiments II-1 to II-42, wherein the method further comprises administering a dexamethasone solution to the subject.

Embodiment II-44. The method, use, compound, medicament, combination, and tacrolimus solution of embodiment II-43, wherein the dexamethasone solution comprises about 0.5 mg/5 mL dexamethasone.

Embodiment II-45. The method, use, compound, medicament, combination, and tacrolimus solution of embodiment II-43 or II-44, wherein the subject is administered about 2.5 mL of the dexamethasone solution.

Embodiment II-46. The method, use, compound, medicament, combination, and tacrolimus solution of embodiments II-43 to II-45, wherein the dexamethasone solution is administered 1, 2, 3, or 4 times daily.

Embodiment II-47. The method, use, compound, medicament, and combination of embodiments II-1 to II-18 and II-28 to II-46, wherein the method further comprises administering a tacrolimus solution to the subject.

Embodiment II-48. The method, use, compound, medicament, combination, and tacrolimus solution of embodiments II-19 to II-27 and II-47, wherein the tacrolimus solution comprises about 0.1 mg/mL tacrolimus.

Embodiment II-49. The method, use, compound, medicament, combination, and tacrolimus solution of embodiments II-19 to 11-27, 11-47, and II-48, wherein the tacrolimus solution comprises about 0.1 mg/mL tacrolimus.

Embodiment II-50. The method, use, compound, medicament, combination, and tacrolimus solution of embodiments II-19 to II-27 and II-47 to II-49, wherein the subject is administered about 2.5 mL of the tacrolimus solution.

Embodiment II-51. The method, use, compound, medicament, combination, and tacrolimus solution of embodiments II-19 to II-27 and II-47 to II-50, wherein the tacrolimus solution is administered 1, 2, 3, or 4 times daily.

Embodiment II-52. The method, use, compound, medicament, combination, and tacrolimus solution of embodiments II-19 to II-27 and II-47 to II-51, wherein the tacrolimus solution is administered on the day of administering the dosage or just prior to administering the dosage.

Embodiment II-53. The method, use, compound, medicament, combination, and tacrolimus solution of embodiments II-1 to II-52, wherein the method further comprises administering a combination solution to the subject, wherein the combination solution comprises dexamethasone and tacrolimus.

Embodiment II-54. The method, use, compound, medicament, combination, and tacrolimus solution of embodiment II-53, wherein the combination solution comprises about 0.5 mg/5 mL dexamethasone.

Embodiment II-55. The method, use, compound, medicament, combination, and tacrolimus solution of embodiment II-53 or II-54, wherein the combination solution comprises about 0.5 mg/mL tacrolimus.

Embodiment II-56. The method, use, compound, medicament, combination, and tacrolimus solution of embodiments II-53 to II-55, wherein the subject is administered about 2.5 mL of the combination solution.

Embodiment II-57. The method, use, compound, medicament, combination, and tacrolimus solution of embodiments II-53 to II-56, wherein the combination solution is administered 1, 2, 3, or 4 times daily.

Embodiment II-58. The method, use, compound, medicament, combination, and tacrolimus solution of embodiments II-53 to II-57, wherein the combination solution is administered on the day of administering the dosage or just prior to administering the dosage.

Embodiment II-59. The method, use, compound, medicament, combination, and tacrolimus solution of embodiments II-1 to II-58, wherein the method further comprises ice being applied to the mouth of the subject.

Embodiment II-60. The method, use, compound, medicament, combination, and tacrolimus solution of embodiment II-59, wherein the ice is applied for about 10 minutes before administering the dosage, during administering the dosage, and for about 10 minutes after administering the dosage.

Embodiment II-61. The method, use, compound, medicament, combination, and tacrolimus solution of embodiments II-27 and II-43 to II-60, wherein the dosage is about 6 mg/week to about 25 mg/week, about 6 mg/week to about 20 mg/week, about 6 mg/week to about 16 mg/week, about 6 mg/week to about 14 mg/week, about 6 mg/week to about 12 mg/week, about 6 mg/week to about 9 mg/week, about 6 mg/week to about 8 mg/week, or about 7 mg/week to about 8 mg/week.

Embodiment II-62. The method, use, compound, medicament, combination, and tacrolimus solution of embodiments II-27 and II-43 to II-61, wherein the dosage is about 7 mg/week, about 7.5 mg/week, about 8 mg/week, about 8.5 mg/week, about 9 mg/week, about 9.5 mg/week, about 10 mg/week, about 10.5 mg/week, about 11 mg/week, about 11.5 mg/week, about 12 mg/week, about 12.5 mg/week, about 13 mg/week, about 13.5 mg/week, about 14 mg/week, about 14.5 mg/week, about 15 mg/week, about 16 mg/week, about 18 mg/week, about 20 mg/week, about 22 mg/week, or about 25 mg/week.

Embodiment II-63. The method, use, compound, medicament, combination, and tacrolimus solution of embodiments II-1 to II-62, wherein the method further comprises administering a RAS inhibitor to the subject.

Embodiment II-64. The method, use, compound, medicament, combination, and tacrolimus solution of embodiment II-63, further comprising administering to the subject an effective amount of the RAS inhibitor.

Embodiment II-65. The method, use, compound, medicament, combination, and tacrolimus solution of embodiment II-63 or II-64, wherein the RAS inhibitor targets a specific RAS mutation.

Embodiment II-66. The method, use, compound, medicament, combination, and tacrolimus solution of embodiments II-63 to II-65, wherein the RAS inhibitor targets a KRAS mutation.

Embodiment II-67. The method, use, compound, medicament, combination, and tacrolimus solution of embodiment II-65 or II-66, wherein the RAS inhibitor targets the $KRAS^{G12C}$ mutation.

Embodiment II-68. The method, use, compound, medicament, combination, and tacrolimus solution of embodiments II-63 to II-67, wherein the RAS inhibitor is a KRAS (OFF) inhibitor.

Embodiment II-69. The method, use, compound, medicament, combination, and tacrolimus solution of embodiment 11-68, wherein the KRAS(OFF) inhibitor is AMG 510, MRTX849, JDQ443, MRTX1133, ERAS-3490, ERAS-4, BPI-421286, D-1553, JAB-21822, GH-35, ICP-915, IBI351, LY3537982, GDC-6036, B11823911, RSC-1255, or a pharmaceutically acceptable salt of any of the foregoing.

Embodiment II-70. The method, use, compound, medicament, combination, and tacrolimus solution of embodiments 11-63 to 11-67, wherein the RAS inhibitor is a RAS(ON) inhibitor.

Embodiment II-71. The method, use, compound, medicament, combination, and tacrolimus solution of embodiment II-70, wherein the RAS(ON) inhibitor is a KRAS(ON) inhibitor.

Embodiment II-72. The method, use, compound, medicament, combination, and tacrolimus solution of embodiment 11-71, wherein the KRAS(ON) inhibitor is RMC-6236, RMC-6291, RMC-9805, RMC-8839, or a pharmaceutically acceptable salt of any of the foregoing.

Embodiment II-73. The method, use, compound, medicament, combination, and tacrolimus solution of embodiment II-71 or II-75, wherein the KRAS(ON) inhibitor is a $KRAS^{G12C}$(ON) inhibitor.

Embodiment II-74. The method, use, compound, medicament, combination, and tacrolimus solution of embodiment 11-75 or 11-73, wherein the $KRAS^{G12C}$ (ON) inhibitor is RMC-6291 or a pharmaceutically acceptable salt thereof.

Embodiment II-75. The method, use, compound, medicament, combination, and tacrolimus solution of embodiments II-7, II-8, and II-11 to II-74, wherein the subject has cancer.

Embodiment II-76. The method, use, compound, medicament, combination, and tacrolimus solution of embodiments II-1 to 11-6, 11-9, II-10, and II-75, wherein the cancer is characterized by a genotypic aberration that activates the mammalian target of rapamycin (mTOR) pathway.

Embodiment II-77. The method, use, compound, medicament, combination, and tacrolimus solution of embodiments II-1 to 11-6, 11-9, 1-10, 11-75, and II-76, wherein the cancer comprises a mutation in the mTOR pathway.

Embodiment II-78. The method, use, compound, medicament, combination, and tacrolimus solution of embodiment II-75 or II-77, wherein the genotypic aberration or the mutation is of mTOR, STK11, PIK3CA, PTEN, KEAP1, TSC1, or TSC2, or a combination thereof.

Embodiment II-79. The method, use, compound, medicament, combination, and tacrolimus solution of embodiments II-75 to II-78, wherein the genotypic aberration or the mutation is of PTEN.

Embodiment II-80. The method, use, compound, medicament, combination, and tacrolimus solution of embodiment II-79, wherein the PTEN mutation is a dominant negative mutation.

Embodiment II-81. The method, use, compound, medicament, combination, or tacrolimus solution embodiments II-1 to 11-6, 11-9, II-10, and II-74 to II-79, wherein cancer is characterized by increased mTORC1 activity 75-80, wherein the cancer comprises greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, or greater than about 99% clonality of pathogenic variants in one or more of PIK3CA, PTEN, TSC1, and TSC2.

Embodiment II-82. The method, use, compound, medicament, combination, and tacrolimus solution of embodiments II-1 to 11-6, 11-9, II-10, and II-75 to II-81, wherein cancer is characterized by increased mTORC1 activity.

Embodiment II-83. The method, use, compound, medicament, combination, and tacrolimus solution of embodiments II-1 to 11-6, 11-9, II-10, and II-75 to II-82, wherein the cancer is characterized by decreased 4EBP1 activity.

Embodiment II-84. The method, use, compound, medicament, combination, and tacrolimus solution of embodiments 11-1 to 11-6, 11-9, 11-10, and 11-75 to 11-83, wherein the cancer comprises a mutation of the Myc family.

Embodiment II-85. The method, use, compound, medicament, combination, and tacrolimus solution of embodiment II-84, wherein the cancer comprises an amplification of MYC, MYCL, MYCN, or a combination thereof and/or dependence on MYC, MYCL, MYCN, or a combination thereof.

Embodiment II-86. The method, use, compound, medicament, combination, and tacrolimus solution of embodiments II-1 to 11-6, 11-9, II-10, and II-75 to II-85, wherein the cancer comprises a mutation of NFE2L2.

Embodiment II-87. The method, use, compound, medicament, combination, and tacrolimus solution of embodiments II-1 to 11-6, 11-9, II-10, and II-75 to II-86, wherein the cancer comprises a BRAF fusion.

Embodiment II-88. The method, use, compound, medicament, combination, and tacrolimus solution of embodiments II-1 to 11-6, 11-9, II-10, and II-75 to II-87, wherein the cancer comprises a $KRAS^{G12C}$ mutation.

Embodiment II-89. The method, use, compound, medicament, combination, and tacrolimus solution of embodiments II-1 to 11-6, 11-9, II-10, and II-75 to II-88, wherein the cancer comprises co-occurring $KRAS^{G12C}$ and STK11 mutations.

Embodiment II-90. The method, use, compound, medicament, combination, and tacrolimus solution of embodiments II-1 to 11-6, 11-9, II-10, and II-75 to II-89, wherein the cancer comprises co-occurring $KRAS^{G12C}$ and $PIK3CA^{E545K}$ mutations.

Embodiment II-91. The method, use, compound, medicament, combination, and tacrolimus solution of embodiments II-1 to 11-5, 11-9, II-10, and II-75 to II-90, wherein cancer is selected from the group consisting of bladder cancer, breast cancer, colorectal cancer, endometrial cancer, glioma, head and neck cancer, hematological cancer, liver cancer, lung cancer, neuro-endocrine cancer, ovarian cancer, pancreatic cancer, renal cancer, and rhabdomyosarcoma.

Embodiment II-92. The method, use, compound, medicament, combination, and tacrolimus solution of embodiments II-1 to II-5, II-9, II-10, and II-75 to II-91, wherein the cancer is a solid tumor.

Embodiment II-93. The method, use, compound, medicament, combination, and tacrolimus solution of embodiments II-1 to II-5, II-9, II-10, and II-75 to II-02, wherein the cancer is head and neck cancer.

Embodiment II-94. The method, use, compound, medicament, combination, and tacrolimus solution of embodiments 11-1 to 11-5, 11-9, 1-10, and 11-75 to 11-93, wherein the cancer is salivary gland cancer.

Embodiment II-95. The method, use, compound, medicament, combination, and tacrolimus solution of embodiments II-1 to II-5, II-9, II-10, and II-75 to II-92, wherein the cancer is colorectal cancer and comprises a mutation of PIK3CA, an amplification of MYC, or a mutation of PIK3CA and an amplification of MYC.

Embodiment II-96. The method, use, compound, medicament, combination, and tacrolimus solution of embodiments II-1 to II-5, II-9, II-10, and II-75 to II-92, wherein the cancer is head and neck cancer and comprises a mutation of PIK3CA, a mutation of PTEN, or a mutation of PIK3CA and a mutation of PTEN.

Embodiment II-97. The method, use, compound, medicament, combination, and tacrolimus solution of embodiments II-1 to II-5, II-9, II-10, and II-75 to II-92, wherein the cancer is hepatocellular carcinoma and comprises a mutation of NFE2L2.

Embodiment II-98. The method, use, compound, medicament, combination, and tacrolimus solution of embodiments II-1 to II-5, II-9, II-10, and II-75 to II-92, wherein the cancer is ovarian cancer and comprises a mutation of TSC2.

Embodiment II-99. The method, use, compound, medicament, combination, and tacrolimus solution of embodiments II-1 to II-5, II-9, II-10, and II-75 to II-92, wherein the cancer is pancreatic cancer and comprises a mutation of STK11, a $KRAS^{G12C}$ mutation, or a mutation of STK11 and a $KRAS^{G12C}$ mutation.

Embodiment II-100. The method, use, compound, medicament, combination, and tacrolimus solution of embodiments II-1 to II-5, II-9, II-10, and II-75 to II-92, wherein the cancer is prostate cancer and comprises a mutation of PTEN.

Embodiment II-101. The method, use, compound, medicament, combination, and tacrolimus solution of embodiments II-1 to II-5, II-9, II-10, and II-75 to II-92, wherein the cancer is uterine cancer and comprises a mutation of PIK3CA, a mutation of PIK3CA, a mutation of TSC2, or a combination thereof.

Embodiment II-102. The method, use, compound, medicament, combination, and tacrolimus solution of embodiments II-1 to II-5, II-9, II-10, and II-72 to II-92, wherein the cancer is lung cancer and comprises a BRAF fusion.

Embodiment II-103. The method, use, compound, medicament, combination, and tacrolimus solution of embodiments II-1 to II-102, wherein the method results in tumor regression.

Embodiment II-104. The method, use, compound, medicament, combination, and tacrolimus solution of embodiments II-1 to II-103, wherein the method results in tumor apoptosis.

EXAMPLES

The following examples are provided to illustrate the present disclosure and should not be construed as limiting thereof.

Example 1—Primary Pharmacodynamics 1.2.1.1. In Vitro Studies

The in vitro profile of RMC-5552 was characterized using standard biochemical and cellular assays to determine the mode of interaction with mTORC1 and mTORC2. The effect of RMC-5552 on established cellular readouts for mTORC1 activity (including phosphorylation of P70S6K at Thr389 and 4EBP1 at Thr37/46), mTORC2 activity (including phosphorylation of Akt at Ser473), and cellular proliferation was monitored.

RMC-5552 binds to the intracellular protein FKBP12 and engages the FRB allosteric site and the ATP binding site on the mTORC1 complex, leading to inhibition of mTOR kinase activity. In human carcinoma cell lines, RMC-5552 potently suppresses phosphorylation of P70S6K and 4EBP1, with $IC_{50}$ values ranging from 0.13 to 0.51 nM, and 0.48 to 2.4 nM, respectively. The cellular selectivity for inhibition of mTORC1 over mTORC2, defined as the ratio of potency for inhibition of phosphorylation of 4EBP1 to Akt, ranges from 15.8- to 38.9-fold. RMC-5552 exhibits similar potency for inhibition of mTORC1, and selectivity over mTORC2, in human, mouse, and rat cells. Inhibition of mTORC1 by RMC-5552 results in inhibition of cell proliferation, with potencies ranging from 0.05 to 0.56 nM in cell lines with activating mutations in the PI3K/mTOR pathway, and 0.10 to 0.46 nM in HNSCC cell lines.

1.2.1.2. In Vivo Studies

The antitumor activity of RMC-5552 as a single agent against tumors predicted to be dependent on the mTOR pathway and/or bearing specific PI3K/mTOR pathway-activating mutations (i.e., PIK3CA$^{mut}$, phosphatase and tensin homolog [PTEN$^{LOF}$], or co-mutation of both and tuberous sclerosis complex [TSC$^{LOF}$]) was evaluated in selected CDX and/or PDX models Table 1. RMC-5552 was administered IP once weekly at 1, 3, 10, and 30 mg/kg. In the breast cancer MCF7 PIK3CA$^{E45K}$ model, a higher dose of 50 mg/kg once weekly and an alternate dose regimen of 30 mg/kg every 10 days were also evaluated.

The in vivo PK-pharmacodynamic relationship for inhibition of activated mTOR pathway signaling of RMC-5552 as a single agent was determined in the breast cancer MCF7 and HCC-1954 PIK3CA mutant CDX models.

Figure 1B:
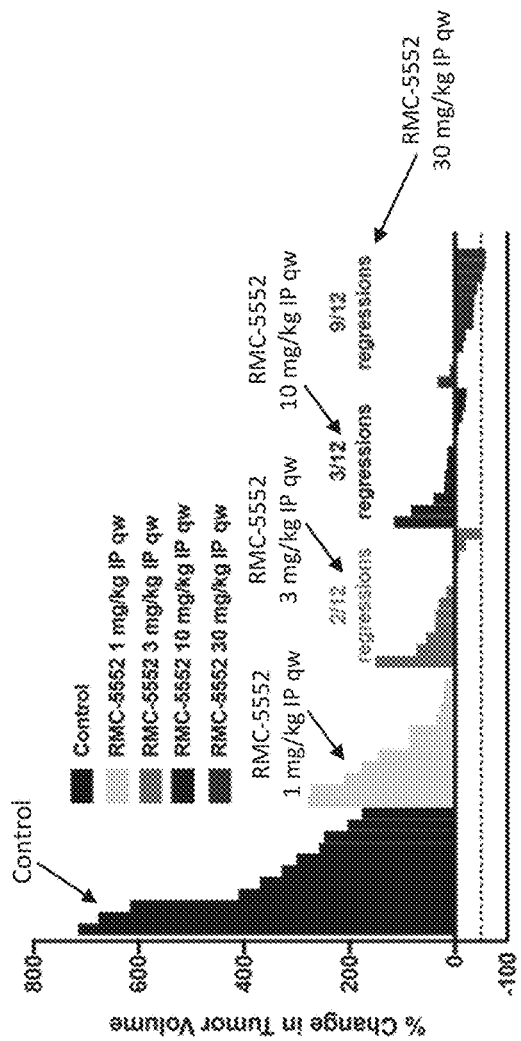
Figure 2A:
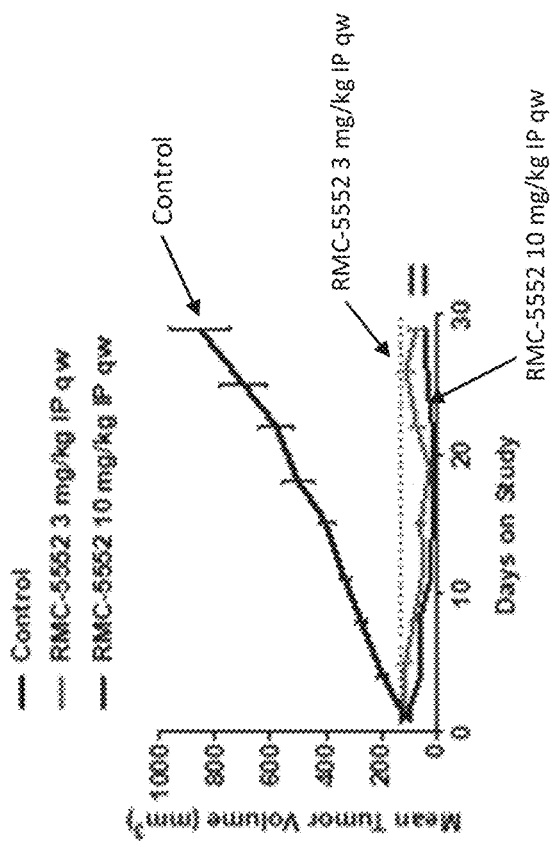
FIGS. 2A-2D show Antitumor Activity of RMC-5552 in the TOV21G Cell Line-Derived Xenograft Model of Human Ovarian Cancer Following Once-Weekly Administration. Abbreviations: ANOVA=analysis of variance; IP=intraperitoneal; QW=once weekly.
Figure 2B:
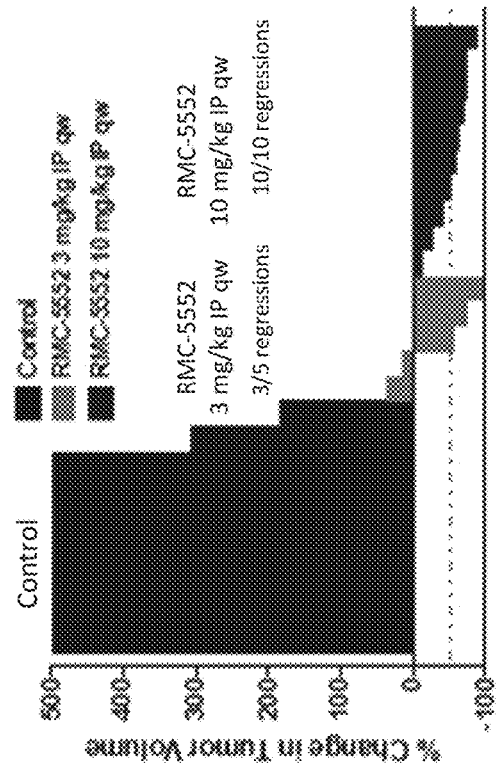
Figure 2C:
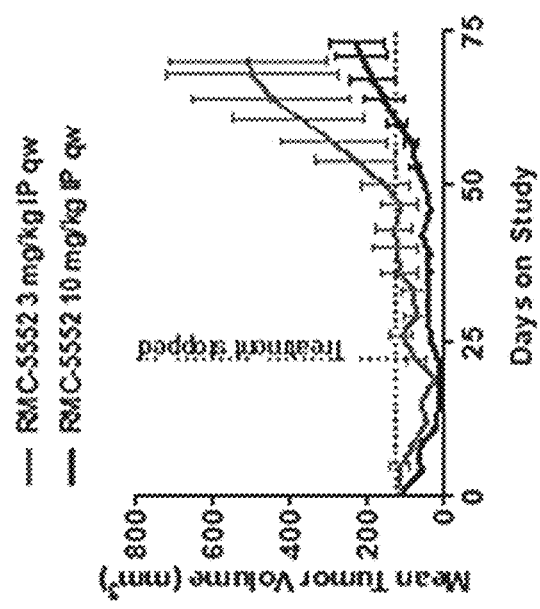
Figure 2D:
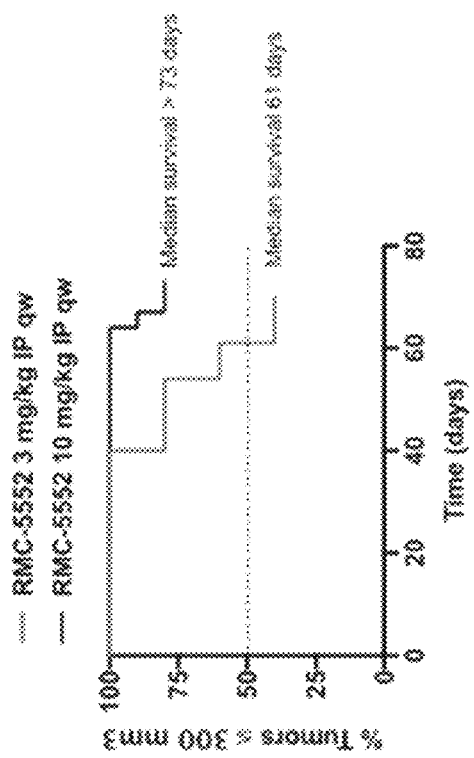
Figure 3A:
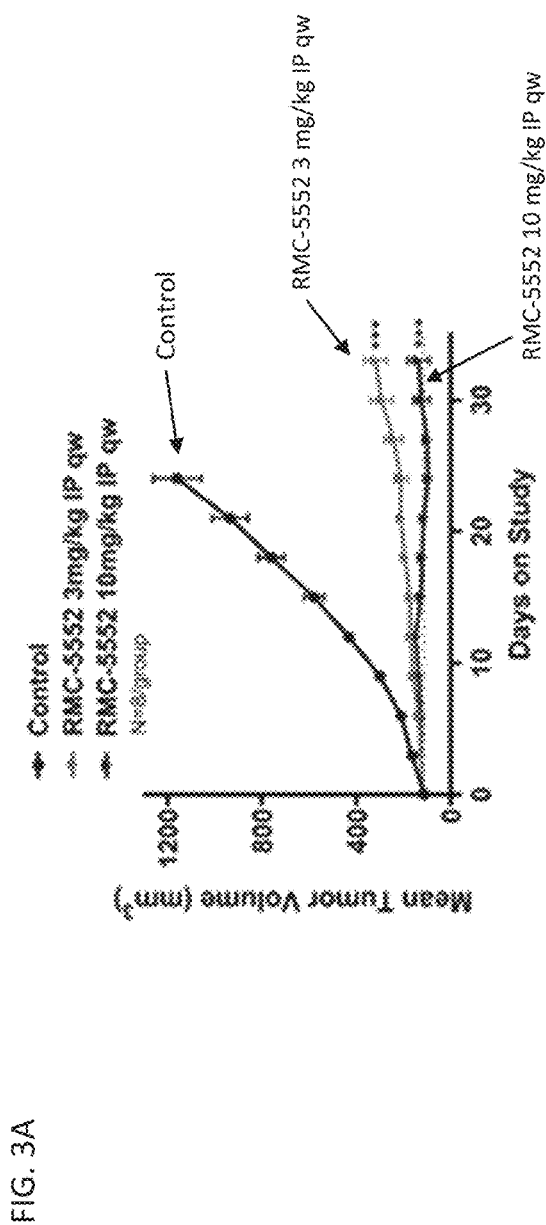
FIGS. 3A-3B show Antitumor Activity of RMC-5552 in the HN009 Patient-Derived Xenograft Model of Human HNSCC Following Once-Weekly Administration. Abbreviations: ANOVA=analysis of variance; IP=intraperitoneal; QW=once weekly.
Figure 3B:
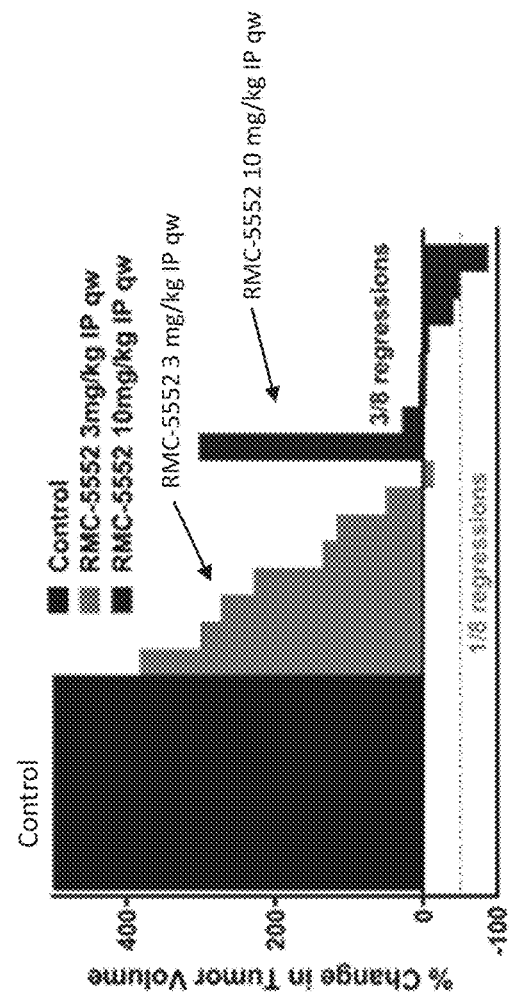

In solid-tumor CDX or PDX models that represent a variety of human cancers with genetic aberrations driving activated mTOR signaling, weekly IP administration of RMC-5552 produced significant TGI at doses as low as 1 mg/kg; robust antitumor activity, with tumor regression apparent in some models, was observed at doses of 3 and 10 mg/kg (and 30 mg/kg where tested) (summarized in Table 1, representative results in FIGS. 1A-1B for a CDX model of PIK3CA$^{mut}$ breast cancer, FIGS. 2A-2D for a CDX model of PIK3CA$^{mut}$ PTEN$^{mut}$ ovarian cancer, and FIGS. 3A-3B for a PDX model of HNSCC).

Figure 4A:
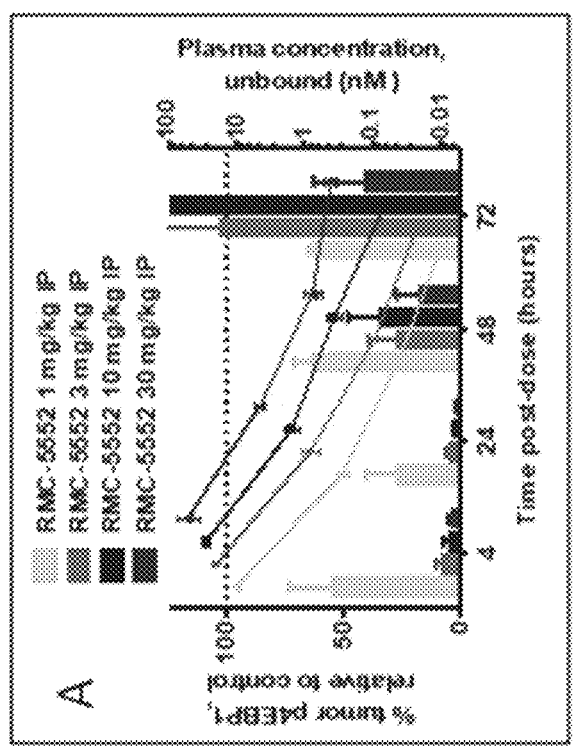
FIGS. 4A-4C show Pharmacokinetic-Pharmacodynamic Profile for RMC-5552 Modulation of Tumor p4EBP1 and pS6RP in MCF7 Tumor Bearing Athymic Nude Mice. Abbreviations: IP=intraperitoneal; p4EBP1=phosphorylated eukaryotic translation initiation factor 4E-binding protein 1.
Figure 4B:
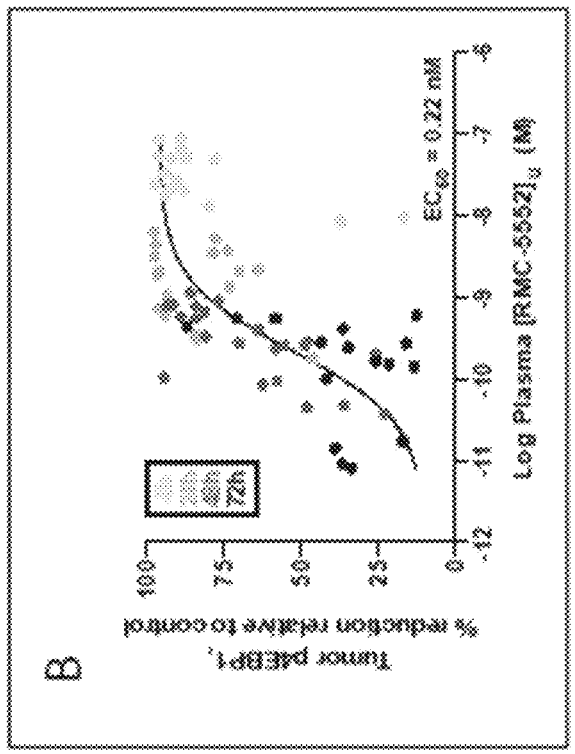
Figure 4C:
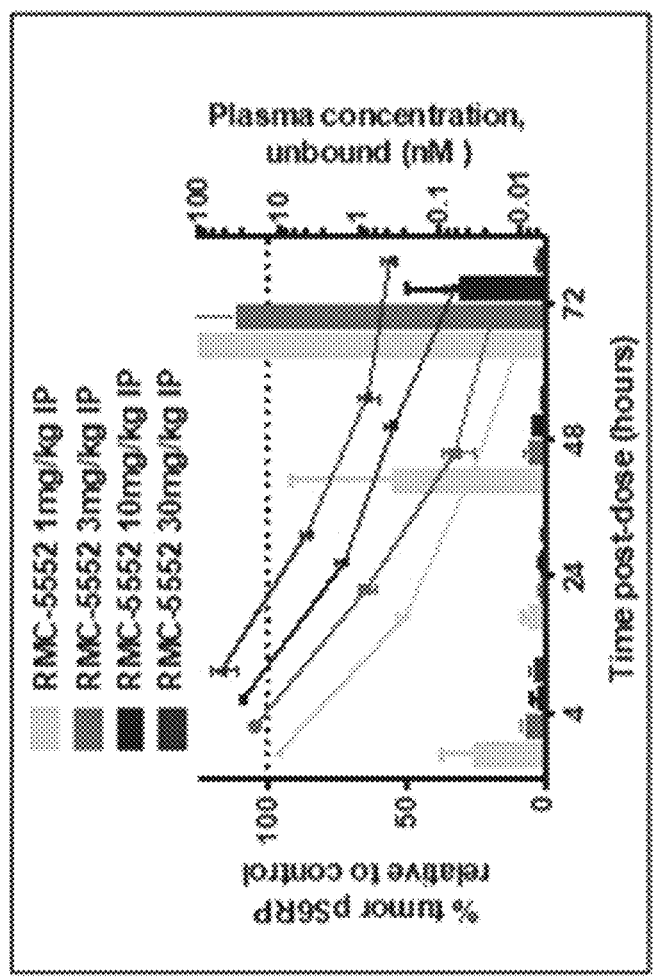

Across all models, these doses and regimens were generally well-tolerated. In 2 xenograft models of different human cancers with mTOR pathway-activation mutations (i.e., ovarian cancer and bladder cancer), RMC-5552 treatment resulted in durable responses and significantly delayed tumor regrowth following treatment cessation (see FIGS. 4A-4C for representative results in an ovarian cancer model).

Figure 5:
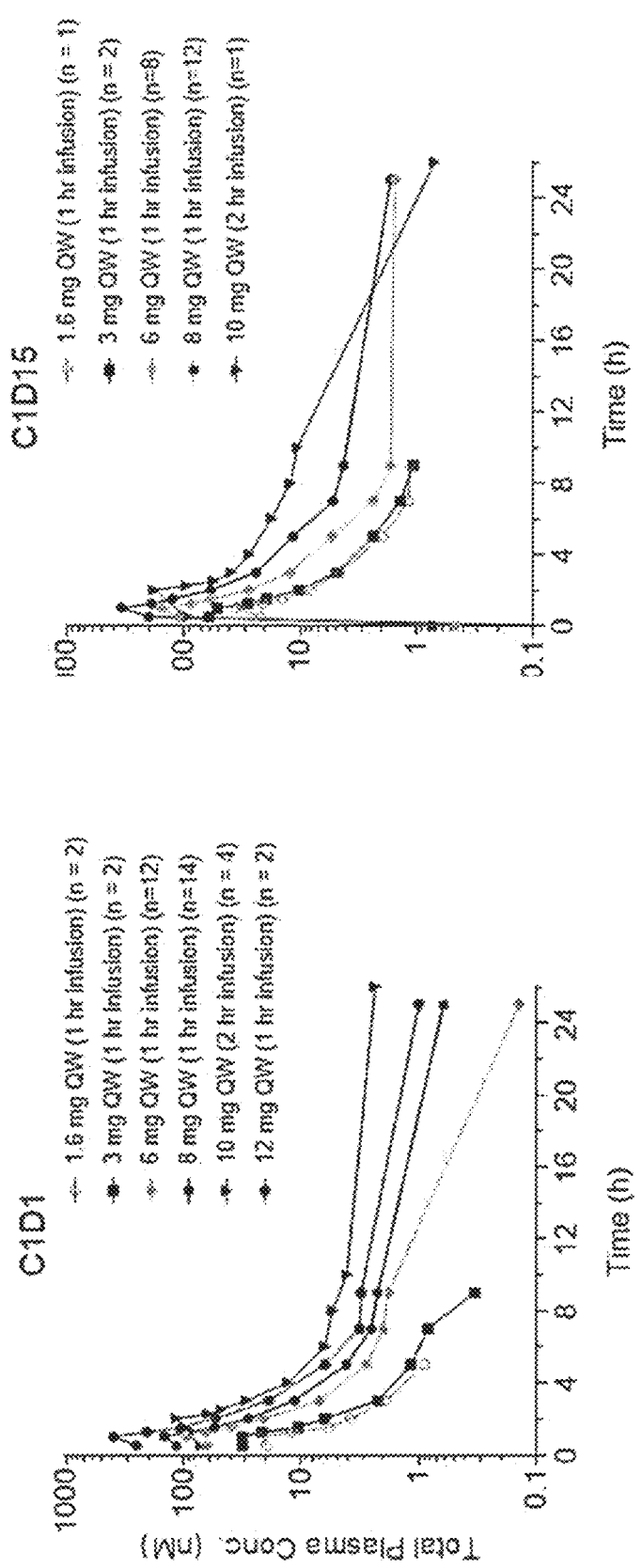
FIG. 5 shows Human Plasma Concentration Over Profiles of RMC-5552 on Cycle 1 Days 1 and 15. Abbreviations: CID1=Cycle 1 Day 1; CID15=Cycle 1 Day 15.

Consistent with inhibition of mTORC1 signaling in vitro, IP administration of RMC-5552 to nude mice produced a dose and plasma concentration-dependent-inhibition of tumor p4EBP1 and pS6RP (a direct substrate of P70S6K) in PI3K mutant breast cancer MCF7 xenograft models FIG. 5. Inhibition of p4EBP1 was maximal at 24 to 48 hours after treatment. The in vivo half-maximal effective concentration ($EC_{50}$) for inhibition of p4EBP1 was 0.22 nM (unbound) in MCF7, and a maximum level of inhibition of >90% relative to control was observed.

Interestingly, weekly dosing was active despite absence of continuous p4EBP1 inhibition. In summary, the MED of RMC-5552 in murine models of mTORC1-activated cancers is estimated to be between 1 and 3 mg/kg once weekly, which resulted in a mean $C_{max,u}$ of 2.0 to 14.7 nM and unbound mean AUC of 21 to 210 nM×h, respectively (adjusted for concentration-dependent unbound fraction in mouse plasma).

TABLE 1

Antitumor Activity of RMC 5552 in Solid-Tumor Cell Line-Derived or Patient-Derived Xenograft Models with Specific Activating Mutations of the PI3K/mTOR Pathway

| CDX/PDX Model | Genotype | Histotype | Dose (mg/kg, IP) | TGI |
|---|---|---|---|---|
| MCF7 | PIK3CA$^{E545K}$ | Breast cancer | 1 | 64% |
|  |  |  | 3 | 93% |
|  |  |  | 10 | 93% |
|  |  |  |  | 15% regression |
| HCC-1954 | PIK3CA$^{H1047R}$ | Breast cancer | 1 | 79%, 81% |
|  |  |  | 3 | 94%, 96% |
|  |  |  | 10 | 95%, 92% |
| HN009 | pEGFR- and p4EBP1-positive | HNSCC | 3 | 91% |
|  |  |  | 10 | 17% regression |
| TOV21G | PIK3CA$^{H1047Y}$; PTEN$^{p.L265fs, p.R142fs}$; KRAS$^{G13C}$ | Ovarian cancer | 3 | 34% regression |
|  |  |  | 10 | 61% regression |
| BLC1521 | TSC1 protein-negative | Bladder cancer | 3 | 94% |
|  |  |  | 10 | 45% regression |
| BXF 2211 | TSC1$^{-/-}$ | Bladder cancer | 3 | 91% regression |
|  |  |  | 10 | 94% regression |

Abbreviations: CDX = cell line-derived xenograft; HNSCC = head and neck squamous cell carcinoma; IP = intraperitoneal; p4EBP1 = phosphorylated eukaryotic translation initiation factor 4E-binding protein 1; PDX = patient-derived xenograft; pEGFR = phosphorylated epidermal growth factor receptor; PI3K = phosphatidylinositol 3-kinase; mTOR = mammalian/mechanistic target of rapamycin; PIK3CA = phosphatidylinositol 4,5-bisphosphate 3-kinase catalytic subunit alpha; PTEN = phosphatase and tensin homolog; TGI = tumor growth inhibition; TSC1 = tuberous sclerosis complex subunit 1.

Note:

In all studies, RMC-5552 was administered in a transcutol/solutol-based formulation.

Example 2—Monotherapy Effects in Humans

The studies used as a basis for clinical data presented in this section were conducted in compliance with GCP, as required by the ICH E6 Guideline for Good Clinical Practice. The studies also meet with the requirements of the Declaration of Helsinki, standard operating procedures for clinical investigations and documentation of the Sponsor, applicable national laws and regulations and the ethical principles of the Directive 2001/20/EC.

RMC-5552 is currently being evaluated as a monotherapy in a FIH, dose-escalation, Phase 1/1b study (RMC-5552-001) in adult subjects with advanced relapsed/refractory solid tumors (see Example 3 for additional study protocol details.) The purpose of this study is to evaluate safety, tolerability, preliminary efficacy, PK, and pharmacodynamics of RMC-5552 monotherapy. The primary objective is to characterize the safety and tolerability of RMC-5552 monotherapy and to define the MTD and the Recommended Phase 2 Dose (RP2DS) and schedule for RMC-5552 monotherapy in subjects with relapsed/refractory solid tumors.

A total of 39 subjects were treated with RMC-5552 monotherapy across 6 dose levels in a weekly IV injection schedule: 1.6 mg over 1-hour infusion (n=2), 3.0 mg over 1-hour infusion (n=3), 6.0 mg over 1-hour infusion (n=12), 8 mg over 1-hour infusion (n=15), 12 mg over 1-hour infusion (n=2), and 10 mg over 2-hour infusion (n=5).

Of 27 subjects evaluable for efficacy (with a postbaseline response assessment or who died or had clinical progression prior to the first postbaseline response assessment) with subjects who received 6 mg IV weekly as their majority doses and subjects who received 8 mg IV weekly as their majority doses, 19 subjects had stable disease as best response and one subject had confirmed partial response with 77.6% reduction in Response Evaluation Criteria in Solid Tumors (RECIST) measurements. The Disease Control Rate (DCR) of this cohort was 74.1%.

The plasma PK of RMC-5552 in subjects was characterized after single- and repeat-dose administration via IV infusion. PK samples were collected up to 48 hours post-dose on Cycle 1 Day 1 (C1D1) and Cycle 1 Day 15 (C1D15). Sparse PK samples were collected on other visit days as indicated in the clinical study protocol, including End of Infusion (EOI) samples on Cycle 1 Day 8 (C1D8), Cycle 2 Day 1 (C2D1), Cycle 3 Day 1 (C3D1), and Cycle 4 Day 1 (C4D1) to approximate maximum concentration ($C_{max}$).

RMC-5552 exhibited a dose-proportional increase in exposure from 1.6 to 6 mg, but more than dose-proportional exposure increase from 6 to 12 mg on C1D1. After weekly repeat dosing, RMC-5552 exposure was about 2-fold higher on CID15 than that on C1D1 at dose levels of 1.6 to 8 mg. The mean $C_{max}$ on C2D1, C3D1, and C4D1 was similar to that on C1D15 at dose levels of 1.6 to 8 mg, suggesting that exposure increase stabilized by Cycle 2.

The most common (>20%) drug-related adverse events were fatigue (41%), stomatitis/mucositis (41%), nausea (36%), decreased appetite (32%), and vomiting (23%). Treatment-emergent hyperglycemia occurred in 6.8% of patients and was not dose limiting. The most common grade 3 drug-related adverse event was mucositis/stomatitis, which limited tolerability and was dose-dependent. In patients treated at doses between 8 and 12 mg IV weekly, the rate of mucositis/stomatitis was 75% (15% grade 3) in patients treated without TM (N=20) versus 14% (no grade 3) in patients treated with TM (N=7). RMC-5552 plasma exposures at these dose levels were within the range that induced significant anti-tumor activity in preclinical models. Reduction in ctDNA consistent with anti-tumor activity was seen in tumors with pathogenic mTOR pathway variants, as well as loss of pathogenic mTOR pathway variant ctDNA at active doses.

2.1. Clinical Pharmacokinetics and Product Metabolism

The plasma PK of RMC-5552 in subjects was characterized after single- and repeat dose administration via intravenous (IV) infusion. Plasma PK samples were collected in the dose-escalation phase across 6 dose levels: 1.6 mg, 3 mg, 6 mg, 8 mg, and 12 mg over a 1-hour IV infusion and 10 mg over a 2-hour infusion once weekly in 21-day treatment cycles. PK samples were collected up to 48 hours post-dose on C1D1 and C1D15. Sparse PK samples were collected on other visit days as indicated in the clinical study protocol, including EOI samples on C1D8, C2D1, C3D1, and C4D1 to approximate $C_{m}ax$. FIG. 5 shows plasma RMC-5552 concentration-time profiles across 6 dose levels, in which concentrations measured below the limit of quantification were not plotted. Preliminary noncompartmental PK analysis was performed by the Sponsor using Phoenix 8.3 software; results are summarized in Table 2. On C1D1, exposure of RMC-5552 was generally dose-proportionally increased from 1.6 to 6 mg. The mean total $C_{max}$ and $AUC_{0-last}$ were increased from 21.6 to 101 nM (unbound: 1.2 to 5.8 nM), and 29.7 to 137 nM×h (unbound: 1.7 to 7.8 nM×h), respectively, from 1.6 to 6 mg. However, exposure was more than dose-proportionally increased from 6 to 12 mg. The mean $C_{max}$ and $AUC_{0-last}$ were increased from 101 to 396 nM (unbound: 5.8 to 22.6 nM), and 137 to 490 nM×h (unbound: 7.8 to 28.0 nM×h), respectively from 6 to 12 mg. The $C_{max}$ and $AUC_{0-last}$ were 115 nM (unbound: 6.6 nM) and 366 nM×h (unbound: 20.9 nM×h) at 10 mg via a 2-hour IV infusion. On C1D15, exposure of RMC-5552 ($C_{max}$ and $AUC_{0-last}$) was higher than that on C1D1 at doses of 1.6 to 8 mg, with mean AUC accumulation ratios ranging from 1.6 to 2.6, although the levels of RMC-5552 were near or below the limit of quantification in all pre-dose samples including Days 8 and 15. On C2D1, C3D1, and C4D1, the mean $C_{max}$, which was the mean EOI DocuSign concentration, was comparable to that on CID15 at doses of 1.6 to 8 mg. $AUC_{0-last}$ value was not calculated on C1D8, C2D1, C3D1, or C4D1 due to limited PK time points (pre-dose and EOI).

In conclusion, RMC-5552 exhibited dose-proportional increase in exposure from 1.6 to 6 mg, but more than dose-proportional from 6 to 12 mg on C1D1. After weekly repeat dosing, RMC-5552 exposure ($C_{max}$ and $AUC_{0-last}$) was about 2-fold higher on CD15 than that on C1D1 at dose levels of 1.6 to 8 mg. The mean $C_{max}$ on C2D1, C3D1, and C4D1 was similar to that on C1D15 at dose levels of 1.6 to 8 mg, suggesting that exposure increase stabilized by Cycle 2.

TABLE 2

Preliminary PK Parameters of RMC-5552

| Dose Level | Number of Subjects | Cycle Day | Mean $C_{max}$ (nM) | Mean Unbound $C_{max}$ (nM) | Mean $AUC_{0-last}$ (nM × h) | Mean Unbound $AUC_{0-last}$ (nM × h) | Mean $t_{1/2}$ (h) | Mean Accumulation Ratio ($AUC_{0-last}$ on D15/D1) | Mean Dose Normalized $AUC_{0-last}$ (nM × h/mg) |
|---|---|---|---|---|---|---|---|---|---|
| 1.6 mg | 2 | C1D1 | 21.6 | 1.2 | 29.7 | 1.7 | ND | — | 18.6 |
| | 1[a] | C1D15 | 35.3 | 2.0 | 55.5 | 3.2 | ND | 2.4 | 34.7 |
| | 1[a] | C2D1[b] | 24.7 | 1.4 | — | — | — | — | — |
| 3 mg | 2[a] | C1D1 | 32.0 | 1.8 | 43.9 | 2.5 | ND | — | 14.6 |
| | 2[a] | C1D15 | 67.5 | 3.8 | 87.5 | 5.0 | ND | 2.1 | 29.2 |
| | 1[a] | C2D1[b] | 74.2 | 4.2 | — | — | — | — | — |
| 6 mg | 12 | C1D1 | 101 | 5.8 | 137 | 7.8 | 8.1 | — | 22.1 |
| | 8 | C1D8[b] | 150 | 8.5 | — | — | — | — | — |
| | 8 | C1D15 | 155 | 8.9 | 219 | 12.5 | 8.2 | 1.6 | 36.6 |
| | 8 | C2D1[b] | 159 | 9.1 | — | — | — | — | — |
| | 4 | C3D1[b] | 187 | 10.7 | — | — | — | — | — |
| | 3 | C4D1[b] | 220 | 12.5 | — | — | — | — | — |
| 8 mg | 14 | C1D1 | 152 | 8.6 | 219 | 12.5 | 11.4 | — | 27.4 |
| | 10 | C1D8[b] | 242 | 13.8 | — | — | — | — | — |
| | 12 | C1D15 | 340 | 19.4 | 466 | 26.6 | 10.6 | 2.6 | 58.3 |
| | 9 | C2D1[b] | 282 | 16.1 | — | — | — | — | — |
| | 5 | C3D1[b] | 295 | 16.8 | — | — | — | — | — |
| | 6 | C4D1[b] | 208 | 11.8 | — | — | — | — | — |
| 12 mg | 2 | C1D1 | 396 | 22.6 | 490 | 28 | 8.3 | — | 40.9 |
| | 0[c] | C1D15 | — | — | — | — | — | — | — |
| 10 mg (2 hr inf) | 4[a] | C1D1 | 115 | 6.6 | 366 | 20.9 | 13.5 | — | 36.6 |
| | 1[a] | C1D15 | 181 | 10.3 | 527 | 30.0 | 4.2 | 1.7 | 52.7 |
| | 4 | C2D1 | 290 | 16.5 | — | — | — | — | — |

Abbreviations: $AUC_{0-last}$ = area under the concentration-time curve from dosing time to the last quantifiable time point; C1D1 = Cycle 1 Day 1; C1D8 = Cycle 1 Day 8; C1D15 = Cycle 1 Day 15; C2D1 = Cycle 2 Day 1; C3D1 = Cycle 3 Day 1; C4D1 = Cycle 4 Day 1; $C_{max}$ = maximum concentration; EOI = End of inf.; inf = infusion; ND = not determined; $t_{1/2}$ = terminal elimination half-life; PK = pharmacokinetic(s).

Note:
Unbound fraction in human plasma: 0.057 at 0.5 μM.

[a] PK samples were collected in 2 subjects at 1.6 mg on C1D15 and C2D1, 3 subjects at 3 mg on C1D1 and C1D15, 2 subjects at 3 mg on C2D1, 5 subjects at 10 mg on C1D1, and 2 subjects at 10 mg on C1D15; 1 subject in each dose group was excluded in PK analysis due to missing samples or possible sample contamination by drawing blood directly from the same line that RMC-5552 being administered.

[b] On C1D8, C2D1, C3D1, and C4D1, PK samples were collected pre-dose and at EOI. $C_{max}$ represents the concentration at EOI.

[c] On C1D15, 1 subject was administered RMC-5552 at a reduced dose of 6 mg; PK results not reported.

2.2. Clinical Pharmacodynamics

Figure 6:
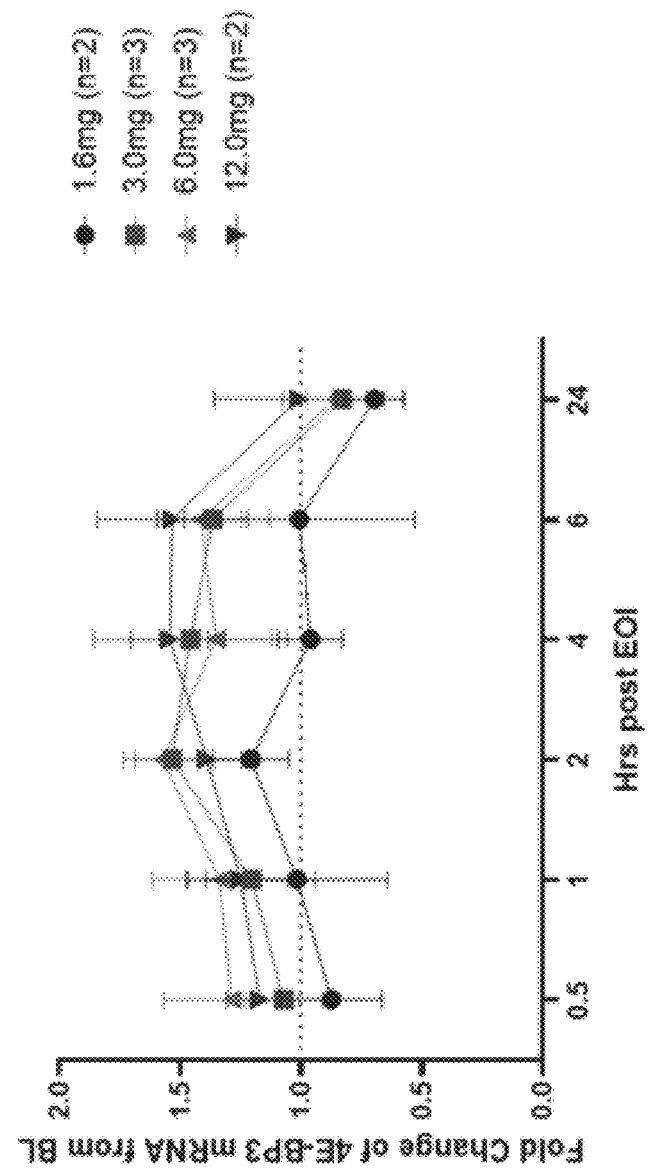
FIG. 6 shows 4EBP3 mRNA Expression in Human Blood Samples.

In preclinical studies, sustained inhibition of mTORC1 resulted in an induction of 4EBP3 mRNA expression in in vitro and in vivo models (Lee Bianca J, Dinglasan Nuntana, Nguyen Tram, et al., 4EBP3 mRNA as a Biomarker of Therapeutic Response to Treatment with mTORC1 Inhibitors. Presented at AACR-NCI-EORTC International Conference on Molecular Targets and Cancer Therapeutics; Oct. 26-30, 2019; Boston, MA; Poster B108). Whole blood was collected from all subjects in dose escalation at C1D1 prior to dosing, and 6 timepoints after EOI. In each sample, 4EBP3 mRNA expression was quantified as a pharmacodynamic indicator of mTORC1 inhibition. In cohorts treated with at least 3.0 mg RMC-5552, 4EBP3 was increased from baseline, and the increase sustained over a 6-hour period as seen in FIG. 6.

2.3. Baseline Characteristics and Disposition

A total of 39 subjects were enrolled and dosed in the dose-escalation phase across 6 dose levels: 1.6 mg (n=2), 3 mg (n=3), 6 mg (n=12), 8 mg (n=15), 12 mg (n=2) over a 1-hour infusion and 10 mg (n=5) over a 2-hour infusion once weekly in 21-day treatment cycles. The median age reported for this subject population was 62 years (range 44-80). Subjects have received a median of 3 prior systemic therapies (range 0-15), with 25 (64.1%) having received at least 3 or more prior systemic therapies. Nineteen (48.7%) subjects had an Eastern Cooperative Oncology Group (ECOG) score of 0, and 20 (57.3%) subjects had ECOG score of 1. Nine (23.1%) subjects had head and neck cancer, 6 (15.4%) subjects had colorectal cancer, 5 (12.8%) had ovarian cancer, 3 (7.7%) had lung cancer, and the rest of the subjects had other types of solid tumors such as cholangiocarcinoma, prostate cancer, melanoma, and liposarcoma. Many of the subjects carried pathogenic mutations in the mTOR or mitogen-activated protein kinase (MAPK) pathway on historic genetic reports.

Two subjects were continuing treatment as of the data cut-off and 37 subjects have discontinued treatment with RMC-5552. Fifteen (38.5%) subjects have discontinued treatment due to disease progression per RECIST assessment, 10 (25.6%) due to withdrawal of consent, 8 (20.5%) due to clinical progression, and others due to alternative anticancer therapy, death, non-compliance, or other (1 subject each). Median duration on study was 2.9 months (range 0.2-15.2 months).

2.4. Clinical Efficacy

Figure 7:
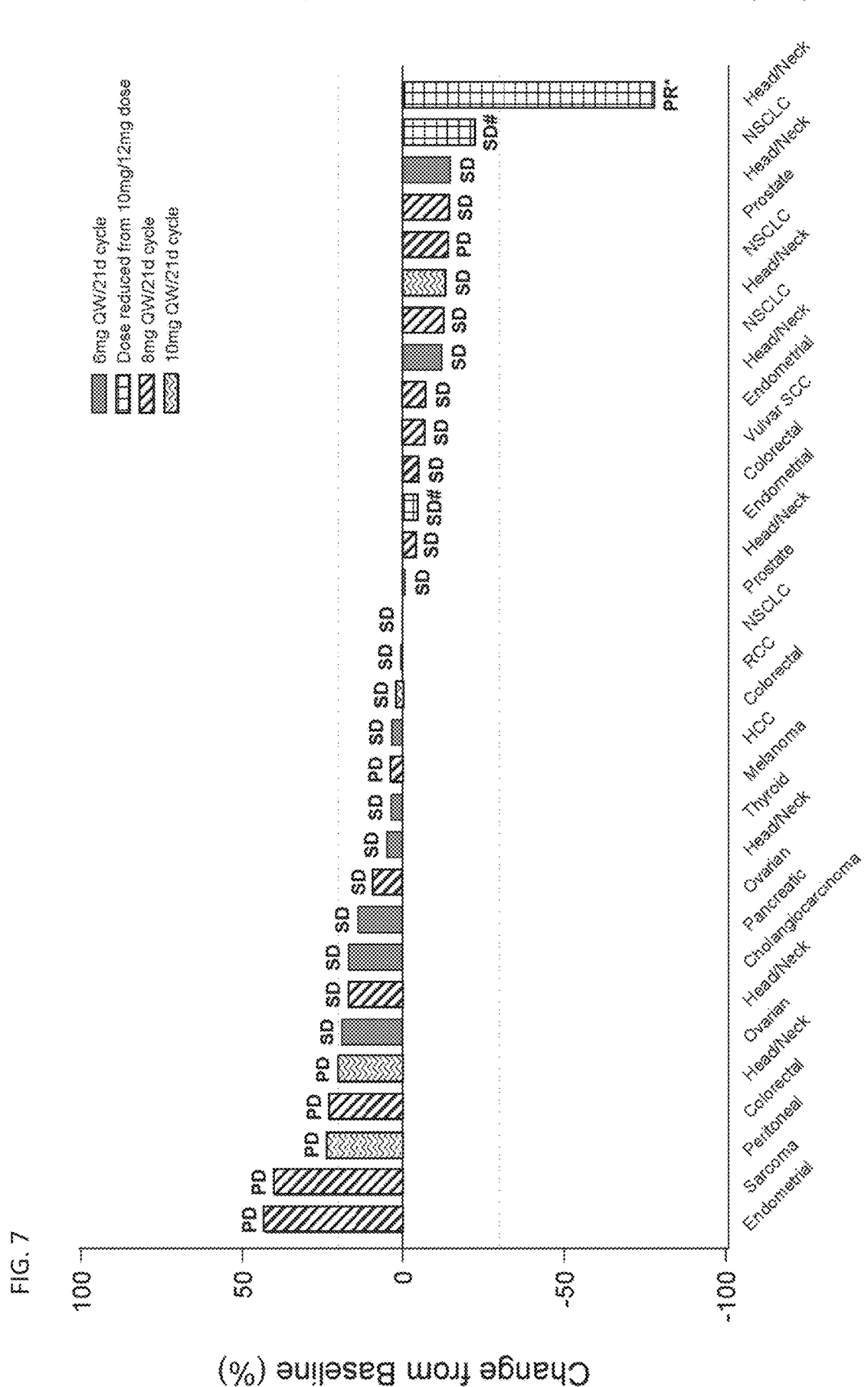
FIG. 7 shows the Best Percent Change from Baseline in Target Lesions for Efficacy-Evaluable Patients Treated With >6 mg RMC-5552. Abbreviations: HCC=hepatocellular carcinoma; PD=progressive disease; PR=partial response; SD=stable disease; QW=once weekly. *Patient received one dose of 12 mg, followed by weekly doses of 6 mg. Patient classified as PR due to persistence of non-target lesions. The patient had been on RMC-5552 for 6 months. #Patient received one dose of 10 mg, followed by weekly doses of 6 mg.

Of 27 subjects evaluable for efficacy (with a postbaseline response assessment or who died or had clinical progression prior to the first postbaseline response assessment) at majority doses of 6 mg or 8 mg IV weekly, 19 subjects had stable disease as best response, and one subject with head and neck cancer (specifically, salivary gland cancer) with a pathogenic mutation in PTEN had a confirmed partial response with 77.6% reduction in the sum of target lesions per RECIST v1.1 measurements. The Disease Control Rate of this cohort was 74.1%. Refer to FIG. 7 for a waterfall plot of best response in subjects treated at majority dose of 6 mg or 8 mg IV weekly (one hour infusion).

Subjects were evaluated at doses of 6 mg and higher. Among 13 efficacy-evaluable patients at dose levels of ≥6 mg RMC-5552, 1 confirmed partial response (PR) observed in a subject with head and neck cancer (specifically, salivary gland cancer) with a pathogenic mutation in PTEN, and 8 subjects had a best response of stable disease (SD). One patient discontinued treatment due to clinical progression without post-baseline scans. Three patients experienced radiographic progressive disease (PD). Results are shown in FIG. 7.

2.4.1 Exposure Levels

Table 3 shows plasma exposure levels for patients treated with RMC-5552 at dose levels between 6 mg and 12 mg. Table 3 also shows mean plasma exposure for mice dosed with 1 mg/kg or 3 mg/kg. The human plasma unbound exposure levels at a dosage of 6 mg to 12 mg IV weekly was equivalent to the murine plasma unbound exposure at 1 mg/kg to 3 mg/kg, which correspond to plasma exposure levels at which tumor regressions were observed in preclinical models (see Example 1.)

2.4.2 Molecular Response

Figure 8:
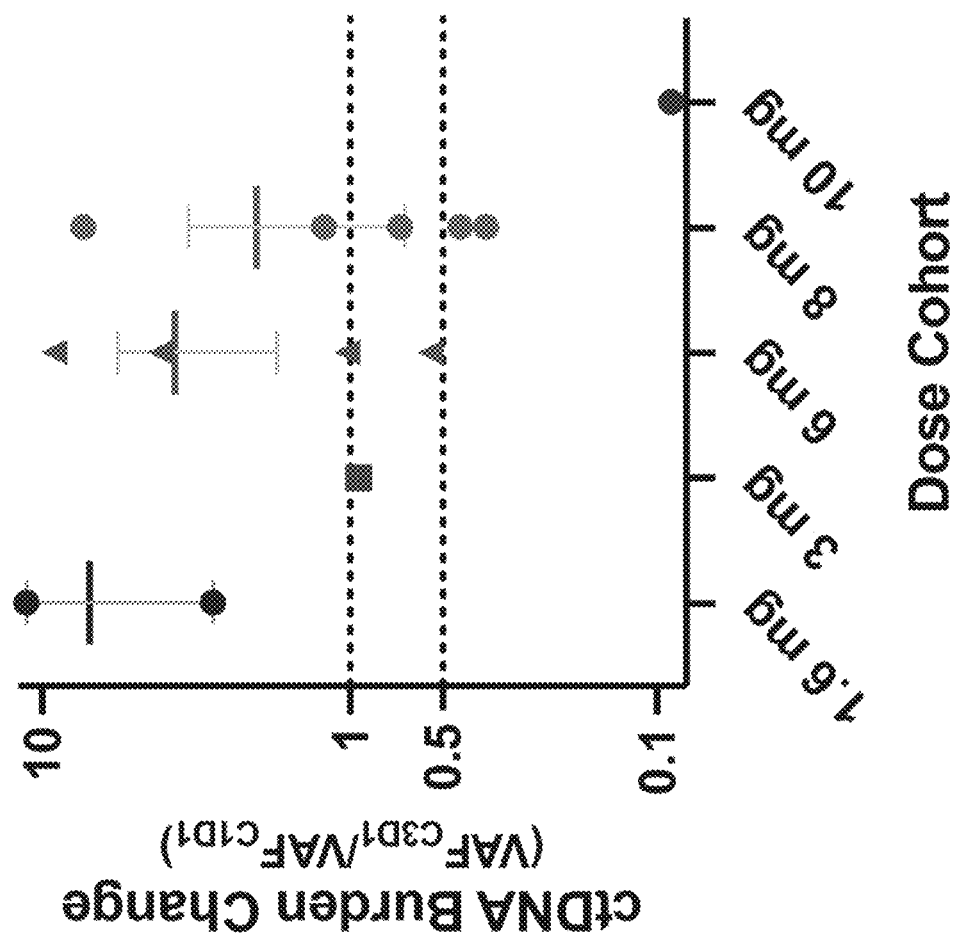
FIG. 8 shows the change in ctDNA burden for dose cohorts treated at a dosage of 1.6 mg to 10 mg of RMC-5552.
Figure 9:
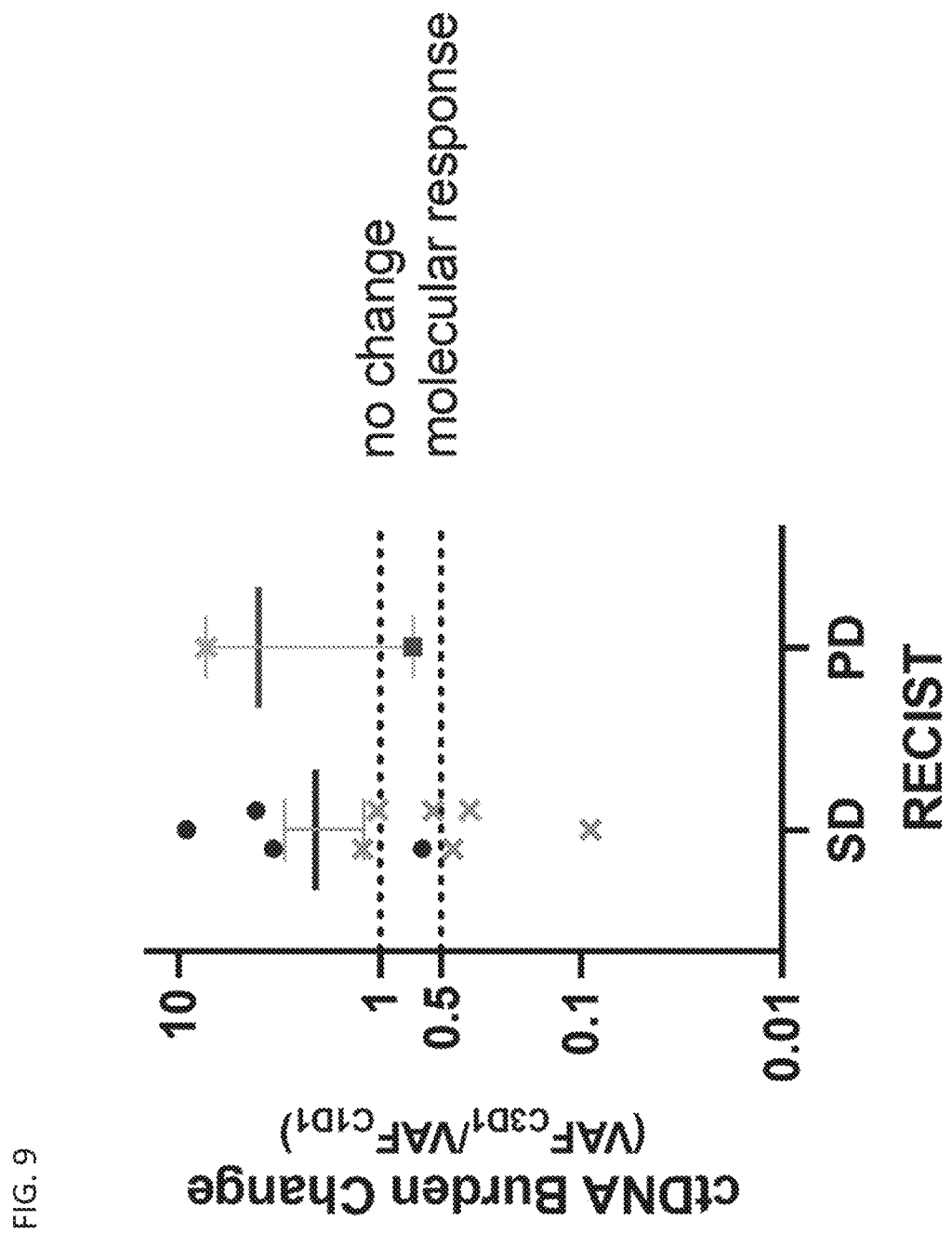
FIG. 9 shows molecular and radiographic responses to RMC-5552 for a subject treated with 6 mg and above of RMC-5552 as evaluated by RECIST (Response Evaluation Criteria in Solid Tumors). X=Subject with pathogenic PTEN, PIK3CA, or TSC1/2 Variant at Baseline.

Further results are shown in FIG. 8, which shows the change in ctDNA burden for dose cohorts treated at a dosage of 1.6 mg to 10 mg. The mean±SEM of fractional change in mean VAF from C1D1 to C3D1 was determined by the Guardant Health Molecular Response Algorithm. In addition to the results shown in FIG. 8, one subject on 12 mg initial dose had effective molecular complete response and clinical PR (with 77% tumor burden reduction). The molecular response data suggest a dose-response relationship among all doses explore. Moreover, FIG. 9 shows molecular and radiographic responses to RMC-5552 for a subject treated with 6 mg and above of RMC-5552 as evaluated by RECIST v1.1 (Response Evaluation Criteria in Solid Tumours). Change in ctDNA is presented as mean±SEM of % change in mean VAF from C1D1 to C3D1. A molecular response was observed in 3 of 6 subjects that had SD (Stable Disease) as their best response by RECIST v1.1 and that had a pathogenic mTOR pathway variant. A subject with PD (Progressive Disease) as their best response by RECIST v1.1 and that had an mTOR pathway variant had myxoid liposarcoma with PIK3CA Q546E (not a canonical hotpsot mutation). The results presented in FIGS. 8 and 9, supported by preclinical data, indicate that the dose range of 6 mg to 12 mg represents a "steep" dose-exposure-response relationship.

Figure 10:
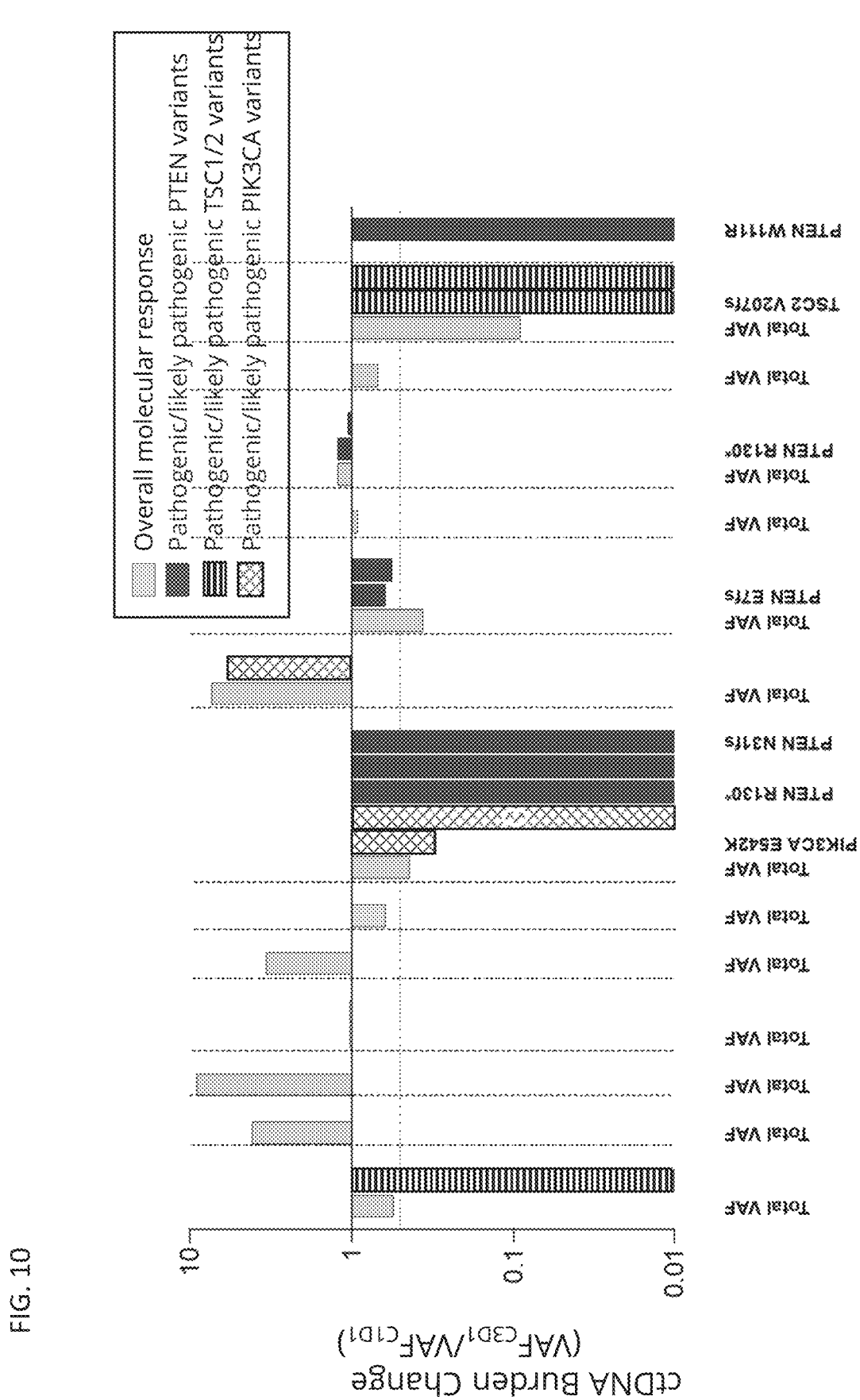
FIG. 10 graphically depicts the ctDNA burden change for overall molecular response, pathogenic/likely pathogenic PTEN variants, pathogenic/likely pathogenic TSC1/2 variants, and pathogenic/likely pathogenic PIK3CA variants.

FIG. 10 shows the change in ctDNA from baseline to C3D1 grouped by patient for overall molecular response (grey bars) and for specific mTOR pathway pathogenic variants (colored bars). This data supports usage of RMC-5552 for treatment of sub-patient populations associated with PTEN, TSC1/2, and/or PIK3CA variants, and the loss of mTOR pathway variants and supports the usage of RMC-5552 in particular for the treatment of a sub-population with high clonality (for example, greater than 50% clonality) of pathogenic variants in PTEN, TSC1/2, and/or PIK3CA.

TABLE 3

Human vs Mouse PK

| PK Parameter | Human PK | | | | | | Mean Mouse Exposure[2] | |
|---|---|---|---|---|---|---|---|---|
| | 6 mg | | 8 mg | | 10 mg[1] | 12 mg[1] | | |
| | C1D1 | C1D15 | C1D1 | C1D15 | C1D1 | C1D1 | 1 mg/kg | 3 mg/kg |
| Unbound $C_{max}$ (nM) | 5.6 | 8.7 | 8.6 | 20.1 | 11 | 22.6 | 2-8 | 3.7-14.7 |
| Unbound $AUC_{0-last}$ (nM × h) | 7.8 | 12.1 | 11.7 | 26.6 | 14.2 | 28.2 | 21-84 | 53-210 |

[1]C1D15 measurements pending; N = 2 each for 10 mg and 12 mg data points
[2]Mouse unbound exposure is calculated at fu: 0.001-0.004

2.4.3 Subject-Level Evidence of Anti-Tumor Activity

Table 4 presents Individual case studies providing evidence of anti-tumor activity.

TABLE 4

Anti-tumor activity

| Evidence of Anti-tumor Activity | Subject Histology Mutation | Dose Level | Best RECIST response | Time on treatment |
|---|---|---|---|---|
| Strong: PR by RECIST; Loss of clonal PTEN DN mutation; >1 yr SD | H&N (Salivary) PTEN DN | 12 mg single dose, 6 mg QW x12 mo, 6 mg 2 on/1 off x2 mo | PR 77% reduction | >13 mo |
| Strong: 37% reduction in CA125; progression only after prolonged hold; MR 91% | Uterine CaSarc TSC1 LOF | 10 mg single dose, 6 mg QW | SD 4.4% reduction | 7 mo |
| Strong: 50% reduction in FDG avidity by PET/CT; 72% reduction in CA125 | Ovarian CA TSC1 LOF | 6 mg QW | SD 19% increase (mixed) | 5 mo |
| Strong: Decrease of CA125 from peak of 1465 to nadir of 254; 9+ months SD; MR 64% | Endometrial PIK3CA, PTEN, TSC2 | 8 mg QW | SD 7% reduction | >9 mo |
| Strong: >6 mo SD despite poor adherence, continual decrease in lesions | 76F w NSCLC BRAF fusion | 10 mg single dose, 6 mg "QW" (Missed 16 of 28 doses) | SD 22% reduction | >6 mo |
| Moderate: 12.2% reduction in fast progressor/widely metastatic | 70F w NSCLC STK11 | 8 mg QW | SD 12% reduction | 3 mo |
| Strong: >4 mo stable disease w modest reduction in lesion; 31% decrease in VAF | 67F w NSCLC STK11, TSC2, KRAS L19F | 8 mg QW | SD 4% reduction | >4 mo |

2.5. Clinical Safety

Adverse events (AEs) were based on the Medical Dictionary for Regulatory Activities (MedDRA) preferred terms and included the grouped preferred term of stomatitis/mucositis using mucosal inflammation, oral pain, and stomatitis. No events of non-oral mucositis were reported. Frequently reported (in 1500 of subjects) treatment-emergent AEs of any grade by MedDRA preferred term (PT) or grouped PTs, regardless of relationship to study drug, included fatigue (61.5%), stomatitis/mucositis (56.40%), decreased appetite (43.6%), nausea (41.0%), vomiting, (30.80%), dyspnea and rash (grouped term) (each 28.20%), anemia (25.6%), diarrhea (23.10%), headache and abdominal pain (each 20.5%). Frequently reported (in ≥5% of subjects) Grade ≥3 TEAEs included anemia (15.4%), stomatitis/mucositis (10.3%), fatigue, dysphagia, rash (grouped term) and urinary tract infection (each 5.1%). Of note, the grouped term of stomatitis/mucositis comprised events of (based on MedDRA PT) mucosal inflammation, oral pain, and stomatitis. No events of non-oral mucositis were reported. Other events of interest (which are based on observations from other agents that inhibit the mTOR signaling pathway) reported in clinical study RMC-5552-001, include rash maculo-papular (17.9%), edema peripheral (10.3%), and hyperglycemia (7.7%). Refer to Table 5 for Treatment-Emergent Adverse Events.

The dose of 6 mg RMC-5552 IV once weekly was well tolerated and dose of 8 mg was cleared with no dose-limiting toxicities. No related Grade 4 or 5 adverse events (AEs) were reported. Across all dose levels, the most common (≥25%) treatment-related AEs (TRAEs) were mucositis/stomatitis (35%), decreased appetite (25%), diarrhea (25%), fatigue (25%) and nausea (25%). The most common Grade 3 TRAEs were mucositis/stomatitis observed in 3 patients at dose levels ≥10 mg (15%) and were dose-limiting. Refer to Table 6 for TRAEs.

Most of the treatment-emergent SAEs were Grade 3, with the exception of 1, Grade 2 SAE of ileal perforation. There were no Grade 4 or 5 SAEs. No SAEs were assessed as treatment-related by investigators. Refer to Table 7 for all reported treatment-emergent SAEs.

Based on the protocol definition of Dose Limiting Toxicity (DLT), no DLT events were observed for 8 DLT evaluable subjects at doses from 1.6 to 6 mg. At a dose of 12 mg over a 1-hour infusion, both enrolled subjects had events of Grade 3 mucositis within the first week of treatment. One subject skipped their second dose and restarted study drug at Week 3 at a reduced dose of 6 mg while the other subject withdrew consent and discontinued the study. These 2 subjects were not considered DLT evaluable due to not receiving at least 67% of the study drug during the DLT period (first cycle) and did not experience a DLT per the protocol. The Dose Committee (DC) decided to discontinue enrollment in the 12-mg over a 1-hour infusion dose level due to intolerability and deescalate the dose to 10 mg over a 2-hour infusion. Of the 4 subjects enrolled at 10 mg, 2 subjects were DLT evaluable at the time of the data cutoff date and 1 had a DLT event of Grade 3 mucositis.

Table 8. The dose finding portion of the study is ongoing.

TABLE 5

| | Incidence of Treatment-Emergent Adverse Events in ≥10% of Subjects | | | | | | | |
|---|---|---|---|---|---|---|---|---|
| | Number (%) of Subjects | | | | | | | |
| MedDRA System Organ Class | 1.6 mg QW 21-day cycle (N = 2) | | 3 mg QW 21-day cycle (N = 3) | | 6 mg QW 21-day cycle (N = 12) | | 12 mg QW 21-day cycle (N = 2) | |
| Preferred Term | Any Grade | Grade ≥3 | Any Grade | Grade ≥3 | Any Grade | Grade ≥3 | Any Grade | Grade ≥3 |
| Subjects with any TEAE | 2 (100) | 1 (50.0) | 3 (100) | 1 (33.3) | 12 (100) | 6 (50) | 2 (100) | 2 (100) |
| Blood and Lymphatic System Disorders | | | | | | | | |
| Anaemia | 1 (50.0) | 1 (50.0) | 2 (66.7) | 1 (33.3) | 2 (16.7) | 1 (8.3) | 0 | 0 |
| Gastrointestinal Disorders | | | | | | | | |
| Nausea | 1 (50.0) | 0 | 0 | 0 | 6 (50.0) | 0 | 0 | 0 |
| Stomatitis/mucositis[a] | 0 | 0 | 0 | 0 | 8 (66.7) | 1 (8.3) | 2 (100) | 2 (100) |
| Vomiting | 1 (50.0) | 0 | 0 | 0 | 6 (50.0) | 1 (8.3) | 0 | 0 |
| Diarrhea | 0 | 0 | 1 (33.3) | 0 | 1 (8.3) | 0 | 0 | 0 |
| Abdominal pain | 1 (50.0) | 0 | 0 | 0 | 1 (8.3) | 0 | 0 | 0 |
| Constipation | 0 | 0 | 1 (33.3) | 0 | 2 (16.7) | 0 | 0 | 0 |
| Dysphagia | 0 | 0 | 0 | 0 | 2 (16.7) | 1 (8.3) | 0 | 0 |
| General Disorders and Administration Site Conditions | | | | | | | | |
| Fatigue | 2 (100) | 0 | 1 (33.3) | 0 | 7 (58.3) | 2 (16.7) | 1 (50.0) | 0 |
| Oedema peripheral | 0 | 0 | 1 (33.3) | 0 | 1 (8.3) | 0 | 0 | 0 |
| Pain | 0 | 0 | 1 (33.3) | 0 | 1 (8.3) | 0 | 0 | 0 |
| Infections and Infestations | | | | | | | | |
| Urinary tract infection | 1 (50.0) | 0 | 0 | 0 | 3 (25) | 2 (16.7) | 0 | 0 |
| Candida infection | 0 | 0 | 1 (33.3) | 0 | 2 (16.7) | 1 (8.3) | 1 (50.0) | 0 |
| Investigations | | | | | | | | |
| ALT increased | 0 | 0 | 1 (33.3) | 1 (33.3) | 0 | 0 | 0 | 0 |
| Weight decreased | 0 | 0 | 1 (33.3) | 0 | 3 (25.0) | 0 | 0 | 0 |
| AST increased | 0 | 0 | 1 (33.3) | 0 | 0 | 0 | 0 | 0 |
| Metabolism and Nutrition Disorders | | | | | | | | |
| Decreased appetite | 2 (100) | 0 | 1 (33.3) | 0 | 9 (75.0) | 0 | 0 | 0 |
| Hyponatremia | 0 | 0 | 1 (33.3) | 0 | 2 (16.7) | 0 | 1 (50.0) | 1 (50.0) |
| Dehydration | 1 (50.0) | 0 | 1 (33.3) | 0 | 2 (16.7) | 1 (8.3) | 0 | 0 |
| Hypokalemia | 0 | 0 | 2 (66.7) | 0 | 1 (8.3) | 0 | 0 | 0 |
| Hyperglycemia[b] | 0 | 0 | 0 | 0 | 1 (8.3) | 0 | 0 | 0 |
| Musculoskeletal and Connective Tissue Disorders | | | | | | | | |
| Pain in extremity | 1 (50.0) | 0 | 0 | 0 | 1 (8.3) | 0 | 0 | 0 |
| Arthralgia | 0 | 0 | 0 | 0 | 0 | 0 | 1 (50.0) | 0 |
| Nervous System Disorders | | | | | | | | |
| Headache | 0 | 0 | 1 (33.3) | 0 | 2 (16.7) | 0 | 1 (50.0) | 0 |

TABLE 5-continued

Incidence of Treatment-Emergent Adverse Events in ≥10% of Subjects

| | | | | | | | | |
|---|---|---|---|---|---|---|---|---|
| Psychiatric Disorders | | | | | | | | |
| Insomnia | 0 | 0 | 0 | 0 | 2 (16.7) | 0 | 0 | 0 |
| Respiratory, Thoracic, and Mediastinal Disorders | | | | | | | | |
| Dyspnoea | 0 | 0 | 0 | 0 | 5 (41.7) | 0 | 0 | 0 |
| Skin and Subcutaneous Tissue Disorders | | | | | | | | |
| Rash[c] | 0 | 0 | 0 | 0 | 5 (41.7) | 1 (8.3) | 1 (50.0) | 0 |

| MedDRA System Organ Class Preferred Term | 10 mg (2-hour inf) QW 21-day cycle (N = 5) | | 8 mg QW 21-day cycle (N = 15) | | Overall (N = 39) | |
|---|---|---|---|---|---|---|
| | Any Grade | Grade ≥3 | Any Grade | Grade ≥3 | Any Grade | Grade ≥3 |
| Subjects with any TEAE | 5 (100) | 1 (60) | 15 (100) | 10 (66.7) | 39 (100) | 23 (59.0) |
| Blood and Lymphatic System Disorders | | | | | | |
| Anaemia | 0 | 0 | 5 (33.3) | 3 (20.0) | 10 (25.6) | 6 (15.4) |
| Gastrointestinal Disorders | | | | | | |
| Nausea | 2 (40.0) | 0 | 7 (46.7) | 1 (6.7) | 16 (41.0) | 1 (2.6) |
| Stomatitis/mucositis[a] | 4 (80.0) | 1 (20.0) | 8 (53.3) | 0 | 22 (56.4) | 4 (10.3) |
| Vomiting | 1 (20.0) | 0 | 4 (26.7) | 0 | 12 (30.8) | 1 (2.6) |
| Diarrhea | 3 (60) | 0 | 4 (26.7) | 0 | 9 (23.1) | 0 |
| Abdominal pain | 2 (40.0) | 0 | 4 (26.7) | 1 (6.7) | 8 (20.5) | 1 (2.6) |
| Constipation | 0 | 0 | 3 (20.0) | 0 | 6 (15.4) | 0 |
| Dysphagia | 0 | 0 | 2 (13.3) | 1 (6.7) | 4 (10.3) | 2 (5.1) |
| General Disorders and Administration Site Conditions | | | | | | |
| Fatigue | 3 (60.0) | 0 | 10 (66.7) | 0 | 24 (61.5) | 2 (5.1) |
| Oedema peripheral | 0 | 0 | 2 (13.3) | 0 | 4 (10.3) | 0 |
| Pain | 0 | 0 | 2 (13.3) | 0 | 4 (10.3) | 0 |
| Infections and Infestations | | | | | | |
| Urinary tract infection | 1 (20.0) | 0 | 2 (13.3) | 0 | 7 (17.9) | 2 (5.1) |
| Candida infection | 0 | 0 | 2 (13.3) | 0 | 6 (15.4) | 1 (2.6) |
| Investigations | | | | | | |
| ALT increased | 1 (20.0) | 0 | 3 (20) | 0 | 5 (12.8) | 1 (2.6) |
| Weight decreased | 0 | 0 | 1 (6.7) | 0 | 5 (12.8) | 0 |
| AST increased | 1 (20.0) | 0 | 2 (13.3) | 0 | 4 (10.3) | 0 |
| Metabolism and Nutrition Disorders | | | | | | |
| Decreased appetite | 1 (20.0) | 0 | 4 (26.7) | 0 | 17 (43.6) | 0 |
| Hyponatremia | 0 | 0 | 2 (13.3) | 0 | 6 (15.4) | 1 (2.6) |
| Dehydration | 0 | 0 | 0 | 0 | 4 (10.3) | 1 (2.6) |
| Hypokalemia | 0 | 0 | 1 (6.7) | 0 | 4 (10.3) | 0 |

TABLE 5-continued

Incidence of Treatment-Emergent Adverse Events in ≥10% of Subjects

| | | | | | | | |
|---|---|---|---|---|---|---|---|
| Hyperglycemia [b] | 0 | 0 | 2 (13.3) | 0 | 3 (7.7) | 0 | |

Musculoskeletal and Connective Tissue Disorders

| | | | | | | | |
|---|---|---|---|---|---|---|---|
| Pain in extremity | 1 (20.0) | 0 | 3 (20) | 1 (6.7) | 6 (15.4) | 1 (2.6) | |
| Arthralgia | 1 (20.0) | 0 | 2 (13.3) | 0 | 4 (10.3) | 0 | |

Nervous System Disorders

| | | | | | | | |
|---|---|---|---|---|---|---|---|
| Headache | 0 | 0 | 4 (26.7) | 0 | 8 (20.5) | 0 | |

Psychiatric Disorders

| | | | | | | | |
|---|---|---|---|---|---|---|---|
| Insomnia | 2 (40.0) | 0 | 0 | 0 | 4 (10.3) | 0 | |

Respiratory, Thoracic, and Mediastinal Disorders

| | | | | | | | |
|---|---|---|---|---|---|---|---|
| Dyspnoea | 3 (60) | 1 (20.0) | 3 (20.0) | 0 | 11 (28.2) | 1 (2.6) | |

Skin and Subcutaneous Tissue Disorders

| | | | | | | | |
|---|---|---|---|---|---|---|---|
| Rash[c] | 1 (20.0) | 0 | 4 (26.7) | 1 (6.7) | 11 (28.2) | 2 (5.1) | |

Abbreviations: ALT = alanine aminotransferase; AST = aspartate aminotransferase; inf = infusion; MedDRA = Medical Dictionary for Regulatory Activities; TEAE = treatment - emergent adverse events; QW = once weekly.
Subjects were summarized based on Cycle 1 Day 1 Dose received.
[a] Includes preferred terms of stomatitis, mucosal inflammation, oral pain.
[b] Hyperglycemia included in table regardless of frequency.
[c] Preferred terms for Rash (group term): dermatitis allergic, erythema, rash, rash maculopapular, rash pustular.

TABLE 6

Incidence of Treatment-related Adverse Events in ≥10% of Subjects

| | Number (%) of Subjects | | | | | | | |
|---|---|---|---|---|---|---|---|---|
| MedDRA System Organ Class | 1.6 mg QW 21-day cycle (N = 2) | | 3 mg QW 21-day cycle (N = 3) | | 6 mg QW 21-day cycle (N = 12) | | 12 mg QW 21-day cycle (N = 2) | |
| Preferred Term | Any Grade | Grade ≥3 | Any Grade | Grade ≥3 | Any Grade | Grade ≥3 | Any Grade | Grade ≥3 |
| Subjects with any TEAE | 2 (100) | 1 (50.0) | 2 (66.7) | 1 (33.3) | 10 (83.3) | 4 (33.3) | 2 (100) | 2 (100) |
| Blood and Lymphatic System Disorders | | | | | | | | |
| Anaemia | 1 (50.0) | 1 (50.0) | 0 | 0 | 1 (8.3) | 0 | 0 | 0 |
| Gastrointestinal Disorders | | | | | | | | |
| Nausea | 0 | 0 | 0 | 0 | 6 (50.0) | 0 | 0 | 0 |
| Stomatitis/ mucositis[a] | 0 | 0 | 0 | 0 | 5 (41.7) | 1 (8.3) | 2 (100) | 2 (100) |
| Vomiting | 0 | 0 | 0 | 0 | 5 (41.7) | 0 | 0 | 0 |
| Diarrhea | 0 | 0 | 1 (33.3) | 0 | 0 | 0 | 0 | 0 |
| General Disorders and Administration Site Conditions | | | | | | | | |
| Fatigue | 1 (50.0) | 0 | 0 | 0 | 6 (50.0) | 2 (16.7) | 1 (50.0) | 0 |
| Metabolism and Nutrition Disorders | | | | | | | | |
| Decreased appetite | 1 (50.0) | 0 | 1 (33.3) | 0 | 7 (58.3) | 0 | 0 | 0 |
| Hyponatremia | 0 | 0 | 0 | 0 | 2 (16.7) | 0 | 1 (50.0) | 1 (50.0) |
| Hyperglycemia [b] | 0 | 0 | 0 | 0 | 1 (8.3) | 0 | 0 | 0 |
| Respiratory, Thoracic, and Mediastinal Disorders | | | | | | | | |
| Dyspnoea | 0 | 0 | 0 | 0 | 2 (16.7) | 0 | 0 | 0 |

TABLE 6-continued

Incidence of Treatment-related Adverse Events in ≥10% of Subjects

Skin and Subcutaneous Tissue Disorders

| Rash maculopapular | 0 | 0 | 0 | 0 | 3 (25.0) | 1 (8.3) | 0 | 0 |

| MedDRA System Organ Class | 10 mg QW (2-hour infusion) 21-day cycle (N = 5) | | 8 mg QW 21-day cycle (N = 15) | | Overall (N = 39) | |
|---|---|---|---|---|---|---|
| Preferred Term | Any Grade | Grade ≥3 | Any Grade | Grade ≥3 | Any Grade | Grade ≥3 |
| Subjects with any TEAE | 5 (100) | 1 (20.0) | 13 (86.7) | 4 (26.7) | 34 (87.2) | 13 (33.3) |
| Blood and Lymphatic System Disorders | | | | | | |
| Anaemia | 0 | 0 | 4 (26.7) | 2 (13.3) | 6 (15.4) | 3 (7.7) |
| Gastrointestinal Disorders | | | | | | |
| Nausea | 2 (40.0) | 0 | 5 (33.3) | 1 (6.7) | 13 (33.3) | 1 (2.6) |
| Stomatitis/mucositis[a] | 4 (80.0) | 1 (20.0) | 6 (40.0) | 0 | 17 (43.6) | 4 (10.3) |
| Vomiting | 1 (20.0) | 0 | 4 (26.7) | 0 | 10 (25.6) | 0 |
| Diarrhea | 2 (40.0) | 0 | 4 (26.7) | 0 | 7 (17.9) | 0 |
| General Disorders and Administration Site Conditions | | | | | | |
| Fatigue | 2 (40.0) | 0 | 6 (40.0) | 0 | 16 (41.0) | 2 (5.1) |
| Metabolism and Nutrition Disorders | | | | | | |
| Decreased appetite | 1 (20.0) | 0 | 3 (20.0) | 0 | 13 (33.3) | 0 |
| Hyponatremia | 0 | 0 | 1 (6.7) | 0 | 4 (10.3) | 1 (2.6) |
| Hyperglycemia [b] | 0 | 0 | 0 | 0 | 1 (2.6) | |
| Respiratory, Thoracic, and Mediastinal Disorders | | | | | | |
| Dyspnoea | 1 (20.0) | 0 | 2 (13.3) | 0 | 5 (12.8) | 0 |
| Skin and Subcutaneous Tissue Disorders | | | | | | |
| Rash maculopapular | 0 | 0 | 2 (13.3) | 1 (6.7) | 5 (12.8) | 2 (5.1) |

Abbreviations: TEAE = treatment - emergent adverse events; QW = once a week.
The event relationship to the study drug is assessed by the investigator. Subjects were summarized based on Cycle 1 Day 1 dose received.
[a] Stomatitis/mucositis includes PTs of stomatitis, mucosal inflammation, oral pain.
[b] Hyperglycemia included in table regardless of frequency

TABLE 7

Incidence of Treatment-Emergent Serious Adverse Events in RMC-5552-001

| | Number (%) of Subjects | | | | | | |
|---|---|---|---|---|---|---|---|
| Preferred Term | 1.6 mg QW 21-Day cycle (N = 2) | 3 mg QW 21-Day cycle (N = 3) | 6 mg QW 21-Day cycle (N = 12) | 12 mg QW 21-Day cycle (N = 2) | 10 mg QW (2-hour infusion) 21-Day cycle (N = 5) | 8 mg QW 21-Day cycle (N = 15) | Overall (N = 39) |
| Number of subjects with any SAE | 0 | 0 | 6 (50.0) | 0 | 3 (60.0) | 5 (33.3) | 14 (35.9) |
| Anemia along with occlusion[a] | 0 | 0 | 0 | 0 | 0 | 1 (6.7) | 1 (2.6) |
| Acute kidney injury | 0 | 0 | 0 | 0 | 1 (20.0) | 0 | 1 (2.6) |

TABLE 7-continued

Incidence of Treatment-Emergent Serious Adverse Events in RMC-5552-001

Number (%) of Subjects

| Preferred Term | 1.6 mg QW 21-Day cycle (N = 2) | 3 mg QW 21-Day cycle (N = 3) | 6 mg QW 21-Day cycle (N = 12) | 12 mg QW 21-Day cycle (N = 2) | 10 mg QW (2-hour infusion) 21-Day cycle (N = 5) | 8 mg QW 21-Day cycle (N = 15) | Overall (N = 39) |
|---|---|---|---|---|---|---|---|
| Anaemia | 0 | 0 | 0 | 0 | 0 | 1 (6.7) | 1 (2.6) |
| Atrial fibrillation | 0 | 0 | 1 (8.3) | 0 | 0 | 0 | 1 (2.6) |
| Dehydration | 0 | 0 | 1 (8.3) | 0 | 0 | | 1 (2.6) |
| Dyspnea | 0 | 0 | 0 | 0 | 1 (20.0) | 0 | 1 (2.6) |
| Embolism | 0 | 0 | 0 | 0 | 1 (20.0) | 0 | 1 (2.6) |
| Face Oedema | 0 | 0 | 1 (8.3) | 0 | 0 | 0 | 1 (2.6) |
| Failure to Thrive | 0 | 0 | 1 (8.3) | 0 | 0 | 0 | 1 (2.6) |
| Fatigue | 0 | 0 | 0 | 0 | 1 (20.0) | 0 | 1 (2.6) |
| Hypotension | 0 | 0 | 1 (8.3) | 0 | 0 | | 1 (2.6) |
| Large intestinal obstruction | 0 | 0 | 0 | 0 | 0 | 1 (6.7) | 1 (2.6) |
| Lower gastrointestinal hemorrhage | 0 | 0 | 0 | 0 | 0 | 1 (6.7) | 1 (2.6) |
| Oedema peripheral | 0 | 0 | 1 (8.3) | 0 | 0 | 0 | 1 (2.6) |
| Pain in extremity | 0 | 0 | 0 | 0 | 0 | 1 (6.7) | 1 (2.6) |
| Pleural effusion | 0 | 0 | 0 | 0 | 1 (20.0) | 0 | 1 (2.6) |
| Pneumonia | 0 | 0 | 0 | 0 | 0 | 1 (6.7) | 1 (2.6) |
| Pneumonia aspiration | 0 | 0 | 0 | 0 | 0 | 1 (6.7) | 1 (2.6) |
| Pneumothorax | 0 | 0 | 0 | 0 | 1 (20.0) | 0 | 1 (2.6) |
| Rash maculopapular | 0 | 0 | 1 (8.3) | 0 | 0 | 0 | 1 (2.6) |
| Rectourethral fistula | 0 | 0 | 1 (8.3) | 0 | 0 | 0 | 1 (2.6) |
| Small intestinal obstruction | 0 | 0 | 1 (8.3) | 0 | 0 | 0 | 1 (2.6) |
| Small intestinal perforation | 0 | 0 | 1 (8.3) | 0 | 0 | 0 | 1 (2.6) |
| Stomatitis/mucositis | 0 | 0 | 1 (8.3) | 0 | 0 | 0 | 1 (2.6) |
| Urinary tract infection | 0 | 0 | 1 (8.3) | 0 | 0 | 0 | 1 (2.6) |
| Vascular occlusion | 0 | 0 | 0 | 0 | 0 | 1 (6.7) | 1 (2.6) |
| Wound infection | 0 | 0 | 0 | 0 | 0 | 1 (6.7) | 1 (2.6) |

Abbreviations: SAE = serious adverse events; QW = once a week.
Subjects were summarized based on Cycle 1 Day 1 dose received.
[a]This event was uncoded at the time of the data cut-off date.

TABLE 8

Summary of Dose Limiting Toxicity in Dose Escalation Phase of RMC-5552-001

| Parameter | 1.6 mg QW 21-day cycle (N = 2) | 3 mg QW 21-day cycle (N = 3) | 6 mg QW 21-day cycle (N = 12) | 12 mg QW 21-day cycle (N = 2) | 10 mg QW (2-hour infusion)/ 21-day cycle (N = 5) | 8 mg QW 21-day cycle (N = 15) | Overall (N = 39) |
|---|---|---|---|---|---|---|---|
| DLT Evaluable Subjects, N | 2 | 3 | 11 | 0 | 3 | 14 | 33 |
| Subjects with DLT, n | 0 | 0 | 0 | 0[a] | 1 | 0 | 1 |
| n/N (DLT rate) | 0 | 0 | 0 | 0 | 1/3 (33.3%)[b] | 0 | 1/33 (3.0%) |

Abbreviations: DLT = dose limiting toxicity; QW = once a week.
Percentage is calculated based on DPT evaluable subjects. Subjects were summarized based on Cycle 1 Day 1 Dose received.
[a]Dose not tolerated and enrollment discontinued due to both subjects experiencing Grade 3 stomatitis (not DLT per protocol) immediately prior to second dose.
[b]One subject in the 10 mg group experienced a DLT of Grade 3 stomatitis.

2.5.1 Clinical Safety-Tacrolimus Ameliorates AEs

Table 9 presents data from all patients (N=27) treated either with dexamethasone mouthwash alone, or dexamethasone mouthwash plus tacrolimus mouthwash at 8 mg (N=16), 10 mg (N=8), and 12 mg (N=3) IV QW. Median time on treatment (min, max) was 2.6 months for patients treated at 8 mg IV QW with dexamethasone mouthwash alone (N=13), 1.2 months for patients treated at 8 mg IV QW with dexamethasone mouthwash plus tacrolimus mouthwash (N=3), 0.9 months for patients treated at 10 mg IV QW with dexamethasone mouthwash alone (N=5), 2.0 months for patients treated at 10 mg IV QW with dexamethasone mouthwash plus tacrolimus mouthwash (N=3), 9.1 months for patients treated at 12 mg IV QW with dexamethasone mouthwash alone (N=2), and 0.4 months for patients treated at 12 mg IV QW with dexamethasone mouthwash plus tacrolimus mouthwash (N=1). At the 10 mg and 12 mg IV QW dose levels, mean relative dose intensity (RDI) was higher in the tacrolimus mouthwash subgroups, suggesting improved tolerability. Among all dose levels, the frequency of Grade 3 or worse events, frequency and severity of mucositis, and frequency of AEs leading to dose modification were lower in those patients treated with tacrolimus mouthwash.

Subjects received dexamethasone alone or dexamethasone plus tacrolimus mouthwash(es). Subjects swish either 2.5 mL of 0.5 mg/5 mL dexamethasone alcohol-free solution or 2.5 mL of 0.5 mg/5 mL dexamethasone alcohol-free solution and 2.5 mL of 0.5 mg/5 mL tacrolimus in oral sweet/oral plus solution for 2 minutes, 4 times each day, and do not eat or drink for at least 1 hour after each mouthwash rinse. At baseline (C1D1 predose), subjects rinse with the mouthwash(es) once at least 15 minutes prior to the first dose of study intervention.
As tacrolimus mitigated the tolerability-limiting toxicity, this allowed for further dose escalation (cleared above 10-12 mg), increased anti-tumor activity (evidenced by the ctDNA dose-response, and by the PR patient, who was initially treated at 12 mg).

measured by the incidence of dose-limiting toxicities (DLTs), treatment-emergent adverse events (TEAEs), and serious adverse events (SAEs). The starting dose of RMC-5552 will be 1.6 mg once weekly (QW) via intravenous (IV) infusion. The first cycle of treatment (i.e., first 21 days after treatment initiation) constitutes the DLT evaluation period.

Enrollment in the Dose-Expansion Phase at the candidate RP2DS will be initiated after the Dose-Escalation Phase has ended and at maximum tolerated dose (MTD) and/or the candidate RP2DS have been established. Once the candidate RP2DS is declared, the Dose-Expansion Phase at the candidate RP2DS will commence and enroll up to 60 additional subjects with specific genotypic aberrations of the mTOR pathway.

RMC-5552 study treatment will be continued until disease progression or unacceptable toxicity. Subjects who have stable disease (SD) as best response will be allowed to continue on treatment, provided the investigator believes it is in the subject's best interest and none of the criteria for discontinuation have been met. Subjects who discontinue study intervention should complete the safety follow-up/end of treatment (EOT) visit 30 days (±5 days) after the last dose, or prior to initiation of alternative anticancer therapy, whichever is earlier. Subjects who do not withdraw consent will also undergo long-term follow-up by telephone contact every 3 months (+2 weeks) from the last dose of study intervention for survival. The anticipated duration of the study is approximately 3 years.

Up to approximately 132 subjects will be enrolled in this study. For the Dose-Escalation Phase of the study, enrollment will include up to 48 subjects (assuming 8 dose cohorts

TABLE 9

Data demonstrating benefit of tacrolimus for prophylaxis or on-treatment of mucositis in patients treated with RMC-5552

| | 8 mg IV QW | | 10 mg IV QW[1] | | 12 mg IV QW | |
| --- | --- | --- | --- | --- | --- | --- |
| | Dex | Dex + Tacro | Dex | Dex + Tacro | Dex | Dex + Tacro |
| N | 13 | 3 | 5 | 3 | 2 | 1 |
| Median time on treatment (min, max) | 2.6 mo (0.5, 10.8) | 1.2 mo (0.3, 1.2) | 0.9 mo (0.03, 6.9) | 2.0 mo (0.9, 2.1) | 9.1 mo (0.03, 18.1) | 0.4 mo |
| Mean RDI | 85% | 72% | 56% | 90% | 71% | 100% |
| Gr ≥3 related AEs (Specific terms) | 30.8% (15.4% anemia, 7.7% rash, 7.7% nausea) | 0 | 20% (20% mucositis) | 0 | 100% (100% mucositis) | 0 |
| AEs leading to dose modification | 30.8% | 0 | 100% | 33.3% | 50% | 0 |
| Mucositis, any grade (includes "oral pain") | 69.2% | 0 | 80% | 33.3% | 100% | 0 |
| Fatigue (all Gr1-2) | 69.2% | 66.7% | 60% | 66.7% | 50% | 0 |
| Neutropenia (all Gr1-2) | 0 | 0 | 0 | 66.7% | 0 | 0 |

[1]Includes all patients treated at 10 mg IV QW, including both 1 hour infusion and 2 hour infusion.

Example 3—Phase 1/1b Study of RMC-5552 Monotherapy in Subjects with Advanced Relapsed/Refractory Solid Tumors There are 2 components in this study: a Dose-Escalation Phase and a Dose-Expansion Phase at the candidate recommended Phase 2 dose (RP2DS).

In the Dose-Escalation Phase, assessment of safety and tolerability will be the primary endpoints and will be directly with approximately 6 subjects per cohort) and up to 24 additional subjects in the optionally expanded dose-escalation cohorts at doses that have cleared DLT assessment but prior to determination of the candidate RP2DS (maximum of 12 subjects per dose level). Up to 60 additional subjects will be enrolled in the Dose-Expansion Phase at the candidate RP2DS.

Intervention Groups and Duration: RMC-5552 will be administered QW via a 1 to 2 hour(s) IV infusion in 21-day cycles. Subjects in the Dose-Escalation Phase will receive RMC-5552 QW at doses ranging from 1.6 mg to up to 24 mg. Subjects in the Dose-Expansion Phase at the candidate RP2DS will receive RMC-5552 at the candidate RP2DS/schedule determined in the Dose-Escalation Phase.

3.2 Objectives and Endpoints

Objectives and endpoints for the study are described in Table 10.

TABLE 10

Objectives and Endpoints

| Objectives | Endpoints |
| --- | --- |
| Primary | |
| To characterize the safety and tolerability of RMC-5552 monotherapy in subjects with relapsed/refractory solid tumors To define the MTD and/or candidate RP2DS for RMC-5552 monotherapy in subjects with relapsed/refractory solid tumors | Incidence, nature, and severity of TEAEs, SAEs, and clinically significant changes in laboratory test values or vital sign measurements for RMC-5552 monotherapy Incidence and nature of DLTs with RMC-5552 monotherapy for determination of the MTD |
| Secondary | |
| To characterize the plasma PK of RMC-5552 after single- and repeat-dose administration To evaluate the preliminary antitumor effects of RMC-5552 monotherapy in subjects with relapsed/refractory solid tumors harboring specific genotypic aberrations | PK parameters including, but not limited to, $C_{max}$, $t_{max}$, $AUC_{0-t}$, $AUC_{inf}$, $t_{1/2}$, and accumulation ratio ORR and DOR of subjects treated with RMC-5552 monotherapy |
| Exploratory | |
| To further characterize preliminary efficacy of RMC-5552 by DCR, PFS, and OS in subjects with relapsed/refractory solid tumors harboring specific genotypic aberrations To assess pharmacodynamic markers of drug activity, including biochemical markers of mTORC1 pathway inhibition in blood and/or tumor tissue To characterize the relationship between plasma PK of RMC-5552 and pharmacodynamic changes To explore predictive biomarkers of response to RMC-5552 in tumor tissue or blood | DCR of subjects treated with RMC-5552 monotherapy PFS of subjects treated with RMC-5552 monotherapy OS of subjects treated with RMC-5552 monotherapy Pharmacodynamic activity measured by treatment-emergent changes in blood and/or tumor tissue biomarkers Correlation of plasma concentrations of RMC-5552 and pharmacodynamic changes Correlation of pharmacodynamic biomarker changes with antitumor activity Correlation of predictive biomarkers with antitumor activity |

Abbreviations: $AUC_{0-t}$, area under the concentration-time curve from dosing time 0 to time t; $AUC_{inf}$, area under the concentration-time curve extrapolated to infinity; $C_{max}$, maximum concentration; DCR, disease control rate; DOR, duration of response; DLTs, dose-limiting toxicities; MTD, maximum tolerated dose; ORR, overall response rate; mTORC1, mammalian/mechanistic target of rapamycin complex 1; OS, overall survival; PFS, progression-free survival; PK, pharmacokinetic(s); RP2DS, recommended Phase 2 dose and schedule; SAEs, serious adverse events; $t_{1/2}$, terminal elimination half-life; TEAE, treatment-emergent adverse event; $t_{max}$, time to achieve maximum concentration.

3.3 Dose Escalation Phase Design

Dose escalation/de-escalation will follow a modified toxicity probability interval 2 (mTPI-2) algorithm (Guo W, Wang S J, Yang S, et al. A Bayesian interval dose-finding design addressing Ockham's razor: mTPI-2. *Contemp Clin Trials*. 2017; 58:23-33), with a target DLT probability of 0.30 and an acceptable toxicity probability interval of (0.25, 0.35).

The starting dose of RMC-5552 will be 1.6 mg QW via IV infusion. See Table 11 for possible dose escalations. The first cycle of treatment (i.e., first 21 days after treatment initiation) constitutes the DLT evaluation period.

TABLE 11

Dose Escalation

| Dose Level | Dosage (mg) | Incremental Increase (×) |
| --- | --- | --- |
| 1 (starting dose) | 1.6 | N/A |
| 2 | 3 | ~2 |

TABLE 11-continued

Dose Escalation

| Dose Level | Dosage (mg) | Incremental Increase (×) |
| --- | --- | --- |
| 3 | 6 | 2 |
| 4C | 8 | ~1.3 |

TABLE 11-continued

Dose Escalation

| Dose Level | Dosage (mg) | Incremental Increase (×) |
| --- | --- | --- |
| 4B | 10 | 1.25 |
| 4A | 12 | 2 |
| 5 | 16 | ~1.3 |
| 6 | 24 | ~1.5 |

Abbreviations: DC, Dose Committee; N/A, not applicable; PK, pharmacokinetic.
Note:
In addition to the planned dose levels, further degree of dose exploration (e.g., intermediate dose levels and/or dose level skipping) may also be implemented based on emerging safety and PK data and the DC decision.

A minimum of 3 to 4 subjects will be enrolled in each dose cohort. Generally, 3 DLT-evaluable subjects are required for DLT assessment. In the lower-dose cohorts of 1.6 mg (Dose Level 1), 3 mg (Dose Level 2), 6 mg (Dose Level 3), 8 mg (Dose Level 4C), 10 mg (Dose Level 4B), and 12 mg (Dose Level 4A), a decision to dose-escalate to the next dose level can be made if there are 2 DLT-evaluable subjects with zero DLTs and the other subjects become non-evaluable for reasons other than missing or discontinuing treatment due to a study drug-related adverse event (AE). If 1 DLT is observed in these 2 DLT-evaluable subjects, the third subject will be replaced and the cohort expanded, as guided by mTPI-2 design (see Table 12). Starting at 16 mg (Dose Level 5), or at any dose level explored after the dose with at least 1 DLT observed, a minimum of 3 DLT-evaluable subjects will be required for DLT assessment. To gain additional confidence at a dose level, 2 subjects may be enrolled in addition to the 4 subjects initially enrolled in the dosing cohort if the first 2 subjects have cleared the DLT period and did not experience any DLTs. If 1 DLT is observed in the first 3 evaluable DLT subjects of any dose cohort, additional subjects will be enrolled as guided by mTPI-2 design. A minimum of 6 subjects will be evaluated at the candidate RP2DS that may or may not be the MTD.

DLT assessment will be performed on the DLT-evaluable population. Replacement subjects may be enrolled if a subject becomes unevaluable for DLT, as guided by mTPI-2 design.

In addition to the planned dose levels, a further degree of dose exploration (e.g., intermediate dose levels and/or dose level skipping) may also be implemented based on emerging safety and PK data and the DC decision. Safety signals will be closely monitored, and smaller escalation increments may be considered, or it may be permitted to skip dose levels based on safety and PK data, provided the next-higher dose level studied is no more than twice the previous dose level.

Alternative dosing schedules may also be explored based on emerging safety and PK data.

based on the new cohort at the lowest dose still recommends dose de-escalation, new lower dose levels may be explored.
4. If the mTPI-2 rule indicates dose escalation at the highest planned dose level cohort, additional subjects may be enrolled to further evaluate the safety profile of the dose level. If the totality of safety data continues to indicate dose escalation, new dose levels may be explored.

To further assess the safety profile of RMC-5552, additional subjects may be enrolled at a dose level below the candidate RP2DS that has cleared DLT assessment and has been deemed to be tolerable. Up to a total of 12 subjects, including the initial subjects, may be enrolled in any dose-escalation cohort. These additional subjects will not be included in the mTPI-2 model.

Intrasubject dose modification to the highest dose level that has cleared DLT assessment may be permitted for subjects 1) who have not experienced a DLT, 2) who have not experienced any treatment-related Grade 3 or higher AEs, and 3) following approval from the Sponsor Medical Monitor. Similarly, subjects whose dose is above the candidate RP2DS may be dose-reduced to the candidate RP2DS, following approval from the Sponsor Medical Monitor. All subjects considered for intrasubject dose escalation must have completed at least 3 treatment cycles and have had at least 1 postbaseline tumor evaluation prior to dose increase. Upon selection of the candidate RP2DS, all subjects who remain on study intervention may have the option of dose modification to receive the RP2DS.

TABLE 12

Dose Escalation Rule of the Modified Toxicity Probability Interval 2 Method

| | | Number of Dose-Limiting Toxicity-Evaluable Subjects Treated at Current Dose | | | | | | | | | |
|---|---|---|---|---|---|---|---|---|---|---|---|
| | | 2 | 3 | 4 | 5 | 6 | 7 | 8 | 9 | 10 | 11 | 12 |
| Number of Dose-Limiting Toxicities | 0 | E | E | E | E | E | E | E | E | E | E | E |
| | 1 | D[a] | S | S | E | E | E | E | E | E | E | E |
| | 2 | DU | D | D | D | S | S | S | E | E | E | E |
| | 3 | | DU | DU | D | D | D | D | S | S | S | S |
| | 4 | | | DU | DU | DU | D | D | D | D | D | S |
| | 5 | | | | DU | DU | DU | DU | DU | D | D | D |
| | 6 | | | | | DU | DU | DU | DU | DU | DU | D |
| | 7 | | | | | | DU | DU | DU | DU | DU | DU |
| | 8 | | | | | | | DU | DU | DU | DU | DU |
| | 9 | | | | | | | | DU | DU | DU | DU |
| | 10 | | | | | | | | | DU | DU | DU |
| | 11 | | | | | | | | | | DU | DU |
| | 12 | | | | | | | | | | | DU |

Abbreviations: D, de-escalate to the next-lower dose; DU, de-escalate to the next-lower dose and the current dose will never be used again because of unacceptable high toxicity; E, escalate to the next-higher dose; N, number; S, stay at the current dose.
[a]"D" will not be applied for the cohorts of Dose Levels 1 to 4 (1.6 to 12 mg, respectively) at N = 2 as the exception; however, "DU" will give priority to the exception (i.e., if 2 of 2 subjects have a dose-limiting toxicity).

When using Table 12, note the following:
1. The first subject in the first dose cohort (1.6 mg QW) will be observed for the first 3 days of dosing prior to dosing additional subjects.
2. If the next dose level is considered to have unacceptable high toxicity (i.e., the probability that the DLT rate is higher than 30% at the next dose is greater than 95%), then the next enrolled cohort should be kept on the last current dose.
3. If the current dose is the lowest dose and the rule indicates dose de-escalation, then the new subjects should be treated at the lowest dose unless there is unacceptable high toxicity ("DU"), at which point, new lower dose levels may be explored. If the decision 3.3.1 Dose-Limiting Toxicity Criteria A DLT is defined as a toxicity that is considered at least possibly related to study intervention, occurs within the first 21 days of treatment initiation (i.e., during Cycle 1), and meets at least 1 of the following criteria (with severity graded according to Common Terminology Criteria for Adverse Events [CTCAE] v5):

Non-Hematologic DLTs:
  Any Grade ≥4 non-hematologic AE
  In general, any Grade 3 non-hematologic AE that remains uncontrolled for >72 hours despite optimal supportive therapy unless otherwise defined in the DLT criteria.
  Grade 3 allergic or hypersensitivity reactions lasting >24 hours Any Grade 4 gastrointestinal toxicity Any Grade 3 gastrointestinal toxicity requiring any procedural intervention (e.g., total parenteral nutrition, tube feeding, endoscopy, transfusion, hospitalization, surgery, manual evacuation, etc.)

Elevated liver transaminases and/or total bilirubin meeting the following criteria:

Grade 4 aspartate aminotransferase (AST), alanine aminotransferase (ALT), or bilirubin (direct or total), regardless of duration, presence of liver metastases, or Gilbert's syndrome Grade 3 AST, ALT, or bilirubin (direct or total), that does not resolve to Grade 1 or within normal limits or baseline grade within 14 days, regardless of the presence of liver metastases or Gilbert's syndrome Concurrent elevation of ALT or AST ≥3×upper limit of normal (ULN) and total bilirubin >2×ULN (>35% direct bilirubin) (>3×ULN total bilirubin for subjects with Gilbert's syndrome) or ALT or AST ≥3×ULN and international normalized ratio (INR) >1.5, which may indicate severe liver injury (potential Hy's Law), in the absence of cholestasis and other causes (e.g., viral hepatitis, other preexisting or acute liver disease, or another drug capable of the observed)

DLT exceptions: The following non-hematologic AEs will not be considered DLTs:

Grade 3 fatigue lasting ≤14 days

Grade 3 chills of any duration

Grade 3 rash (e.g., acneiform, pustular, or maculopapular type) that resolves to Grade ≤2 within 7 days and does not recur at the same severity level upon rechallenge at the same dose in the setting of optimal medical management.

Grade 3 nausea, vomiting, or diarrhea that resolves to Grade 1 or within normal limits or baseline grade within 72 hours, with supportive care.

Hematologic DLTs:

Grade ≥3 febrile neutropenia (defined as absolute neutrophil count [ANC]<1000 mm$^3$, with a single temperature of 38.3° C. [101° F.] or a sustained temperature of 38.0° C. [100.4° F.] for >1 hour)

Grade 4 neutropenia that does not resolve to Grade 1 or within normal limits or baseline grade within 7 days or that requires growth factor therapy Grade 4 thrombocytopenia, or Grade 3 thrombocytopenia with clinically significant bleeding Grade 3 or 4 lymphopenia that is deemed clinically significant by the investigator 3.4 Dose-Expansion Phase at the Candidate Recommended Phase 2 Dose Once the candidate RP2DS is established, the Dose-Expansion Phase will commence and enroll up to 60 additional subjects with specific histologies and genotypic aberrations. If necessary, expansion cohorts might include more than one candidate RP2DS. Expansion cohorts would permit the evaluation of histology-specific toxicities and assessment of preliminary anti-tumor activity. Subjects with the following three histology/genotype groups will be enrolled in the expansion cohorts:

Head and neck cancers with mTOR-pathway mutations

Non-small-cell lung carcinoma (NSCLC) with mutations of serine/threonine kinase 11 (STK11)/Kelch-like ECH-associated protein 1 (KEAP1)/nuclear factor, erythroid 2 like 2 (NFE2L2) and other mTOR-pathway mutations Solid tumors with MYC proto-oncogene, bHLH transcription factor (MYC) amplification A final determination of the RP2DS may include data for all subjects from the dose-escalation and the dose-expansion cohorts.

3.5 Prophylaxis for Mucositis and Stomatitis

Adverse events (AEs) specific to stomatitis/mucositis (bundled term comprising multiple MedDRA PTs) of any grade were reported in 56.4% (22/39) of subjects in the overall population of study RMC-5552-001. Grade 3 AEs of stomatitis/mucositis were reported in 10.3% (4/39) of subjects in the overall population. No subjects had a Grade 4 or 5 AE. The median time to first onset of stomatitis/mucositis was 12.5 days (range: 1-56 days) from the start of study treatment and the median duration of resolved events was 12.0 days (range: 1-144 days).

For Grade 2 events, provide corticosteroid mouthwash and manage pain per institutional guidelines. Study intervention interruption and/or dose reduction may be considered but is not required.

For Grade 3 events, consider the use of analgesics, corticosteroid mouthwash, and other supportive care per institutional guidelines. For the first occurrence, hold the study intervention until improvement to Grade 1 or normal or baseline grade. Resume study intervention at the same dose and provide topical corticosteroid mouthwash prophylaxis. For second and subsequent occurrences, hold the study intervention until improvement to Grade 1 or normal or baseline grade. Resume the study intervention at 1 dose level lower and provide topical corticosteroid mouthwash prophylaxis. Dose reductions for Grade 3 stomatitis/mucositis are permitted until the lowest biologically active dose (consult with the Sponsor Medical Monitor) has been reached.

For Grade 4 events, consider the use of analgesics and other supportive care per institutional guidelines. For the first occurrence, hold the study intervention until improvement to Grade 1 or normal or baseline grade. Resume the study intervention at 1 dose level lower if the event duration is ≤21 days and provide topical corticosteroid mouthwash prophylaxis. For a second occurrence, discontinue the study intervention. If, at any time, the study drug interruption for the event is >21 days, discontinue study intervention.

As a preventive measure, subjects will be instructed to suck on ice chips for 10 minutes before infusion, during infusion, and 10 minutes after infusion for a total of 80 minutes (1-hr infusion) or 140 minutes (2-hr infusion). Subjects will also be assigned to a mucositis/stomatitis mouthwash prophylaxis regimen provided by the sponsor. All subjects will be required to use corticosteroid mouthwash (dexamethasone alone or dexamethasone plus tacrolimus mouthwash) for the duration of the study. All subjects will be instructed to swish 2.5 mL dexamethasone mouthwash (0.5 mg/5 mL dexamethasone alcohol-free solution) and/or 2.5 mL tacrolimus mouthwash (0.5 mg/5 mL tacrolimus in oral sweet/oral plus solution) for 2 minutes, 4 times each day (starting on C1D1 at least 15 minutes prior to the first dose of RMC-5552), and not to eat or drink for at least 1 hour after each mouthwash rinse. Prophylaxis and/or treatment for oral thrush secondary to oral corticosteroids may be given through the use of oral clotrimazole lozenge 10 mg three times each day. All subjects will be instructed to record each dose of the mouthwash in a diary.

Subjects might receive dexamethasone alone or dexamethasone plus tacrolimus mouthwash(es). Instruct subjects to swish either 2.5 mL of 0.5 mg/5 mL dexamethasone alcohol-free solution or 2.5 mL of 0.5 mg/5 mL dexamethasone alcohol-free solution and 2.5 mL of 0.5 mg/5 mL tacrolimus in oral sweet/oral plus solution for 2 minutes, 4 times each day, and not eat or drink for at least 1 hour after each mouthwash rinse. At baseline (CID1 predose), the subject should rinse with the mouthwash(es) once at least 15 minutes prior to the first dose of study intervention. Instruct subjects to record each dose of mouthwash(es) in a diary.

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:

1. A method of treating a subject having a cancer, the method comprising administering a dosage of about 6 mg/week to about 25 mg/week of a compound to the subject: wherein the compound is

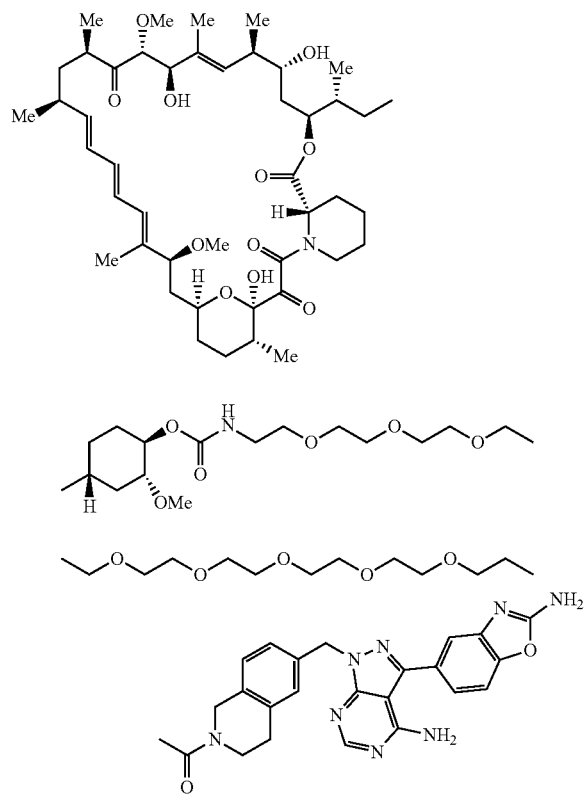

or a stereoisomer, tautomer, or oxepane isomer thereof, or a pharmaceutically acceptable salt of any of the foregoing
wherein the cancer is selected from the group consisting of breast cancer, colorectal cancer, endometrial cancer, head and neck cancer, liver cancer, lung cancer, ovarian cancer, pancreatic cancer, renal cancer, thyroid cancer, vulvar cancer, and prostate cancer.

2. The method of claim 1, wherein the dosage is about 6 mg/week to about 14 mg/week.

3. The method of claim 1, wherein the dosage is administered via IV infusion.

4. The method of claim 3, wherein the dosage is administered over about 0.5 hour to about 2 hours.

5. The method of claim 3, wherein the dosage is administered over about 1 hour.

6. The method of claim 1, wherein the subject is human.

7. The method of claim 1, wherein the method further comprises administering a tacrolimus solution to the subject.

8. The method of claim 7, wherein the tacrolimus solution comprises about 0.1 mg/mL to about 1 mg/mL tacrolimus.

9. The method of claim 7, wherein the tacrolimus solution is administered 1, 2, 3, or 4 times daily.

10. The method of claim 7, wherein the tacrolimus solution is administered on the day of administering the dosage or just prior to administering the dosage.

11. The method of claim 1, wherein the liver cancer is hepatocellular carcinoma or cholangiocarcinoma, and rhabdomyosarcoma.

12. The method of claim 1, wherein the cancer is a solid tumor.

13. The method of claim 1, wherein the cancer is head and neck cancer.

14. The method of claim 1, wherein the cancer is colorectal cancer and comprises a mutation of PIK3CA, an amplification of MYC, or a mutation of PIK3CA and an amplification of MYC.

15. The method of claim 1, wherein the cancer is head and neck cancer and comprises a mutation of PIK3CA, a mutation of PTEN, or a mutation of PIK3CA and a mutation of PTEN.

16. The method of claim 11, wherein the hepatocellular carcinoma comprises a mutation of NFE2L2.

17. The method of claim 1, wherein the cancer is ovarian cancer and comprises a mutation of TSC2.

18. The method of claim 1, wherein the cancer is pancreatic cancer and comprises a mutation of STK11, a $KRAS^{G12C}$ mutation, or a mutation of STK11 and a $KRAS^{G12C}$ mutation.

19. The method of claim 7, wherein the tacrolimus solution treats or prevents mucositis in the subject that has been, is being, or will be treated with the compound inhibitor.

20. The method of claim 19, wherein the mucositis is stomatitis.

21. A method of treating a subject having a cancer, the method comprising administering a dosage of about 6 mg/week to about 25 mg/week of a compound to the subject:

wherein the compound is

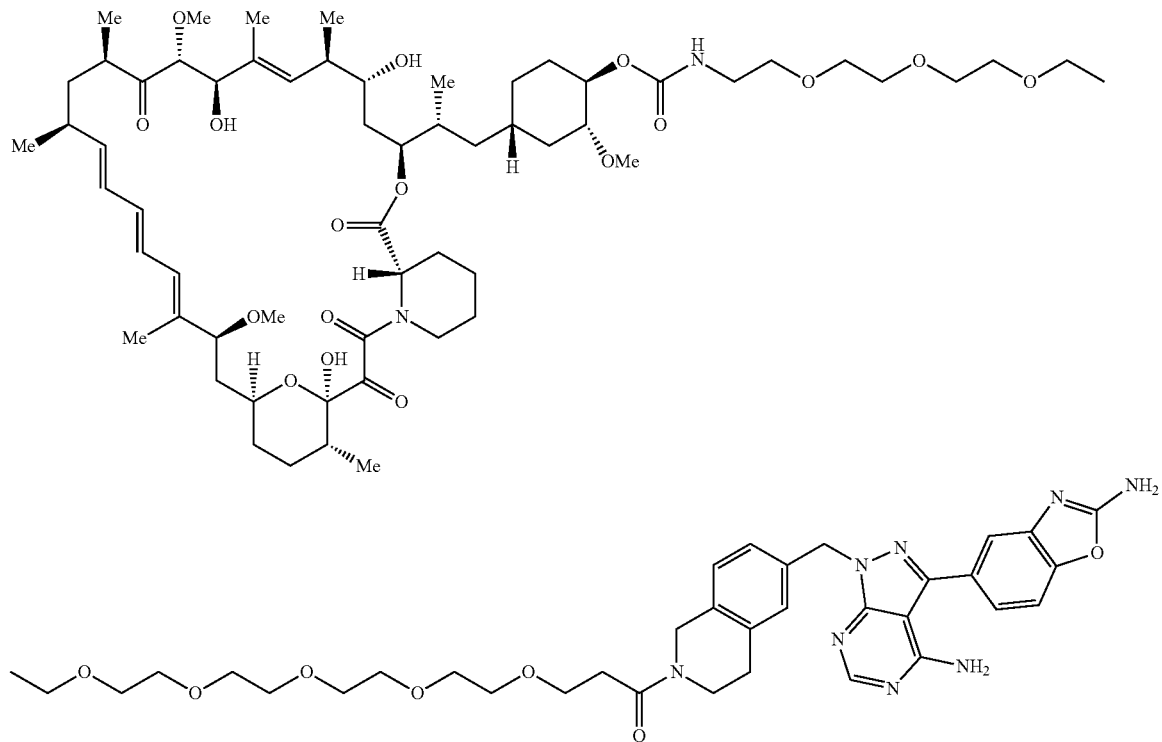

or a stereoisomer, tautomer, or oxepane isomer thereof, or pharmaceutically acceptable salt of any of the foregoing wherein the cancer comprises a PIK3CA mutation, a PTEN mutation, a TSC1 mutation, a TSC2 mutation, or a combination thereof.

22. The method of claim 21, wherein the cancer comprises a PTEN mutation.

23. The method of claim 22, wherein the PTEN mutation is a dominant negative mutation.

24. The method of claim 21, wherein the cancer comprises greater than about 95% clonality of pathogenic variants in one or more of PIK3CA, PTEN, TSC1, and TSC2, wherein the PTEN mutation is a dominant negative mutation.

* * * * *

```
SEQUENCE LISTING

Sequence total quantity: 5
SEQ ID NO: 1            moltype = AA   length = 2549
FEATURE                 Location/Qualifiers
source                  1..2549
                        mol_type = protein
                        organism = Homo sapiens
SEQUENCE: 1
MLGTGPAAAT TAATTSSNVS VLQQFASGLK SRNEETRAKA AKELQHYVTM ELREMSQEES   60
TRFYDQLNHH IFELVSSSDA NERKGGILAI ASLIGVEGGN ATRIGRFANY LRNLLPSNDP  120
VVMEMASKAI GRLAMAGDTF TAEYVEFEVK RALEWLGADR NEGRRHAAVL VLRELAISVP  180
TFFFQQVQPF FDNIFVAVWD PKQAIREGAV AALRACLILT TQREPKEMQK PQWYRHTFEE  240
AEKGFDETLA KEKGMNRDDR IHGALLILNE LVRISSMEGE RLREEMEEIT QQQLVHDKYC  300
KDLMGFGTKP RHITPFTSFQ AVQPQQSNAL VGLLGYSSHQ GLMGFGTSPS PAKSTLVESR  360
CCRDLMEEKF DQVCQWVLKC RNSKNSLIQM TILNLLPRLA AFRPSAFTDT QYLQDTMNHV  420
LSCVKKEKER TAAFQALGLL SVAVRSEFKV YLPRVLDIIR AALPPKDFAH KRQKAMQVDA  480
TVFTCISMLA RAMGPGIQQD IKELLEPMLA VGLSPALTAV LYDLSRQIPQ LKKDIQDGLL  540
KMLSLVLMHK PLRHPGMPKG LAHQLASPGL TTLPEASDVG SITLALRTLG SFEFEGHSLT  600
QFVRHCADHF LNSEHKEIRM EAARTCSRLL TPSIHLISGH AHVVSQTAVQ VVADVLSKLL  660
VVGITDPDPD IRYCVLASLD ERFDAHLAQA ENLQALFVAL NDQVFEIREL AICTVGRLSS  720
MNPAFVMPFL RKMLIQILTE LEHSGIGRIK EQSARMLGHL VSNAPRLIRP YMEPILKALI  780
LKLKDPDPDP NPGVINNVLA TIGELAQVSG LEMRKWVDEL FIIIMDMLQD SSLLAKRQVA  840
LWTLGQLVAS TGYVVEPYRK YPTLLEVLLN FLKTEQNQGT RREAIRVLGL LGALDPYKHK  900
VNIGMIDQSR DASAVSLSES KSSQDSSDYS TSEMLVNMGN LPLDEFYPAV SMVALMRIFR  960
DQSLSHHHTM VVQAITFIFK SLGLKCVQFL PQVMPTFLNV IRVCDGAIRE FLFQQLGMLV 1020
SFVKSHIRPY MDEIVTLMRE FWVMNTSIQS TIILLIEQIV VALGGEFKLY LPQLIPHMLR 1080
VFMHDNSPGR IVSIKLLAAI QLFGANLDDY LHLLLPPIVK LFDAPEAPLP SRKAALETVD 1140
RLTESLDFTD YASRIIHPIV RTLDQSPELR STAMDTLSSL VFQLGKKYQI FIPMVNKVLV 1200
RHRINHQRYD VLICRIVKGY TLADEEEDPL IYQHRMLRSG QGDALASGPV ETGPMKKLHV 1260
STINLQKAWG AARRVSKDDW LEWLRRLSLE LLKDSSSPSL RSCWALAQAY NPMARDLFNA 1320
AFVSCWSELN EDQQDELIRS IELALTSQDI AEVTQTLLNL AEFMEHSDKG PLPLRDDNGI 1380
VLLGERAAKC RAYAKALHYK ELEFQKGPTP AILESLISIN NKLQQPEAAA GVLEYAMKHF 1440
GELEIQATWY EKLHEWEDAL VAYDKKMDTN KDDPELMLGR MRCLEALGEW GQLHQQCCEK 1500
WTLVNDETQA KMARMAAAAA WGLGQWDSME EYTCMIPRDT HDGAFYRAVL ALHQDLFSLA 1560
QQCIDKARDL LDAELTAMAG ESYSRAYGAM VSCHMLSELE EVIQYKLVPE RREIIRQIWW 1620
ERLQGCQRIV EDWQKILMVR SLVVSPHEDM RTWLKYASLC GKSGRLALAH KTLVLLLGVD 1680
PSRQLDHPLP TVHPQVTYAY MKNMWKSARK IDAFQHMQHF VQTMQQQAQH AIATEDQQHK 1740
QELHKLMARC FLKLGEWQLN LQGINESTIP KVLQYYSAAT EHDRSWYKAW HAWAVMNFEA 1800
VLHYKHQNQA RDEKKKLRHA SGANITNATT AATTAATATT TASTEGSNSE SEAESTENSP 1860
TPSPLQKKVT EDLSKTLLMY TVPAVQGFFR SISLSRGNNL QDTLRVLTLW FDYGHWPDVN 1920
EALVEGVKAI QIDTWLQVIP QLIARIDTPR PLVGRLIHQL LTDIGRYHPQ ALIYPLTVAS 1980
KSTTTARHNA ANKILKNMCE HSNTLVQQAM MVSEELIRVA ILWHEMWHEG LEEASRLYFG 2040
ERNVKGMFEV LEPLHAMMER GPQTLKETSF NQAYGRDLME AQEWCRKYMK SGNVKDLTQA 2100
WDLYYHVFRR ISKQLPQLTS LELQYVSPKL LMCRDLELAV PGTYDPNQPI IRIQSIAPSL 2160
QVITSKQRPR KLTLMGSNGH EFVFLLKGHE DLRQDERVMQ LFGLVNTLLA NDPTSLRKNL 2220
SIQRYAVIPL STNSGLIGWV PHCDTLHALI RDYREKKKIL LNIEHRIMLR MAPDYDHLTL 2280
MQKVEVFEHA VNNTAGDDLA KLLWLKSPSS EVWFDRRTNY TRSLAVMSMV GYILGLGDRH 2340
PSNLMLDRLS GKILHIDFGD CFEVAMTREK FPEKIPPRLT RMLTNAMEVT GLDGNYRITC 2400
HTVMEVLREH KDSVMAVLEA FVYDPLLNWR LMDTNTKGNK RSRTRTDSYS AGQSVEILDG 2460
VELGEPAHKK TGTTVPESIH SFIGDGLVKP EALNKKAIQI INRVRDKLTG RDFSHDDTLD 2520
VPTQVELLIK QATSHENLCQ CYIGWCPFW                                  2549

SEQ ID NO: 2            moltype = DNA   length = 8733
FEATURE                 Location/Qualifiers
source                  1..8733
                        mol_type = other DNA
                        organism = Homo sapiens
SEQUENCE: 2
gctcccggct tagaggacag cggggaaggc gggcggtggg gcaggggggcc tgaagcggcg   60
gtaccggtgc tggcggcggc agctgaggcc ttggccgaag ccgcgcgaac ctcagggcaa  120
gatgcttgga accggacctg ccgccgccac caccgctgcc accacatcta gcaatgtgag  180
cgtcctgcag cagtttgcca gtggcctaaa gagccggaat gaggaaacca gggccaaagc  240
cgccaaggag ctccagcact atgtcaccat ggaactccga gaatgagtc aagaggagtc  300
tactcgcttc tatgaccaac tgaaccatca cattttttgaa ttggttttcca gctcagatgc  360
caatgagagg aaagtggcat tcttggccat agctagcctc ataggagtgg aaggtgggaa  420
tgccacccga attggcagat ttgccaacta tcttcggaac ctcctcccct ccaatgaccc  480
agttgtcatg gaaatggcat ccaaggccat tggccgtctt gccatggcag gggacacttt  540
taccgctgag tacgtggaat ttgaggtgaa gcgagccctg gaatggctgg gtgctgaccg  600
```

```
caatgagggc cggagacatg cagctgtcct ggttctccgt gagctggcca tcagcgtccc    660
taccttcttc ttccagcaag tgcaacccte ctttgacaac attttgtgg ccgtgtggga     720
ccccaaacag gccatccgtg agggagctgt agccgccctt cgtgcctgtc tgattctcac    780
aacccagcgt gagccgaagg agatgcagaa gcctcagtgg tacaggcaca catttgaaga    840
agcagagaag ggatttgatg agaccttggc caaagagaag ggcatgaatc gggatgatcg    900
gatccatgga gccttgttga tccttaacga gctggtccga atcagcagca tggagggaga    960
gcgtctgaga gaagaaatgg aagaaatcac acagcagcag ctggtacacg acaagtactg   1020
caaagatctc atgggcttcg gaacaaaacc tcgtcacatt accccttca ccagtttcca    1080
ggctgtacag cccagcagt caaatgcctt ggtggggctg ctggggtaca gctctcacca    1140
aggcctcatg ggatttggga cctccccag tccagctaag tccaccctgg tggagagccg    1200
gtgttgcaga gacttgatgg aggagaaatt tgatcaggtg tgccagtggg tgctgaaatg   1260
caggaatagc aagaactcgc tgatccaaat gacaatcctt aatttgttgc cccgcttggc   1320
tgcattccga ccttctgcct tcacagatac ccagtatctc caagatacca tgaaccatgt   1380
cctaagctgt gtcaagaagg agaaggaacg tacagccgcc ttccaagccc tggggctact   1440
ttctgtggct gtgaggtctg agtttaaggt ctatttgcct cgcgtgctgg acatcatccg   1500
agcggccctg cccccaaagg acttcgccca taagaggcag aaggcaatgc aggtggatgc   1560
cacagtcttc acttgcatca gcatgctggc tcgagcaatg gggccaggca tccagcagga   1620
tatcaaggag ctgctggagc ccatgctggc agtgggacta agccctgcct tcactgcagt   1680
gctctacgac ctgagccgtc agattccaca gctaaagaag gacattcaag atgggcact    1740
gaaaatgctg tccctggtcc ttatgcacaa acccttcgc cacccaggca tgcccaaggg    1800
cctggcccat cagctggcct ctcctggcct cacgaccctc cctgaggcca gcgatgtggg   1860
cagcatcact cttgccctcc gaacgcttgg cagctttgaa tttgaaggcc actctctgaa   1920
ccaatttgtt cgccactgtg cggatcattt cctgaacagt gagcacaagg agatccgcat   1980
ggaggctgcc cgcacctgct cccgcctgct cacaccctcc atccacctca tcagtggcca   2040
tgctcatgtg gttagccaga ccgcagtgca agtggtggca gatgtgctta gcaaactgct   2100
cgtagttggg ataacagatc ctgaccctga cattcgctac tgtgtcttgg cgtccctgga   2160
cgagcgcttt gatgcacacc tggcccagc ggagaacttg caggccttgt ttgtggctct    2220
gaatgaccag gtgtttgaga tccgggagct ggccatctgc actgtgggcc gactcagtag   2280
catgaaccct gcctttgtca tgcctttcct gcgcaagatg ctcatccaga ttttgacaga   2340
gttggagcac agtgggattg gaagaatcaa agagcagagt gcccgcatgc tgggcaccct   2400
ggtctccaat gccccgac tcatccgccc ctacatctga aggcattaat                2460
tttgaaactg aaagatccag accctgatcc aaacccaggt gtgatcaata atgtcctggc   2520
aacaatagga gaattggcac aggttagtgg cctggaaatg aggaaatggg ttgatgaact   2580
ttttattatc atcatggaca tgctccagga ttcctcttg ttggccaaaa ggcaggtggc    2640
tctgtggacc ctgggacagt tggtggccag cactggctat gtagtagagc cctacaggaa   2700
gtaccctact ttgcttgagg tgctactgaa ttttctgaag actgagcaga accagggtac   2760
acgcagagag gccatccgtg tgttagggct tttaggggct ttggatccct acaagcacaa   2820
agtgaacatt ggcatgatag accagtcccg ggatgcctct gctgtcagcc tgtcagaatc   2880
caagtcaagt caggattcct ctgactatag cactagtgaa atgctggtca atgggaaa     2940
cttgcctctg gatgagttct acccagctgt gtccatggtg gccctgatgc ggatcttccg   3000
agaccagtca ctctctcatc atcacaccat ggttgtccag gccatcacct tcatcttcaa   3060
gtccctggga ctcaaatgtg tgcagttcct gccccaggtc atgccacgt tccttaacgt    3120
cattcagtc tgtgatgggg ccatccggga atttttgtgc cagcagctgg gaatgtggt     3180
gtcctttgtg aagagccaca tcagaccta tatggatgaa atagtcaccc tcatgagaga    3240
attctgggtc atgaacacct caattcagag cacgatcatt cttctcattg agcaaattgt   3300
ggtagctctt ggggtgaat ttaagctcta cctgcccag ctgatccac acatgctgcg      3360
tgtcttcatg catgacaaca gcccaggccg cattgtctct atcaagttac tggctgcaat   3420
ccagctgttt ggcgccaacc tggatgacta cctgcattta ctgctgcctc ctattgttaa   3480
gttgtttgat gccctgaag ctccactgcc atctcgaaag gcagcgctag agactgtgga    3540
ccgcctgacg gagtccctgg atttcactga ctatgcctcc cggatcattc ccctattgt    3600
tcgaacactg gaccagagcc cagaactgcg ctccacagcc atggacacgc tgtcttcact   3660
tgtttttcag ctggggaaga agtaccaaat tttcattcca atggtgaata agttctggt     3720
gcgcacccga atcaatcatc agcgctatga tgtgctcatc tgcagaattg tcaagggata   3780
cacttgct gatgaagagg aggatccttt gatttaccag catcggatgc ttaggagtgg     3840
ccaagggat ggcattggcta gtggaccagt ggaaacagga cccatgaaga aactgcacgt    3900
cagcaccate aacctccaaa aggcctgggg cgctgccagg agggtctcca agatgactg    3960
gctgaatgg ctgagacggc tgagcctgga gctgctgaag gactcatcat cgccctccct    4020
gcgctcctgc tgggccctgg cacaggccta caacccgatg ccagggatc tcttcaatgc    4080
tgcatttgtg tcctgctggt ctgaactgaa tgaagatcaa caggatgagc tcatcagaag   4140
catcgagttg gccctcacct cacaagacat cgctgaagtc acacagaccc tcttaaactt   4200
ggctgaattc atggaacaca gtgacaaggg cccctgcca ctgagagatg acaatggcat    4260
tgttctgctg ggtgagagag ctgccaagtg ccgagcatat gccaaagcac tacactacaa   4320
agaactggag ttcagaaaag gccccacccc tgccattgta gaatctctca tcagcattaa   4380
taataagcta cagcagccgg aggcagcggc tggagtgtta gaatatgcca tgaaacactt   4440
tggagagctg gagatccagg ctacctggta tgagaaactg cacgagtggg aggatgccct   4500
tgtggcctat gacaagaaaa tggacaccaa caaggacgac ccagagctga tgctgggccg   4560
catgcgctgc ctcgaggcct tggggaatgg ggtcaactc caccagcagt gctgtgaaaa    4620
gtggaccctg gttaatgatg agaccaagc caagatggcc cggatggctg ctgcagctgg   4680
atggggttta ggtcagtggg acagcatgga agaatacacc tgtatgatcc ctcggacac    4740
ccatgatggg gcattttata gagctgtgct ggcactgcat caggacctct tctccttggc   4800
acaacagtgc attgacaagg ccagggacct gctggatgct gaattaactg cgatggcagg   4860
agagagttac agtcgggcat atgggccat ggtttcttgc cacatgctgt ccgagctgga    4920
ggaggttatc cagtacaaac ttgtcccga gcgacgagag atcatccgcc agatctggtg    4980
ggagagactg cagggctgcc agcgtatcgt agaggactgg cagaaaatcc ttatggtgcg   5040
gtcccttgtg gtcagccctc atgaagacat gagaacctgg ctcaagtatg caagcctgtg   5100
cggcaagagt ggcaggctgg ctcttgctca taaactttta gtgttgctcc tgggagttga   5160
tccgtctcgg caacttgacc atcctctgcc aacagttcac cctcaggtga cctatgccta   5220
catgaaaaac atgtggaaga gtgccgcaa gatcgatgcc ttccagcaca tgcagcatt    5280
tgtccagacc atgcagcaac aggcccagca tgccatcgct actgaggacc agcagcataa   5340
```

-continued

```
gcaggaactg cacaagctca tggcccgatg cttcctgaaa cttggagagt ggcagctgaa    5400
tctacagggc atcaatgaga gcacaatccc caaagtgctg cagtactaca gcgccgccac    5460
agagcacgac cgcagctggt acaaggcctg gcatgcgtgg gcagtgatga acttcgaagc    5520
tgtgctacac tacaaacatc agaaccaagc ccgcgatgag aagaagaaac tgcgtcatgc    5580
cagcggggcc aacatcacca cgccaccac tgccgccacc acggccgcca ctgccaccac    5640
cactgccagc accgagggca gcaacagtga gagcgaggcc gagagcaccg agaacagccc    5700
cacccatcg ccgctgcaga agaaggtcac tgaggatctg tccaaaaccc tcctgatgta    5760
cacggtgcct gccgtccagg gcttcttccg ttccatctcc ttgtcacgag caacaacct    5820
ccaggataca ctcagagttc tcaccttatg gtttgattat ggtcactggc cagatgtcaa    5880
tgaggcctta gtgaggggg tgaaagccat ccagattgat acctggctac aggttatacc    5940
tcagctcatt gcaagaattg atacgcccag acccttggtg ggacgtctca ttcaccagct    6000
tctcacagac attggtcggt accaccccca ggccctcatc tacccactga ctggcttc    6060
taagtctacc acgacagccc ggcacaatgc agccaacaag attctgaaga acatgtgtga    6120
gcacagcaac ccctggtcc agcaggccat gatggtgagc gaggagctga tccgagtggc    6180
catcctctgg catgagatgt ggcatgaagg cctggaagag gcatctcgtt tgtactttgg    6240
ggaaaggaac gtgaaaggca tgtttgaggt gctggagccc ttgcatgcta tgatggaacg    6300
gggccccccag actctgaagg aaacatcctt taatcagtgc tatgtcgag atttaatgga    6360
ggcccaagag tggtcaggga agtacatgaa atcaggaat gtcaaggacc tcacccaagc    6420
ctgggacctc tattatcatg tgttccgacg aatctcaaag cagctgcctc agctcacatc    6480
cttagagctg caatatgttt ccccaaaact tctgatgtgc cgggaccttg aattggctgt    6540
gccaggaaca tatgacccca accagccaat cattcgcatt cagtccatag caccgtcttt    6600
gcaagtcatc acatccaagc agaggcccccg gaaattgaca cttatgggca gcaacggaca    6660
tgagtttgtt ttccttctaa aaggccatga agatctgcgc caggatgagc gtgtgatgca    6720
gctcttcggc ctggttaaca cccttctggc caatgaccca acatctcttc ggaaaaacct    6780
cagcatccag agatacgctg tcatcccttt atcgaccaac tcgggcctca ttggctgggt    6840
tccccactgt gacacactgc acgccctcat ccgggactac agggagaaga agaagatcct    6900
tctcaacatc gagcatccgca tacatgttgcg gatggctccg gactatgacc acttgactct    6960
gatgcagaag gtggaggtgt ttgagcatgc cgtcaataat acagctgggg acgacctggc    7020
caagctgctg tggctgaaaa gccccagctc cgaggtgtgg tttgaccgaa gaaccaatta    7080
tacccgttct ttagcggtca tgtcaatggt tgggtatatt ttaggcctgg gagatagaca    7140
cccatccaac ctgatgctgg accgtctgag tgggaagatc ctgcacattg actttgggga    7200
ctgctttgag gttgctatga cccgagagaa gtttccagag aagattccat ttagactaac    7260
aagaatgttg accaatgcta tggaggttac aggcctggat ggcaactaca gaatcacatg    7320
ccacacagtg atgaggtgc tgcgagagca caaggacagt gtcatggccg tgctggaagc    7380
cttgtctat gacccctctg tgaactggag gctgatggac acaaataca aaggcaacaa    7440
gcgatcccga acgaggacgg attcctactc tgctggccag tcagtcgaaa tttggacgt    7500
tgtggaactt ggagagccag cccataagaa acgggaccc acagtgccag aatctattca    7560
ttcttcatt ggagacggtt tggtgaaacc agaggcccta aataagaaag ctatccagat    7620
tattaacagg gttcgagata agctcactgg tcgggacttc tctcatgatg acactttgga    7680
tgttccaacg caagttgagc tgctcatcaa acaagcgaca tcccatgaaa acctctgcca    7740
gtgctatatt ggctggtgcc ctttctggta actggaggcc cagatgtgcc catcacgttt    7800
tttctgaggc ttttgtactt tagtaaatgc ttccactaaa ctgaaaccat ggtgagaaag    7860
tttgactttg ttaaatattt tgaaatgtaa atgaaaagaa ctatgctgta ttaaaagttg    7920
gtttgaacca actttctagc tgctgttgaa gaatatattg tcagaaacac aaggcttgat    7980
ttggttccca ggacagtgaa acatagtaat accacgtaaa tcaagccatt cattttgggg    8040
aacagaagat ccataacttt agaaatacgg ttttgacttt aactcacaag gaactcatc    8100
ataagtactt gctgatggaa gaatgaccta gttgctcctc tcaacatggg tacagcaaac    8160
tcagcacagc caagagcct caggtcgtgg agaacatgga ttaggatcct agactgtaaa    8220
gacacagaag atgctgacct caccctgcc acctatccca agacctcact ggtctgtgga    8280
cagcagcaga aatgtttgca agataggcca aaatgagtac aaaaggtctg tcttccatca    8340
gacccagtga tgctgcgact cacacagctt aattcaagac ctgaccgcta gtagggaggt    8400
ttattcagat cgctggcagc ctcggctgag cagatgcaca gaggggatca ctgtgcagtg    8460
ggaccaccct cactggcctt ctgcagcagg gttctgggat gttttcagtg gtcaaaatac    8520
tctgtttaga gcaagggctc agaaaacaga aatactgtca tggaggtgct gaacacaggg    8580
aaggtctggt acatattgga aattatgagc agaacaaata ctcaactaaa tgcacaaagt    8640
ataaagtgta gccatgtcta gacaccatgt tgtatcagaa taattttgt gccaataaat    8700
gacatcagaa ttttaaacat atgtaaaaaa aaa                                 8733
```

```
SEQ ID NO: 3        moltype = AA  length = 108
FEATURE             Location/Qualifiers
source              1..108
                    mol_type = protein
                    organism = Homo sapiens
SEQUENCE: 3
MGVQVETISP GDGRTFPKRG QTCVVHYTGM LEDGKKFDSS RDRNKPFKFM LGKQEVIRGW    60
EEGVAQMSVG QRAKLTISPD YAYGATGHPG IIPPHATLVF DVELLKLE                108

SEQ ID NO: 4        moltype = AA  length = 118
FEATURE             Location/Qualifiers
source              1..118
                    mol_type = protein
                    organism = Homo sapiens
SEQUENCE: 4
MSGGSSCSQT PSRAIPATRR VVLGDGVQLP PGDYSTTPGG TLFSTTPGGT RIIYDRKFLM    60
ECRNSPVTKT PPRDLPTIPG VTSPSSDEPP MEASQSHLRN SPEDKRAGGE ESQFEMDI     118
```

```
SEQ ID NO: 5           moltype = AA  length = 480
FEATURE                Location/Qualifiers
source                 1..480
                       mol_type = protein
                       organism = Homo sapiens
SEQUENCE: 5
MSDVAIVKEG  WLHKRGEYIK  TWRPRYFLLK  NDGTFIGYKE  RPQDVDQREA  PLNNFSVAQC   60
QLMKTERPRP  NTFIIRCLQW  TTVIERTFHV  ETPEEREEWT  TAIQTVADGL  KKQEEEEMDF  120
RSGSPSDNSG  AEEMEVSLAK  PKHRVTMNEF  EYLKLLGKGT  FGKVILVKEK  ATGRYYAMKI  180
LKKEVIVAKD  EVAHTLTENR  VLQNSRHPFL  TALKYSFQTH  DRLCFVMEYA  NGGELFFHLS  240
RERVFSEDRA  RFYGAEIVSA  LDYLHSEKNV  VYRDLKLENL  MLDKDGHIKI  TDFGLCKEGI  300
KDGATMKTFC  GTPEYLAPEV  LEDNDYGRAV  DWWGLGVVMY  EMMCGRLPFY  NQDHEKLFEL  360
ILMEEIRFPR  TLGPEAKSLL  SGLLKKDPKQ  RLGGGSEDAK  EIMQHRFFAG  IVWQHVYEKK  420
LSPPFKPQVT  SETDTRYFDE  EFTAQMITIT  PPDQDDSMEC  VDSERRPHFP  QFSYSASGTA  480
```